(12) United States Patent
Zhan

(10) Patent No.: US 8,962,810 B2
(45) Date of Patent: Feb. 24, 2015

(54) MACROCYCLIC HETEROCYCLIC COMPOUND FOR INHIBITING HEPATITIS C VIRUS AND PREPARATION AND USE THEREOF

(75) Inventor: Zheng-yun James Zhan, Shanghai (CN)

(73) Assignee: AB Pharma Ltd., Shanghai (CN)

( * ) Notice: Subject to any disclaimer, the term of this patent is extended or adjusted under 35 U.S.C. 154(b) by 0 days.

(21) Appl. No.: 14/126,554

(22) PCT Filed: Jun. 14, 2012

(86) PCT No.: PCT/CN2012/000821
§ 371 (c)(1),
(2), (4) Date: Mar. 21, 2014

(87) PCT Pub. No.: WO2012/171332
PCT Pub. Date: Dec. 20, 2012

(65) Prior Publication Data
US 2014/0205567 A1    Jul. 24, 2014

(30) Foreign Application Priority Data
Jun. 16, 2011  (CN) .......................... 2011 1 0162701

(51) Int. Cl.
*A61K 38/00* (2006.01)
*C07K 16/00* (2006.01)
(Continued)

(52) U.S. Cl.
CPC ............ *C07D 498/20* (2013.01); *C07K 5/0808* (2013.01); *C07K 5/06034* (2013.01); *A61K 31/407* (2013.01); *A61K 45/06* (2013.01); *C07D 498/16* (2013.01); *C07D 498/22* (2013.01)
USPC ........................................ 530/388.3; 514/3.7

(58) Field of Classification Search
None
See application file for complete search history.

(56) References Cited

U.S. PATENT DOCUMENTS 5,990,276 A  11/1999  Zhang et al.
2003/0207861 A1  11/2003  Arasappan et al.
(Continued)

FOREIGN PATENT DOCUMENTS

WO  89/04669  6/1989
WO  99/50230  3/1998
(Continued)

OTHER PUBLICATIONS

Alberti, et al., "Natural history of hepatitis C", Journal of Hepatology, vol. 31 (Suppl. 1), pp. 17-24, (1999).
(Continued)

*Primary Examiner* — James H Alstrum Acevedo
*Assistant Examiner* — Jeanette Lieb
(74) *Attorney, Agent, or Firm* — Greenberg Traurig, LLP; Fang Xie

(57) ABSTRACT

The present invention discloses a class of novel macro-heterocyclic compounds represented by the formula Ia or Ib, and their intermediates, preparation methods and the uses. The macro-heterocyclic compounds of the present invention have good inhibitory activities against hepatitis C virus (HCV), and can be used to treat HCV infection effectively by its excellent inhibition against HCV, low toxicity and side effects.

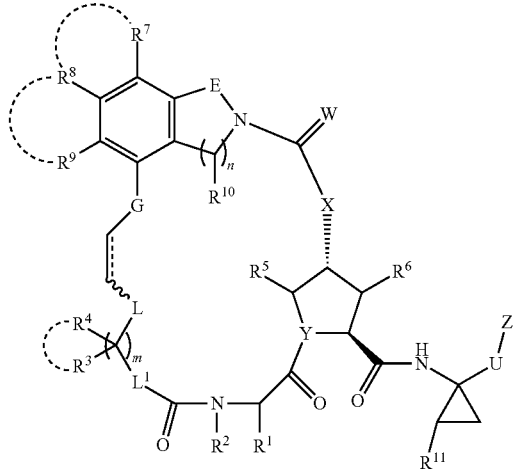

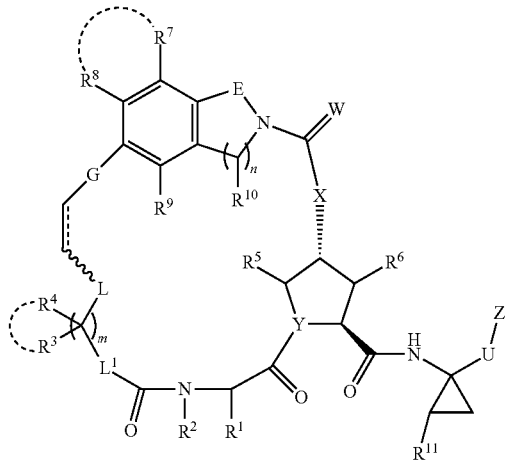

17 Claims, No Drawings

(51) Int. Cl.
*C07D 498/20* (2006.01)
*C07K 5/083* (2006.01)
*C07K 5/062* (2006.01)
*A61K 31/407* (2006.01)
*A61K 45/06* (2006.01)
*C07D 498/16* (2006.01)
*C07D 498/22* (2006.01)

(56) References Cited

U.S. PATENT DOCUMENTS

| | | | |
|---|---|---|---|
| 2005/0267018 | A1 | 12/2005 | Blatt et al. |
| 2007/0027071 | A1* | 2/2007 | Holloway et al. .............. 514/9 |
| 2009/0269305 | A1 | 10/2009 | Seiwert et al. |
| 2010/0003214 | A1 | 1/2010 | Gai et al. |
| 2010/0022578 | A1 | 1/2010 | Raboisson et al. |
| 2010/0029715 | A1 | 2/2010 | Stokbroekx et al. |
| 2010/0041889 | A1 | 2/2010 | Horvath et al. |
| 2011/0183895 | A1 | 7/2011 | Zhan |

FOREIGN PATENT DOCUMENTS

| | | |
|---|---|---|
| WO | 98/17679 | 4/1998 |
| WO | 98/46630 | 10/1998 |
| WO | 99/07733 | 2/1999 |
| WO | 99/07734 | 2/1999 |
| WO | 99/64442 | 12/1999 |
| WO | 00/09543 | 2/2000 |
| WO | 00/09558 | 2/2000 |
| WO | 02/18369 | 3/2002 |
| WO | 2005/037214 | 4/2005 |
| WO | 2007/014920 | 2/2007 |
| WO | 2007/015787 | 2/2007 |
| WO | 2007/016476 | 2/2007 |
| WO | 2007/148135 | 12/2007 |
| WO | 2008/051477 | 5/2008 |
| WO | 2008/057208 | 5/2008 |
| WO | 2008/057209 | 5/2008 |
| WO | 2008/074035 | 6/2008 |
| WO | 2008/106130 | 9/2008 |
| WO | 2008/134397 | 11/2008 |
| WO | 2009/010804 | 1/2009 |
| WO | 2009/064955 | 5/2009 |
| WO | 2009/134624 | 11/2009 |
| WO | 2010/033466 | 3/2010 |
| WO | 2010/075127 | 7/2010 |
| WO | 2011/025849 | 3/2011 |
| WO | 2011/091757 | 8/2011 |

OTHER PUBLICATIONS

Alter, Miriam J., "Hepatitis C virus infection in the United States", Journal of Hepatology, vol. 31 (Suppl. 1), pp. 88-91, (1999).

Asami, et al., "Synthesis and Biological Activity of 4'-Methoxy Derivatives of Abscisic Acid", Bioorganic & Medicinal Chemistry Letters, vol. 10, pp. 1571-1574, (2000).

Chambers, et al., "Evidence that the N-terminal domain of nonstructural protein NS3 from yellow fever virus is a serine protease responsible for site-specific cleavages in the viral polyprotein", Proc. Natl. Acad. Sci. USA, vol. 87, pp. 8898-8902, Nov. 1990.

Kolykhalov, et al., "Hepatitis C Virus-Encoded Enzymatic Activities and Conserved RNA Elements in the 3' Nontranslated Region Are Essential for Virus Replication In Vivo", Journal of Virology, vol. 74, No. 4, pp. 2046-2051, (2000).

LaPlante, et al., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, vol. 10, pp. 2271-2274, (2000).

Llinas-Brunet, et al., "Highly Potent and Selective Peptide-Based Inhibitors of the Hepatitis C Virus Serine Protease: Towards Smaller Inhibitors", Bioorganic & Medicinal Chemistry Letters, vol. 10, pp. 2267-2270, (2000).

Walker, Michael A., "Hepatitis C virus: an overview of current approaches and progress", Drug Discoveries and Therapeutics (DDT), vol. 4, No. 11, pp. 518-529, Nov. 1999.

Weiland, Ola, "Interferon therapy in chronic hepatitis C virus infection", FEMS Microbiology Reviews, vol. 14, pp. 279-288, (1994).

Zacuto, et al., "Preparation of 4-Allylisoindoline via a Kumada Coupling with Allylmagnesium Chloride", Organic Process Research & Development, vol. 15, pp. 158-161, (2011).

"Global surveillance and control of hepatitis C", Report of a WHO Consultation organized in collaboration with the Viral Hepatitis Prevention Board, Antwerp, Belgium, Journal of Viral Hepatitis, vol. 6, pp. 35-47, (1999).

International Search Report PCT/CN2012/000821 mailed Dec. 20, 2012.

* cited by examiner

MACROCYCLIC HETEROCYCLIC COMPOUND FOR INHIBITING HEPATITIS C VIRUS AND PREPARATION AND USE THEREOF

CROSS-REFERENCE TO RELATED APPLICATIONS

This application is a National Phase application of International Application No. PCT/CN12/00821 filed Jun. 14, 2012, which claims the benefit of and priority to Chinese Application No. CN201110162701.1 filed Jun. 16, 2011, the contents of both of which applications are incorporated by reference herein in their entirety.

FIELD OF THE INVENTION

This present invention relates to a kind of macro-heterocyclic based compounds highly potent as HCV inhibitor and their intermediates, preparation and uses.

BACKGROUND OF THE INVENTION

Hepatitis C virus (HCV) infection leads to chronic liver disease such as cirrhosis and hepatocellular carcinoma. So far, HCV infection is one of the major infection diseases, due to the fact that the number of HCV infected individuals is estimated 5-15% of the world's population while no any effective vaccines or therapeutic agents are available, so how to control or cure HCV is an urgent human health problem needed to be solved. [Reference: WO 89/04669; Lavanchy, J. Viral Hepatitis, 6, 35-47 (1999); Alter, J. Hepatology, 31 (Suppl. 1), 88-91 (1999); and Alberti et al, J. Hepatology, 31 (Suppl. 1), 17-24 (1999)].

Currently, due to lack of immunity or remission associated with HCV infection, hepatitis caused by HCV infection is more difficult to treat comparing to other forms of hepatitis. Now, the only available anti-HCV therapies are interferon-α, interferon-α/ribavirin combination, and pegylated interferon-α. However, sustained response rates for interferon-α or interferon-α/ribavirin combination were found to be <50% and patients suffer greatly from side effects of these therapeutic agents [Reference: Walker, DDT, 4, 518-529 (1999); Weiland, FEMS Microbial. Rev., 14, 279-288 (1994); and WO 02/18369]. Now, a linear molecule HCV inhibitor VX950 as a HCV new drug from Vertex (US) is expected to be approved during second half of 2011, which can control and cure HCV infection but the activity to inhibit HCV is quite low while the dosage is high and the side effects are potential. Besides, some patients could have antibodies, so it is necessary to develop more effective therapeutic drugs with lower dosage and side effects for inhibiting HCV.

So far, Hepatitis C virus (HCV) is the major causative agent for most cases of non-A, non-B hepatitis, and it is a single-stranded positive RNA virus in the Flaviviridae family. It includes a nucleocapsid protein (C), envelope proteins (E1 and E2), and several non-structural proteins (NS1, NS2, NS3, NS4a, NS5a, and NS5b). The NS3 protein possesses serine protease activity and is considered essential for viral replication and infectivity, and the essentiality of the NS3 protease was inferred from the fact that mutations in the yellow fever virus NS3 protease decreased viral infectivity [Reference: Chamber et al, Proc. Natl. Acad. Sci. USA 1990, 87, 8898-8902; Rice et al, J. Virol. 2000, 74 (4) 2046-51]. Furthermore, the HCV NS3 serine protease has been found to facilitate proteolysis at the NS3/NS4a, NS4a/NS4b, NS4b/NS5a, NS5a/NS5b junctions and is thus responsible for generating four viral proteins during viral replication [Reference: US 2003/0207861]. Consequently, the HCV NS3 serine protease enzyme is an attractive and effective target to develop new inhibitors for HCV infection.

Many European and American research institutes and pharmaceuticals have deeply and widely developed different kinds of the linear and cyclic molecules as HCV inhibitors since 1999. Some representative potential NS3 HCV protease inhibitors have been reported in patents and articles, such as WO2010033466, WO2010075127, US20100003214, US20100022578, US20100029715, US20100041889, WO2009134624, WO2009010804, US20090269305, WO2008057209, WO2008057208, WO2007015787, WO2005037214, WO200218369, WO200009558, WO200009543, WO199964442, WO199907733, WO199907734, WO199950230, WO199846630, WO199817679, U.S. Pat. No. 5,990,276, Dunsdon et al, Biorg. Med. Chem. Lett. 2000, 10, 1571-1579; Llinas-Brunet et al, Biorg. Med. Chem. Lett. 2000, 10, 2267-2270; and S. LaPlante et al., Biorg. Med. Chem. Lett. 2000, 10, 2271-2274.

Besides, other HCV NS3 protease inhibitors such as a kind of macro-cyclic peptide compounds were derived from bicyclic rings formed by one aromatic ring and another saturated heterocyclic ring on HCV NS3 protease P2 site, which was reported in patent US2005/0267018 of InterMune. The patent WO2007/016476 of Phenomix published in 2007 disclosed a linear peptide compound formed by connection of special boric acid on HCV NS3 protease P1 site; The patent WO2007/014920 of Tibotec and Medivir published in 2007 disclosed a macro-cyclic peptide compound derived from N-serined carbamates; The patent WO2008/074035 of Abbott published in 2008 disclosed a linear peptide compound derived from special cycloalkanes; The patent WO2008/106130 of Achillion published in 2008 disclosed a linear and macro-cyclic peptide derived from special piperidines; The patent WO2008/134397 of Enanta published in 2008 disclosed a linear peptide compound derived from connection of hydrazine groups on HCV NS3 protease P3 site; Also, The patent WO2008/057209 of Merck published in 2008 disclosed a macro-cyclic peptide compound by connection of aromatic rings on HCV NS3 protease P2 site.

So far, some different kinds of macro cyclic HCV inhibitors were developed by famous global pharmaceuticals have entered into Phase III in the US, EU and in Japan, such as ITMN-191 (RG-7227) of InterMune (US) and MK-7009 of Merck (US) by Structure Figure 1. Other potent molecules ZN2007, ZN2012 and ZN2017 (Reference: CN102140100 A; US2011/0183895 A1; WO2011/091757 A1) were developed by Zannan to inhibit HCV, is now taking the pre-clinical research. The character of Zannan's macro-heterocyclic HCV drugs is to design a macro-cyclic molecule by synthesis of 14-20 membered macrocyclic molecules prepared by both amido bond and olefin double-bond.

Structure FIG. 1

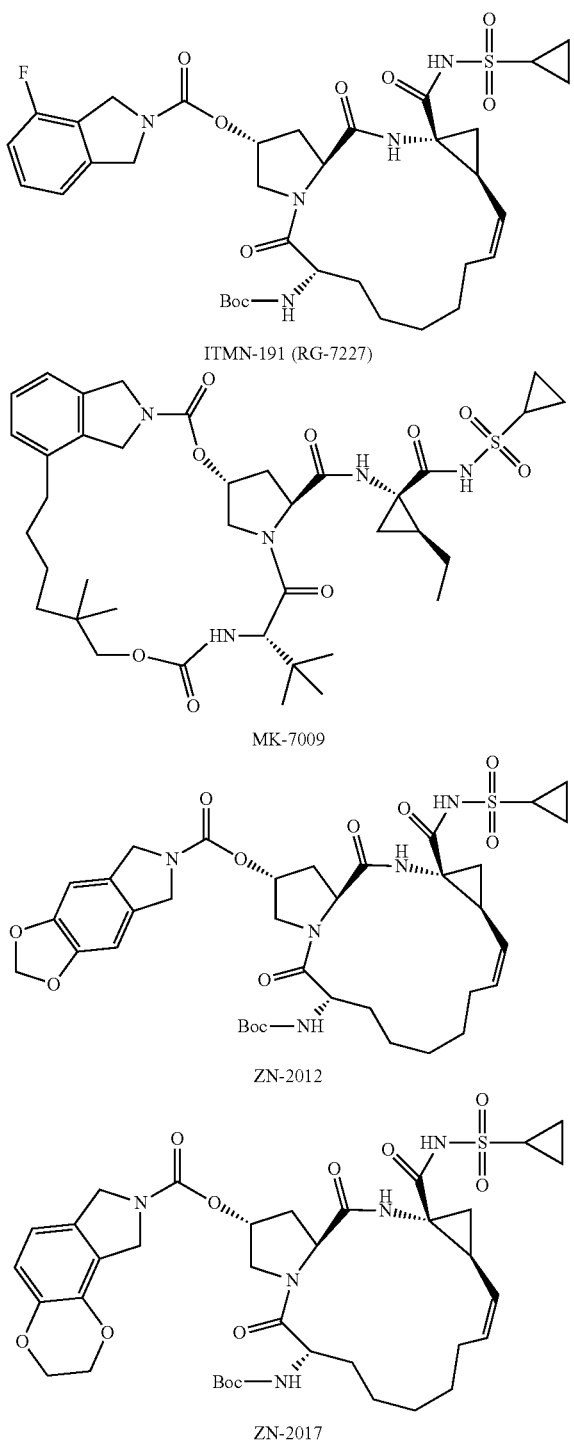

ITMN-191 (RG-7227)

MK-7009

ZN-2012

ZN-2017

SUMMARY OF THE INVENTION

The purpose in the present invention was to develop new macro-heterocyclic based compounds different from present structures, based on 17-25 heterocyclic ring structure, and their intermediates, preparation methods and uses thereof. The new developed macro-heterocyclic compounds had good inhibitory activities against hepatitis C virus and could be used effectively to cure HCV patients by excellent inhibition against HCV and low toxicity and side effects.

The present invention in the first aspect provides a kind of novel macro-heterocyclic based compounds represented by the formula Ia or Ib, and their stereoisomers, tautomers, esterification or amidation prodrugs, pharmaceutically acceptable salts, or mixtures thereof;

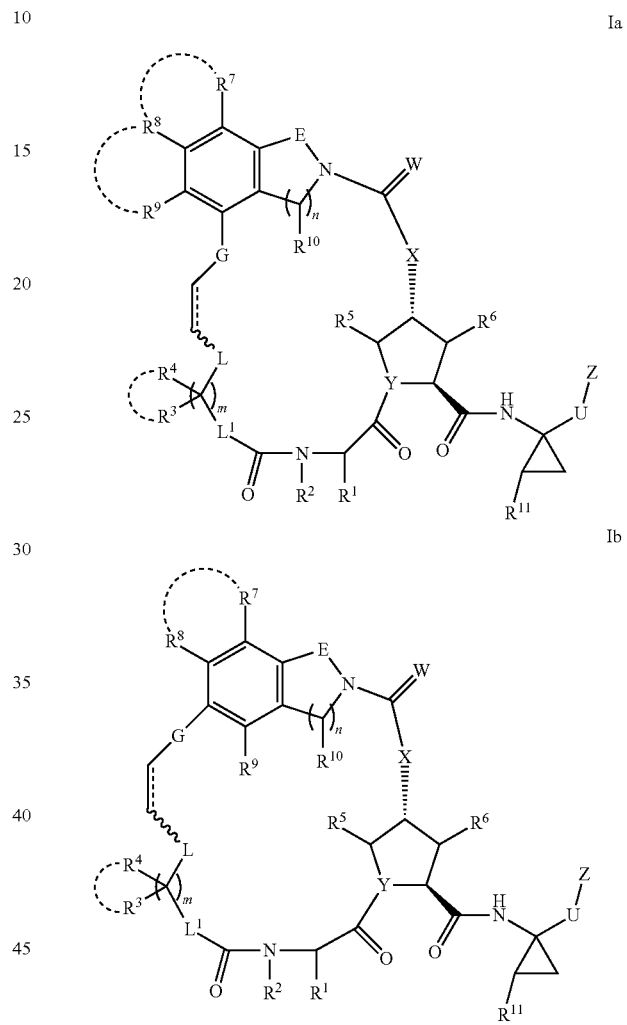

Ia

Ib

Wherein:
m=1 or 2; n=0, 1 or 2;
" ----- " is a single bond or double bond;
E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkylcarbonyl, $C_1$-$C_{20}$ alkoxycarbonyl, $C_6$-$C_{20}$ aryloxycarbonyl, $C_2$-$C_{20}$ heterocyclic oxycarbonyl, aminocarbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ arylamino aminosulfonyl group.

Rb and Rc are each independently selected from hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxyl, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic-oxycarbonyl, $C_2$-$C_{20}$ heterocyclic aryl, $C_1$-$C_{20}$ alkylamino, $C_2$-$C_{20}$ heterocyclic amino, $C_6$-$C_{20}$ arylamino, aminocarbonyl, $C_1$-$C_{20}$ alkylaminocarbonyl, carbonylamino, $C_1$-$C_{20}$ alkylcarbonylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{20}$ alkoxyl, $C_1$-$C_{20}$ alkylamino, $C_1$-$C_{20}$ alkyl-oxygen, $C_1$-$C_{20}$ alkyl, $C_1$-$C_{20}$ alkoxycarbonyl, carbonyl, carbonylamino or $C_1$-$C_{20}$ alkylcarbonylamino group; when $R^7$ and $R^8$ or $R^8$ and $R^9$ are connected each other as a cyclic structure, G is methylene or does not exist (ie. "═" connected directly with the phenyl group of polyheterocyclic group); wherein the definition of Ra, Rb and Rc are the same as that in E.

L and $L^1$ are each independently selected from oxygen, sulfur, $C_2$-$C_{20}$ alkenyl, $C_1$-$C_{20}$ alkyl, $C_3$-$C_{20}$ cycloalkyl, $C_2$-$C_{20}$ heterocyclic, $C_6$-$C_{20}$ aryl, $C_3$-$C_{20}$ heterocyclic aryl, $C_1$-$C_{20}$ alkylthio, $C_1$-$C_{20}$ alkoxyl, $C_3$-$C_{20}$ cycloalkoxyl, $C_2$-$C_{20}$ heterocyclic oxyl, $C_1$-$C_{20}$ alkylamino, $C_1$-$C_{20}$ alkoxycarbonyl, $C_6$-$C_{20}$ aryl, or $C_6$-$C_{20}$ aryloxy group;

U is selected from carbonyl, sulfoxide (—SO—), sulfone (—$SO_2$—), —P(O)(ORd)- or —B(ORe)-; Wherein Rd and Re are independently selected from hydrogen (H), $C_1$-$C_{20}$ alkyl, $C_3$-$C_{20}$ cycloalkyl, $C_2$-$C_{20}$ heterocyclic, $C_6$-$C_{20}$ aryl, or $C_3$-$C_{20}$ heterocyclic alkyl group;

W is selected from oxygen or sulfur;

X is selected from oxygen, sulfur, nitrogen or —NRa—; wherein the definition of Ra is the same as that in E and G;

Y is selected from nitrogen or CH;

Z is selected from hydrogen (H), hydroxyl (OH), amino ($NH_2$), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ arylamino, $C_3$-$C_{20}$ heterocyclic arylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkylaminosulfonamido, $C_3$-$C_{20}$ cycloalkylaminosulfonamido, $C_6$-$C_{20}$ aryloxysulfonamido, $C_1$-$C_{20}$ alkylaminosulfonamido, $C_3$-$C_{20}$ cycloalkylaminosulfonamido, $C_6$-$C_{20}$ arylaminosulfonamido, uramido, $C_1$-$C_{20}$ alkyluramido, or $C_1$-$C_{20}$ alkylthiouramido group.

$R^1$ is selected from hydrogen (H), $C_1$-$C_{20}$ alkyl, $C_3$-$C_{20}$ cycloalkyl, $C_6$-$C_{20}$ aryl, $C_3$-$C_{20}$ heterocyclic aryl, $C_1$-$C_{20}$ alkylsulfonamido, $C_2$-$C_{20}$ heterocyclic sulfonamido, or $C_1$-$C_{20}$ alkoxyl carbonylamino group;

$R^2$ is selected from hydrogen (H), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_6$-$C_{20}$ aryl, $C_3$-$C_{20}$ heterocyclic aryl, $C_6$-$C_{20}$ aryloxycarbonyl, $C_1$-$C_{20}$ alkylsulfonyl, $C_3$-$C_{20}$ cycloalkylsulfonyl, $C_1$-$C_{20}$ alkoxysulfonyl, $C_3$-$C_{20}$ cycloalkoxysulfonyl, $C_6$-$C_{20}$ arylsulfonyl, $C_6$-$C_{20}$ aryloxysulfonyl, $C_1$-$C_{20}$ alkylaminosulfonyl, $C_3$-$C_{20}$ cycloalkylaminosulfonyl, or $C_6$-$C_{20}$ arylaminosulfonyl group;

$R^3$, $R^4$, $R^5$ and $R^6$ are each independently selected from hydrogen, halogen atom, hydroxyl, cyano, nitro, $C_1$-$C_{20}$ alkyl, $C_3$-$C_{20}$ cycloalkyl, $C_1$-$C_{20}$ alkoxyl, $C_1$-$C_{20}$ alkylamino, $C_2$-$C_{20}$ heterocyclic amino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_{20}$ alkyl, $C_1$-$C_{20}$ alkoxyl, $C_1$-$C_{20}$ alkylthio, $C_1$-$C_{20}$ alkoxylcarbonyl, aminocarbonyl, $C_1$-$C_{20}$ alkylaminocarbonyl, carbonylamino, $C_1$-$C_{20}$ alkylcarbonylamino, $C_2$-$C_{20}$ heterocyclicoxyl carbonyl, $C_6$-$C_{20}$ aryl, $C_6$-$C_{20}$ aryloxy, $C_6$-$C_{20}$ aryloxycarbonyl or $C_2$-$C_{20}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{20}$ alkyl, $C_3$-$C_{20}$ cycloalkyl, $C_1$-$C_{20}$ alkoxyl, $C_1$-$C_{20}$ alkylthio, $C_1$-$C_{20}$ alkoxylcarbonyl, $C_1$-$C_{20}$ alkylaminocarbonyl, $C_1$-$C_{20}$ alkylcarbonylamino, $C_6$-$C_{20}$ aryl, $C_6$-$C_{20}$ aryloxy, $C_6$-$C_{20}$ aryloxycarbonyl or $C_2$-$C_{20}$ heterocyclic group.

$R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group;

In one preferred embodiment in the present invention by the formula Ia or Ib,

Wherein:

m=1 or 2; n=0, 1 or 2;

"═" is a single bond or double bond;

E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkylcarbonyl, $C_1$-$C_{15}$ alkoxycarbonyl, $C_6$-$C_{15}$ aryloxycarbonyl, $C_2$-$C_{15}$ heterocyclic oxycarbonyl, aminocarbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylamino aminosulfonyl group.

Rb and Rc are each independently selected from hydrogen, halogen atom, cyano, nitro, $C_1$-$C_{15}$ alkyl, $C_3$-$C_{15}$ cycloalkyl, $C_6$-$C_{15}$ aryl, $C_1$-$C_{15}$ alkoxyl, $C_1$-$C_{15}$ alkylthio, $C_1$-$C_{15}$ alkoxycarbonyl, $C_6$-$C_{15}$ aryloxy, $C_6$-$C_{15}$ aryloxycarbonyl, $C_2$-$C_{15}$ heterocyclic-oxycarbonyl, $C_2$-$C_{15}$ heterocyclic aryl, $C_1$-$C_{15}$ alkylamino, $C_2$-$C_{15}$ heterocyclic amino, $C_6$-$C_{15}$ arylamino, aminocarbonyl, $C_1$-$C_{15}$ alkylaminocarbonyl, carbonylamino, $C_1$-$C_{15}$ alkylcarbonylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{15}$ alkoxyl, $C_1$-$C_{15}$ alkylamino, $C_1$-$C_{15}$ alkyl-oxygen, $C_1$-$C_{15}$ alkyl, $C_1$-$C_{15}$ alkoxycarbonyl, carbonyl, carbonylamino or $C_1$-$C_{15}$ alkylcarbonylamino group; when $R^7$ and $R^8$ or $R^8$ and $R^9$ are connected each other as a cyclic structure, G is methylene or does not exist (ie. "═" connected directly with the phenyl group of polyheterocyclic group); wherein the definition of Ra, Rb and Rc are the same as that in E.

L and $L^1$ are each independently selected from oxygen, sulfur, $C_2$-$C_{15}$ alkenyl, $C_1$-$C_{15}$ alkyl, $C_3$-$C_{15}$ cycloalkyl, $C_2$-$C_{15}$ heterocyclic, $C_6$-$C_{15}$ aryl, $C_3$-$C_{15}$ heterocyclic aryl, $C_1$-$C_{15}$ alkylthio, $C_1$-$C_{15}$ alkoxyl, $C_3$-$C_{15}$ cycloalkoxyl, $C_2$-$C_{15}$ heterocyclic oxyl, $C_1$-$C_{15}$ alkylamino, $C_1$-$C_{15}$ alkoxycarbonyl, $C_6$-$C_{15}$ aryl, or $C_6$-$C_{15}$ aryloxy group;

U is selected from carbonyl, sulfoxide (—SO—), sulfone (—$SO_2$—), —P(O)(ORd)- or —B(ORe)-; Wherein Rd and Re are independently selected from hydrogen (H), $C_1$-$C_{15}$ alkyl, $C_3$-$C_{15}$ cycloalkyl, $C_2$-$C_{15}$ heterocyclic, $C_6$-$C_{15}$ aryl, or $C_3$-$C_{15}$ heterocyclic alkyl group;

W is selected from oxygen or sulfur;

X is selected from oxygen, sulfur, nitrogen or —NRa—; wherein the definition of Ra is the same as that in E and G;

Y is selected from nitrogen or CH;

Z is selected from hydrogen (H), hydroxyl (OH), amino ($NH_2$), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_1$-$C_{15}$ alkylamino, $C_3$-$C_{15}$ cycloalkylamino, $C_2$-$C_{15}$ heterocyclic amino, $C_6$-$C_{15}$ aryl, $C_6$-$C_{15}$ arylamino, $C_3$-$C_{15}$ heterocyclic arylamino, $C_1$-$C_{15}$ alkylsulfonamido, $C_3$-$C_{15}$ cycloalkylsulfonamido, $C_6$-$C_{15}$ arylsulfonamido, $C_1$-$C_{15}$ alkylaminosulfonamido, $C_3$-$C_{15}$ cycloalkylaminosulfonamido, $C_6$-$C_{15}$ aryloxysulfonamido, $C_1$-$C_{15}$ alkylaminosulfonamido, $C_3$-$C_{15}$ cycloalkylaminosulfonamido, $C_6$-$C_{15}$ arylaminosulfonamido, uramido, $C_1$-$C_{15}$ alkyluramido, or $C_1$-$C_{15}$ alkylthiouramido group.

$R^1$ is selected from hydrogen (H), $C_1$-$C_{15}$ alkyl, $C_3$-$C_{15}$ cycloalkyl, $C_6$-$C_{15}$ aryl, $C_3$-$C_{15}$ heterocyclic aryl, $C_1$-$C_{15}$ alkylsulfonamido, $C_2$-$C_{15}$ heterocyclic sulfonamido, or $C_1$-$C_{15}$ alkoxyl carbonylamino group;

$R^2$ is selected from hydrogen (H), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_6$-$C_{15}$ aryl, $C_3$-$C_{15}$ heterocyclic aryl, $C_6$-$C_{15}$ aryloxycarbonyl, $C_1$-$C_{15}$ alkylsulfonyl, $C_3$-$C_{15}$ cycloalkylsulfonyl, $C_1$-$C_{15}$ alkoxysulfonyl, $C_3$-$C_{15}$ cycloalkoxysulfonyl, $C_6$-$C_{15}$ arylsulfonyl, $C_6$-$C_{15}$ aryloxysulfonyl, $C_1$-$C_{15}$ alkylaminosulfonyl, $C_3$-$C_{15}$ cycloalkylaminosulfonyl, or $C_6$-$C_{15}$ arylaminosulfonyl group;

$R^3$, $R^4$, $R^5$ and $R^6$ are each independently selected from hydrogen, halogen atom, hydroxyl, cyano, nitro, $C_1$-$C_{15}$ alkyl, $C_3$-$C_{15}$ cycloalkyl, $C_1$-$C_{15}$ alkoxyl, $C_1$-$C_{15}$ alkylamino, $C_2$-$C_{15}$ heterocyclic amino, $C_6$-$C_{15}$ aryl, $C_6$-$C_{15}$ arylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_{15}$ alkyl, $C_1$-$C_{15}$ alkoxyl, $C_1$-$C_{15}$ alkylthio, $C_1$-$C_{15}$ alkoxylcarbonyl, aminocarbonyl, $C_1$-$C_{15}$ alkylaminocarbonyl, carbonylamino, $C_1$-$C_{15}$ alkylcarbonylamino, $C_2$-$C_{15}$ heterocyclicoxyl carbonyl, $C_6$-$C_{15}$ aryl, $C_6$-$C_{15}$ aryloxy, $C_6$-$C_{15}$ aryloxycarbonyl or $C_2$-$C_{15}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{15}$ alkyl, $C_3$-$C_{15}$ cycloalkyl, $C_1$-$C_{15}$ alkoxyl, $C_1$-$C_{15}$ alkylthio, $C_1$-$C_{15}$ alkoxylcarbonyl, $C_1$-$C_{15}$ alkylaminocarbonyl, $C_1$-$C_{15}$ alkylcarbonylamino, $C_6$-$C_{15}$ aryl, $C_6$-$C_{15}$ aryloxy, $C_6$-$C_{15}$ aryloxycarbonyl or $C_2$-$C_{15}$ heterocyclic group.

$R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group;

In one more preferred embodiment in the present invention by the formula Ia or Ib, Wherein:

m=1 or 2; n=0, 1 or 2;

" " is a single bond or double bond;

E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_8$ alkyl, $C_3$-$C_8$ cycloalkyl, $C_6$-$C_{12}$ aryl, $C_2$-$C_8$ heterocyclic aryl, $C_1$-$C_8$ alkylcarbonyl, $C_1$-$C_8$ alkoxycarbonyl, $C_6$-$C_{12}$ aryloxycarbonyl, $C_2$-$C_8$ heterocyclic oxycarbonyl, aminocarbonyl, $C_1$-$C_8$ alkylaminocarbonyl, $C_1$-$C_8$ alkylaminosulfonyl, $C_2$-$C_8$ heterocyclic aminosulfonyl, or $C_6$-$C_{12}$ arylamino aminosulfonyl group.

Rb and Rc are each independently selected from hydrogen, halogen atom, cyano, nitro, $C_1$-$C_8$ alkyl, $C_3$-$C_8$ cycloalkyl, $C_6$-$C_{12}$ aryl, $C_1$-$C_8$ alkoxyl, $C_1$-$C_8$ alkylthio, $C_1$-$C_8$ alkoxycarbonyl, $C_6$-$C_{12}$ aryloxy, $C_6$-$C_{12}$ aryloxycarbonyl, $C_2$-$C_8$ heterocyclic-oxycarbonyl, $C_2$-$C_{12}$ heterocyclic aryl, $C_1$-$C_8$ alkylamino, $C_2$-$C_8$ heterocyclic amino, $C_6$-$C_{12}$ arylamino, aminocarbonyl, $C_1$-$C_8$ alkylaminocarbonyl, carbonylamino, $C_1$-$C_8$ alkylcarbonylamino, $C_1$-$C_8$ alkylsulfonamido, $C_2$-$C_8$ heterocyclic sulfonamido, $C_6$-$C_{12}$ arylsulfonamido or $C_1$-$C_8$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_8$ alkoxyl, $C_1$-$C_8$ alkylamino, $C_1$-$C_8$ alkyl-oxygen, $C_1$-$C_8$ alkyl, $C_1$-$C_8$ alkoxycarbonyl, carbonyl, carbonylamino or $C_1$-$C_8$ alkylcarbonylamino group; when $R^7$ and $R^8$ or $R^8$ and $R^9$ are connected each other as a cyclic structure, G is methylene or does not exist (ie. " " connected directly with the phenyl group of polyheterocyclic group); wherein the definition of Ra, Rb and Rc are the same as that in E.

L and $L^1$ are each independently selected from oxygen, sulfur, $C_2$-$C_8$ alkenyl, $C_1$-$C_8$ alkyl, $C_3$-$C_8$ cycloalkyl, $C_2$-$C_8$ heterocyclic, $C_6$-$C_{12}$ aryl, $C_3$-$C_8$ heterocyclic aryl, $C_1$-$C_8$ alkylthio, $C_1$-$C_8$ alkoxyl, $C_3$-$C_8$ cycloalkoxyl, $C_2$-$C_8$ heterocyclic oxyl, $C_1$-$C_8$ alkylamino, $C_1$-$C_8$ alkoxycarbonyl, $C_6$-$C_{12}$ aryl, or $C_6$-$C_{12}$ aryloxy group;

U is selected from carbonyl, sulfoxide (—SO—), sulfone (—SO$_2$—), —P(O)(ORd)- or —B(ORe)-; Wherein Rd and Re are independently selected from hydrogen (H), $C_1$-$C_8$ alkyl, $C_3$-$C_8$ cycloalkyl, $C_2$-$C_8$ heterocyclic, $C_6$-$C_{12}$ aryl, or $C_3$-$C_{12}$ heterocyclic alkyl group;

W is selected from oxygen or sulfur;

X is selected from oxygen, sulfur, nitrogen or —NRa—; wherein the definition of Ra is the same as that in E and G;

Y is selected from nitrogen or CH;

Z is selected from hydrogen (H), hydroxyl (OH), amino (NH$_2$), $C_1$-$C_8$ alkyl, $C_3$-$C_8$ cycloalkyl, $C_1$-$C_8$ alkoxyl, $C_3$-$C_8$ cycloalkoxyl, $C_1$-$C_8$ alkylamino, $C_3$-$C_8$ cycloalkylamino, $C_2$-$C_8$ heterocyclic amino, $C_6$-$C_{12}$ aryl, $C_6$-$C_{12}$ arylamino, $C_3$-$C_{12}$ heterocyclic arylamino, $C_1$-$C_8$ alkylsulfonamido, $C_3$-$C_8$ cycloalkylsulfonamido, $C_6$-$C_{12}$ arylsulfonamido, $C_1$-$C_8$ alkylaminosulfonamido, $C_3$-$C_8$ cycloalkylaminosulfonamido, $C_6$-$C_{12}$ aryloxysulfonamido, $C_1$-$C_8$ alkylaminosulfonamido, $C_3$-$C_8$ cycloalkylaminosulfonamido, $C_6$-$C_{12}$ arylaminosulfonamido, uramido, $C_1$-$C_8$ alkyluramido, or $C_1$-$C_8$ alkylthiouramido group.

$R^1$ is selected from hydrogen (H), $C_1$-$C_8$ alkyl, $C_3$-$C_8$ cycloalkyl, $C_6$-$C_{12}$ aryl, $C_3$-$C_{12}$ heterocyclic aryl, $C_1$-$C_8$ alkylsulfonamido, $C_2$-$C_{12}$ heterocyclic sulfonamido, or $C_1$-$C_8$ alkoxyl carbonylamino group;

$R^2$ is selected from hydrogen (H), $C_1$-$C_8$ alkyl, $C_3$-$C_8$ cycloalkyl, $C_1$-$C_8$ alkoxyl, $C_3$-$C_8$ cycloalkoxyl, $C_6$-$C_{12}$ aryl, $C_3$-$C_{12}$ heterocyclic aryl, $C_6$-$C_{12}$ aryloxycarbonyl, $C_1$-$C_8$ alkylsulfonyl, $C_3$-$C_8$ cycloalkylsulfonyl, $C_1$-$C_8$ alkoxysulfonyl, $C_3$-$C_8$ cycloalkoxysulfonyl, $C_6$-$C_{12}$ arylsulfonyl, $C_6$-$C_{12}$ aryloxysulfonyl, $C_1$-$C_8$ alkylaminosulfonyl, $C_3$-$C_8$ cycloalkylaminosulfonyl, or $C_6$-$C_{12}$ arylaminosulfonyl group;

$R^3$, $R^4$, $R^5$ and $R^6$ are each independently selected from hydrogen, halogen atom, hydroxyl, cyano, nitro, $C_1$-$C_8$ alkyl, $C_3$-$C_8$ cycloalkyl, $C_1$-$C_8$ alkoxyl, $C_1$-$C_8$ alkylamino, $C_2$-$C_8$ heterocyclic amino, $C_6$-$C_{12}$ aryl, $C_6$-$C_{12}$ arylamino, $C_1$-$C_8$ alkylsulfonamido, $C_2$-$C_8$ heterocyclic sulfonamido, $C_6$-$C_{12}$ arylsulfonamido or $C_1$-$C_8$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_8$ alkyl, $C_1$-$C_8$ alkoxyl, $C_1$-$C_8$ alkylthio, $C_1$-$C_8$ alkoxylcarbonyl, aminocarbonyl, $C_1$-$C_8$ alkylaminocarbonyl, carbonylamino, $C_1$-$C_8$ alkylcarbonylamino, $C_2$-$C_8$ heterocyclicoxyl carbonyl, $C_6$-$C_{12}$ aryl, $C_6$-$C_{12}$ aryloxy, $C_6$-$C_{12}$ aryloxycarbonyl or $C_2$-$C_8$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_8$ alkyl, $C_3$-$C_8$ cycloalkyl, $C_1$-$C_8$ alkoxyl, $C_1$-$C_8$ alkylthio, $C_1$-$C_8$ alkoxylcarbonyl, $C_1$-$C_8$ alkylaminocarbonyl, $C_1$-$C_8$ alkylcarbonylamino, $C_6$-$C_{12}$ aryl, $C_6$-$C_{12}$ aryloxy, $C_6$-$C_{12}$ aryloxycarbonyl or $C_2$-$C_8$ heterocyclic group.

$R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group;

In one further optimal embodiment of in the present invention by the formula Ia or Ib, Wherein,
m=1; n=1;
p=0, 1 or 2; q=0, 1 or 2; r=0, 1 or 2;
"----" is a single bond or double bond;
E is methylene (—$CH_2$—);
G is selected from oxygen, sulfur, —$SCH_2$—, —N(Ra)$CH_2$—, —NRa—, methylene (—$CH_2$—), —$CH_2OCH_2$—, $C_1$-$C_3$ alkoxycarbonyl, carbonylamino, or $C_1$-$C_3$ alkylcarbonylamino group; When $R^7$ and $R^8$ or $R^8$ and $R^9$ are connected each other as a cyclic structure, G is methylene or does not exist (ie. "----" connected directly with the phenyl group of poyheterocyclic group); wherein Ra is selected from hydrogen, $C_1$-$C_6$ alkyl, $C_1$-$C_6$ alkylcarbonyl, or $C_1$-$C_6$ alkoxycarbonyl group;

L is methylene (—$CH_2$—);
$L^1$ is $C_1$-$C_6$ alkyl, $C_1$-$C_6$ alkoxyl, or $C_1$-$C_6$ alkylamino;
U is carbonyl;
W and X are both oxygen (O);
Y is nitrogen (N);
Z is selected from hydroxyl, $C_1$-$C_6$ alkoxyl, $C_1$-$C_6$ alkylsulfonamido, $C_3$-$C_6$ cycloalkylsulfonamido, or $C_6$-$C_{10}$ arylsulfonamido group;
$R^1$ is selected from $C_1$-$C_6$ alkyl, $C_6$-$C_{10}$ aryl, $C_1$-$C_6$ alkylsulfonamido, $C_2$-$C_6$ heterocyclic sulfonamido, or $C_1$-$C_6$ alkoxylcarbonylamino group;
$R^2$, $R^5$ and $R^6$ are each independently hydrogen;
$R^3$ and $R^4$ are each independently selected from hydrogen, methyl, fluorine, or $R^3$ and $R^4$ are connected each other as cyclopropyl group;
$R^7$, $R^8$ and $R^9$ are each independently selected from hydrogen, halogen, $C_1$-$C_3$ alkyl, or $C_1$-$C_3$ alkoxyl group;
$R^{10}$ is hydrogen;
$R^{11}$ is selected from $C_1$-$C_3$ alkyl or vinyl;

In the most preferred embodiment in the present invention, formula Ia is selected from the following structures;

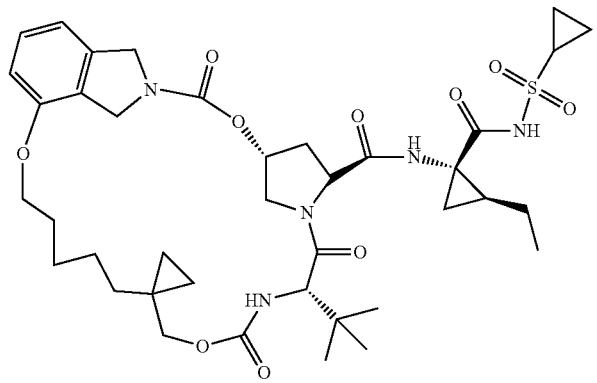

15a

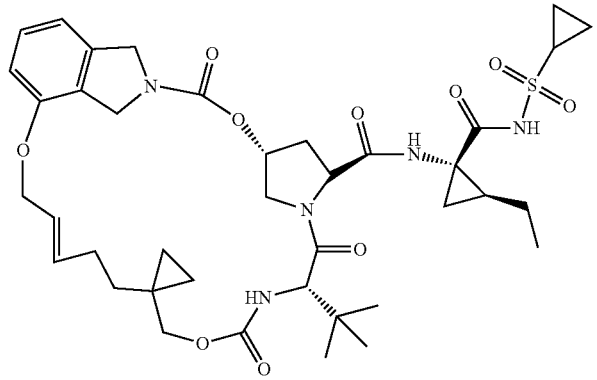

15b

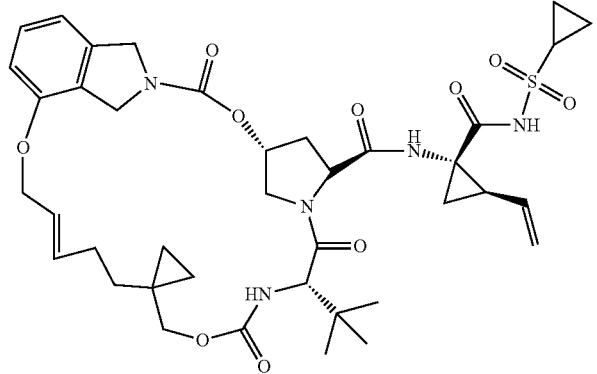

15c

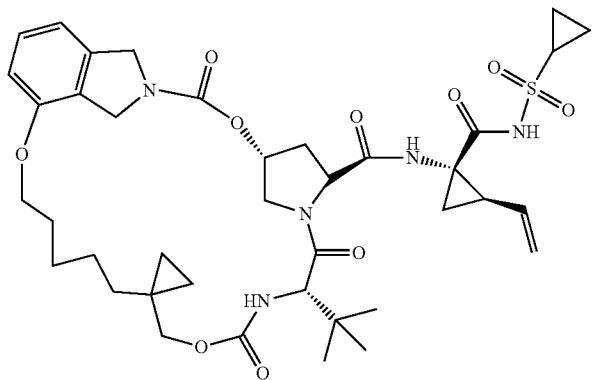
15d
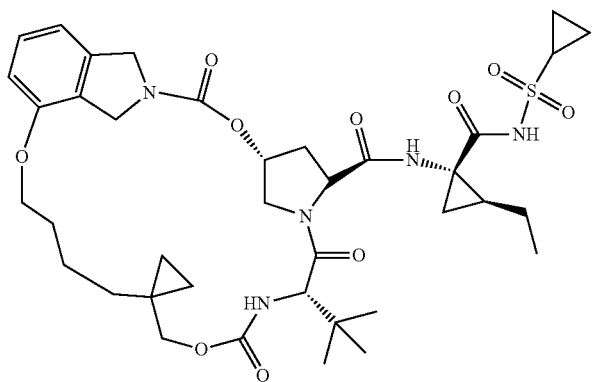
15e
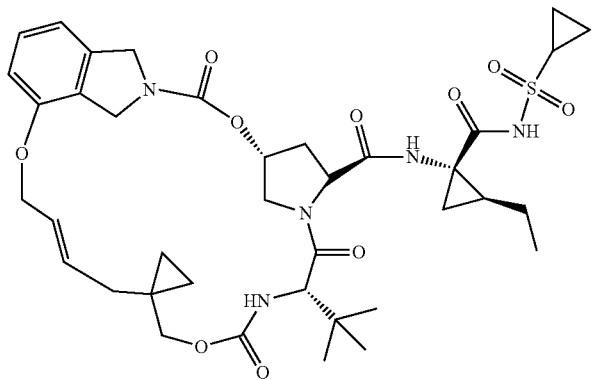
15f
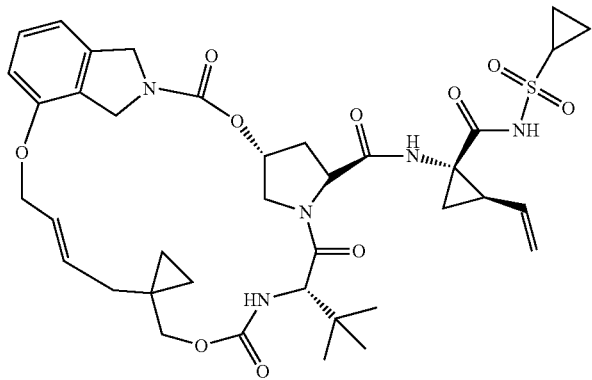
15g

-continued
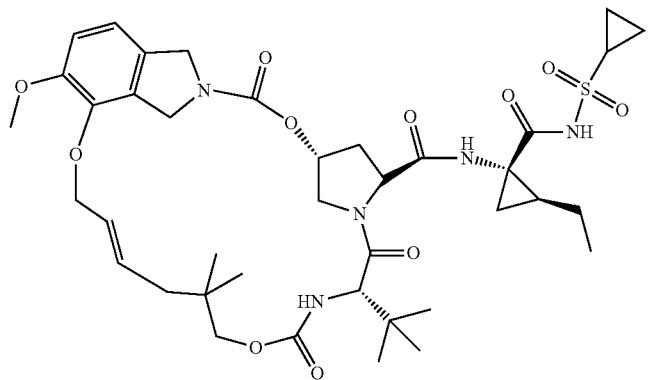
15h
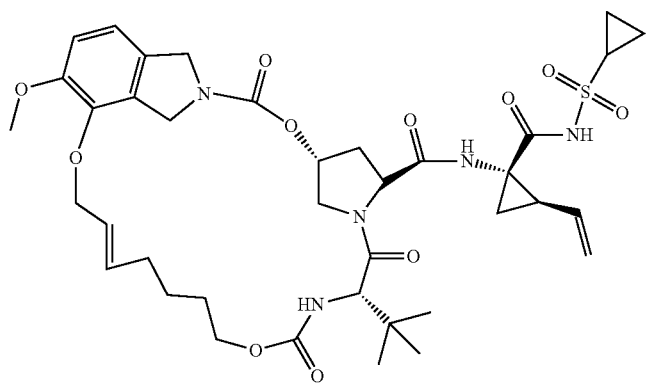
15j
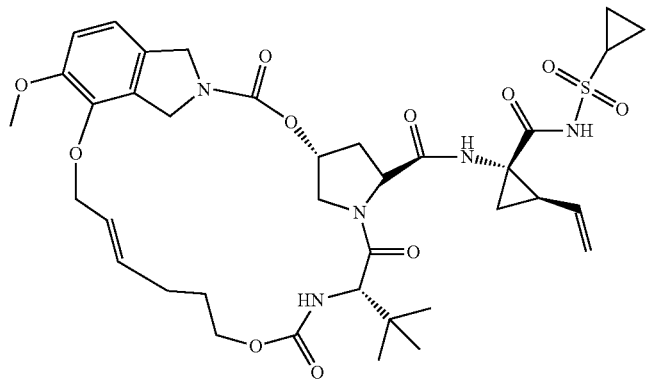
15k
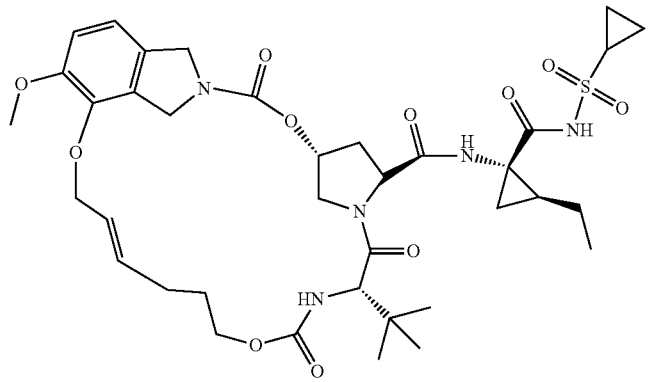
15m

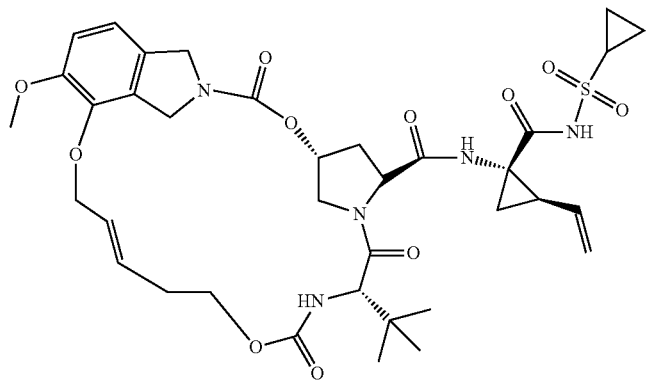
15n
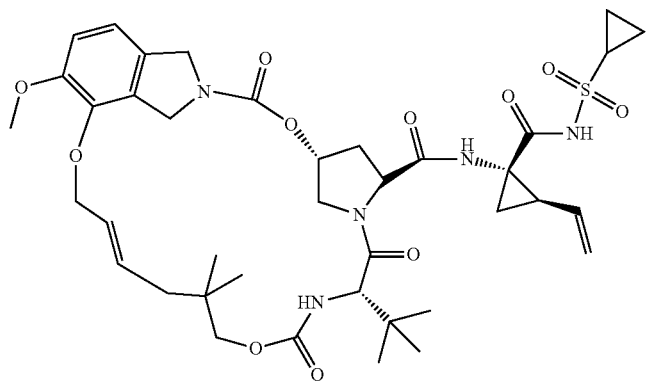
15p
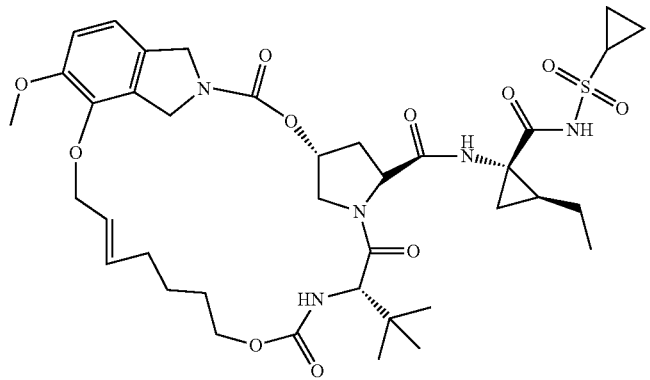
15q
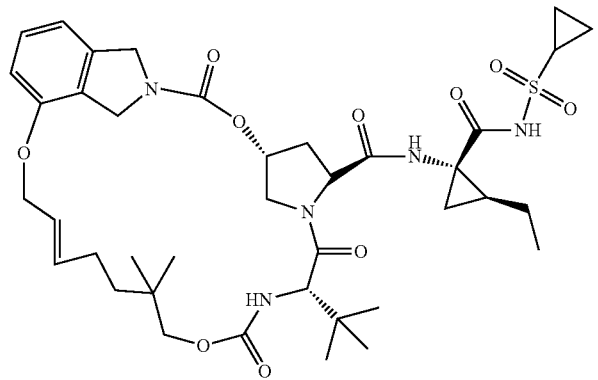
15r

-continued
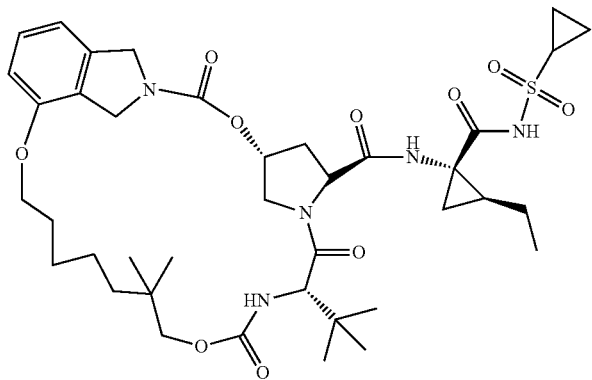
15s
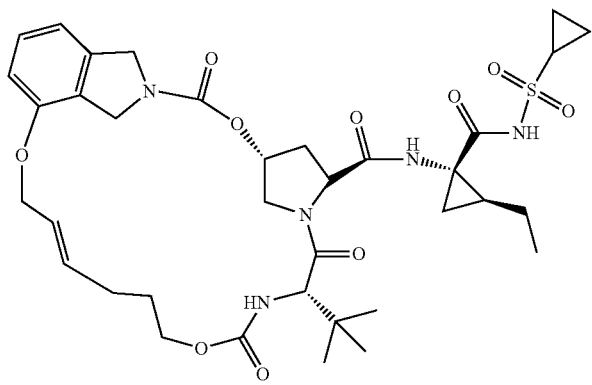
15t
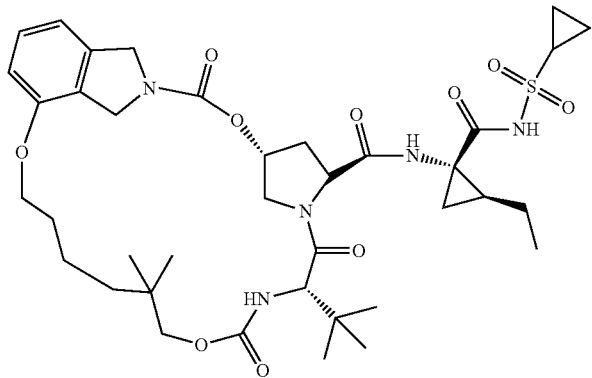
15u
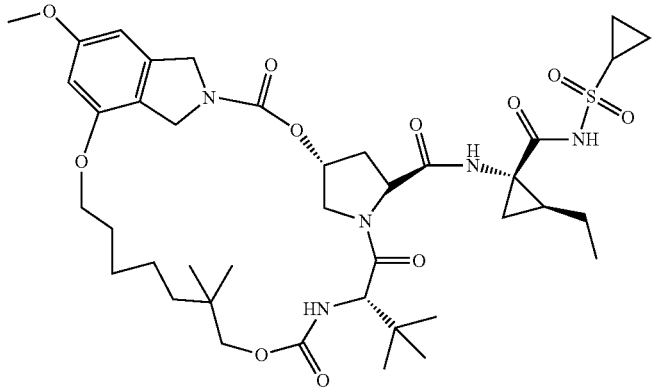
15v

15w
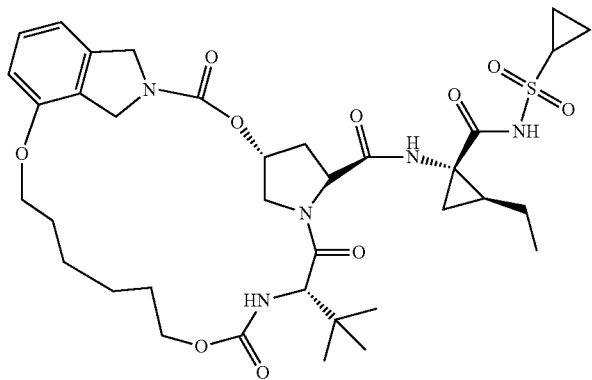
15x
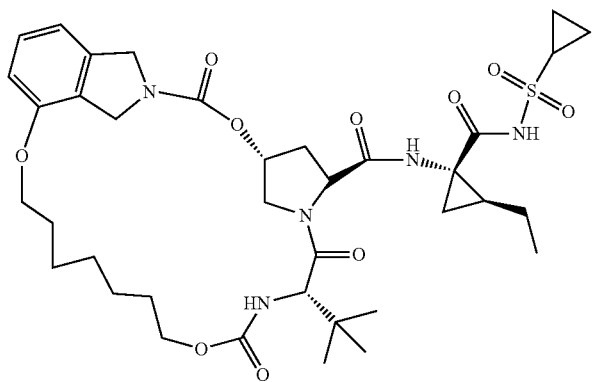
15y
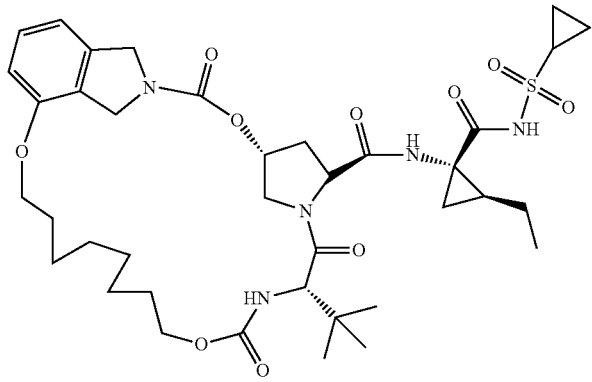
15z
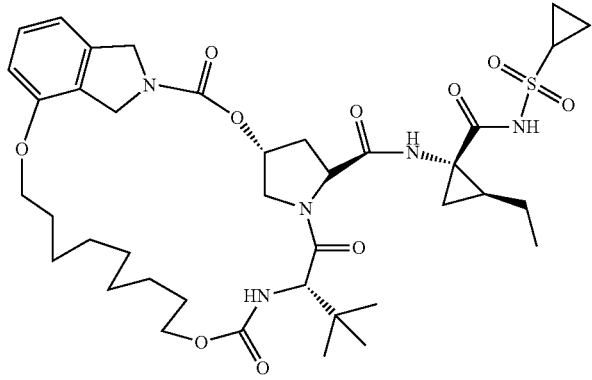

15aa
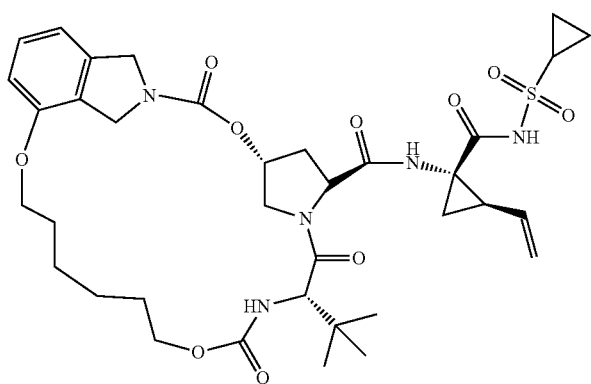
15ab
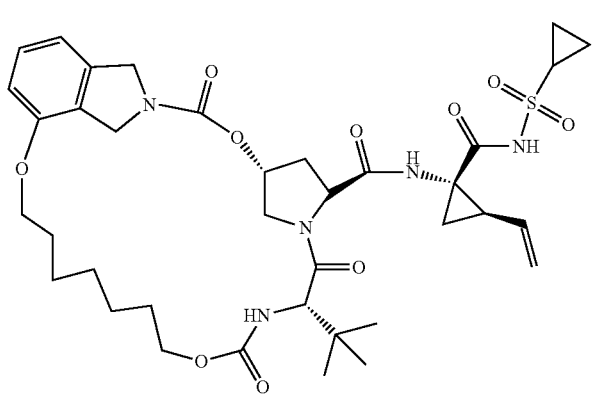
15ac
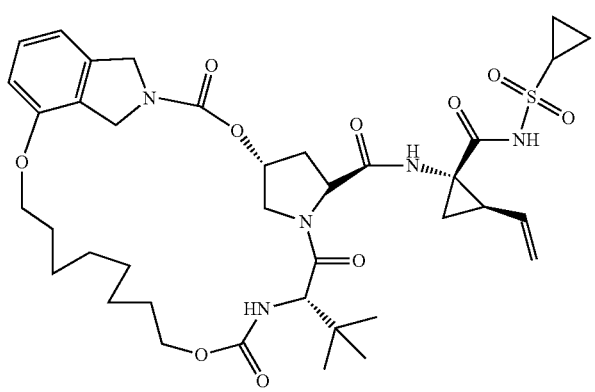
15ad
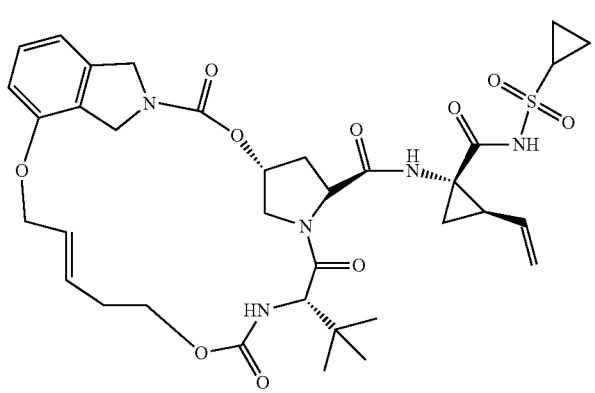

-continued
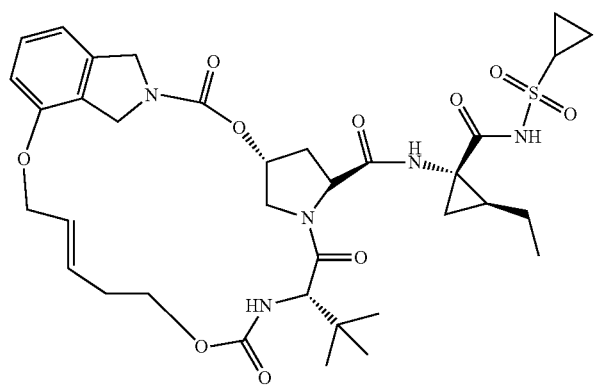
15ae
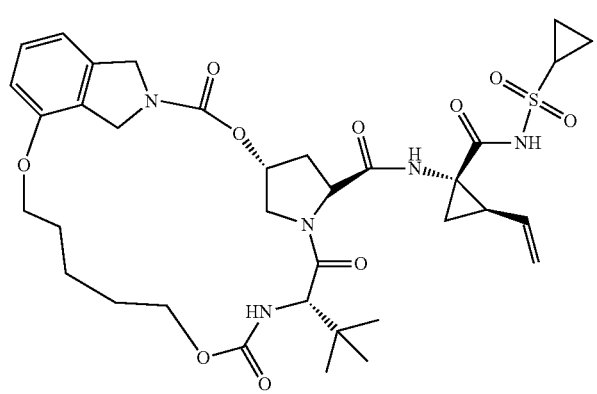
15af
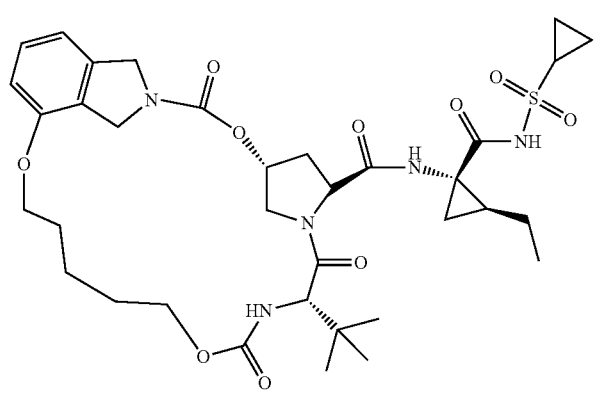
15ag
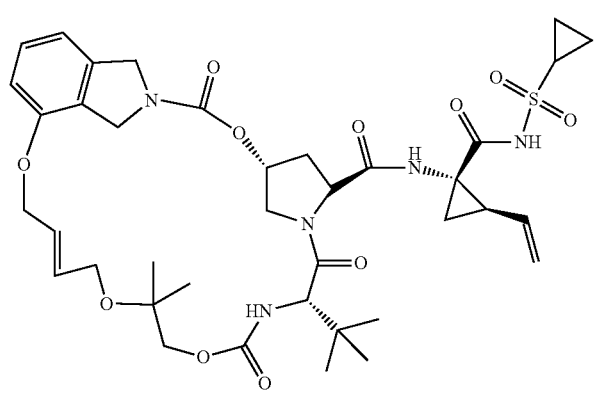
15ah

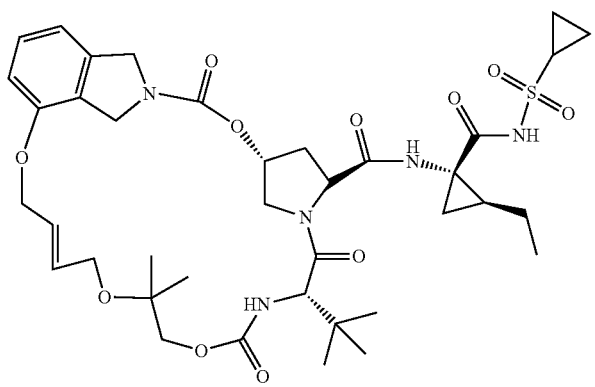
15aj
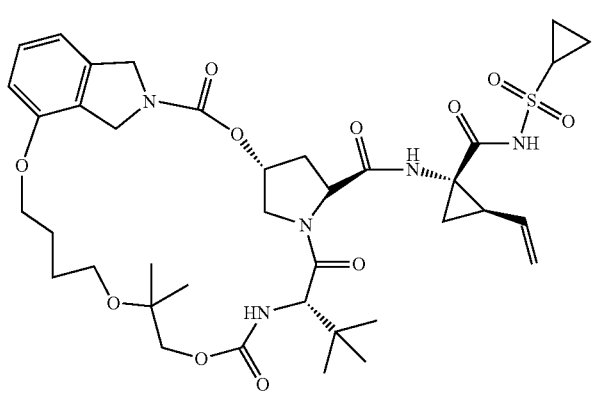
15ak
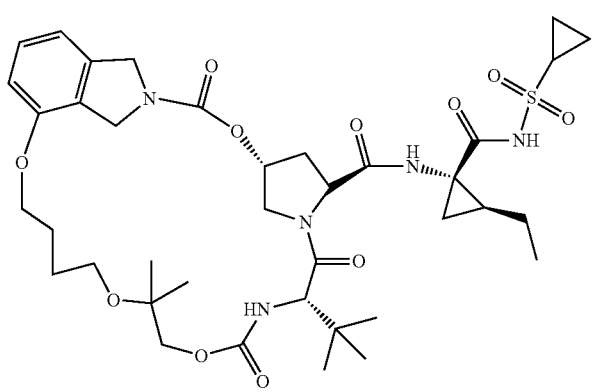
15am
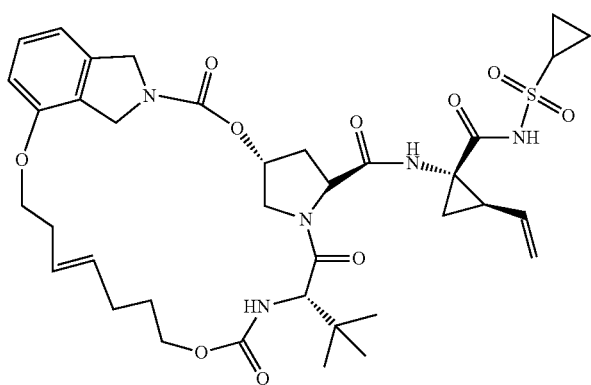
15an

15ap
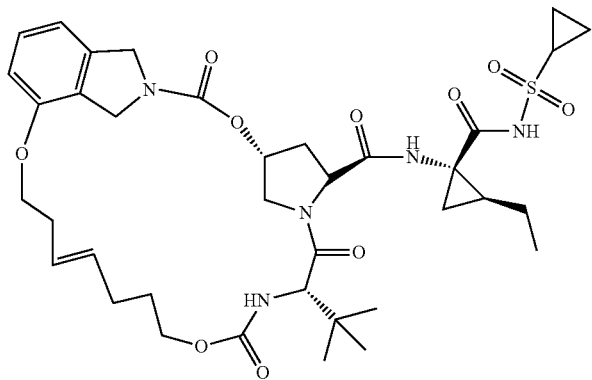
15aq
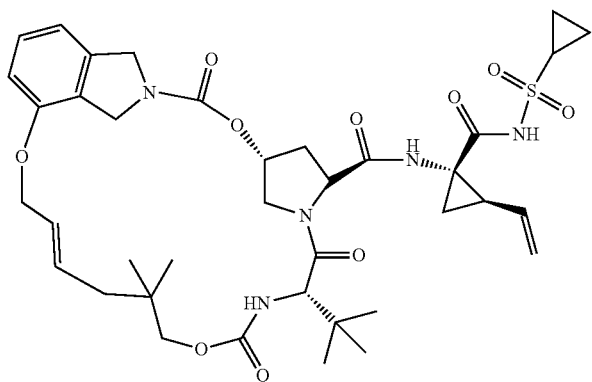
15ar
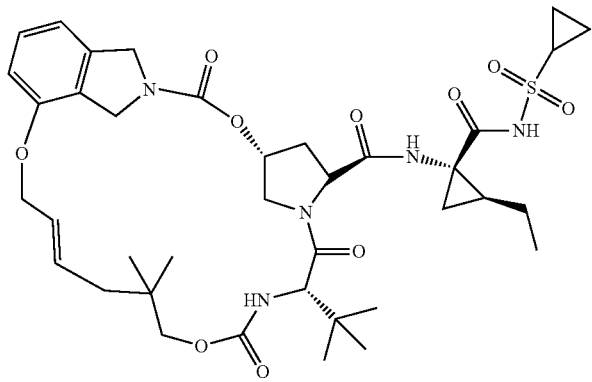
15as
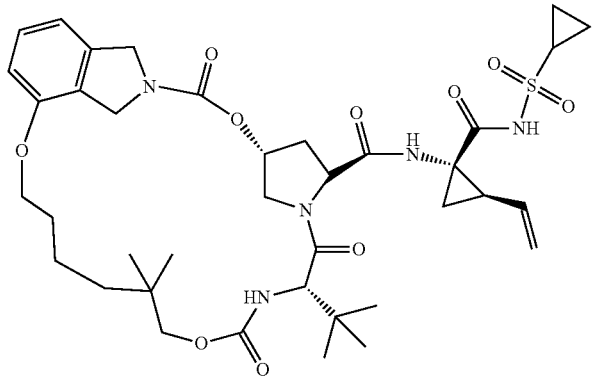

15at
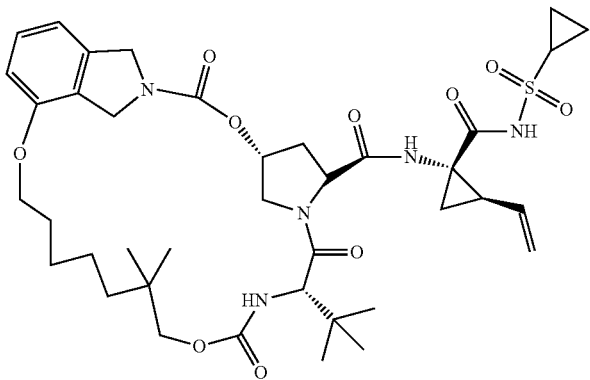
15au
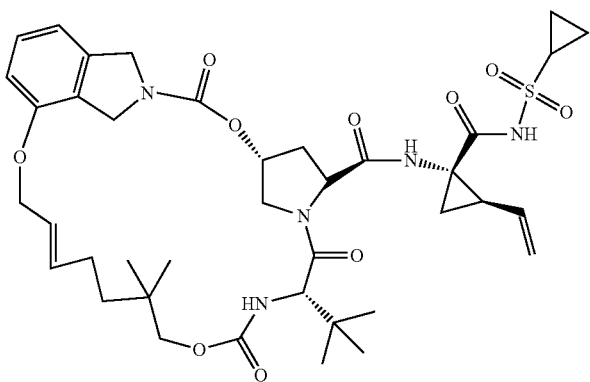
15av
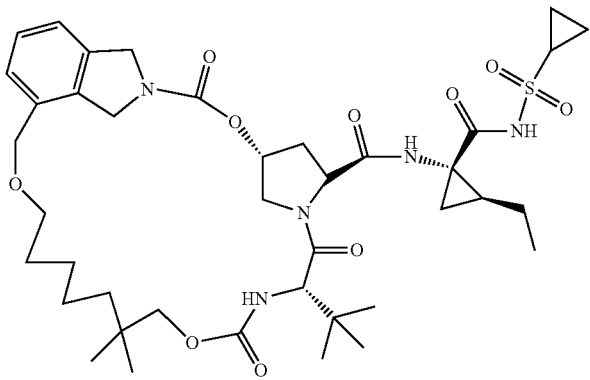
15aw
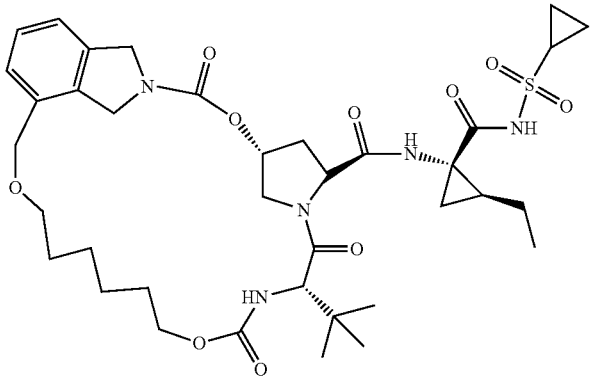

15ax
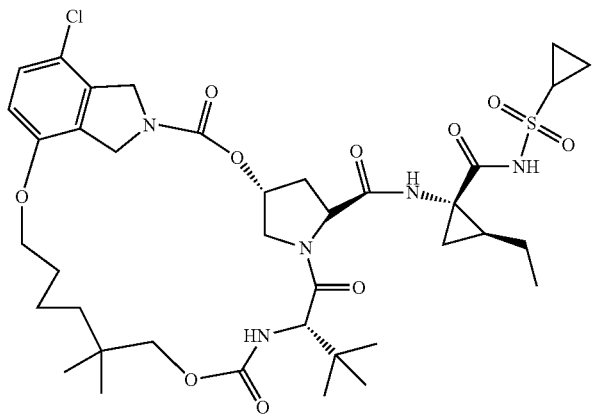
15ba
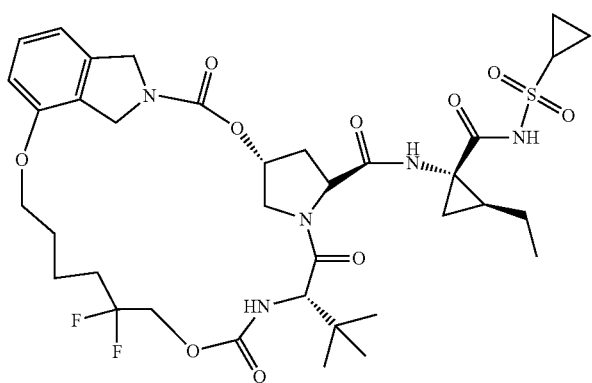
15bb
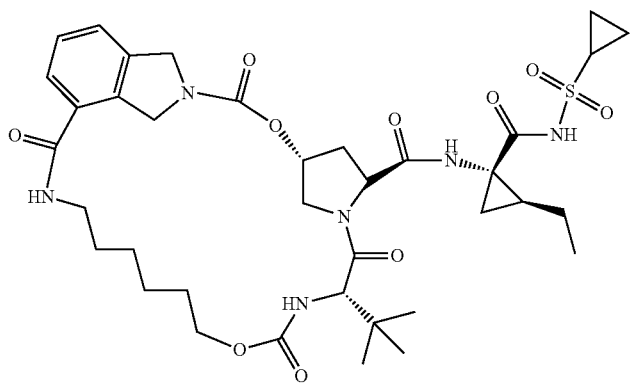
15bc
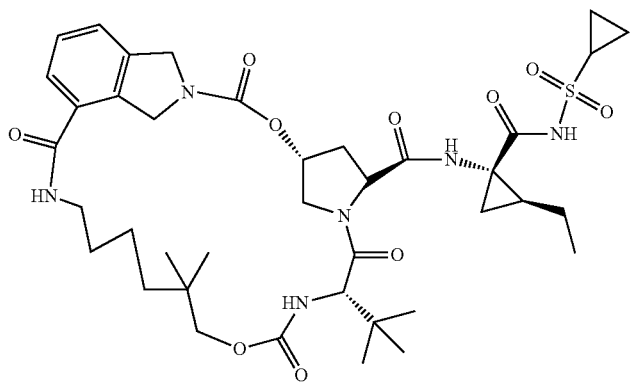

15bd
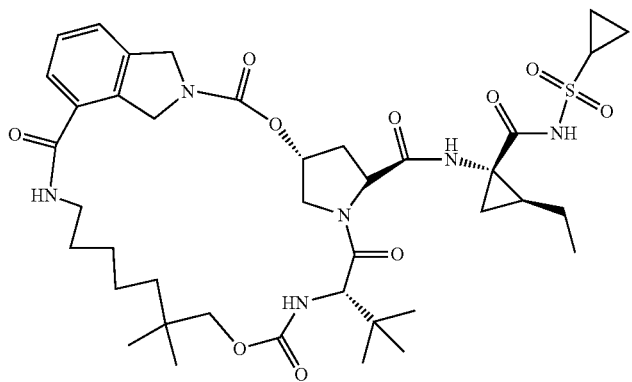
15bt
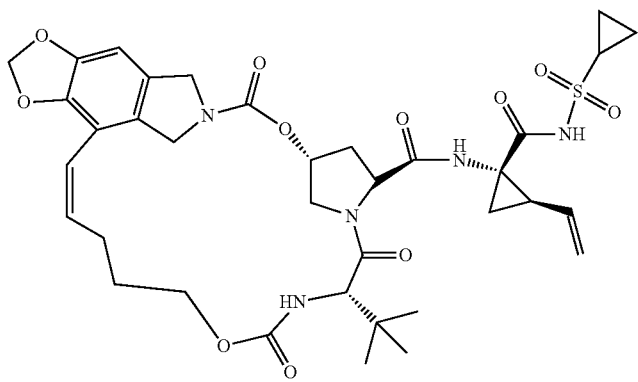
15bu
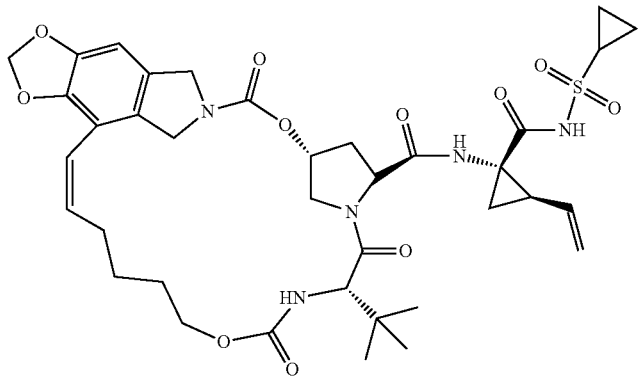
15bv
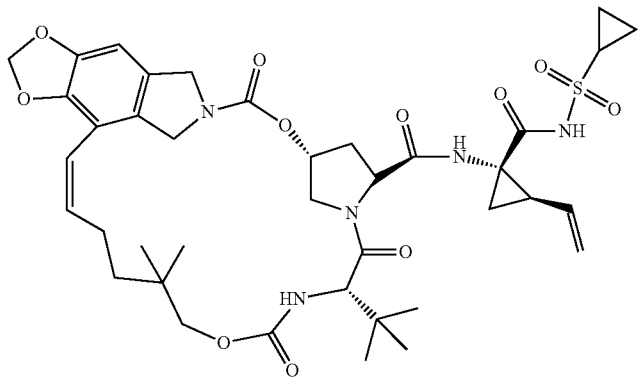

15bw
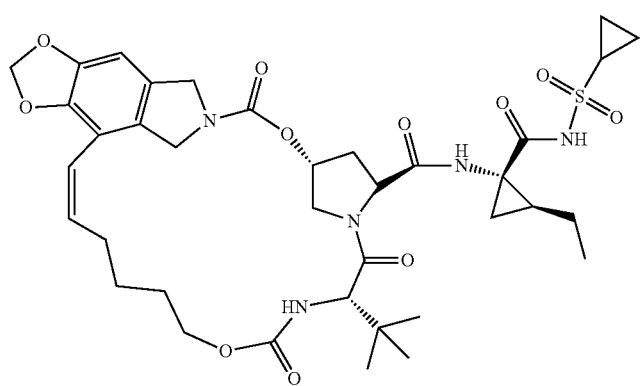
15bx
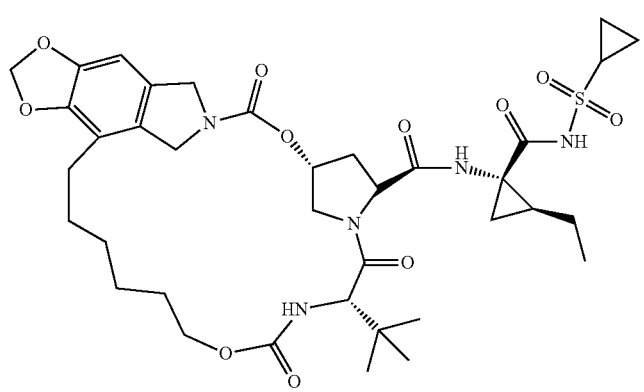
15by
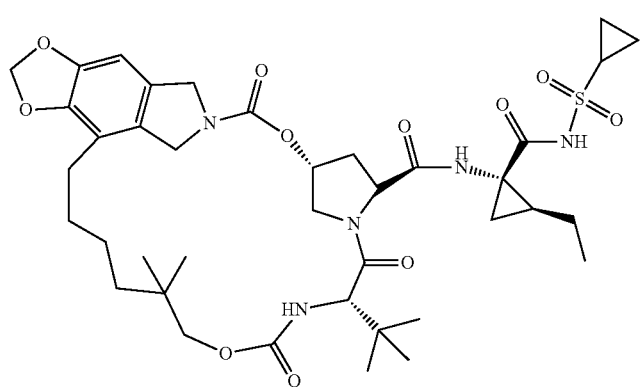
15ca
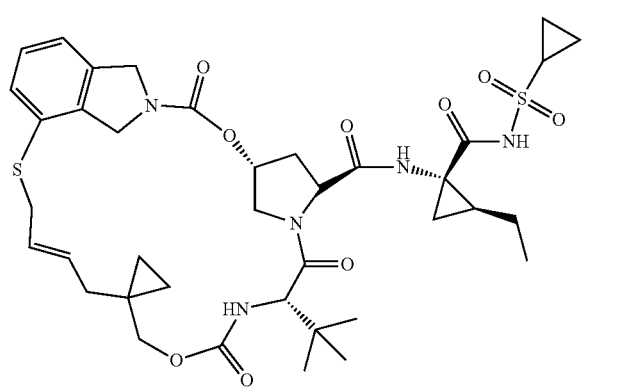

-continued
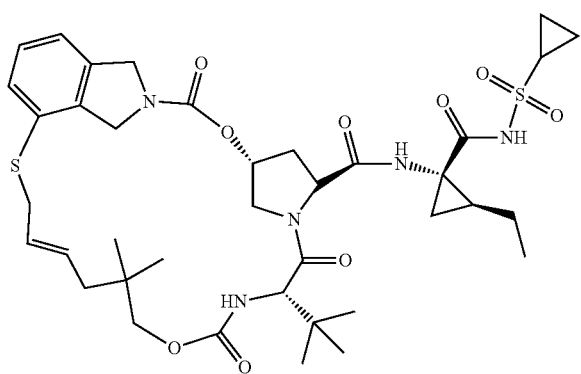
15cb
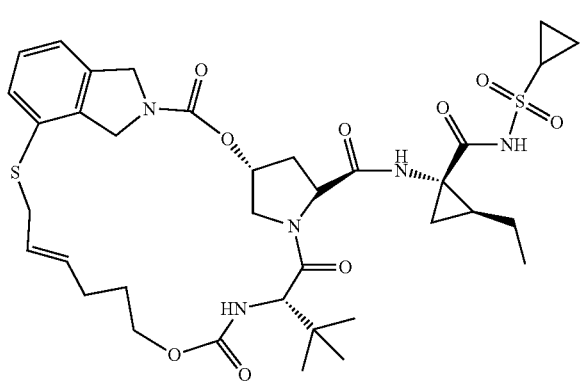
15cc
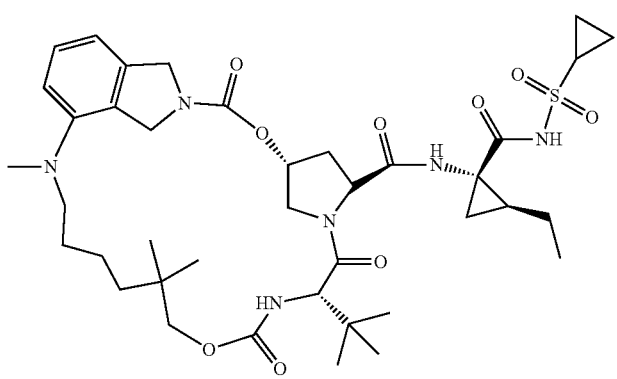
15cd
Formula Ib is selected from the following structures:
-continued
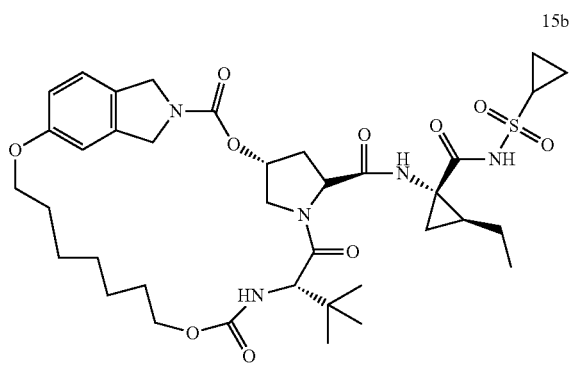
15be
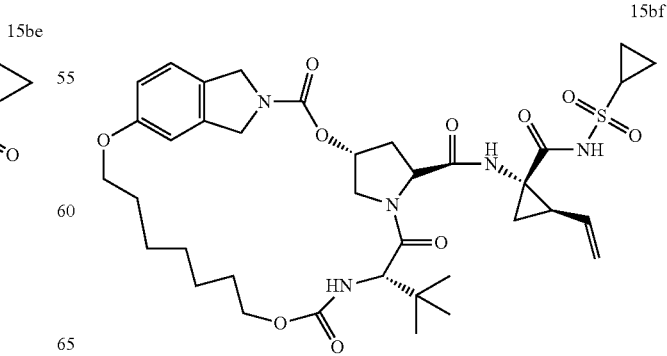
15bf 15bg
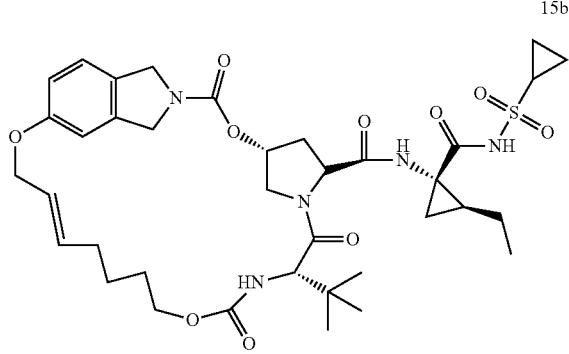
15bm
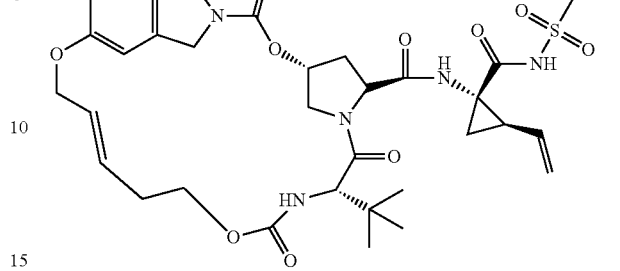
15bh
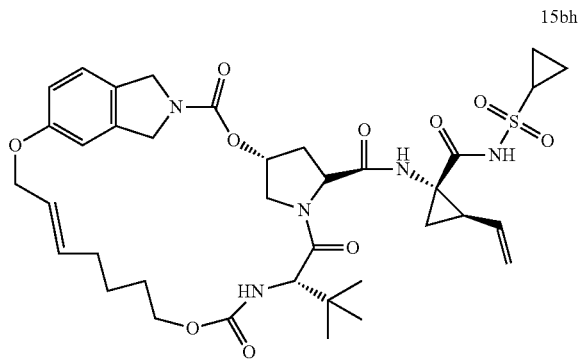
15bn
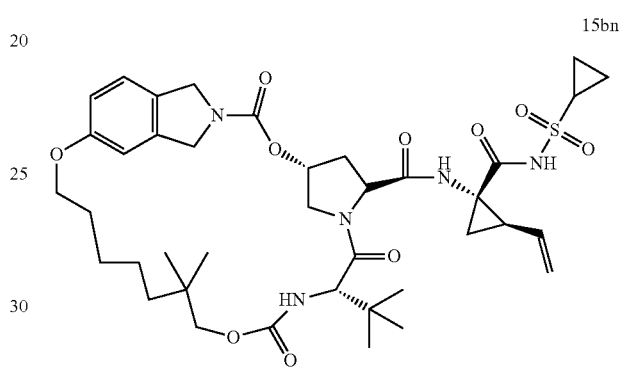
15bj
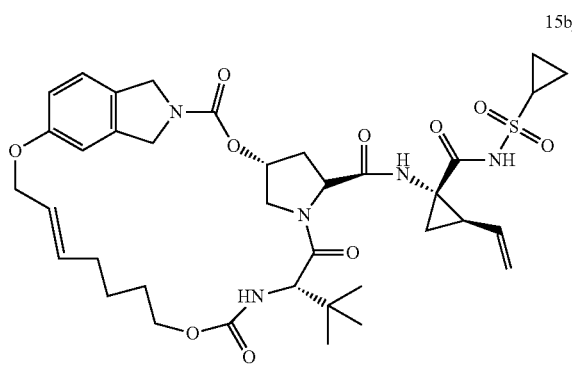
15bp
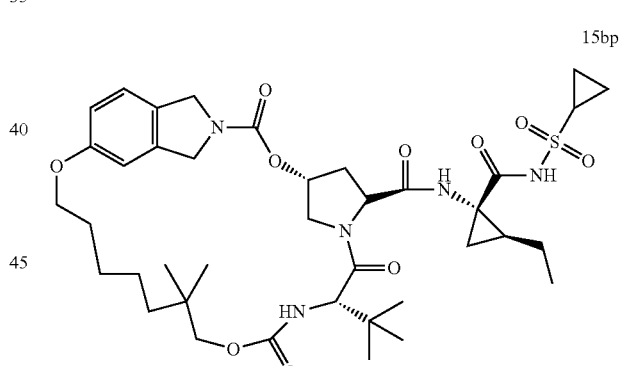
15bk
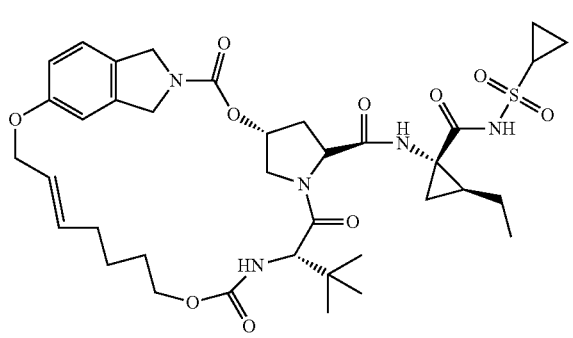
15bq
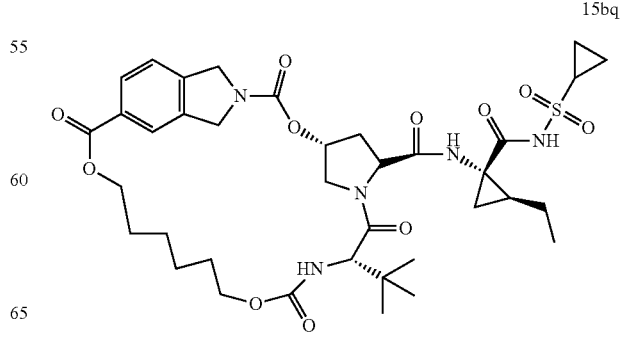

-continued

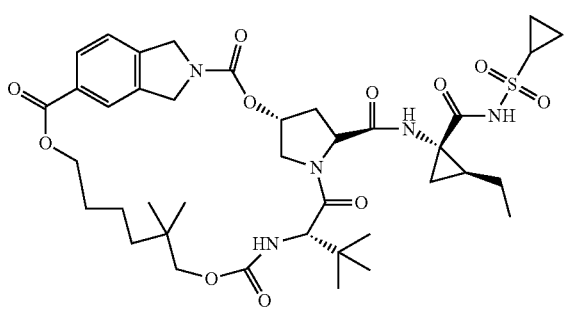

15br

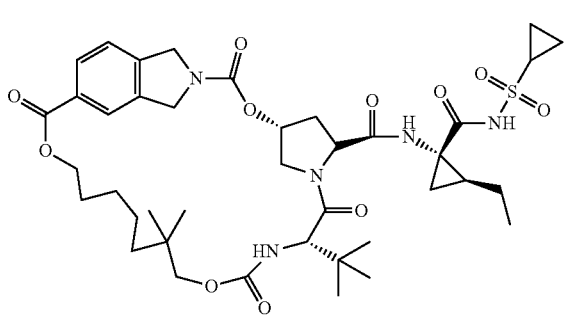

15bs

The present invention in the second aspect provides polycyclic compounds represented by the formula IIa or IIb:

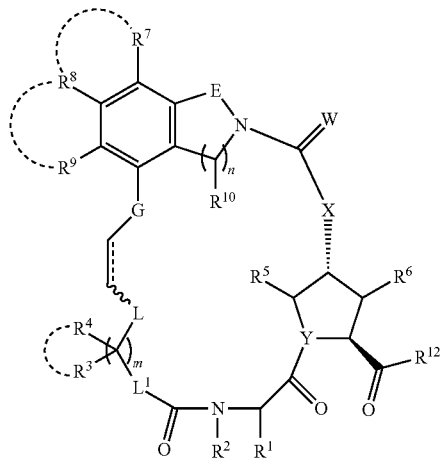

IIa

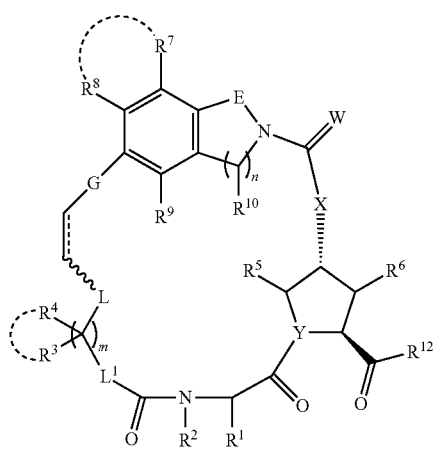

IIb

Wherein:
m=1 or 2; n=0, 1 or 2;
" ⋯ " is a single bond or double bond;
E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkylcarbonyl, $C_1$-$C_{20}$ alkoxycarbonyl, $C_6$-$C_{20}$ aryloxycarbonyl, $C_2$-$C_{20}$ heterocyclic oxycarbonyl, aminocarbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ arylamino aminosulfonyl group.

Rb and Rc are each independently selected from hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxyl, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic-oxycarbonyl, $C_2$-$C_{20}$ heterocyclic aryl, $C_1$-$C_{20}$ alkylamino, $C_2$-$C_{20}$ heterocyclic amino, $C_6$-$C_{20}$ arylamino, aminocarbonyl, $C_1$-$C_{20}$ alkylaminocarbonyl, carbonylamino, $C_1$-$C_{20}$ alkylcarbonylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ alkyl aminosulfonamido.

G is selected from oxygen, sulfur, sulfone, —NRa—, —OC(Rb)(Rc)-, —SC(Rb)(Rc)-, —N(Ra)C(Rb)(Rc)-, $C_1$-$C_{20}$ alkoxyl, $C_1$-$C_{20}$ alkylamino, $C_1$-$C_{20}$ alkyl-oxygen, $C_1$-$C_{20}$ alkyl, $C_1$-$C_{20}$ alkoxycarbonyl, carbonyl, carbonylamino or $C_1$-$C_{20}$ alkylcarbonylamino group; when $R^7$ and $R^8$ or $R^8$ and $R^9$ are connected each other as cyclic structure, G is methylene or does not exist (ie. " ⋯ " connected directly with the phenyl group of polyheterocyclic group); wherein the definition of Ra, Rb and Rc are the same as that in E.

L and $L^1$ are each independently selected from oxygen, sulfur, $C_2$-$C_{20}$ alkenyl, $C_1$-$C_{20}$ alkyl, $C_3$-$C_{20}$ cycloalkyl, $C_2$-$C_{20}$ heterocyclic, $C_6$-$C_{20}$ aryl, $C_3$-$C_{20}$ heterocyclic aryl, $C_1$-$C_{20}$ alkylthio, $C_1$-$C_{20}$ alkoxyl, $C_3$-$C_{20}$ cycloalkoxyl, $C_2$-$C_{20}$ heterocyclic oxyl, $C_1$-$C_{20}$ alkylamino, $C_1$-$C_{20}$ alkoxycarbonyl, $C_6$-$C_{20}$ aryl, or $C_6$-$C_{20}$ aryloxy group;

W is selected from oxygen or sulfur;
X is selected from oxygen, sulfur, nitrogen or —NRa—; wherein the definition of Ra is the same as that in E and G;
Y is selected from nitrogen or CH;
$R^1$ is selected from hydrogen (H), $C_1$-$C_{20}$ alkyl, $C_3$-$C_{20}$ cycloalkyl, $C_6$-$C_{20}$ aryl, $C_3$-$C_{20}$ heterocyclic aryl, $C_1$-$C_{20}$ alkylsulfonamido, $C_2$-$C_{20}$ heterocyclic sulfonamido, or $C_1$-$C_{20}$ alkoxyl carbonylamino group;
$R^2$ is selected from hydrogen (H), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_6$-$C_{20}$ aryl, $C_3$-$C_{20}$ heterocyclic aryl, $C_6$-$C_{20}$ aryloxycarbonyl, $C_1$-$C_{20}$ alkylsulfonyl, $C_3$-$C_{20}$ cycloalkylsulfonyl, $C_1$-$C_{20}$ alkoxysulfonyl, $C_3$-$C_{20}$ cycloalkoxysulfonyl, $C_6$-$C_{20}$ arylsulfonyl, $C_6$-$C_{20}$ aryloxysulfonyl, $C_1$-$C_{20}$ alkylaminosulfonyl, $C_3$-$C_{20}$ cycloalkylaminosulfonyl, or $C_6$-$C_{20}$ arylaminosulfonyl group;
$R^3$, $R^4$, $R^5$ and $R^6$ are each independently selected from hydrogen, halogen atom, hydroxyl, cyano, nitro, $C_1$-$C_{20}$ alkyl, $C_3$-$C_{20}$ cycloalkyl, $C_1$-$C_{20}$ alkoxyl, $C_1$-$C_{20}$ alkylamino, $C_2$-$C_{20}$ heterocyclic amino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_{20}$ alkyl, $C_1$-$C_{20}$ alkoxyl, $C_1$-$C_{20}$ alkylthio, $C_1$-$C_{20}$ alkoxylcarbonyl, aminocarbonyl, $C_1$-$C_{20}$ alkylaminocarbonyl, carbonylamino, $C_1$-$C_{20}$ alkylcarbonylamino, $C_2$-$C_{20}$ heterocyclicoxyl carbonyl, $C_6$-$C_{20}$ aryl, $C_6$-$C_{20}$ aryloxy, $C_6$-$C_{20}$ aryloxycarbonyl or $C_2$-$C_{20}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{20}$ alkyl, $C_3$-$C_{20}$ cycloalkyl, $C_1$-$C_{20}$ alkoxyl, $C_1$-$C_{20}$ alkylthio, $C_1$-$C_{20}$ alkoxylcarbonyl, $C_1$-$C_{20}$ alkylaminocarbonyl, $C_1$-$C_{20}$ alkylcarbonylamino, $C_6$-$C_{20}$ aryl, $C_6$-$C_{20}$ aryloxy, $C_6$-$C_{20}$ aryloxycarbonyl or $C_2$-$C_{20}$ heterocyclic group.

$R^{12}$ is selected from hydrogen (H), hydroxyl (OH), amino ($NH_2$), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ aryloxyl, $C_3$-$C_{20}$ heterocyclic arylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkyloxysulfonamido, $C_3$-$C_{20}$ cycloalkyloxysulfonamido, $C_6$-$C_{20}$ aryloxysulfonamido, $C_1$-$C_{20}$ alkylaminosulfonamido, $C_3$-$C_{20}$ cycloalkylaminosulfonamido, or $C_6$-$C_{20}$ arylaminosulfonamido group;

In one preferred embodiment in the present invention by the formula IIa or IIb,

Wherein:

m=1 or 2; n=0, 1 or 2;

"$=\!=\!=$" is a single bond or double bond;

E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkylcarbonyl, $C_1$-$C_{15}$ alkoxycarbonyl, $C_6$-$C_{15}$ aryloxycarbonyl, $C_2$-$C_{15}$ heterocyclic oxycarbonyl, aminocarbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylamino aminosulfonyl group.

Rb and Rc are each independently selected from hydrogen, halogen atom, cyano, nitro, $C_1$-$C_{15}$ alkyl, $C_3$-$C_{15}$ cycloalkyl, $C_6$-$C_{15}$ aryl, $C_1$-$C_{15}$ alkoxyl, $C_1$-$C_{15}$ alkylthio, $C_1$-$C_{15}$ alkoxycarbonyl, $C_6$-$C_{15}$ aryloxy, $C_6$-$C_{15}$ aryloxycarbonyl, $C_2$-$C_{15}$ heterocyclic-oxycarbonyl, $C_2$-$C_{15}$ heterocyclic aryl, $C_1$-$C_{15}$ alkylamino, $C_2$-$C_{15}$ heterocyclic amino, $C_6$-$C_{15}$ arylamino, aminocarbonyl, $C_1$-$C_{15}$ alkylaminocarbonyl, carbonylamino, $C_1$-$C_{15}$ alkylcarbonylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{15}$ alkoxyl, $C_1$-$C_{15}$ alkylamino, $C_1$-$C_{15}$ alkyl-oxygen, $C_1$-$C_{15}$ alkyl, $C_1$-$C_{15}$ alkoxycarbonyl, carbonyl, carbonylamino or $C_1$-$C_{15}$ alkylcarbonylamino group; when $R^7$ and $R^8$ or $R^8$ and $R^9$ are connected each other as a cyclic structure, G is methylene or does not exist (ie. "$=\!=\!=$" connected directly with the phenyl group of polyheterocyclic group); wherein the definition of Ra, Rb and Rc are the same as that in E.

L and $L^1$ are each independently selected from oxygen, sulfur, $C_2$-$C_{15}$ alkenyl, $C_1$-$C_{15}$ alkyl, $C_3$-$C_{15}$ cycloalkyl, $C_2$-$C_{15}$ heterocyclic, $C_6$-$C_{15}$ aryl, $C_3$-$C_{15}$ heterocyclic aryl, $C_1$-$C_{15}$ alkylthio, $C_1$-$C_{15}$ alkoxyl, $C_3$-$C_{15}$ cycloalkoxyl, $C_2$-$C_{15}$ heterocyclic oxyl, $C_1$-$C_{15}$ alkylamino, $C_1$-$C_{15}$ alkoxycarbonyl, $C_6$-$C_{15}$ aryl, or $C_6$-$C_{15}$ aryloxy group;

W is selected from oxygen or sulfur;

X is selected from oxygen, sulfur, nitrogen or —NRa—; wherein the definition of Ra is the same as that in E and G;

Y is selected from nitrogen or CH;

$R^1$ is selected from hydrogen (H), $C_1$-$C_{15}$ alkyl, $C_3$-$C_{15}$ cycloalkyl, $C_6$-$C_{15}$ aryl, $C_3$-$C_{15}$ heterocyclic aryl, $C_1$-$C_{15}$ alkylsulfonamido, $C_2$-$C_{15}$ heterocyclic sulfonamido, or $C_1$-$C_{15}$ alkoxyl carbonylamino group;

$R^2$ is selected from hydrogen (H), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_6$-$C_{15}$ aryl, $C_3$-$C_{15}$ heterocyclic aryl, $C_6$-$C_{15}$ aryloxycarbonyl, $C_1$-$C_{15}$ alkylsulfonyl, $C_3$-$C_{15}$ cycloalkylsulfonyl, $C_1$-$C_{15}$ alkoxysulfonyl, $C_3$-$C_{15}$ cycloalkoxysulfonyl, $C_6$-$C_{15}$ arylsulfonyl, $C_6$-$C_{15}$ aryloxysulfonyl, $C_1$-$C_{15}$ alkylaminosulfonyl, $C_3$-$C_{15}$ cycloalkylaminosulfonyl, or $C_6$-$C_{15}$ arylaminosulfonyl group;

$R^3$, $R^4$, $R^5$ and $R^6$ are each independently selected from hydrogen, halogen atom, hydroxyl, cyano, nitro, $C_1$-$C_{15}$ alkyl, $C_3$-$C_{15}$ cycloalkyl, $C_1$-$C_{15}$ alkoxyl, $C_1$-$C_{15}$ alkylamino, $C_2$-$C_{15}$ heterocyclic amino, $C_6$-$C_{15}$ aryl, $C_6$-$C_{15}$ arylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_{15}$ alkyl, $C_1$-$C_{15}$ alkoxyl, $C_1$-$C_{15}$ alkylthio, $C_1$-$C_{15}$ alkoxylcarbonyl, aminocarbonyl, $C_1$-$C_{15}$ alkylaminocarbonyl, carbonylamino, $C_1$-$C_{15}$ alkylcarbonylamino, $C_2$-$C_{15}$ heterocyclicoxyl carbonyl, $C_6$-$C_{15}$ aryl, $C_6$-$C_{15}$ aryloxy, $C_6$-$C_{15}$ aryloxycarbonyl or $C_2$-$C_{15}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{15}$ alkyl, $C_3$-$C_{15}$ cycloalkyl, $C_1$-$C_{15}$ alkoxyl, $C_1$-$C_{15}$ alkylthio, $C_1$-$C_{15}$ alkoxylcarbonyl, $C_1$-$C_{15}$ alkylaminocarbonyl, $C_1$-$C_{15}$ alkylcarbonylamino, $C_6$-$C_{15}$ aryl, $C_6$-$C_{15}$ aryloxy, $C_6$-$C_{15}$ aryloxycarbonyl or $C_2$-$C_{15}$ heterocyclic group.

$R^{12}$ is selected from hydrogen (H), hydroxyl (OH), amino ($NH_2$), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_1$-$C_{15}$ alkylamino, $C_3$-$C_{15}$ cycloalkylamino, $C_2$-$C_{15}$ heterocyclic amino, $C_6$-$C_{15}$ aryl, $C_6$-$C_{15}$ aryloxyl, $C_3$-$C_{15}$ heterocyclic arylamino, $C_1$-$C_{15}$ alkylsulfonamido, $C_3$-$C_{15}$ cycloalkylsulfonamido, $C_6$-$C_{15}$ arylsulfonamido, $C_1$-$C_{15}$ alkyloxysulfonamido, $C_3$-$C_{15}$ cycloalkyloxysulfonamido, $C_6$-$C_{15}$ aryloxysulfonamido, $C_1$-$C_{15}$ alkylaminosulfonamido, $C_3$-$C_{15}$ cycloalkylaminosulfonamido, or $C_6$-$C_{15}$ arylaminosulfonamido group;

In one more preferred embodiment in the present invention by the formula IIa or IIb, Wherein:

m=1 or 2; n=0, 1 or 2;

"$=\!=\!=$" is a single bond or double bond;

E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_8$ alkyl, $C_3$-$C_8$ cycloalkyl, $C_6$-$C_{12}$ aryl, $C_2$-$C_8$ heterocyclic aryl, $C_1$-$C_8$ alkylcarbonyl, $C_1$-$C_8$ alkoxycarbonyl, $C_6$-$C_{12}$ aryloxycarbonyl, $C_2$-$C_8$ heterocyclic oxycarbonyl, aminocarbonyl, $C_1$-$C_8$ alkylaminocarbonyl, $C_1$-$C_8$ alkylaminosulfonyl, $C_2$-$C_8$ heterocyclic aminosulfonyl, or $C_6$-$C_{12}$ arylamino aminosulfonyl group.

Rb and Rc are each independently selected from hydrogen, halogen atom, cyano, nitro, $C_1$-$C_8$ alkyl, $C_3$-$C_8$ cycloalkyl, $C_6$-$C_{12}$ aryl, $C_1$-$C_8$ alkoxyl, $C_1$-$C_8$ alkylthio, $C_1$-$C_8$ alkoxycarbonyl, $C_6$-$C_{12}$ aryloxy, $C_6$-$C_{12}$ aryloxycarbonyl, $C_2$-$C_8$ heterocyclic-oxycarbonyl, $C_2$-$C_{12}$ heterocyclic aryl, $C_1$-$C_8$ alkylamino, $C_2$-$C_8$ heterocyclic amino, $C_6$-$C_{12}$ arylamino, aminocarbonyl, $C_1$-$C_8$ alkylaminocarbonyl, carbonylamino, $C_1$-$C_8$ alkylcarbonylamino, $C_1$-$C_8$ alkylsulfonamido, $C_2$-$C_8$ heterocyclic sulfonamido, $C_6$-$C_{12}$ arylsulfonamido or $C_1$-$C_8$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_8$ alkoxyl, $C_1$-$C_8$ alkylamino, $C_1$-$C_8$ alkyl-oxygen, $C_1$-$C_8$ alkyl, $C_1$-$C_8$ alkoxycarbonyl, carbonyl, carbonylamino or $C_1$-$C_8$ alkylcarbonylamino group; when $R^7$ and $R^8$ or $R^8$ and $R^9$ are connected each other as a cyclic structure, G is methylene or does not exist (ie. "┄" connected directly with the phenyl group of polyheterocyclic group); wherein the definition of Ra, Rb and Rc are the same as that in E.

L and $L^1$ are each independently selected from oxygen, sulfur, $C_2$-$C_8$ alkenyl, $C_1$-$C_8$ alkyl, $C_3$-$C_8$ cycloalkyl, $C_2$-$C_8$ heterocyclic, $C_6$-$C_{12}$ aryl, $C_3$-$C_8$ heterocyclic aryl, $C_1$-$C_8$ alkylthio, $C_1$-$C_8$ alkoxyl, $C_3$-$C_8$ cycloalkoxyl, $C_2$-$C_8$ heterocyclic oxyl, $C_1$-$C_8$ alkylamino, $C_1$-$C_8$ alkoxycarbonyl, $C_6$-$C_{12}$ aryl, or $C_6$-$C_{12}$ aryloxy group;

W is selected from oxygen or sulfur;

X is selected from oxygen, sulfur, nitrogen or —NRa—; wherein the definition of Ra is the same as that in E and G;

Y is selected from nitrogen or CH;

$R^1$ is selected from hydrogen (H), $C_1$-$C_8$ alkyl, $C_3$-$C_8$ cycloalkyl, $C_6$-$C_{12}$ aryl, $C_3$-$C_{12}$ heterocyclic aryl, $C_1$-$C_8$ alkylsulfonamido, $C_2$-$C_{12}$ heterocyclic sulfonamido, or $C_1$-$C_8$ alkoxyl carbonylamino group;

$R^2$ is selected from hydrogen (H), $C_1$-$C_8$ alkyl, $C_3$-$C_8$ cycloalkyl, $C_1$-$C_8$ alkoxyl, $C_3$-$C_8$ cycloalkoxyl, $C_6$-$C_{12}$ aryl, $C_3$-$C_{12}$ heterocyclic aryl, $C_6$-$C_{12}$ aryloxycarbonyl, $C_1$-$C_8$ alkylsulfonyl, $C_3$-$C_8$ cycloalkylsulfonyl, $C_1$-$C_8$ alkoxysulfonyl, $C_3$-$C_8$ cycloalkoxysulfonyl, $C_6$-$C_{12}$ arylsulfonyl, $C_6$-$C_{12}$ aryloxysulfonyl, $C_1$-$C_8$ alkylaminosulfonyl, $C_3$-$C_8$ cycloalkylaminosulfonyl, or $C_6$-$C_{12}$ arylaminosulfonyl group;

$R^3$, $R^4$, $R^5$ and $R^6$ are each independently selected from hydrogen, halogen atom, hydroxyl, cyano, nitro, $C_1$-$C_8$ alkyl, $C_3$-$C_8$ cycloalkyl, $C_1$-$C_8$ alkoxyl, $C_1$-$C_8$ alkylamino, $C_2$-$C_8$ heterocyclic amino, $C_6$-$C_{12}$ aryl, $C_6$-$C_{12}$ arylamino, $C_1$-$C_8$ alkylsulfonamido, $C_2$-$C_8$ heterocyclic sulfonamido, $C_6$-$C_{12}$ arylsulfonamido or $C_1$-$C_8$ aminosulfonamido group. Wherein $R^3$ and $R^4$ can be connected as a cyclic structure.

$R^7$, $R^8$ and $R^9$ are each independently selected from hydrogen, halogen atom, cyano, nitro, trifluoromethyl, $C_1$-$C_8$ alkyl, $C_1$-$C_8$ alkoxyl, $C_1$-$C_8$ alkylthio, $C_1$-$C_8$ alkoxylcarbonyl, aminocarbonyl, $C_1$-$C_8$ alkylaminocarbonyl, carbonylamino, $C_1$-$C_8$ alkylcarbonylamino, $C_2$-$C_8$ heterocyclicoxyl carbonyl, $C_6$-$C_{12}$ aryl, $C_6$-$C_{12}$ aryloxy, $C_6$-$C_{12}$ aryloxycarbonyl or $C_2$-$C_8$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_8$ alkyl, $C_3$-$C_8$ cycloalkyl, $C_1$-$C_8$ alkoxyl, $C_1$-$C_8$ alkylthio, $C_1$-$C_8$ alkoxylcarbonyl, $C_1$-$C_8$ alkylaminocarbonyl, $C_1$-$C_8$ alkylcarbonylamino, $C_6$-$C_{12}$ aryl, $C_6$-$C_{12}$ aryloxy, $C_6$-$C_{12}$ aryloxycarbonyl or $C_2$-$C_8$ heterocyclic group.

$R^{12}$ is selected from hydrogen (H), hydroxyl (OH), amino ($NH_2$), $C_1$-$C_8$ alkyl, $C_3$-$C_8$ cycloalkyl, $C_1$-$C_8$ alkoxyl, $C_3$-$C_8$ cycloalkoxyl, $C_1$-$C_8$ alkylamino, $C_3$-$C_8$ cycloalkylamino, $C_2$-$C_8$ heterocyclic amino, $C_6$-$C_{12}$ aryl, $C_6$-$C_{12}$ aryloxyl, $C_3$-$C_{12}$ heterocyclic arylamino, $C_1$-$C_8$ alkylsulfonamido, $C_3$-$C_8$ cycloalkylsulfonamido, $C_6$-$C_{12}$ arylsulfonamido, $C_1$-$C_8$ alkyloxysulfonamido, $C_3$-$C_8$ cycloalkyloxysulfonamido, $C_6$-$C_{12}$ aryloxysulfonamido, $C_1$-$C_8$ alkylaminosulfonamido, $C_3$-$C_8$ cycloalkylaminosulfonamido, or $C_6$-$C_{12}$ arylaminosulfonamido group;

In the most preferred embodiment in the present invention by the formula IIa or IIb, Wherein, m=1; n=1;

p=0, 1 or 2; q=0, 1 or 2; r=0, 1 or 2;

"┄" is a single bond or double bond;

E is methylene (—$CH_2$—);

G is selected from oxygen, sulfur, —$SCH_2$—, —N(Ra)$CH_2$—, —NRa—, methylene (—$CH_2$—), —$OCH_2$—, —$CH_2OCH_2$—, $C_1$-$C_3$ alkoxycarbonyl, carbonyl, carbonylamino, or $C_1$-$C_3$ alkylcarbonylamino group; When $R^7$ and $R^8$ or $R^8$ and $R^9$ are connected each other as a cyclic structure, G is methylene or does not exist (ie. "┄" connected directly with the phenyl group of polyheterocyclic group); wherein Ra is selected from hydrogen, $C_1$-$C_6$ alkyl, $C_1$-$C_6$ alkylcarbonyl, or $C_1$-$C_6$ alkoxycarbonyl group;

L is methylene (—$CH_2$—);

$L^1$ is $C_1$-$C_6$ alkyl, $C_1$-$C_6$ alkoxyl, or $C_1$-$C_6$ alkylamino;

W and X are both oxygen (O);

Y is nitrogen (N);

$R^1$ is selected from $C_1$-$C_6$ alkyl, $C_6$-$C_{10}$ aryl, $C_1$-$C_6$ alkylsulfonamido, $C_2$-$C_6$ heterocyclic sulfonamido, or $C_1$-$C_6$ alkoxylcarbonylamino group;

$R^2$, $R^5$ and $R^6$ are each independently hydrogen;

$R^3$ and $R^4$ are each independently selected from hydrogen, methyl, fluorine, or $R^3$ and $R^4$ are connected each other as a cyclopropyl group;

$R^7$, $R^8$ and $R^9$ are each independently selected from hydrogen, halogen, $C_1$-$C_3$ alkyl, or $C_1$-$C_3$ alkoxyl group;

$R^{10}$ is hydrogen;

$R^{12}$ is selected from hydroxyl or $C_1$-$C_3$ alkoxyl;

The present invention in the third aspect provides intermediates IIIa or IIIb for preparation of compounds Ia or Ib;

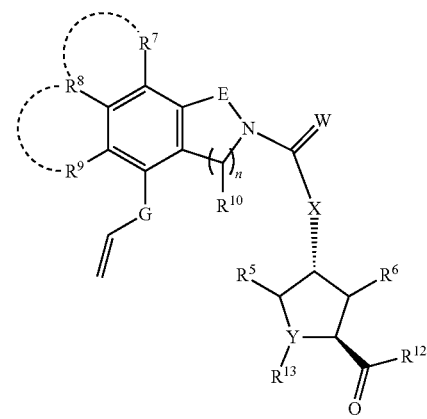

IIIa

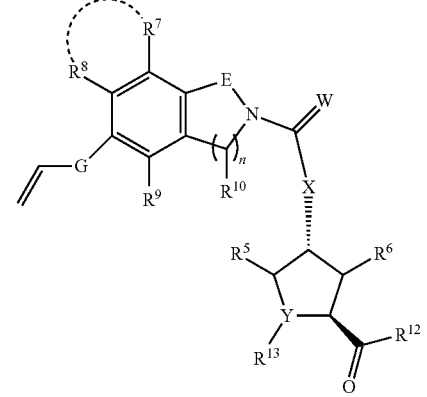

IIIb

Wherein in formula IIIa or IIIb:

n=0, 1 or 2;

"┄" is a single bond or double bond;

E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkylcarbonyl, $C_1$-$C_{20}$ alkoxycarbonyl, $C_6$-$C_{20}$ aryloxycarbonyl, $C_2$-$C_{20}$ heterocyclic oxycarbonyl, aminocarbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ arylamino aminosulfonyl group.

Rb and Rc are each independently selected from hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxyl, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic-oxycarbonyl, $C_2$-$C_{20}$ heterocyclic aryl, $C_1$-$C_{20}$ alkylamino, $C_2$-$C_{20}$ heterocyclic amino, $C_6$-$C_{20}$ arylamino, aminocarbonyl, $C_1$-$C_{20}$ alkylaminocarbonyl, carbonylamino, $C_1$-$C_{20}$ alkylcarbonylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{20}$ alkoxyl, $C_1$-$C_{20}$ alkylamino, $C_1$-$C_{20}$ alkyl-oxygen, $C_1$-$C_{20}$ alkyl, $C_1$-$C_{20}$ alkoxycarbonyl, carbonyl, carbonylamino or $C_1$-$C_{20}$ alkylcarbonylamino group; when $R^7$ and $R^8$ or $R^8$ and $R^9$ are connected each other as a cyclic structure, G is methylene or does not exist (ie. "=" connected directly with the phenyl group of polyheterocyclic group); wherein the definition of Ra, Rb and Rc are the same as that in E.

W is selected from oxygen or sulfur;

X is selected from oxygen, sulfur, nitrogen or —NRa—; wherein the definition of Ra is the same as that in E and G;

Y is selected from nitrogen or CH;

$R^5$ and $R^6$ are each independently selected from hydrogen, halogen atom, hydroxyl, cyano, nitro, $C_1$-$C_{20}$ alkyl, $C_3$-$C_{20}$ cycloalkyl, $C_1$-$C_{20}$ alkoxyl, $C_1$-$C_{20}$ alkylamino, $C_2$-$C_{20}$ heterocyclic amino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ aminosulfonamido group.

$R^7$, $R^8$ and $R^9$ are each independently selected from hydrogen, halogen atom, cyano, nitro, trifluoromethyl, $C_1$-$C_{20}$ alkyl, $C_1$-$C_{20}$ alkoxyl, $C_1$-$C_{20}$ alkylthio, $C_1$-$C_{20}$ alkoxylcarbonyl, aminocarbonyl, $C_1$-$C_{20}$ alkylaminocarbonyl, carbonylamino, $C_1$-$C_{20}$ alkylcarbonylamino, $C_2$-$C_{20}$ heterocycicoxyl carbonyl, $C_6$-$C_{20}$ aryl, $C_6$-$C_{20}$ aryloxy, $C_6$-$C_{20}$ aryloxycarbonyl or $C_2$-$C_{20}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{20}$ alkyl, $C_3$-$C_{20}$ cycloalkyl, $C_1$-$C_{20}$ alkoxyl, $C_1$-$C_{20}$ alkylthio, $C_1$-$C_{20}$ alkoxylcarbonyl, $C_1$-$C_{20}$ alkylaminocarbonyl, $C_1$-$C_{20}$ alkylcarbonylamino, $C_6$-$C_{20}$ aryl, $C_6$-$C_{20}$ aryloxy, $C_6$-$C_{20}$ aryloxycarbonyl or $C_2$-$C_{20}$ heterocyclic group.

$R^{12}$ is selected from hydrogen (H), hydroxyl (OH), amino ($NH_2$), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ aryloxyl, $C_3$-$C_{20}$ heterocyclic arylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkyloxysulfonamido, $C_3$-$C_{20}$ cycloalkyloxysulfonamido, $C_6$-$C_{20}$ aryloxysulfonamido, $C_1$-$C_{20}$ alkylaminosulfonamido, $C_3$-$C_{20}$ cycloalkylaminosulfonamido, or $C_6$-$C_{20}$ arylaminosulfonamido group;

$R^{13}$ is selected from hydrogen (H), $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkoxylcarbonyl, $C_6$-$C_{20}$ aryloxylcarbonyl, $C_2$-$C_{20}$ heterocyclic oxycarbonyl, $C_1$-$C_{20}$ alkylaminocarbonyl, $C_1$-$C_{20}$ alkylaminosulfonyl, $C_2$-$C_{20}$ heterocyclic alkylaminosulfonyl, or $C_6$-$C_{20}$ arylaminosulfonyl group;

In one preferred embodiment in the present invention by the formula Ina or IIIb, Wherein:

n=0, 1 or 2;

"=" is a single bond or double bond;

E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkylcarbonyl, $C_1$-$C_{15}$ alkoxycarbonyl, $C_6$-$C_{15}$ aryloxycarbonyl, $C_2$-$C_{15}$ heterocyclic oxycarbonyl, aminocarbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylamino aminosulfonyl group.

Rb and Rc are each independently selected from hydrogen, halogen atom, cyano, nitro, $C_1$-$C_{15}$ alkyl, $C_3$-$C_{15}$ cycloalkyl, $C_6$-$C_{15}$ aryl, $C_1$-$C_{15}$ alkoxyl, $C_1$-$C_{15}$ alkylthio, $C_1$-$C_{15}$ alkoxycarbonyl, $C_6$-$C_{15}$ aryloxy, $C_6$-$C_{15}$ aryloxycarbonyl, $C_2$-$C_{15}$ heterocyclic-oxycarbonyl, $C_2$-$C_{15}$ heterocyclic aryl, $C_1$-$C_{15}$ alkylamino, $C_2$-$C_{15}$ heterocyclic amino, $C_6$-$C_{15}$ arylamino, aminocarbonyl, $C_1$-$C_{15}$ alkylaminocarbonyl, carbonylamino, $C_1$-$C_{15}$ alkylcarbonylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{15}$ alkoxyl, $C_1$-$C_{15}$ alkylamino, $C_1$-$C_{15}$ alkyl-oxygen, $C_1$-$C_{15}$ alkyl, $C_1$-$C_{15}$ alkoxycarbonyl, carbonyl, carbonylamino or $C_1$-$C_{15}$ alkylcarbonylamino group; when $R^7$ and $R^8$ or $R^8$ and $R^9$ are connected each other as a cyclic structure, G is methylene or does not exist (ie. "=" connected directly with the phenyl group of polyheterocyclic); wherein the definition of Ra, Rb and Rc are the same as that in E.

W is selected from oxygen or sulfur;

X is selected from oxygen, sulfur, nitrogen or —NRa—; wherein the definition of Ra is the same as that in E and G;

Y is selected from nitrogen or CH;

$R^5$ and $R^6$ are each independently selected from hydrogen, halogen atom, hydroxyl, cyano, nitro, $C_1$-$C_{15}$ alkyl, $C_3$-$C_{15}$ cycloalkyl, $C_1$-$C_{15}$ alkoxyl, $C_1$-$C_{15}$ alkylamino, $C_2$-$C_{15}$ heterocyclic amino, $C_6$-$C_{15}$ aryl, $C_6$-$C_{15}$ arylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ aminosulfonamido group.

$R^7$, $R^8$ and $R^9$ are each independently selected from hydrogen, halogen atom, cyano, nitro, trifluoromethyl, $C_1$-$C_{15}$ alkyl, $C_1$-$C_{15}$ alkoxyl, $C_1$-$C_{15}$ alkylthio, $C_1$-$C_{15}$ alkoxylcarbonyl, aminocarbonyl, $C_1$-$C_{15}$ alkylaminocarbonyl, carbonylamino, $C_1$-$C_{15}$ alkylcarbonylamino, $C_2$-$C_{15}$ heterocycicoxyl carbonyl, $C_6$-$C_{15}$ aryl, $C_6$-$C_{15}$ aryloxy, $C_6$-$C_{15}$ aryloxycarbonyl or $C_2$-$C_{15}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{15}$ alkyl, $C_3$-$C_{15}$ cycloalkyl, $C_1$-$C_{15}$ alkoxyl, $C_1$-$C_{15}$ alkylthio, $C_1$-$C_{15}$ alkoxylcarbonyl, $C_1$-$C_{15}$ alkylaminocarbonyl, $C_1$-$C_{15}$ alkylcarbonylamino, $C_6$-$C_{15}$ aryl, $C_6$-$C_{15}$ aryloxy, $C_6$-$C_{15}$ aryloxycarbonyl or $C_2$-$C_{15}$ heterocyclic group.

$R^{12}$ is selected from hydrogen (H), hydroxyl (OH), amino ($NH_2$), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_1$-$C_{15}$ alkylamino, $C_3$-$C_{15}$ cycloalkylamino, $C_2$-$C_{15}$ heterocyclic amino, $C_6$-$C_{15}$ aryl, $C_6$-$C_{15}$ aryloxyl, $C_3$-$C_{15}$ heterocyclic arylamino, $C_1$-$C_{15}$ alkylsulfonamido, $C_3$-$C_{15}$ cycloalkylsulfonamido, $C_6$-$C_{15}$ arylsulfonamido, $C_1$-$C_{15}$ alkyloxysulfonamido, $C_3$-$C_{15}$ cycloalkyloxysulfonamido, $C_6$-$C_{15}$ aryloxysulfonamido, $C_1$-$C_{15}$ alkylaminosulfonamido, $C_3$-$C_{15}$ cycloalkylaminosulfonamido, or $C_6$-$C_{15}$ arylaminosulfonamido group;

$R^{13}$ is selected from hydrogen (H), $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkoxylcarbonyl, $C_6$-$C_{15}$ aryloxylcarbonyl, $C_2$-$C_{15}$ heterocyclic oxycarbonyl, $C_1$-$C_{15}$ alkylaminocarbonyl, $C_1$-$C_{15}$ alkylaminosulfonyl, $C_2$-$C_{15}$ heterocyclic alkylaminosulfonyl, or $C_6$-$C_{15}$ arylaminosulfonyl group;

In one more preferred embodiment in the present invention by the formula IIIa or IIIb, Wherein:

n=0, 1 or 2;

"═" is a single bond or double bond;

E is oxygen, —NRa—, —CRbRc-, ethylidene, propylidene, $C_1$-$C_6$ alkoxyl, carbonyl, amino carbonyl or carbonyl amino Ra is selected from hydrogen, $C_1$-$C_8$ alkyl, $C_3$-$C_8$ cycloalkyl, $C_6$-$C_{12}$ aryl, $C_2$-$C_8$ heterocyclic aryl, $C_1$-$C_8$ alkylcarbonyl, $C_1$-$C_8$ alkoxycarbonyl, $C_6$-$C_{12}$ aryloxycarbonyl, $C_2$-$C_8$ heterocyclic oxycarbonyl, aminocarbonyl, $C_1$-$C_8$ alkylaminocarbonyl, $C_1$-$C_8$ alkylaminosulfonyl, $C_2$-$C_8$ heterocyclic aminosulfonyl, or $C_6$-$C_{12}$ arylamino aminosulfonyl group.

Rb and Rc are each independently selected from hydrogen, halogen atom, cyano, nitro, $C_1$-$C_8$ alkyl, $C_3$-$C_8$ cycloalkyl, $C_6$-$C_{12}$ aryl, $C_1$-$C_8$ alkoxyl, $C_1$-$C_8$ alkylthio, $C_1$-$C_8$ alkoxycarbonyl, $C_6$-$C_{12}$ aryloxy, $C_6$-$C_{12}$ aryloxycarbonyl, $C_2$-$C_8$ heterocyclic-oxycarbonyl, $C_2$-$C_{12}$ heterocyclic aryl, $C_1$-$C_8$ alkylamino, $C_2$-$C_8$ heterocyclic amino, $C_6$-$C_{12}$ arylamino, aminocarbonyl, $C_1$-$C_8$ alkylaminocarbonyl, carbonylamino, $C_1$-$C_8$ alkylcarbonylamino, $C_1$-$C_8$ alkylsulfonamido, $C_2$-$C_8$ heterocyclic sulfonamido, $C_6$-$C_{12}$ arylsulfonamido or $C_1$-$C_8$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_8$ alkoxyl, $C_1$-$C_8$ alkylamino, $C_1$-$C_8$ alkyl-oxygen, $C_1$-$C_8$ alkyl, $C_1$-$C_8$ alkoxycarbonyl, carbonyl, carbonylamino or $C_1$-$C_8$ alkylcarbonylamino group; when $R^7$ and $R^8$ or $R^8$ and $R^9$ are connected each other as a cyclic structure, G is methylene or does not exist (ie. "═" connected directly with the phenyl group of polyheterocyclic group); wherein the definition of Ra, Rb and Rc are the same as that in E.

W is selected from oxygen or sulfur;

X is selected from oxygen, sulfur, nitrogen or —NRa—; wherein the definition of Ra is the same as that in E and G;

Y is selected from nitrogen or CH;

$R^5$ and $R^6$ are each independently selected from hydrogen, halogen atom, hydroxyl, cyano, nitro, $C_1$-$C_8$ alkyl, $C_3$-$C_8$ cycloalkyl, $C_1$-$C_8$ alkoxyl, $C_1$-$C_8$ alkylamino, $C_2$-$C_8$ heterocyclic amino, $C_6$-$C_{12}$ aryl, $C_6$-$C_{12}$ arylamino, $C_1$-$C_8$ alkylsulfonamido, $C_2$-$C_8$ heterocyclic sulfonamido, $C_6$-$C_{12}$ arylsulfonamido or $C_1$-$C_8$ aminosulfonamido group.

$R^7$, $R^8$ and $R^9$ are each independently selected from hydrogen, halogen atom, cyano, nitro, trifluoromethyl, $C_1$-$C_8$ alkyl, $C_1$-$C_8$ alkoxyl, $C_1$-$C_8$ alkylthio, $C_1$-$C_8$ alkoxylcarbonyl, aminocarbonyl, $C_1$-$C_8$ alkylaminocarbonyl, carbonylamino, $C_1$-$C_8$ alkylcarbonylamino, $C_2$-$C_8$ heterocyclicoxyl carbonyl, $C_6$-$C_{12}$ aryl, $C_6$-$C_{12}$ aryloxy, $C_6$-$C_{12}$ aryloxycarbonyl or $C_2$-$C_8$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_8$ alkyl, $C_3$-$C_8$ cycloalkyl, $C_1$-$C_8$ alkoxyl, $C_1$-$C_8$ alkylthio, $C_1$-$C_8$ alkoxylcarbonyl, $C_1$-$C_8$ alkylaminocarbonyl, $C_1$-$C_8$ alkylcarbonylamino, $C_6$-$C_{12}$ aryl, $C_6$-$C_{12}$ aryloxy, $C_6$-$C_{12}$ aryloxycarbonyl or $C_2$-$C_8$ heterocyclic group.

$R^{12}$ is selected from hydrogen (H), hydroxyl (OH), amino ($NH_2$), $C_1$-$C_8$ alkyl, $C_3$-$C_8$ cycloalkyl, $C_1$-$C_8$ alkoxyl, $C_3$-$C_8$ cycloalkoxyl, $C_1$-$C_8$ alkylamino, $C_3$-$C_8$ cycloalkylamino, $C_2$-$C_8$ heterocyclic amino, $C_6$-$C_{12}$ aryl, $C_6$-$C_{12}$ aryloxyl, $C_3$-$C_{12}$ heterocyclic arylamino, $C_1$-$C_8$ alkylsulfonamido, $C_3$-$C_8$ cycloalkylsulfonamido, $C_6$-$C_{12}$ arylsulfonamido, $C_1$-$C_8$ alkyloxysulfonamido, $C_3$-$C_8$ cycloalkyloxysulfonamido, $C_6$-$C_{12}$ aryloxysulfonamido, $C_1$-$C_8$ alkylaminosulfonamido, $C_3$-$C_8$ cycloalkylaminosulfonamido, or $C_6$-$C_{12}$ arylaminosulfonamido group;

$R^{13}$ is selected from hydrogen (H), $C_1$-$C_8$ alkyl, $C_3$-$C_8$ cycloalkyl, $C_6$-$C_{12}$ aryl, $C_2$-$C_{12}$ heterocyclic aryl, $C_1$-$C_8$ alkoxylcarbonyl, $C_6$-$C_{12}$ aryloxylcarbonyl, $C_2$-$C_8$ heterocyclic oxycarbonyl, $C_1$-$C_8$ alkylaminocarbonyl, $C_1$-$C_8$ alkylaminosulfonyl, $C_2$-$C_8$ heterocyclic alkylaminosulfonyl, or $C_6$-$C_{12}$ arylaminosulfonyl group;

In the most preferred embodiment in the present invention by formula IIIa or IIIb, n=1;

E is methylene (—$CH_2$—);

G is selected from oxygen, sulfur, —$SCH_2$—, —N(Ra)$CH_2$—, —NRa—, methylene (—$CH_2$—), —$OCH_2$—, —$CH_2OCH_2$—, $C_1$-$C_3$ alkoxycarbonyl, carbonylamino, or $C_1$-$C_3$ alkylcarbonylamino group; When $R^7$ and $R^8$ or $R^8$ and $R^9$ are connected each other as a cyclic structure, G is methylene or does not exist (ie. "═" connected directly with the phenyl group of polyheterocyclic group); wherein Ra is selected from hydrogen, $C_1$-$C_6$ alkyl, $C_1$-$C_6$ alkylcarbonyl, or $C_1$-$C_6$ alkoxycarbonyl group;

W and X are both oxygen (O);

Y is nitrogen (N);

$R^5$ and $R^6$ are each independently hydrogen;

$R^7$, $R^8$ and $R^9$ are each independently selected from hydrogen, halogen, $C_1$-$C_3$ alkyl, or $C_1$-$C_3$ alkoxyl group;

$R^{10}$ is hydrogen;

$R^{12}$ is selected from hydroxyl (OH) or $C_1$-$C_3$ alkoxyl;

$R^{13}$ is selected from hydrogen, $C_1$-$C_6$ alkylcarbonyl, or $C_1$-$C_6$ alkoxycarbonyl group;

The present invention in the forth aspect provides intermediates IVa or IVb for preparation of compounds Ia or Ib;

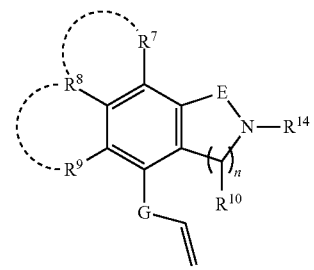

IVa

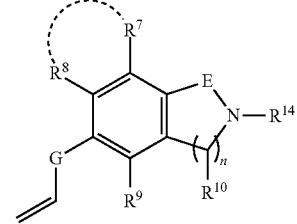

IVb

Wherein in the formula IVa or IVb:

n=0, 1 or 2;

"═" is a single bond or double bond;

E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkylcarbonyl, $C_1$-$C_{20}$ alkoxycarbonyl, $C_6$-$C_{20}$ aryloxycarbonyl, $C_2$-$C_{20}$ heterocyclic oxycarbonyl, aminocarbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ arylamino aminosulfonyl group.

Rb and Rc are each independently selected from hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxyl, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic-oxycarbonyl, $C_2$-$C_{20}$ heterocyclic aryl, $C_1$-$C_{20}$ alkylamino, $C_2$-$C_{20}$ heterocyclic amino, $C_6$-$C_{20}$ arylamino, aminocarbonyl, $C_1$-$C_{20}$ alkylaminocarbonyl, carbonylamino, $C_1$-$C_{20}$ alkylcarbonylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{20}$ alkoxyl, $C_1$-$C_{20}$ alkylamino, $C_1$-$C_{20}$ alkyl-oxygen, $C_1$-$C_{20}$ alkyl, $C_1$-$C_{20}$ alkoxycarbonyl, carbonyl, carbonylamino or $C_1$-$C_{20}$ alkylcarbonylamino group; when $R^7$ and $R^8$ or $R^8$ and $R^9$ are connected each other as a cyclic structure, G is methylene or does not exist (ie. "=" connected directly with the phenyl group of polyheterocyclic group); wherein the definition of Ra, Rb and Rc are the same as that in E.

$R^7$, $R^8$ and $R^9$ are each independently selected from hydrogen, halogen atom, cyano, nitro, trifluoromethyl, $C_1$-$C_{20}$ alkyl, $C_1$-$C_{20}$ alkoxyl, $C_1$-$C_{20}$ alkylthio, $C_1$-$C_{20}$ alkoxylcarbonyl, aminocarbonyl, $C_1$-$C_{20}$ alkylaminocarbonyl, carbonylamino, $C_1$-$C_{20}$ alkylcarbonylamino, $C_2$-$C_{20}$ heterocyclicoxyl carbonyl, $C_6$-$C_{20}$ aryl, $C_6$-$C_{20}$ aryloxy, $C_6$-$C_{20}$ aryloxycarbonyl or $C_2$-$C_{20}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{20}$ alkyl, $C_3$-$C_{20}$ cycloalkyl, $C_1$-$C_{20}$ alkoxyl, $C_1$-$C_{20}$ alkylthio, $C_1$-$C_{20}$ alkoxylcarbonyl, $C_1$-$C_{20}$ alkylaminocarbonyl, $C_1$-$C_{20}$ alkylcarbonylamino, $C_6$-$C_{20}$ aryl, $C_6$-$C_{20}$ aryloxy, $C_6$-$C_{20}$ aryloxycarbonyl or $C_2$-$C_{20}$ heterocyclic group.

$R^{14}$ is selected from hydrogen, $C_1$-$C_{20}$ alkyl, $C_3$-$C_{20}$ cycloalkyl, $C_6$-$C_{20}$ aryl, $C_2$-$C_{20}$ heterocyclic alkyl, $C_1$-$C_{20}$ alkoxylcarbonyl, $C_6$-$C_{20}$ aryloxycarbonyl, $C_2$-$C_{20}$ heterocyclicoxyl carbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ arylaminosulfonyl group;

In one preferred embodiment in the present invention by the formula IVa or IVb,

Wherein:

n=0, 1 or 2;

"=" is a single bond or double bond;

E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkylcarbonyl, $C_1$-$C_{15}$ alkoxycarbonyl, $C_6$-$C_{15}$ aryloxycarbonyl, $C_2$-$C_{15}$ heterocyclic oxycarbonyl, aminocarbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylamino aminosulfonyl group.

Rb and Rc are each independently selected from hydrogen, halogen atom, cyano, nitro, $C_1$-$C_{15}$ alkyl, $C_3$-$C_{15}$ cycloalkyl, $C_6$-$C_{15}$ aryl, $C_1$-$C_{15}$ alkoxyl, $C_1$-$C_{15}$ alkylthio, $C_1$-$C_{15}$ alkoxycarbonyl, $C_6$-$C_{15}$ aryloxy, $C_6$-$C_{15}$ aryloxycarbonyl, $C_2$-$C_{15}$ heterocyclic-oxycarbonyl, $C_2$-$C_{15}$ heterocyclic aryl, $C_1$-$C_{15}$ alkylamino, $C_2$-$C_{15}$ heterocyclic amino, $C_6$-$C_{15}$ arylamino, aminocarbonyl, $C_1$-$C_{15}$ alkylaminocarbonyl, carbonylamino, $C_1$-$C_{15}$ alkylcarbonylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_{15}$ alkoxyl, $C_1$-$C_{15}$ alkylamino, $C_1$-$C_{15}$ alkyl-oxygen, $C_1$-$C_{15}$ alkyl, $C_1$-$C_{15}$ alkoxycarbonyl, carbonyl, carbonylamino or $C_1$-$C_{15}$ alkylcarbonylamino group; when $R^7$ and $R^8$ or $R^8$ and $R^9$ are connected each other as a cyclic structure, G is methylene or does not exist (ie. "=" connected directly with the phenyl group of polyheterocyclic group); wherein the definition of Ra, Rb and Rc are the same as that in E.

$R^7$, $R^8$ and $R^9$ are each independently selected from hydrogen, halogen atom, cyano, nitro, trifluoromethyl, $C_1$-$C_{15}$ alkyl, $C_1$-$C_{15}$ alkoxyl, $C_1$-$C_{15}$ alkylthio, $C_1$-$C_{15}$ alkoxylcarbonyl, aminocarbonyl, $C_1$-$C_{15}$ alkylaminocarbonyl, carbonylamino, $C_1$-$C_{15}$ alkylcarbonylamino, $C_2$-$C_{15}$ heterocyclicoxyl carbonyl, $C_6$-$C_{15}$ aryl, $C_6$-$C_{15}$ aryloxy, $C_6$-$C_{15}$ aryloxycarbonyl or $C_2$-$C_{15}$ heterocyclic group. Wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{15}$ alkyl, $C_3$-$C_{15}$ cycloalkyl, $C_1$-$C_{15}$ alkoxyl, $C_1$-$C_{15}$ alkylthio, $C_1$-$C_{15}$ alkoxylcarbonyl, $C_1$-$C_{15}$ alkylaminocarbonyl, $C_1$-$C_{15}$ alkylcarbonylamino, $C_6$-$C_{15}$ aryl, $C_6$-$C_{15}$ aryloxy, $C_6$-$C_{15}$ aryloxycarbonyl or $C_2$-$C_{15}$ heterocyclic group.

$R^{14}$ is selected from hydrogen, $C_1$-$C_{15}$ alkyl, $C_3$-$C_{15}$ cycloalkyl, $C_6$-$C_{15}$ aryl, $C_2$-$C_{15}$ heterocyclic alkyl, $C_1$-$C_{15}$ alkoxylcarbonyl, $C_6$-$C_{15}$ aryloxycarbonyl, $C_2$-$C_{15}$ heterocyclicoxyl carbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylaminosulfonyl group;

In one more preferred embodiment in the present invention by the formula IVa or IVb, Wherein:

n=0, 1 or 2;

"=" is a single bond or double bond;

E is oxygen, —NRa—, —CRbRc-, ethylidene, propylidene, $C_1$-$C_6$ alkoxyl, carbonyl, amino carbonyl or carbonyl amino.

Ra is selected from hydrogen, $C_1$-$C_8$ alkyl, $C_3$-$C_8$ cycloalkyl, $C_6$-$C_{12}$ aryl, $C_2$-$C_8$ heterocyclic aryl, $C_1$-$C_8$ alkylcarbonyl, $C_1$-$C_8$ alkoxycarbonyl, $C_6$-$C_{12}$ aryloxycarbonyl, $C_2$-$C_8$ heterocyclic oxycarbonyl, aminocarbonyl, $C_1$-$C_8$ alkylaminocarbonyl, $C_1$-$C_8$ alkylaminosulfonyl, $C_2$-$C_8$ heterocyclic aminosulfonyl, or $C_6$-$C_{12}$ arylamino aminosulfonyl group.

Rb and Rc are each independently selected from hydrogen, halogen atom, cyano, nitro, $C_1$-$C_8$ alkyl, $C_3$-$C_8$ cycloalkyl, $C_6$-$C_{12}$ aryl, $C_1$-$C_8$ alkoxyl, $C_1$-$C_8$ alkylthio, $C_1$-$C_8$ alkoxycarbonyl, $C_6$-$C_{12}$ aryloxy, $C_6$-$C_{12}$ aryloxycarbonyl, $C_2$-$C_8$ heterocyclic-oxycarbonyl, $C_2$-$C_{12}$ heterocyclic aryl, $C_1$-$C_8$ alkylamino, $C_2$-$C_8$ heterocyclic amino, $C_6$-$C_{12}$ arylamino, aminocarbonyl, $C_1$-$C_8$ alkylaminocarbonyl, carbonylamino, $C_1$-$C_8$ alkylcarbonylamino, $C_1$-$C_8$ alkylsulfonamido, $C_2$-$C_8$ heterocyclic sulfonamido, $C_6$-$C_{12}$ arylsulfonamido or $C_1$-$C_8$ alkyl aminosulfonamido group.

G is selected from oxygen, sulfur, sulfone, —NRa—, —OC(Rb)(Rc)-, —SC(Rb)(Rc)-, —N(Ra)C(Rb)(Rc)-, $C_1$-$C_8$ alkoxyl, $C_1$-$C_8$ alkylamino, $C_1$-$C_8$ alkyl-oxygen, $C_1$-$C_8$ alkyl, $C_1$-$C_8$ alkoxycarbonyl, carbonyl, carbonylamino or C$_1$-C$_8$ alkylcarbonylamino group; when R$^7$ and R$^8$ or R$^8$ and R$^9$ are connected each other as a cyclic structure, G is methylene or does not exist (ie. "═" connected directly with the phenyl group of polyheterocyclic); wherein the definition of Ra, Rb and Rc are the same as that in E.

R$^7$, R$^8$ and R$^9$ are each independently selected from hydrogen, halogen atom, cyano, nitro, trifluoromethyl, C$_1$-C$_8$ alkyl, C$_1$-C$_8$ alkoxyl, C$_1$-C$_8$ alkylthio, C$_1$-C$_8$ alkoxylcarbonyl, aminocarbonyl, C$_1$-C$_8$ alkylaminocarbonyl, carbonylamino, C$_1$-C$_8$ alkylcarbonylamino, C$_2$-C$_8$ heterocyclicoxyl carbonyl, C$_6$-C$_{12}$ aryl, C$_6$-C$_{12}$ aryloxy, C$_6$-C$_{12}$ aryloxycarbonyl or C$_2$-C$_8$ heterocyclic group. Wherein R$^7$ and R$^8$ or R$^8$ and R$^9$ can be connected each other as a cyclic structure;

R$^{10}$ is selected from hydrogen, halogen atom, cyano, nitro, trifluoromethyl, C$_1$-C$_8$ alkyl, C$_3$-C$_8$ cycloalkyl, C$_1$-C$_8$ alkoxyl, C$_1$-C$_8$ alkylthio, C$_1$-C$_8$ alkoxylcarbonyl, C$_1$-C$_8$ alkylaminocarbonyl, C$_1$-C$_8$ alkylcarbonylamino, C$_6$-C$_{12}$ aryl, C$_6$-C$_{12}$ aryloxy, C$_6$-C$_{12}$ aryloxycarbonyl or C$_2$-C$_8$ heterocyclic group.

R$^{14}$ is selected from hydrogen, C$_1$-C$_8$ alkyl, C$_3$-C$_8$ cycloalkyl, C$_6$-C$_{12}$ aryl, C$_2$-C$_8$ heterocyclic alkyl, C$_1$-C$_8$ alkoxylcarbonyl, C$_6$-C$_{12}$ aryloxycarbonyl, C$_2$-C$_8$ heterocyclicoxyl carbonyl, C$_1$-C$_8$ alkylaminocarbonyl, C$_1$-C$_8$ alkylaminosulfonyl, C$_2$-C$_8$ heterocyclic aminosulfonyl, or C$_6$-C$_{12}$ arylaminosulfonyl group;

In one further optimal embodiment of in the present invention by the formula IVa or IVb, Wherein, n=1;

E is methylene (—CH$_2$—);

G is selected from oxygen, sulfur, —SCH$_2$—, —N(Ra)CH$_2$—, —NRa—, methylene (—CH$_2$—), —OCH$_2$—, —CH$_2$OCH$_2$—, C$_1$-C$_3$ alkoxycarbonyl, carbonylamino, or C$_1$-C$_3$ alkylcarbonylamino group; When R$^7$ and R$^8$ or R$^8$ and R$^9$ are connected each other as a cyclic structure, G is methylene or does not exist (ie. "═" connected directly with the phenyl group of polyheterocyclic group); wherein Ra is selected from hydrogen, C$_1$-C$_6$ alkyl, C$_1$-C$_6$ alkylcarbonyl, or C$_1$-C$_6$ alkoxycarbonyl group;

R$^7$, R$^8$ and R$^9$ are each independently selected from hydrogen, halogen, C$_1$-C$_3$ alkyl, or C$_1$-C$_3$ alkoxyl group;

R$^{10}$ is hydrogen;

R$^{14}$ is selected from hydrogen, C$_1$-C$_6$ alkyl, or C$_1$-C$_6$ alkoxycarbonyl group;

In the most preferred embodiment in the present invention, formula IVa is selected from the following structures:

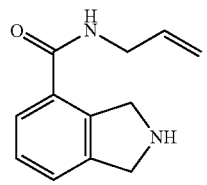

V-1

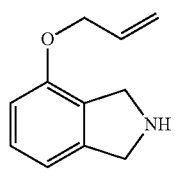

V-2

-continued

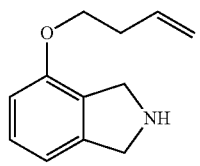

V-3

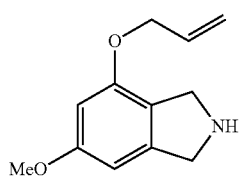

V-4

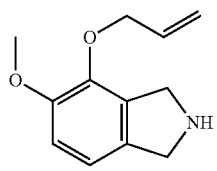

V-5

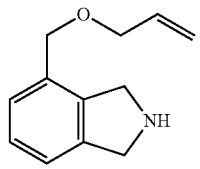

V-6

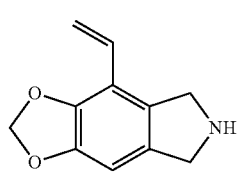

V-7

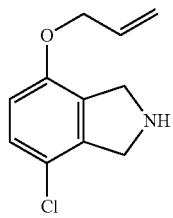

V-10

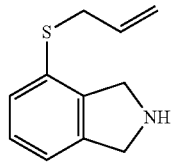

V-11

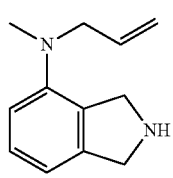

V-12

Formula IVb is selected from the following structures:

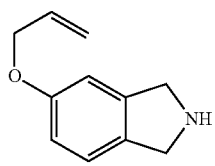

V-8

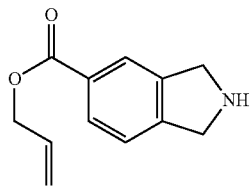

V-9

It is emphasized in the present invention that technicians in the present area understand the description of above groups, wherein any group containing two or more groups between two groups, for example, in group

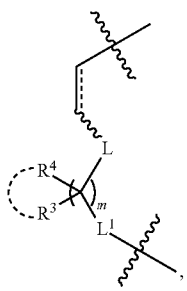

L is between two groups, when L is "methoxycarbonyl", the "methoxycarbonyl" has two ways to connect the cyclic ring, which has either methoxycarbony or carbonyl methoxyl group as the following structure:

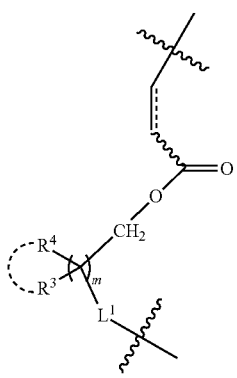

In the following part, the preparation methods of the related compounds in the invention were described:

The critical innovative point in the invention was first to synthesize several novel heterocyclic building blocks, from which heterocyclic intermediates IIIa-IIIb were synthesized. Therefore, the macrocyclic compounds IIa-IIb were obtained through three step's synthesis from IIIa-IIIb, followed by the amidation to prepare compounds Ia-Ib.

The schemes, methods and reaction conditions involved in the preparation of the new compounds in the present invention, were conducted by the regular processes used in this synthetic field. According to the following preparative methods disclosed in the invention, chemists in this field can synthesize each designed formula compound by using the same principle or method presented in the invention.

The preferred preparative methods used in the present invention were described as follows:

Scheme 1:

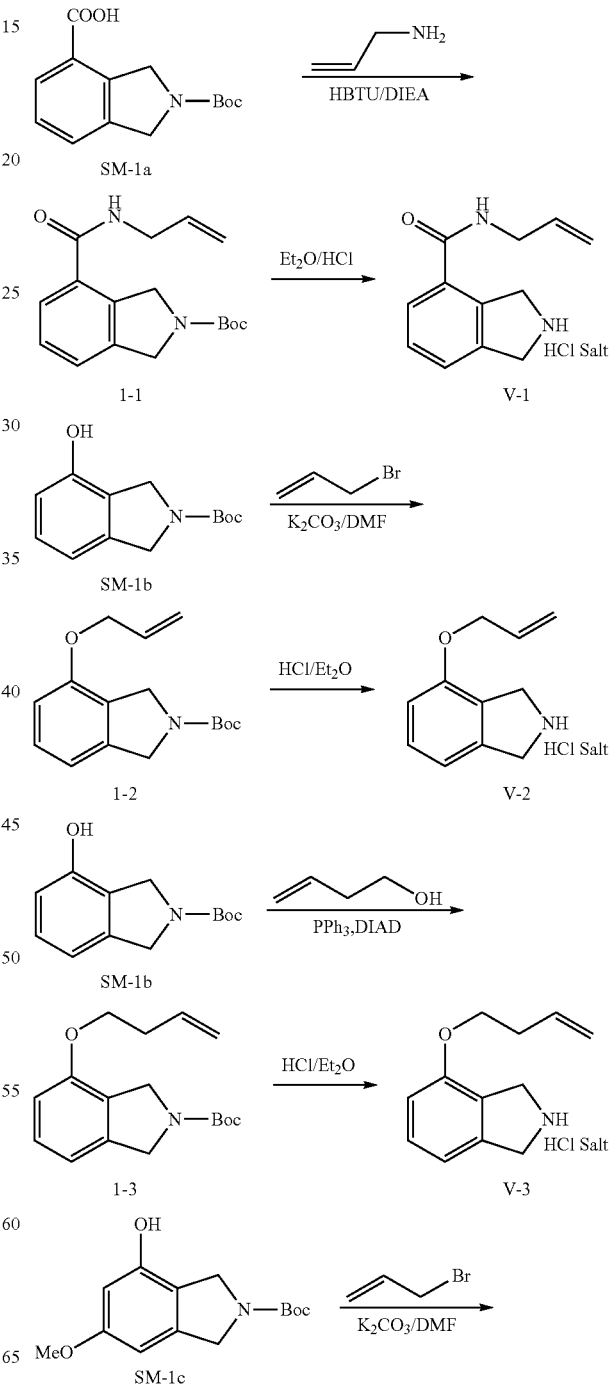

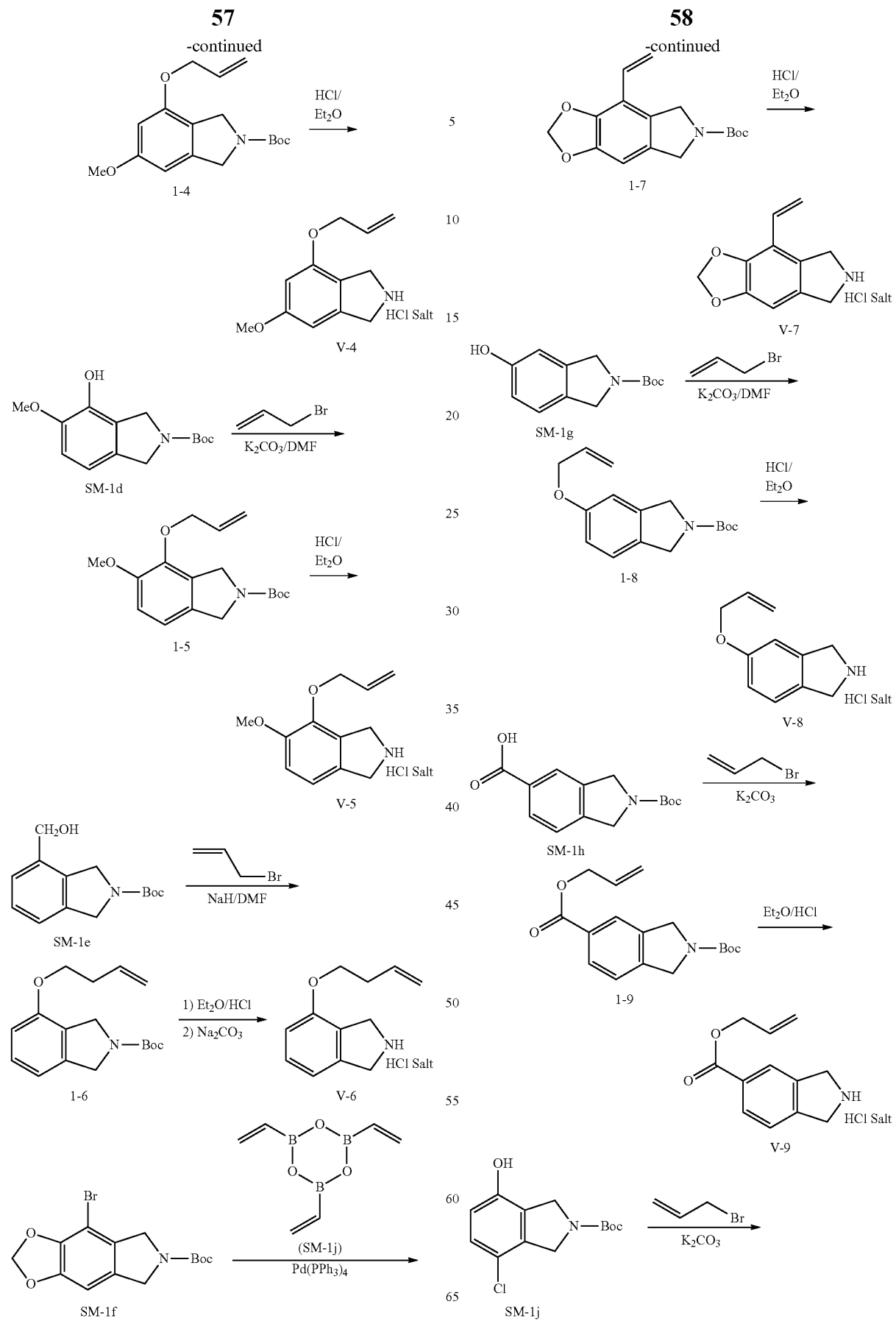

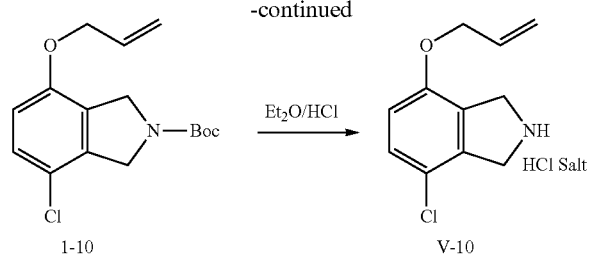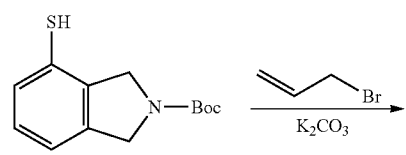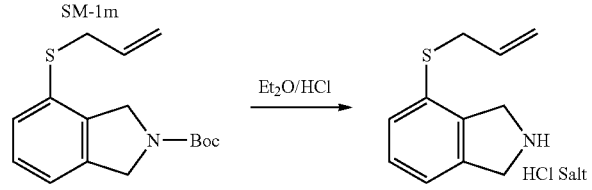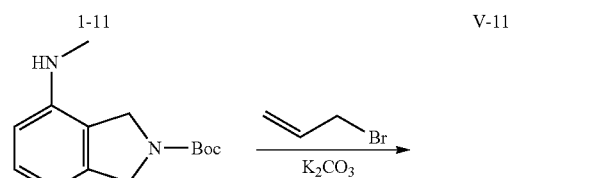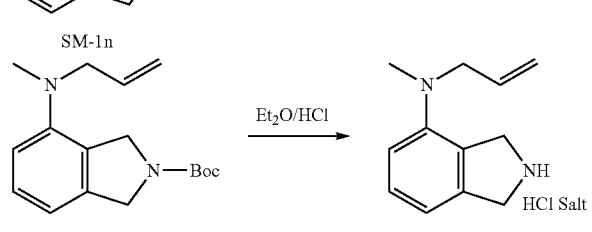
Structural FIG. 2:
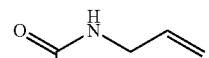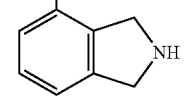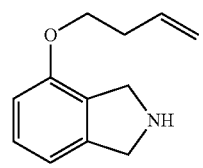
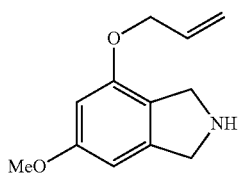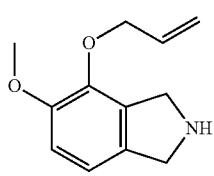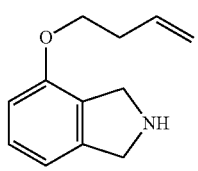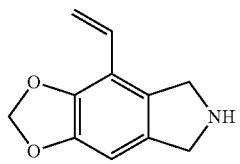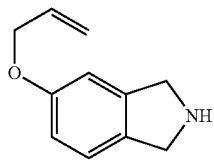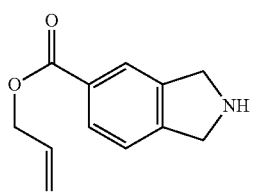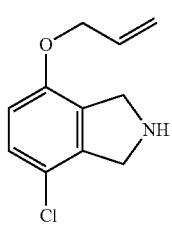

-continued

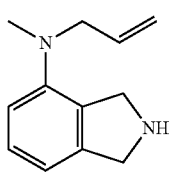

V-12

In scheme 1 described above, the starting materials SM-1a, SM-1b, SM-1c, SM-1d, SM-1e, SM-1f, SM-1g, SM-1h, SM-1j, SM-1m, SM-1n were reacted in the organic solvents (methanol, THF, N,N-dimethylformamide or dimethyl sulfoxide) respectively, of which SM-1a is reacted with $CH_2=CHCH_2NH_2$ to form 1-1 using the coupling reagent HBTU; or SM-1b, SM-1c, SM-1d, SM-1e, SM-1g, SM-1 h, SM-1j, SM-1m, SM-1n were reacted with $CH_2=CHCH_2Br$ respectively to form 1-1, 1-2, 1-3, 1-4, 1-5, 1-6, 1-8, 1-9, 1-10, 1-11 or 1-12 in the treatment of the inorganic bases (such as sodium hydroxide, sodium methoxide or sodium hydride); or SM-1f is reacted with the ethylene borate reagent SM-1j to form 1-7 using palladium catalyst; Subsequently, the obtained products 1-1 to 1-9 were subjected to hydrogenation to cleave the protecting group (Bn) or treated with strong acid (HCl, TFA) as shown in scheme 1 to cleave the protecting group Boc to furnish the key products V-1, V-2, V-3, V-4, V-5, V-6, V-7, V-8, V-9, V-10, V-11 or V-12 shown in structural figure 2.

Scheme 2:

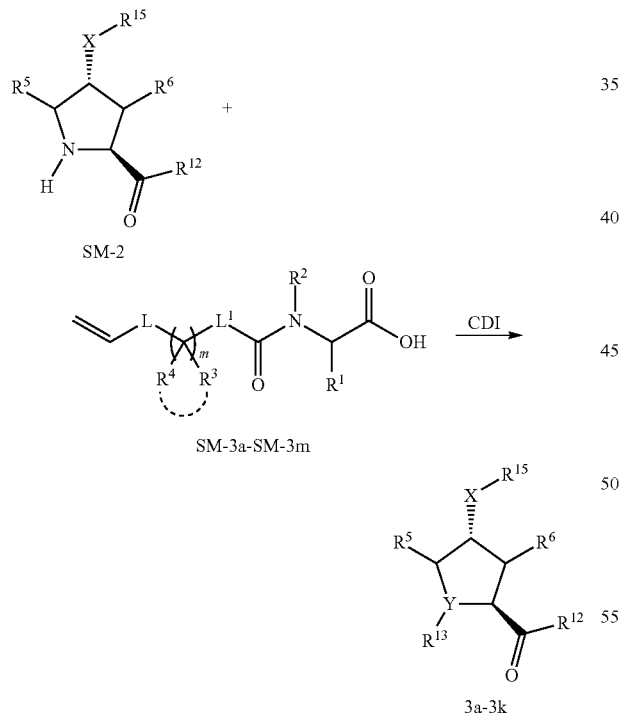

In Scheme 2 shown above, SM-2 is first coupled with SM-3a, SM-3b, SM-3c, SM-3d, SM-3e, SM-3f, SM-3g, SM-3h, SM-3h, SM-3k, SM-3m through amidation in the treatment of CDI or EDCI in organic solvent (dichloromethane, tetrahydrofuran or N,N-dimethylformamide) to give the intermediates 3a, 3b, 3c, 3d, 3e, 3f, 3g, 3h, 3j, 3k, 3m, which is used for the next reaction:

In the product 3a-3m, the definition of m, L, $L^1$ and $R^{13}$ group is the same as that of L, $L^1$ and $R^{13}$ group described above, $R^{15}$ is selected from hydrogen, $C_1$-$C_{15}$ alkylcarbonyl, $C_1$-$C_{15}$ alkoxycarbonyl or $C_1$-$C_{15}$ alkyl aminocarbonyl group; wherein, the amino acid derivative reagents SM-3a-SM-3m ($R^{13}$—OH) were each selected from structural figure 3 shown as below:

Structural FIG. 3:

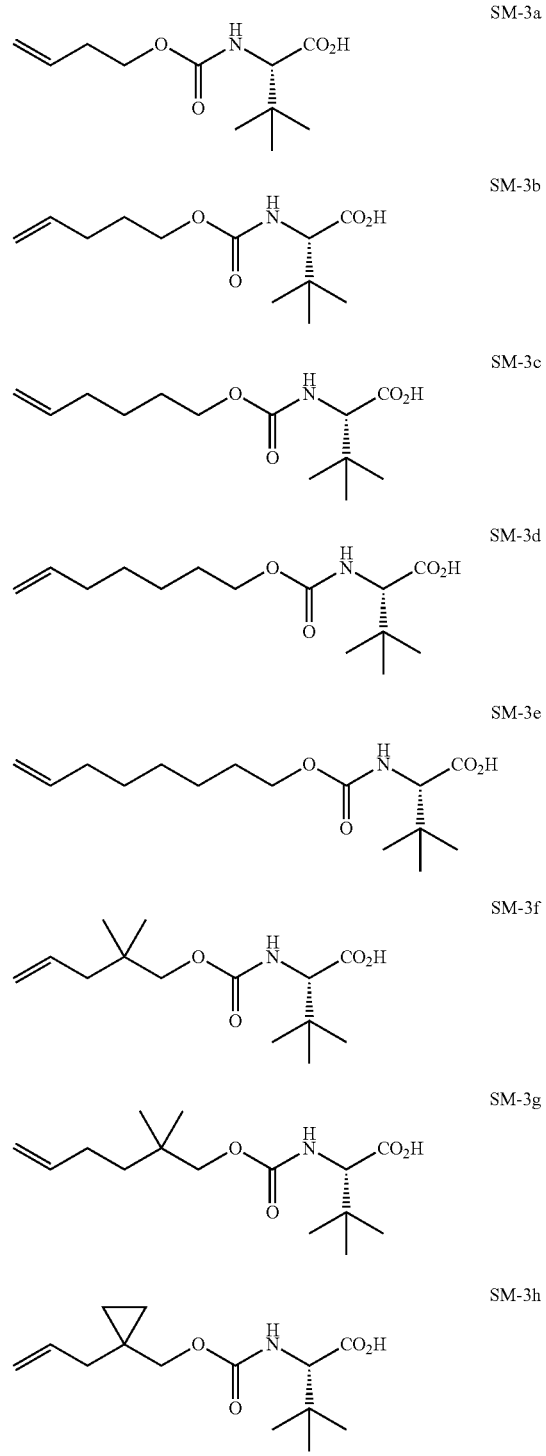

63

-continued

SM-3j

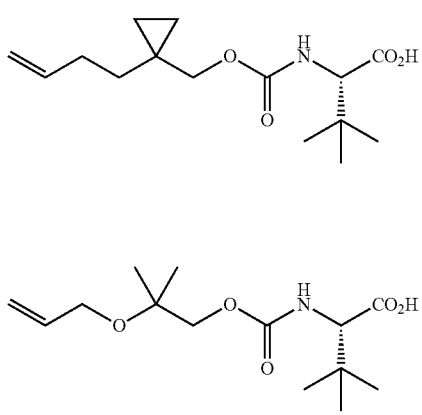

SM-3k

SM-3m

Scheme 3:

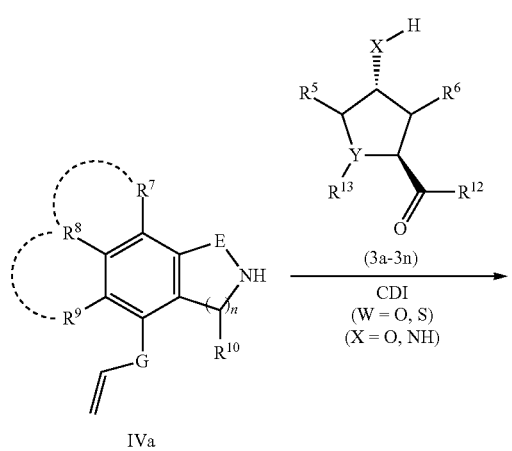

IVa

IIIa

64

-continued

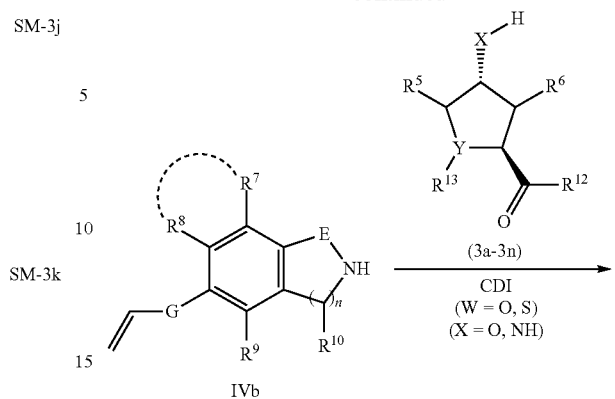

IVb (3a-3n)
CDI
(W = O, S)
(X = O, NH)

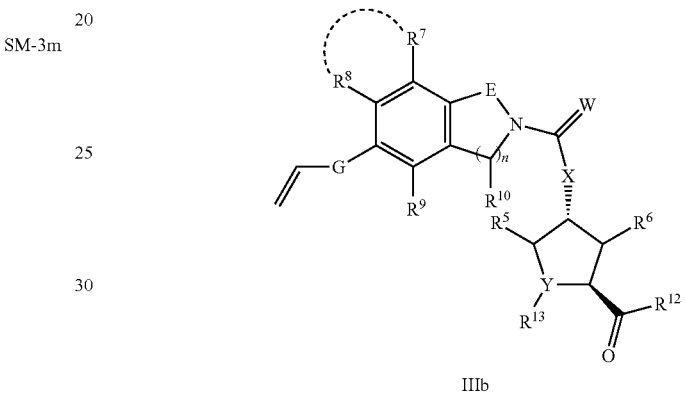

IIIb

Wherein, $R^{13}$ shown above is the same as the definition of $R^{13}$ in claims 11-15 of the invention, n=1 or 2. Scheme 3 shown above gives the example of the preparation of the new compounds IIIa-IIIb with novel structures and properties, in which the intermediates IVa-Ivb (V-1 to V-12) together with SM-3a-SM-3m were coupled with the products (3a-3m) from Scheme 2 respectively through an amidation reaction using CDI or EDCI in the organic solvents (dichloromethane, tetrahydrofuran or N,N-dimethylformamide), leading to the compounds IIIa-IIIb (4a-4n) with different kinds of heterocycles as shown in Structural Figure 4 in the invention.

Structural FIG. 4:

4a

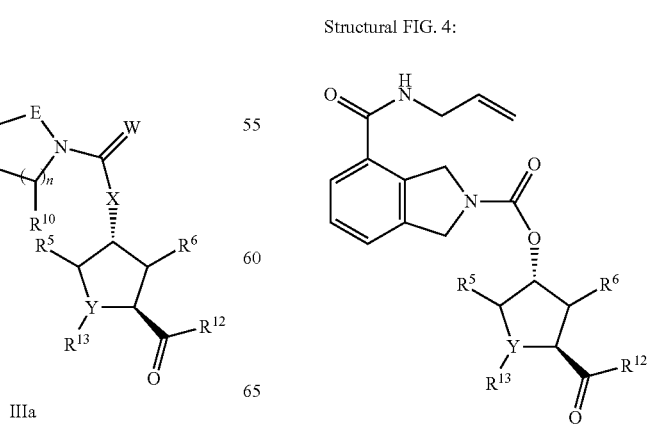

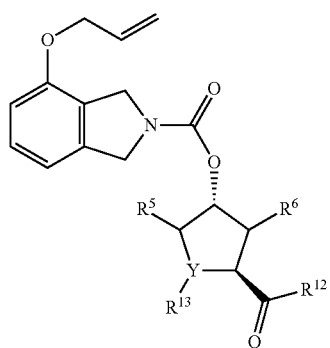 4b
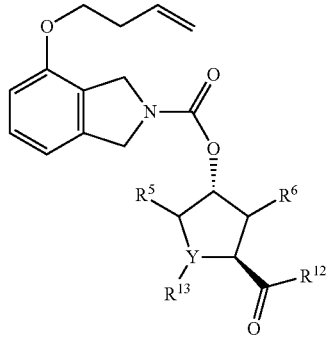 4f
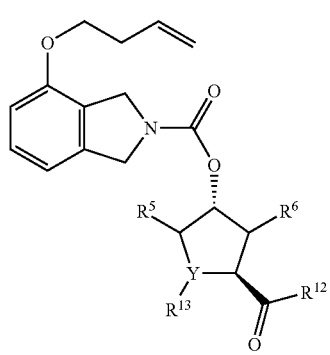 4c
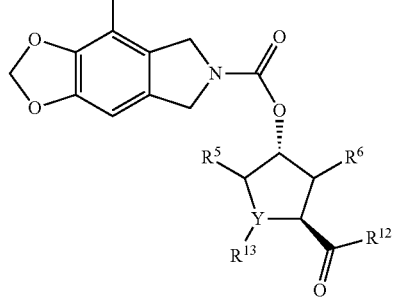 4g
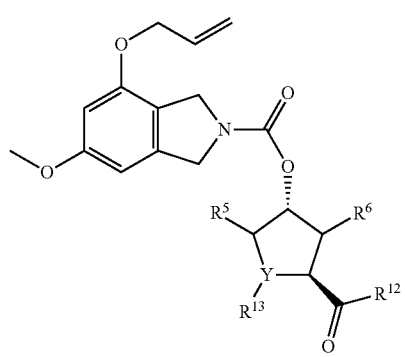 4d
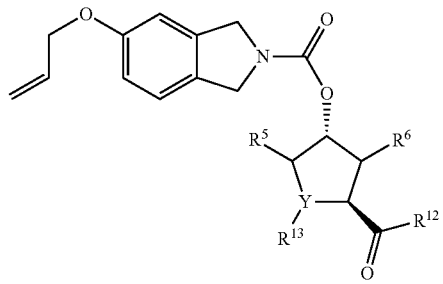 4h
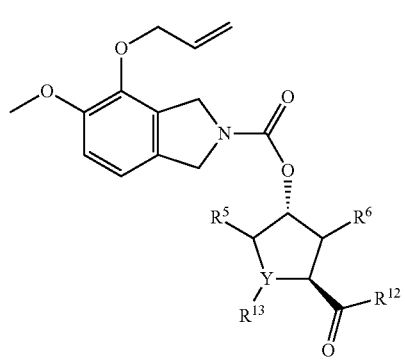 4e
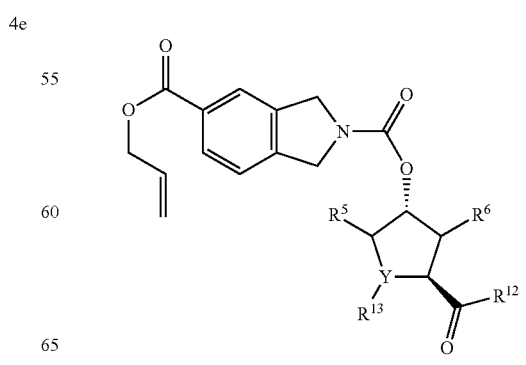 4j

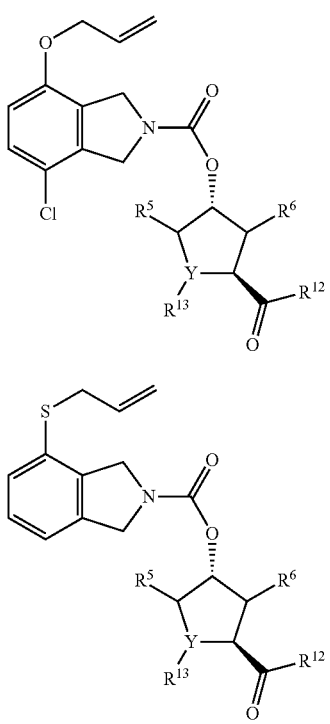

4k

4m

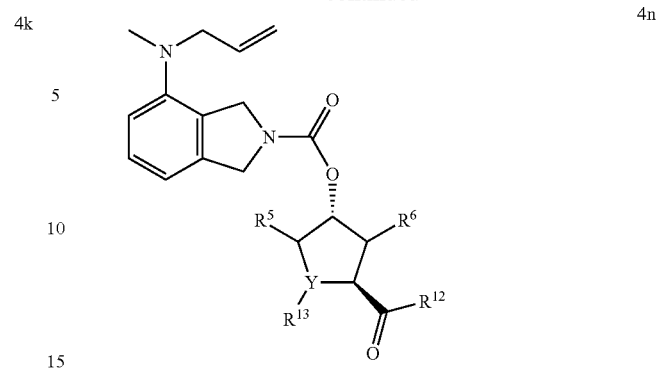

4n

Wherein, $R^{13}$ shown above is selected from H, Boc or amino acid derivative $R^{13}$—OH in Structural Figure 3.

In order to optimize a feasible synthetic method, when "Y" in IIIa-IIIb is the nitrogen atom, we use another synthetic way shown in Scheme 4a and 4b in the invention to synthesize compounds IIIa-IIIb. Therefore, IVa, IVb and SM-4 were first subjected to the coupling reaction respectively using CDI, followed by the cleavage of the protecting group Boc under the acidic treatment (HCl or TFA), to furnish the intermediates 4-A and 4-B (4ba-4bj) respectively. The obtained intermediates 4-A and 4-B were again subjected to an coupling amidation reaction respectively using CDI or EDCI in the organic solvents (dichloromethane, tetrahydrofuran or N,N-dimethyl formamide) to offer compounds IIIa-IIIb (4a-4n) with different kinds of heterocycles as shown in Structural Figure 4 in the invention.

Scheme 4a:

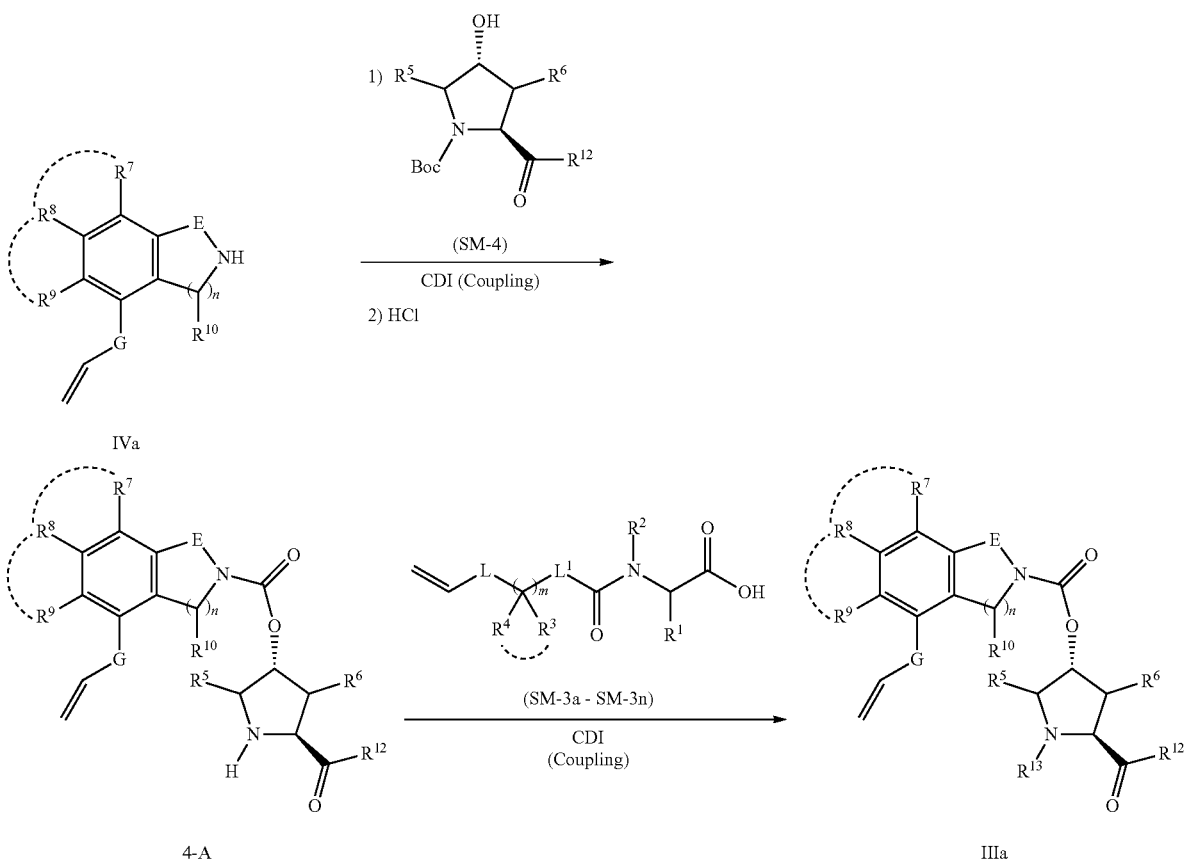

Scheme 4b:
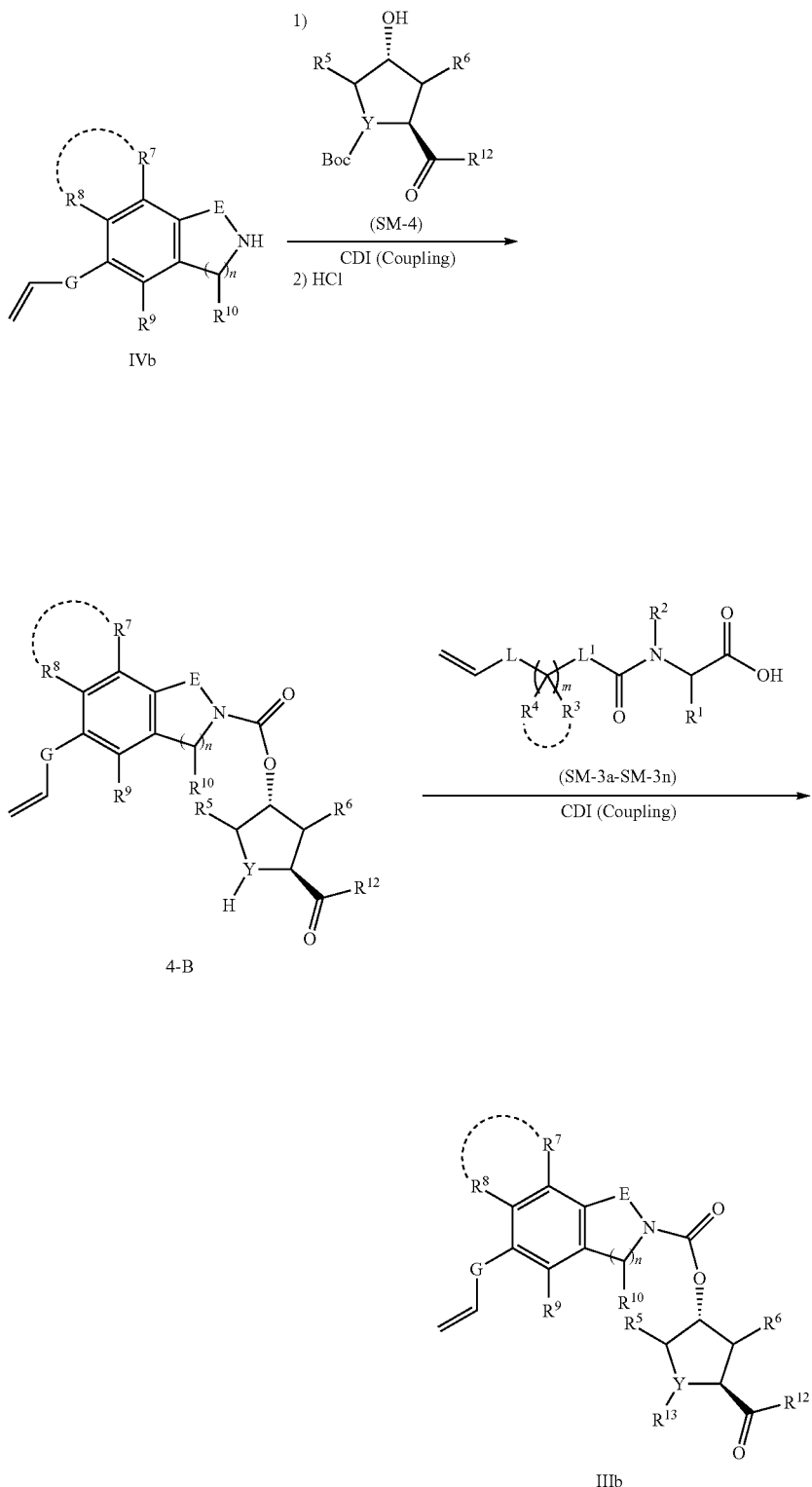
Wherein, $R^{13}$ group is each selected from the amino acid derivatives $R^{13}$—OH in Structural Figure 3. According to Scheme 4a and 4b shown above, Compounds V (V-1-V-10) were reacted with the reagents SM-4a ($R^5$, $R^6$=H; $R^{12}$=OMe) to prepare a varieties of heterocyclic intermediates 4A-4B (4aa-4an and 4ba-4bn), which were shown in Structural Figures 5a and 5b as follows:

Structural FIG. 5a:
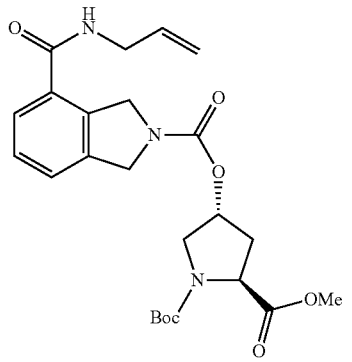
4aa
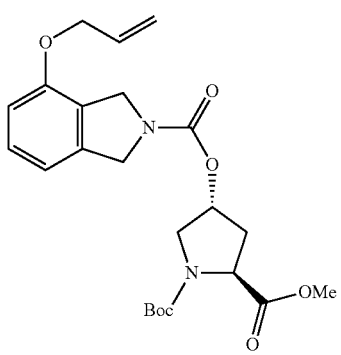
4ab
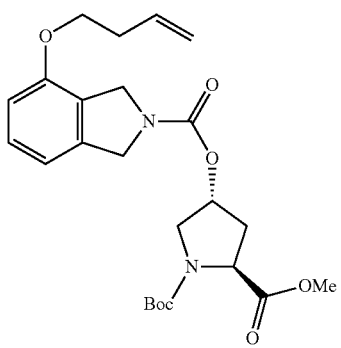
4ac
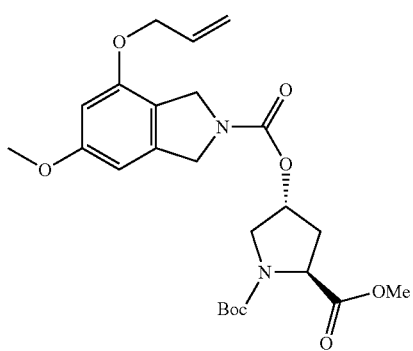
4ad
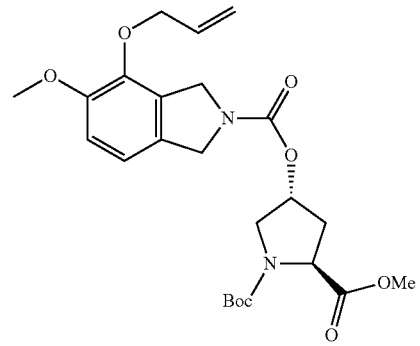
4ae
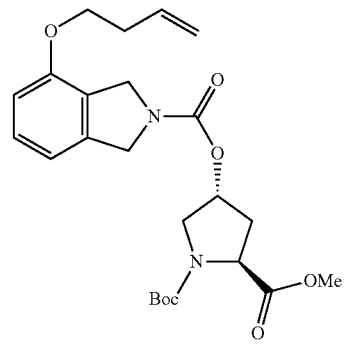
4af
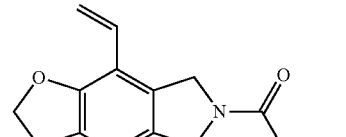
4ag
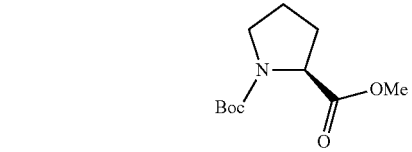
4ah
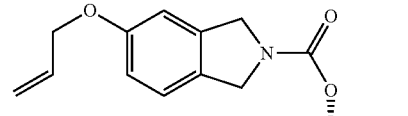
4aj

| | |
|---|---|
| 4ak 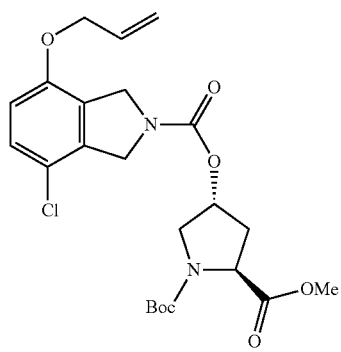 | 4bb 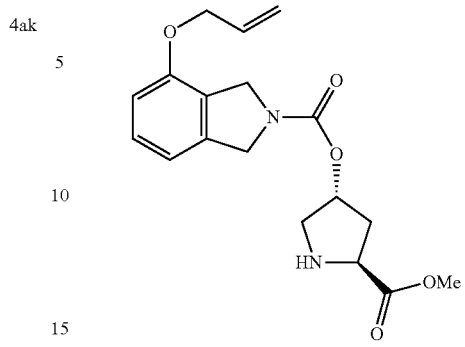 |
| 4am 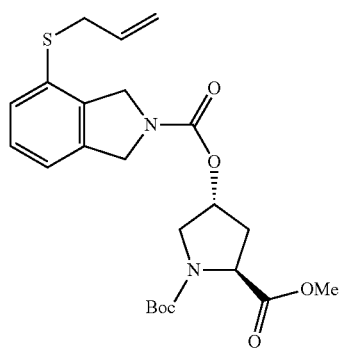 | 4bc 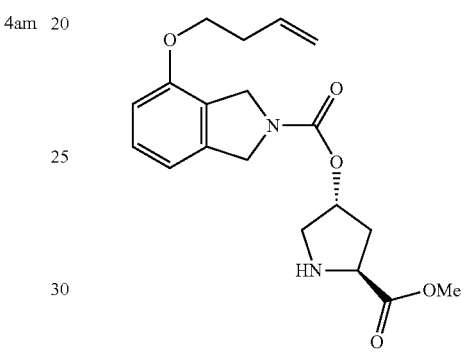 |
| 4an 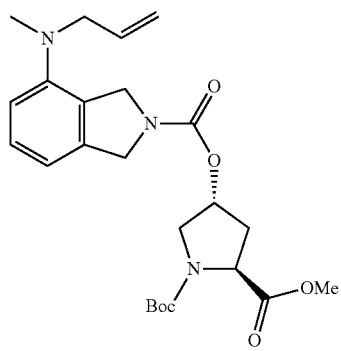 | 4bd 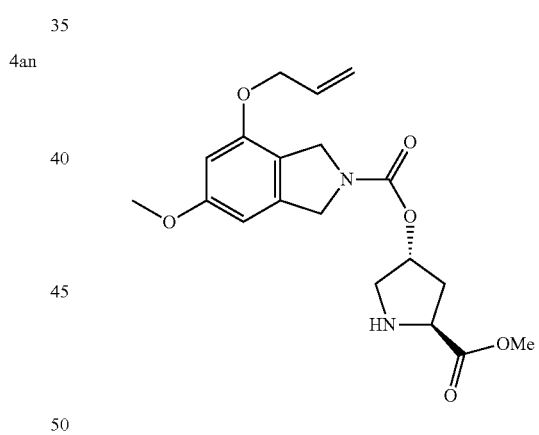 |
Structural FIG. 5b:
| | |
|---|---|
| 4ba 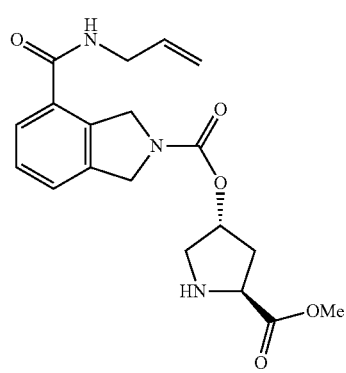 | 4be 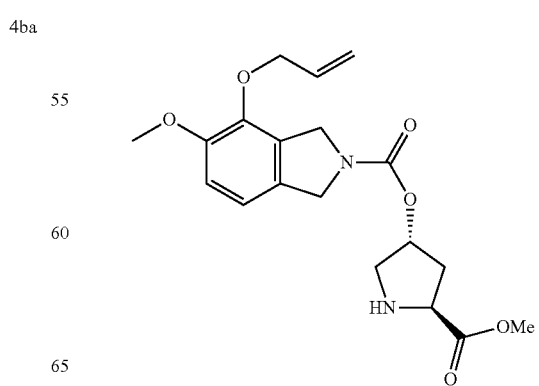 |

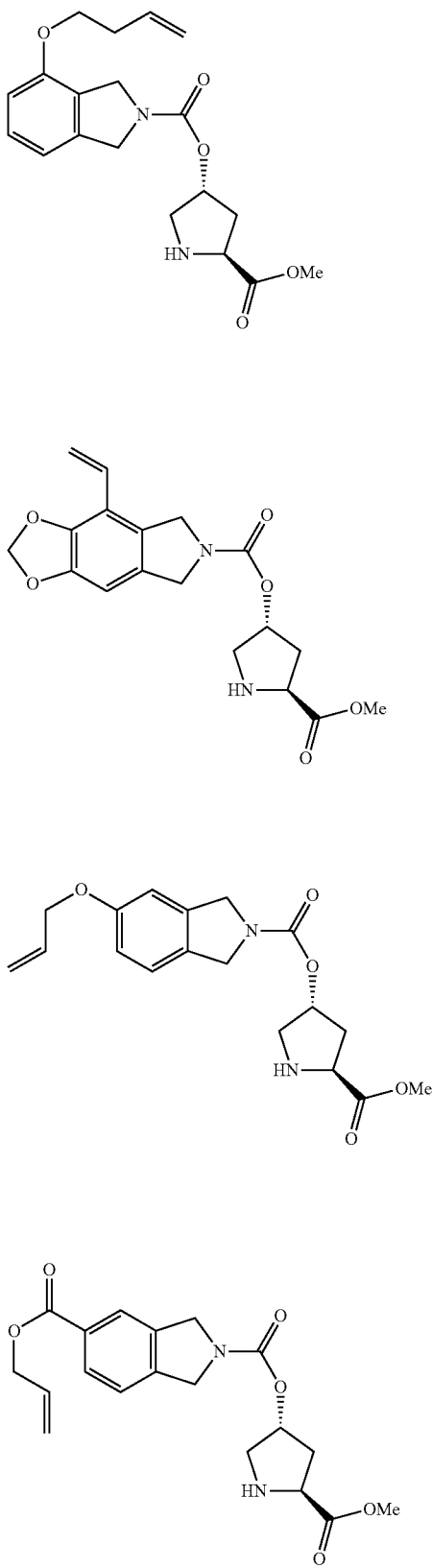

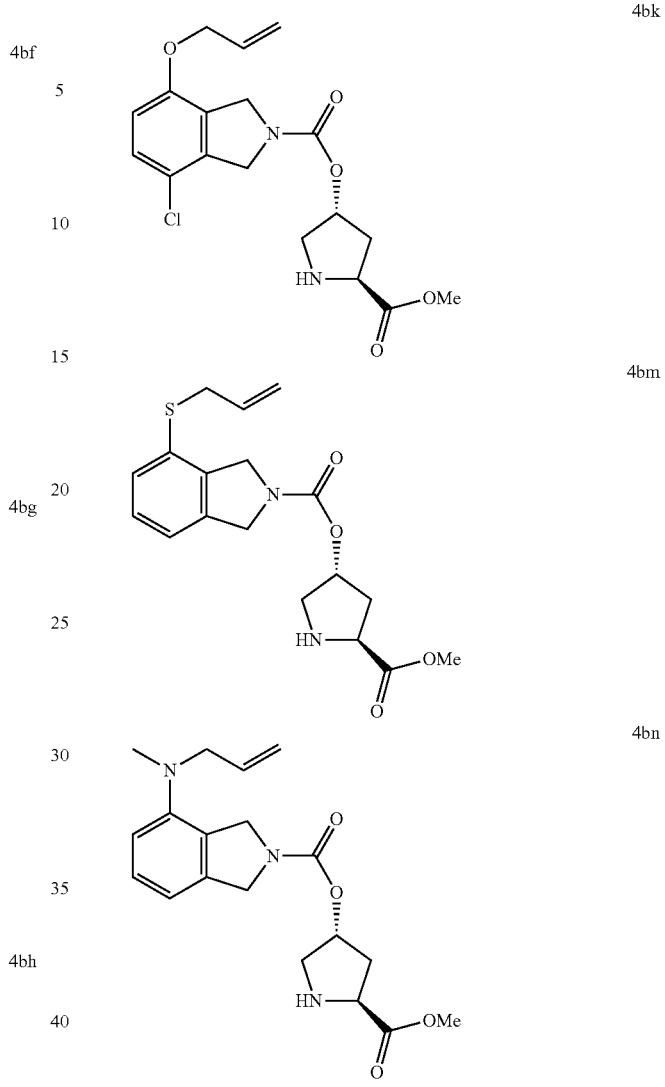

After the key heterocyclic compounds IIIa-IIIb (i.e., 3a-3m) in the invention were synthesized according to Scheme 1-4 shown above, the following synthetic schemes (Scheme 5a-5d) were designed for the purpose of structural and functional optimization and innovation. Therefore, the diene compounds (IIIa or IIIb) obtained from Scheme 4a-4b were conducted for the Ring Closure Metathesis reaction (RCM, 0-100) respectively by using RCM catalysts (such as 0.1-5% mol of Zhan catalyst or Grubbs catalyst, etc) in anhydrous organic solvents (such as dichloromethane, dichloroethane or toluene) to afford the 17-25 membered cyclic olefin products 6a-6b (IIa-IIb). The hydrogenation of the olefin bond in 6a-6b (IIa-IIb) with Pd/C catalyst offered the products 7a-7b, which were subsequently hydrolysed or methanolized with base (LiOH) followed by acidation to offer the macro-heterocyclic compounds 8a-8b. In the end, the obtained compounds 8a-8b were reacted with various amino acid derivatives SM-5 by amidation with their amino groups in the presence of the coupling reagents (i.e., EDCI or HATU) at 0-80 to offer the final novel macro-heterocyclic compounds Ia-Ib (such as compounds 10a-10b). The details of reaction procedure and structural characterization for each compound were shown in the experimental examples, respectively.

Scheme 5a:
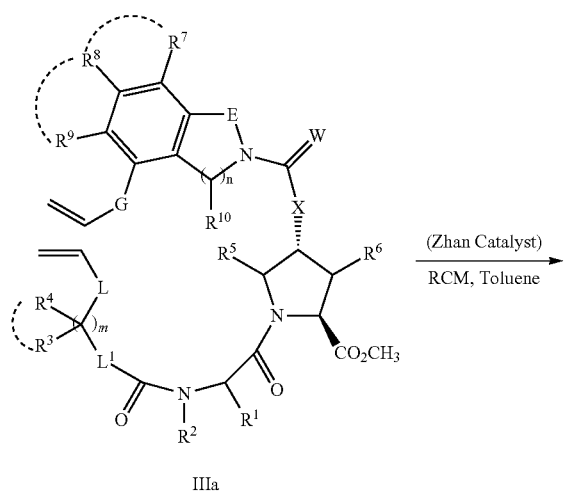
IIIa
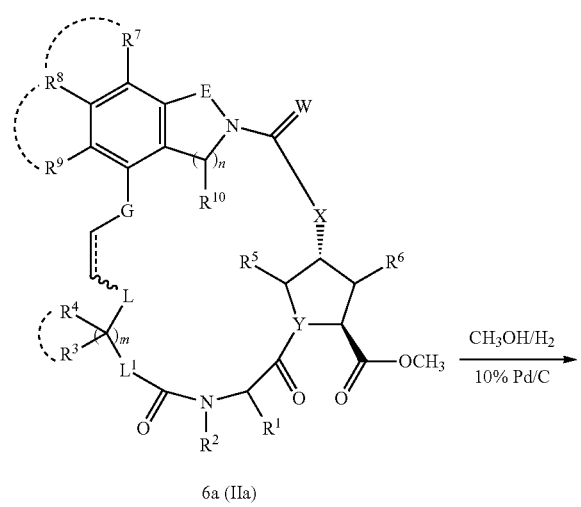
6a (IIa)
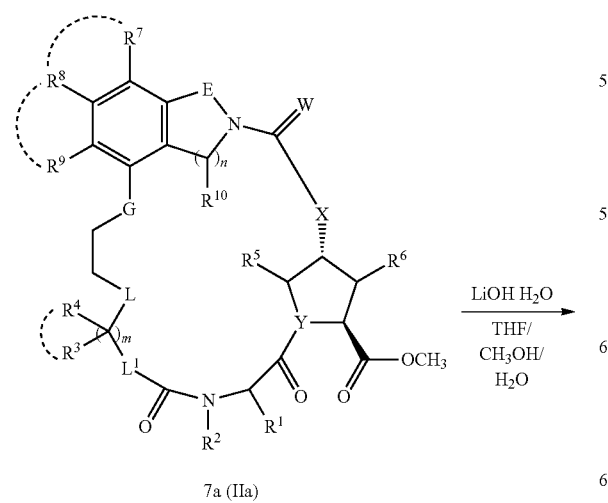
7a (IIa)
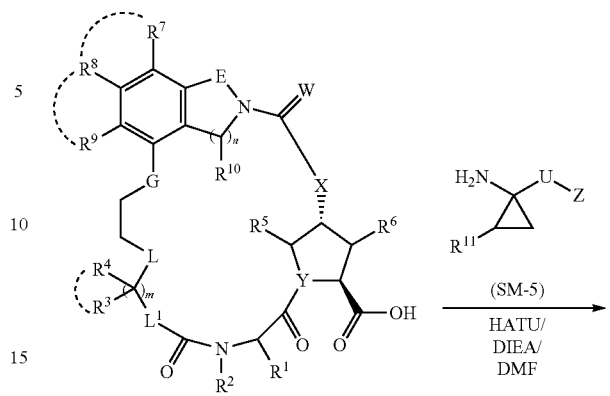
8a (IIa)
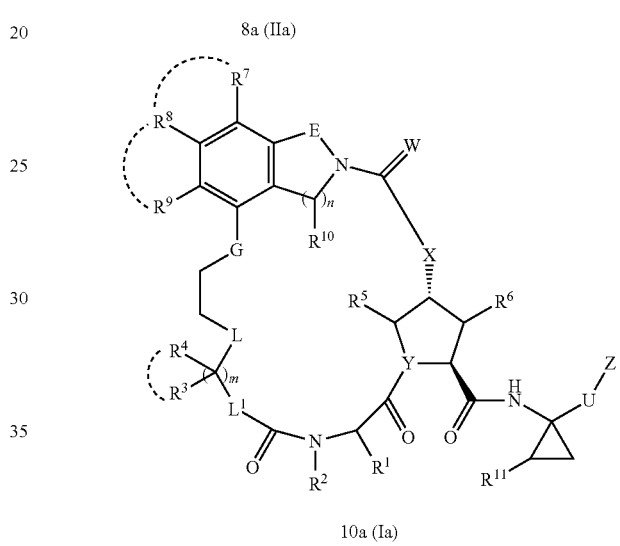
10a (Ia)
Scheme 5b:
6a (IIa) $\xrightarrow[\text{THF/CH}_3\text{OH/H}_2\text{O}]{\text{LiOH H}_2\text{O}}$ $\xrightarrow[\text{HATU/DIEA/DMF}]{\text{(SM-5)}}$
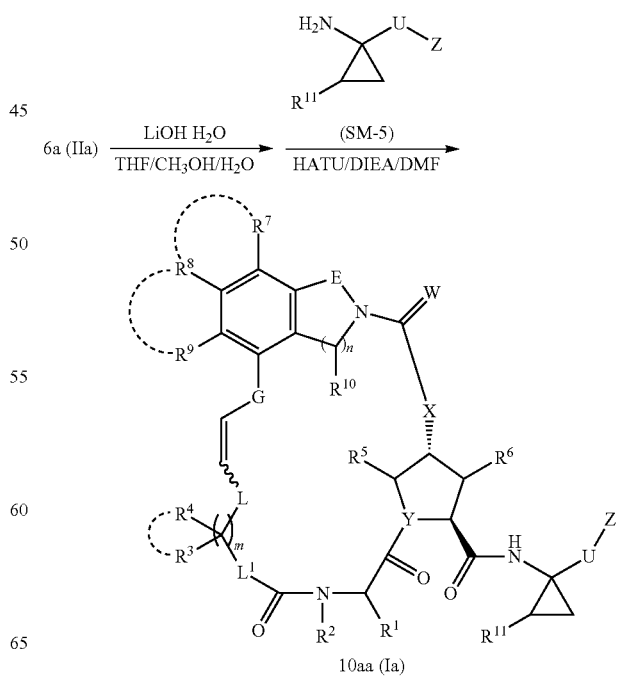
10aa (Ia)

Scheme 5c:
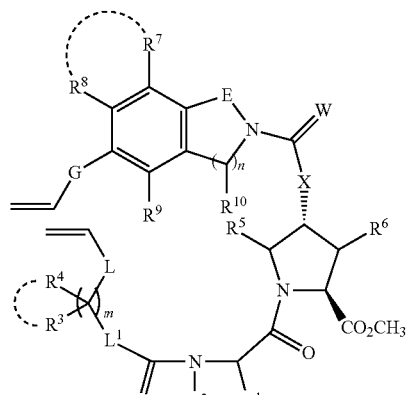
IIIb
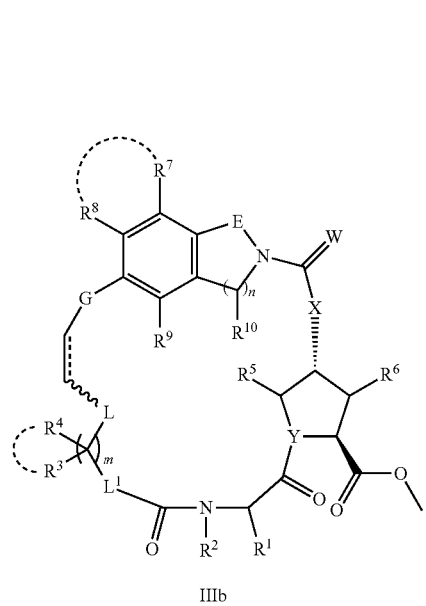
IIIb
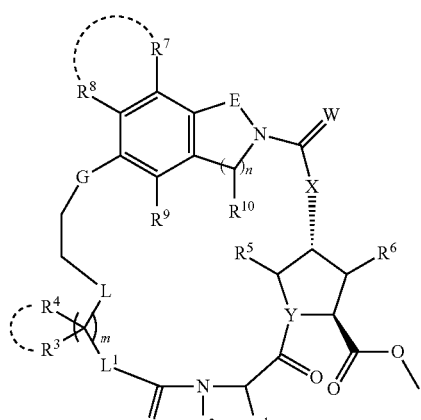
7b (IIb)
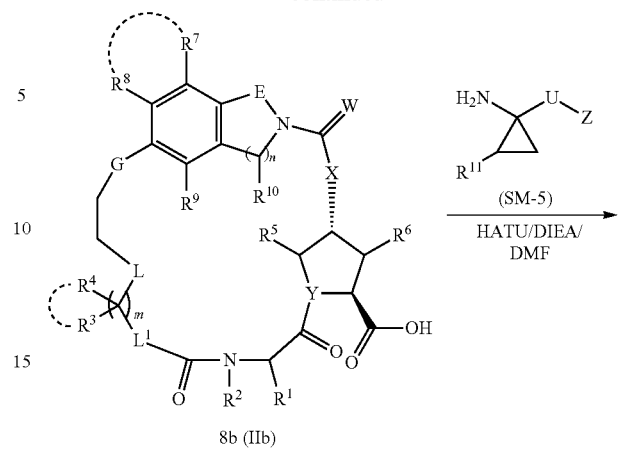
8b (IIb)
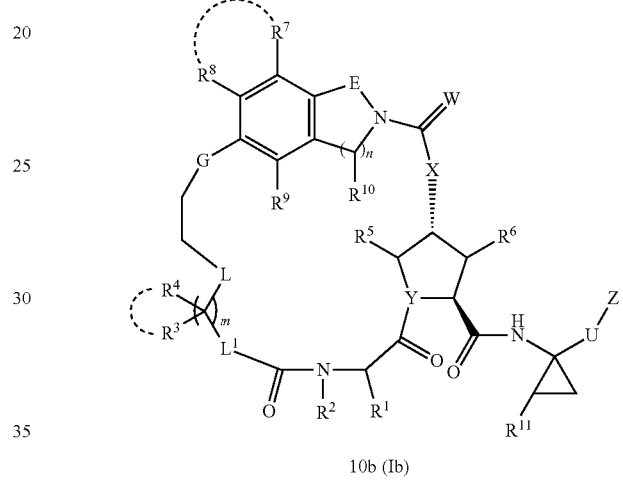
10b (Ib)
Scheme 5d:
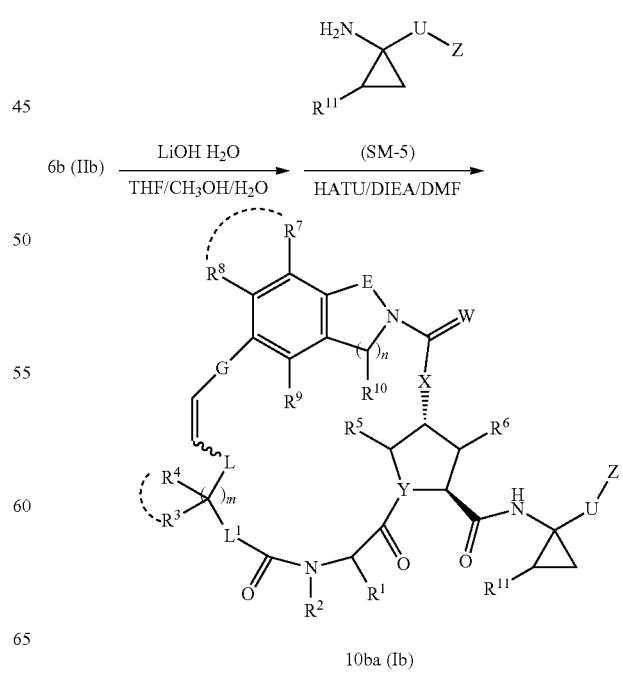
10ba (Ib)

In Scheme 5a-5d, the desired amino acid derivatives SM-5 were optimally selected from Structural Figure 6 (i.e., SM-5a, SM-5b) as below:

Structural FIG. 6

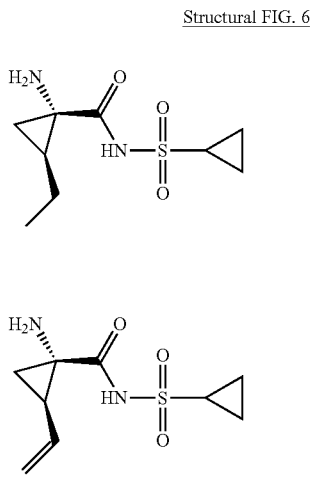

Other than the synthetic scheme described above, in the following synthetic way as shown in Scheme 6a in the invention, compound 4bb (V) is reacted with SM-3j through the amidation reaction in the presence of CDI or EDCI in the organic solvents (dichloromethane, tetrahydrofuran or N,N-dimethylformamide) to give the diene compound IIa (IIIa), which is then subjected to ring closure metathesis (RCM, 0-100) using RCM catalyst (such as 0.1-10% mol of Zhan catalyst or Grubbs catalyst, etc) in anhydrous organic solvents (such as dichloromethane, dichloroethane or toluene) to afford the macro-heterocyclic compounds 12a (IIa). Hydrogenation of the olefin bond in macrocycle of 12a gives compound 13a, which was subsequently hydrolysed or methanolized with base (LiOH) followed by acidation to give the macrocyclic compound 14a. In the end, the obtained compound 14a were reacted with various amino acid derivatives SM-5a through amidation in the presence of the coupling reagents (i.e., EDCI or HATU) at 0-80 to furnish the final novel macro-heterocyclic compound 15a (Ia). In Scheme 6b, the obtained intermediate 12a from Scheme 6a is directly subjected to hydrolization with base (LiOH) followed by acidation to afford compound 14b, neglecting the hydrogenation forementioned. Subsequently, the obtained compound 14b were reacted with various amino acid derivatives SM-5a and SM-5b respectively through amidation in the presence of the coupling reagents (i.e., EDCI or HATU) at 0-80 to furnish the final novel macro-heterocyclic compound 15b and 15c. The details of reaction procedure and structural characterization for each compound (such as 15a-15cd in Structural Figure 9) were shown in the experimental examples, respectively.

Scheme 6a:

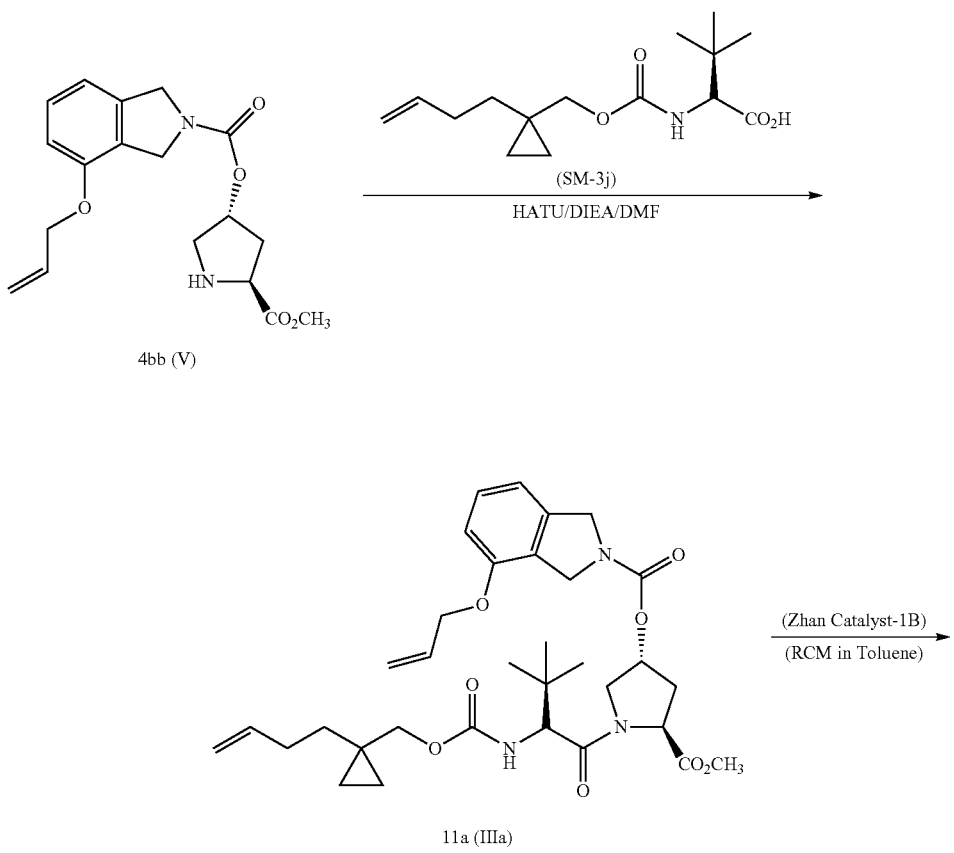

-continued
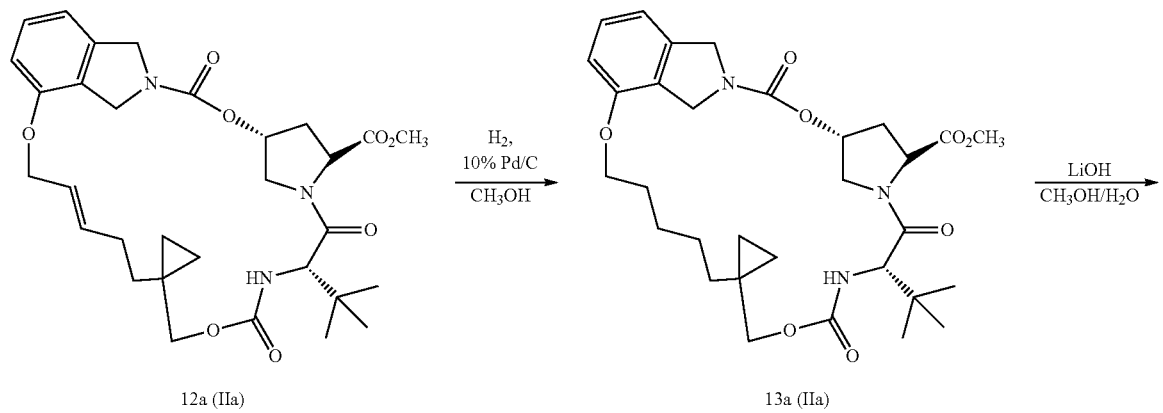
12a (IIa) → 13a (IIa)
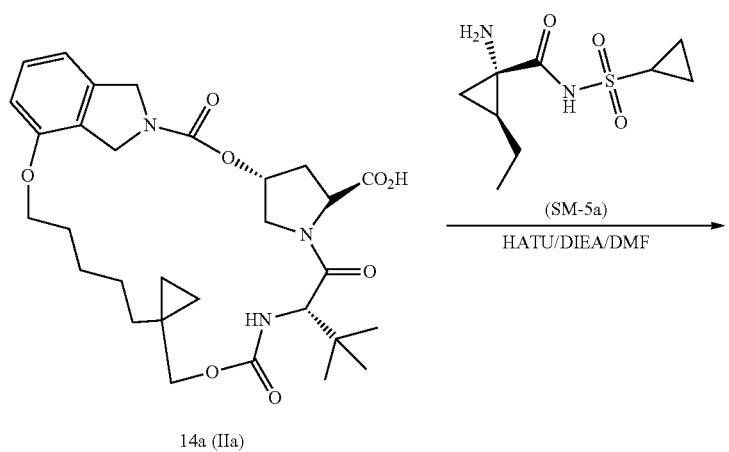
14a (IIa)
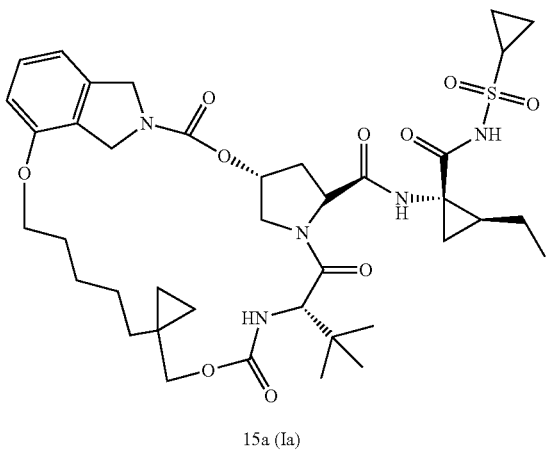
15a (Ia)

Scheme 6b:
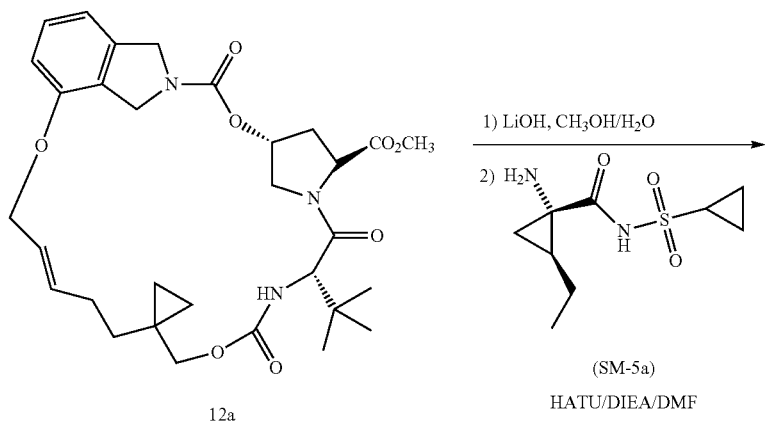
12a
(SM-5a)
HATU/DIEA/DMF
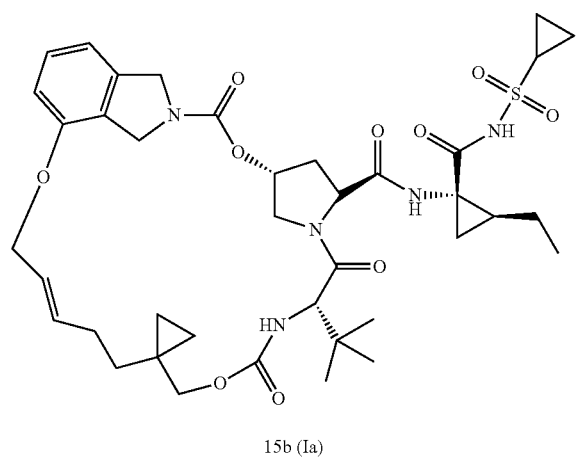
15b (Ia)
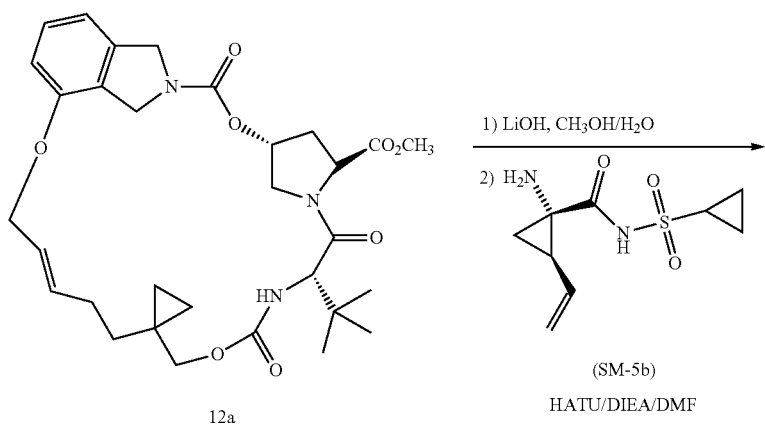
12a
(SM-5b)
HATU/DIEA/DMF

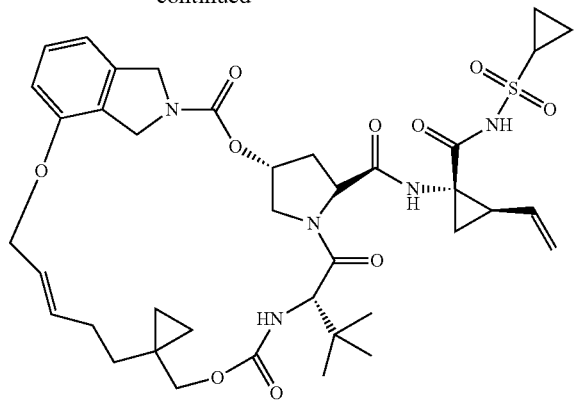

15c (Ia)

Zhan Catalyst-1B used in Ring Closure Metathesis of diene intermediates IIIa-IIIb in Scheme 6 is shown as below:

Structural FIG. 7

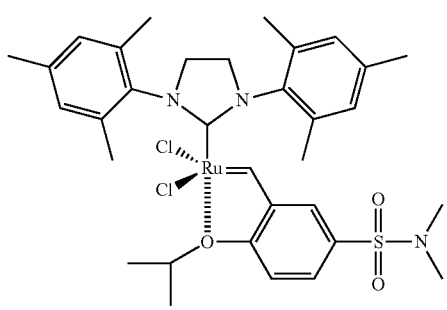

Zhan Catalyst-1B, the patented product of Zannan; Catalogue No. RC-303

Above all, a varieties of macro-heterocyclic based intermediates IIa-IIb and final compounds Ia-Ib which contain different new functional groups were synthesized through multi-steps' reaction shown in Scheme 5 and 6. In Structural Figures 8 and 9, is shown the structure of the novel macro-heterocyclic intermediates IIa-IIb and the final compounds Ia-Ib, which correspond to Formula 12a-14 am (IIa-IIb) in Structural Figure 8 and Formula 15a-15cd (Ia-Ib) in Structural Figure 9:

Structural FIG. 8:

12ak

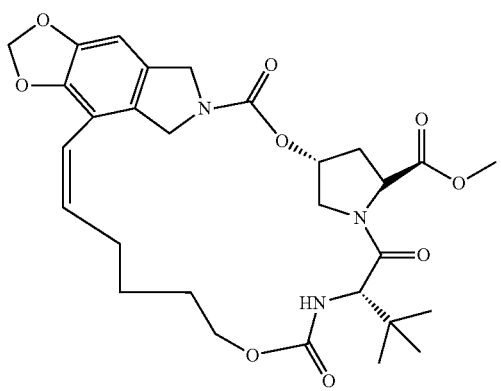

12am

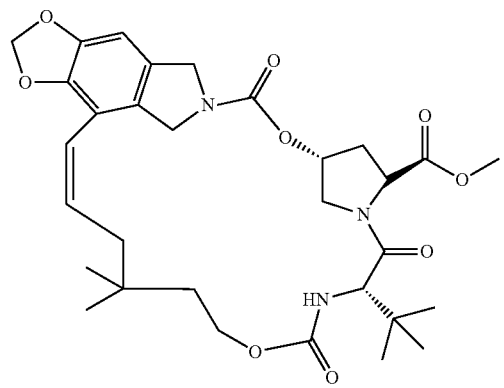

13ak

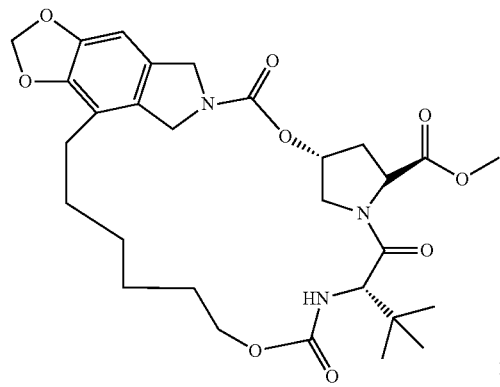

13am

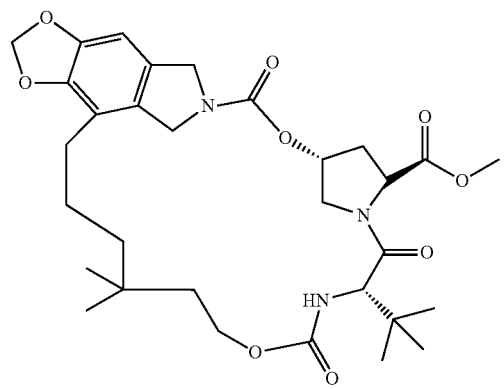

89
-continued
12a
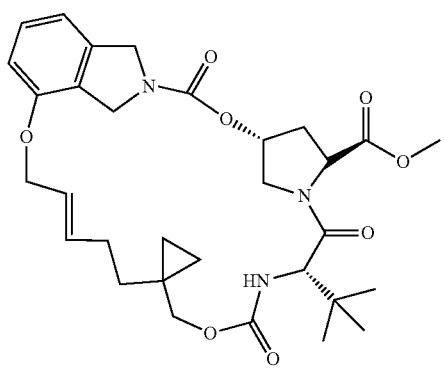
13a
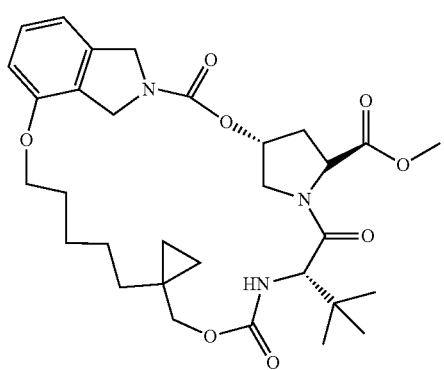
12b
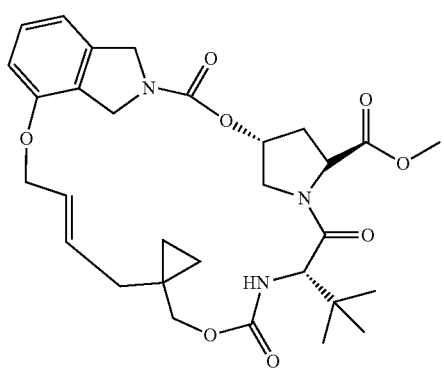
13b
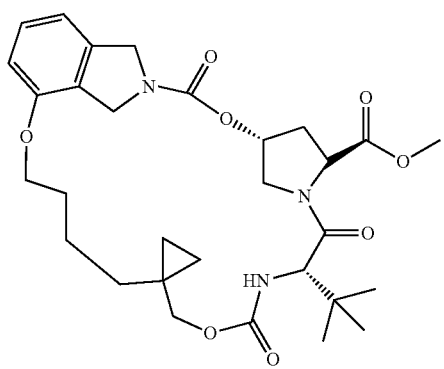
90
-continued
12c
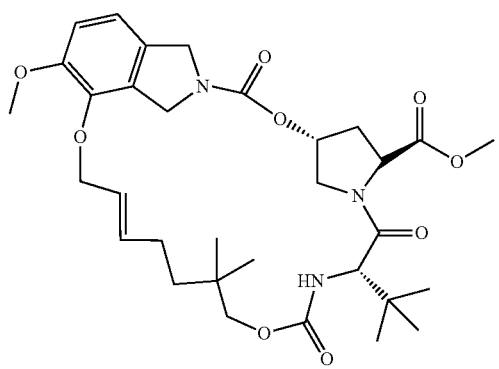
12d
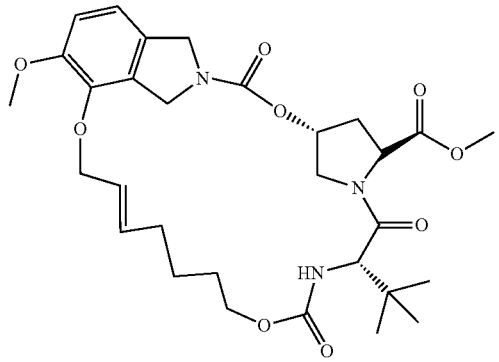
12e
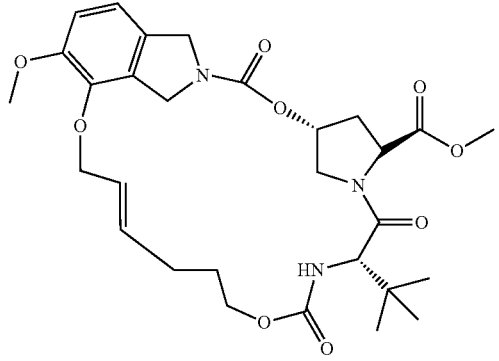
12f
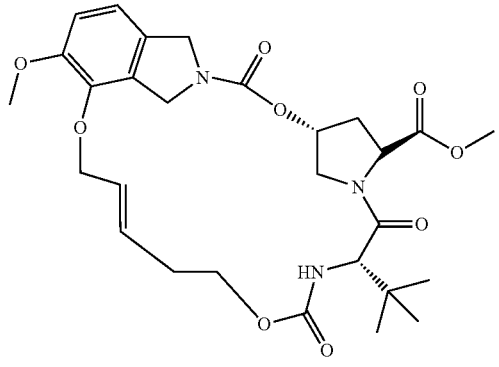

12g
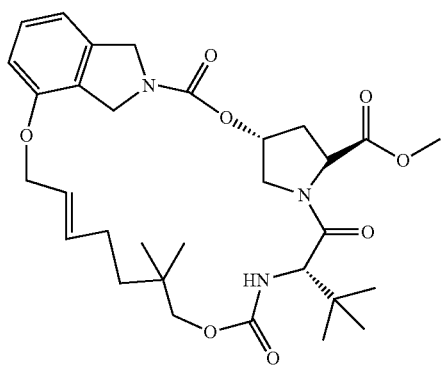
13g
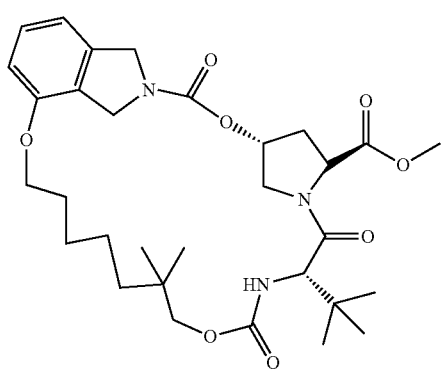
12h
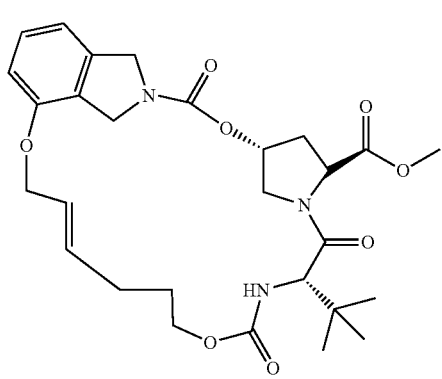
13k
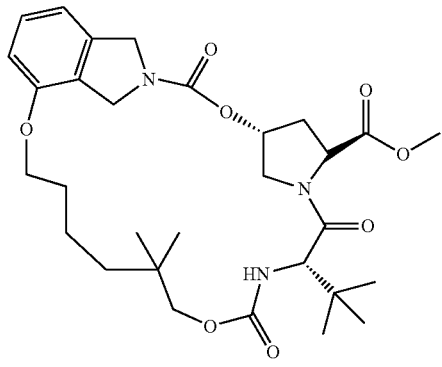
13m
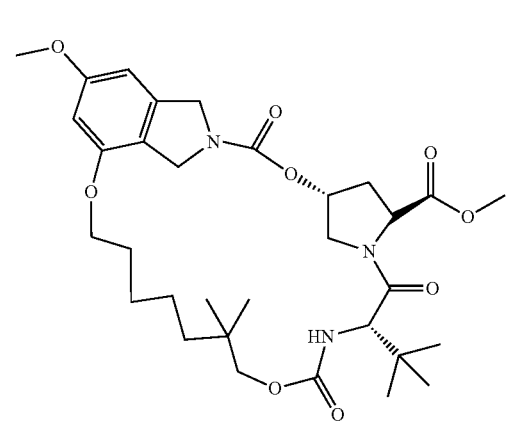
13h
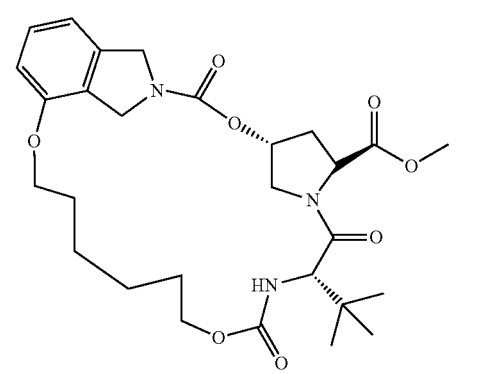
13n
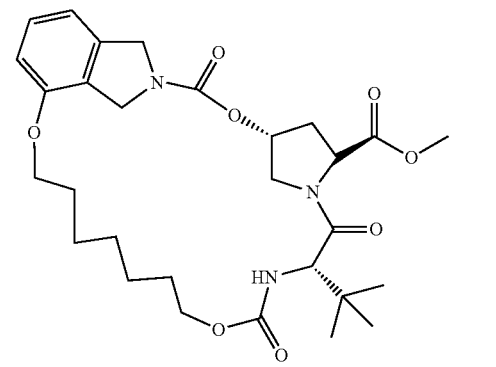
13p
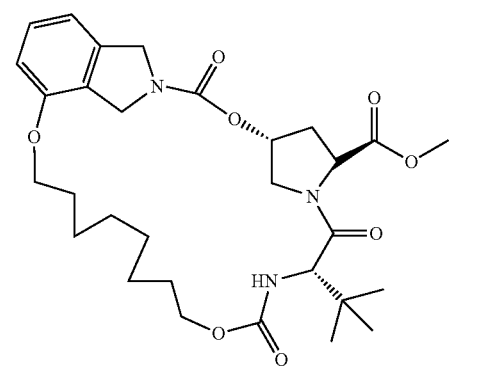

93
-continued
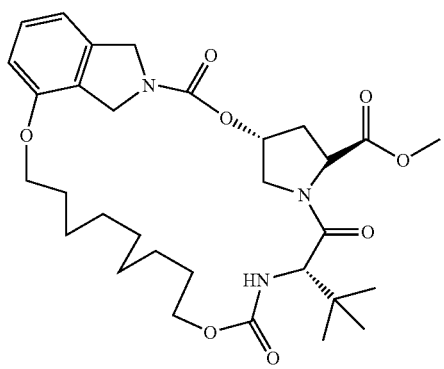
13q
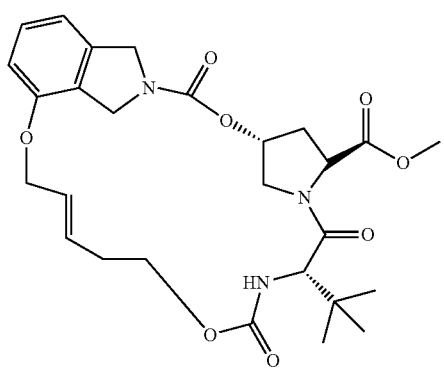
12r
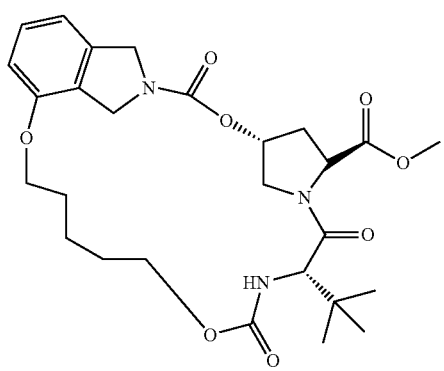
13r
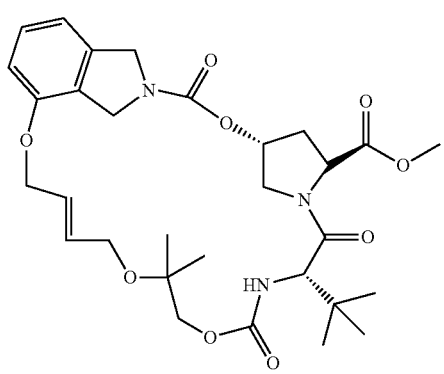
12s
94
-continued
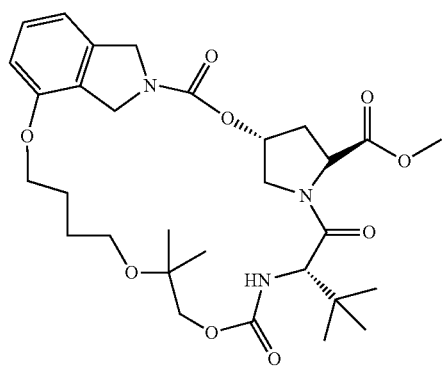
13s
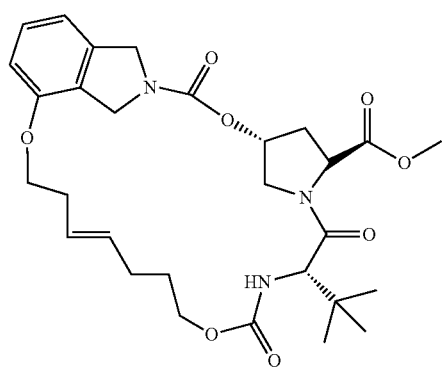
12t
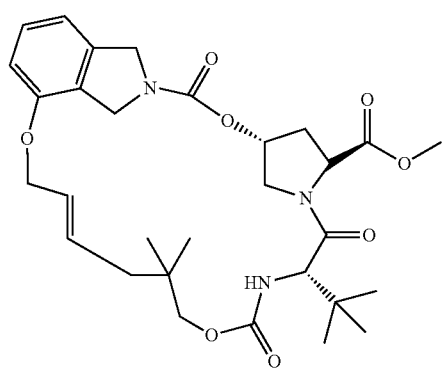
12k
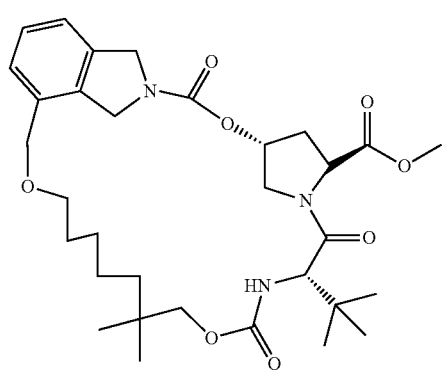
13u

| 13v | 14v |
|---|---|
| 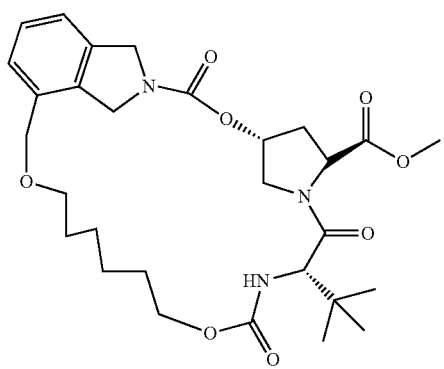 | 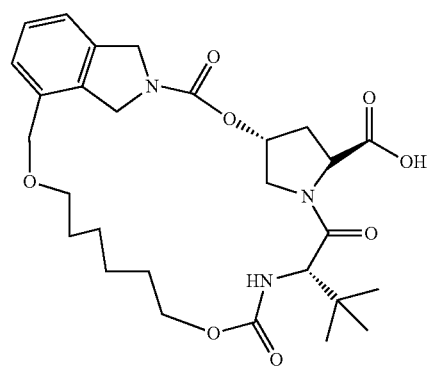 |
| 13w | 14w |
| 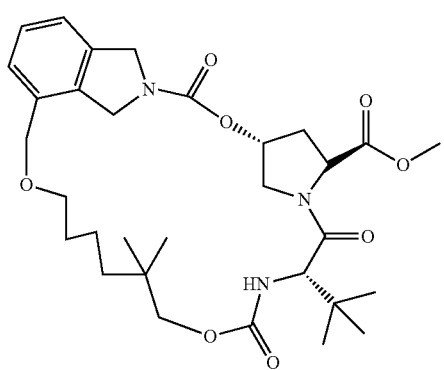 | 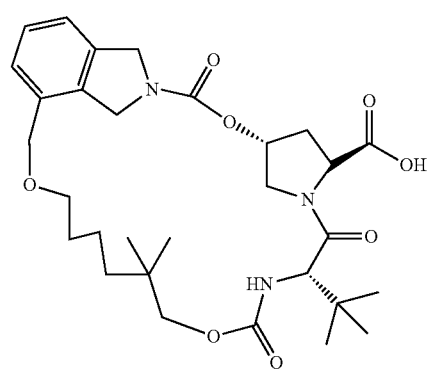 |
| 13x | 14x |
| 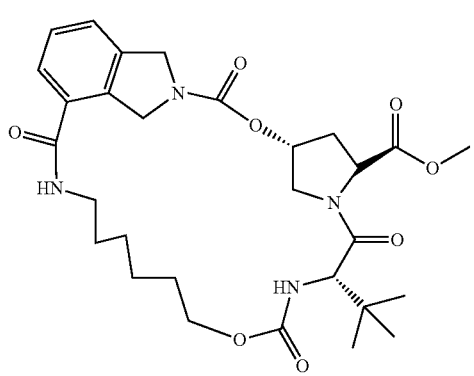 | 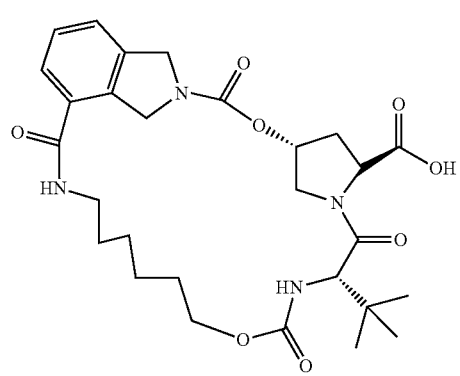 |
| 13y | 14y |
| 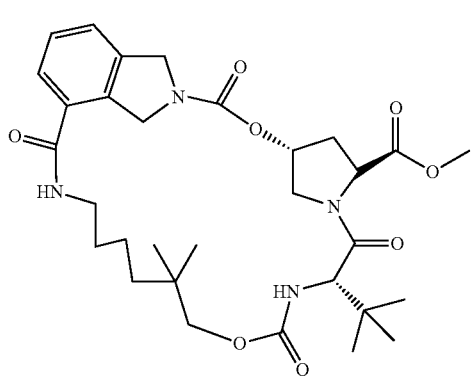 | 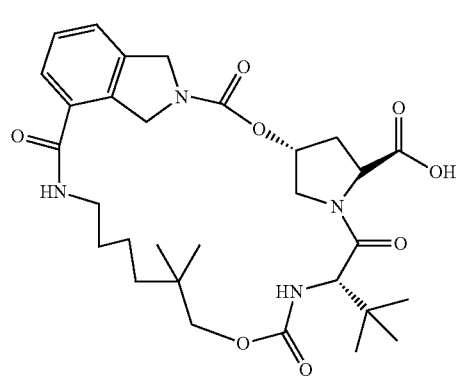 |

14z
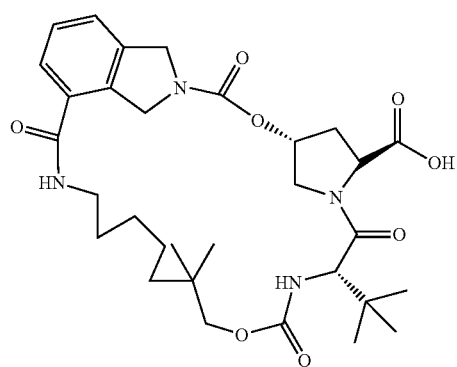
12ah
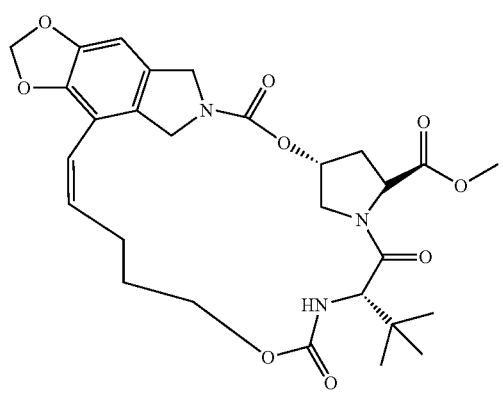
14a-2
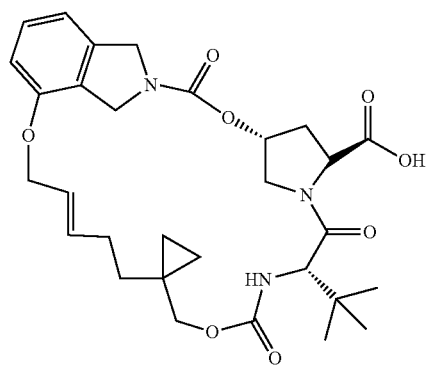
14a
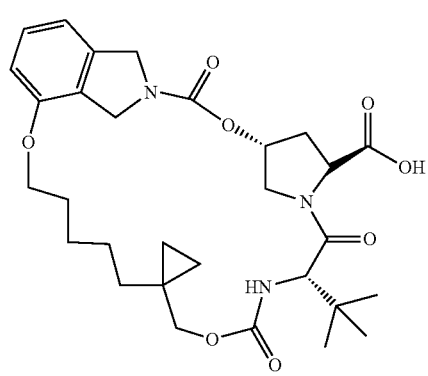
14b-2
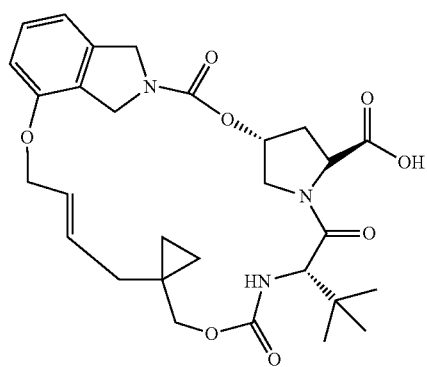
14b
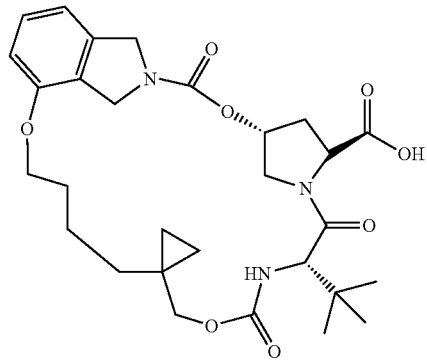
14c-2
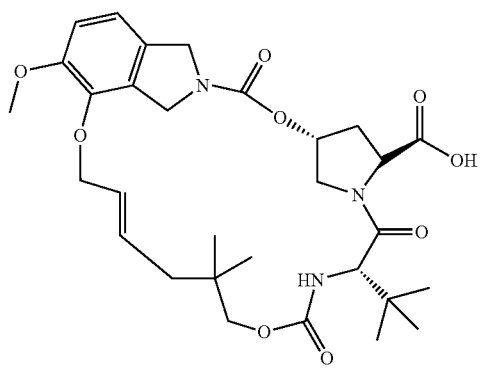
14d-2
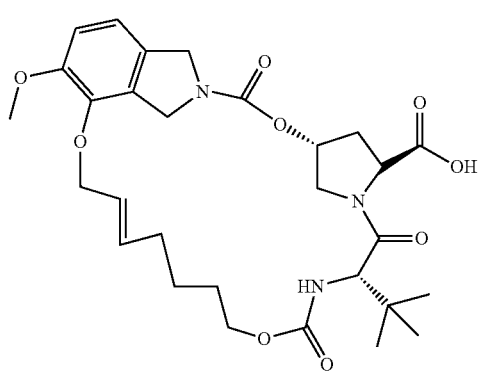

99
-continued
14e-2
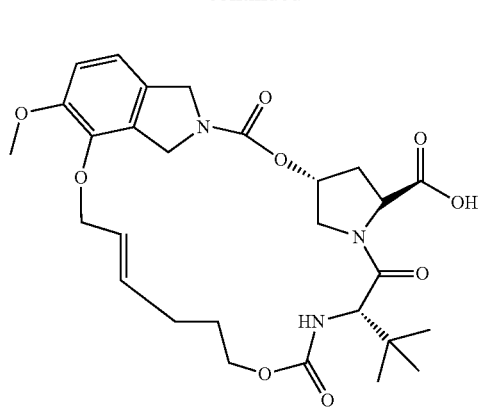
14f-2
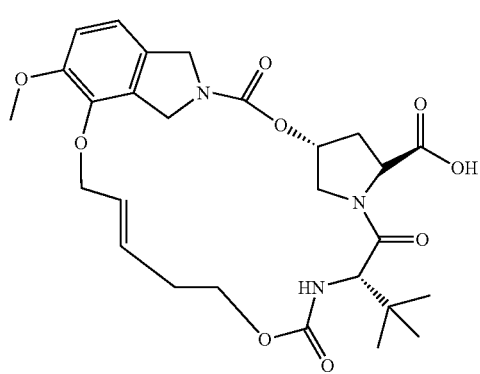
14g-2
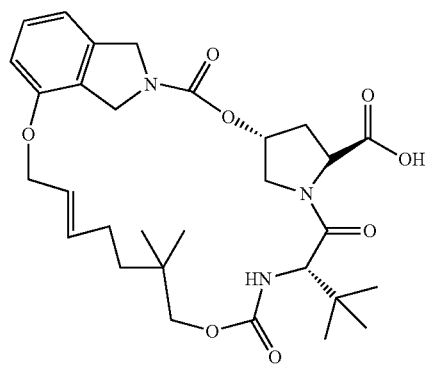
14g
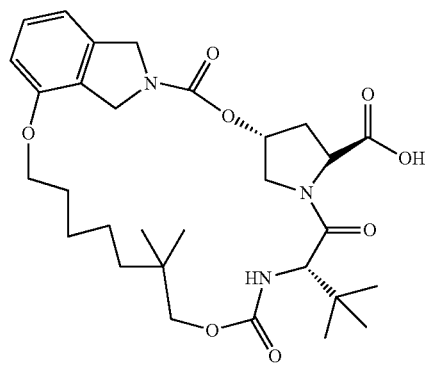
100
-continued
14h-2
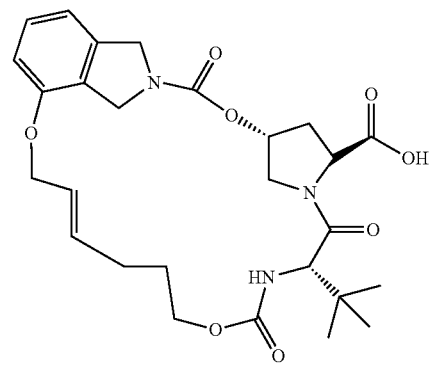
14k
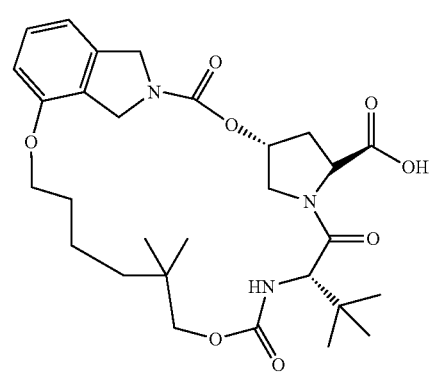
14m
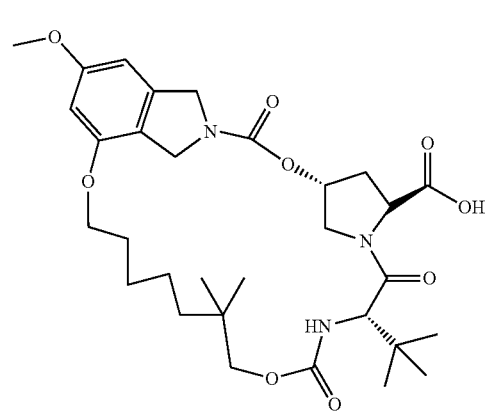
14h
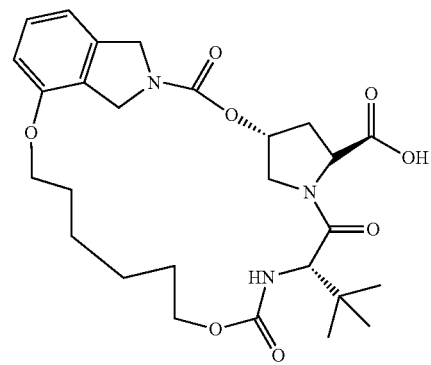

14n
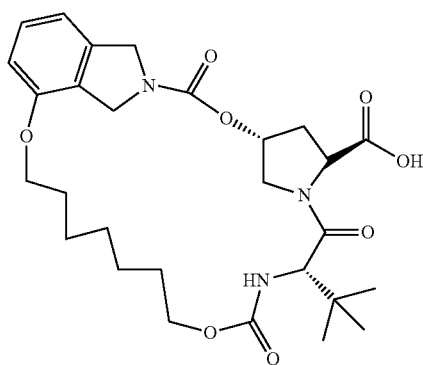
14r
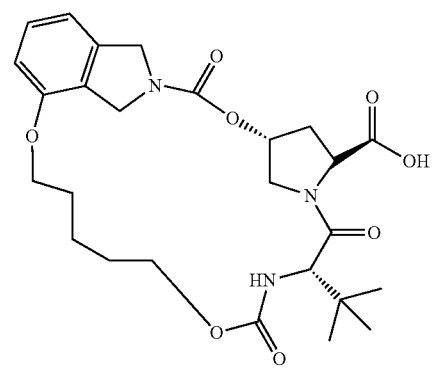
14p
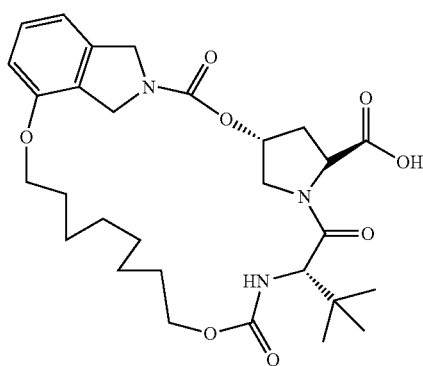
14s-2
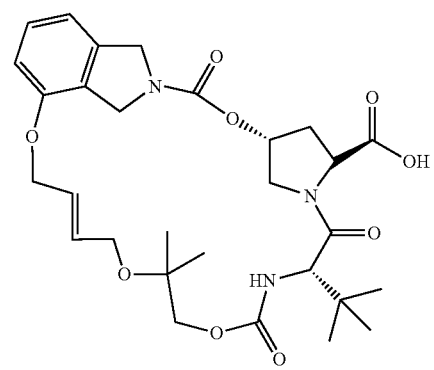
14q
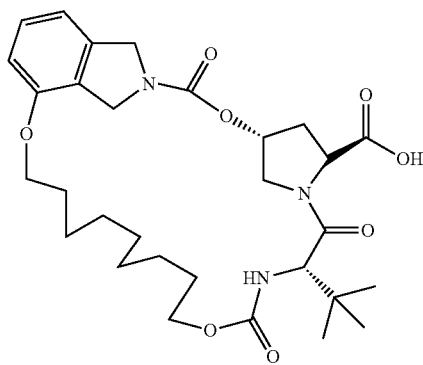
14s
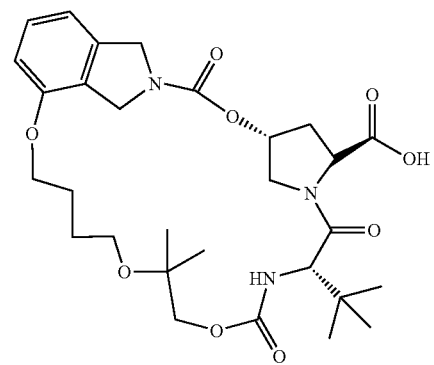
14r2
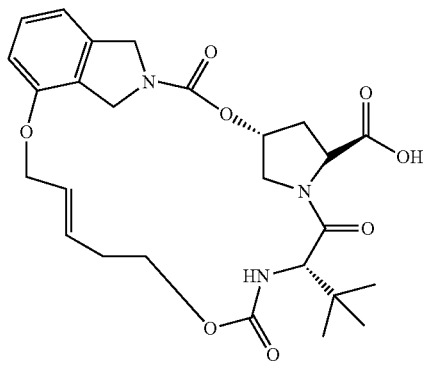
14t-2
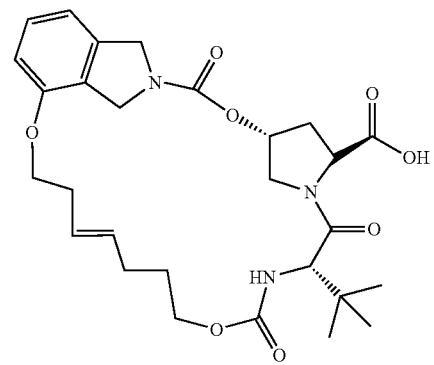

103
-continued
14k-2
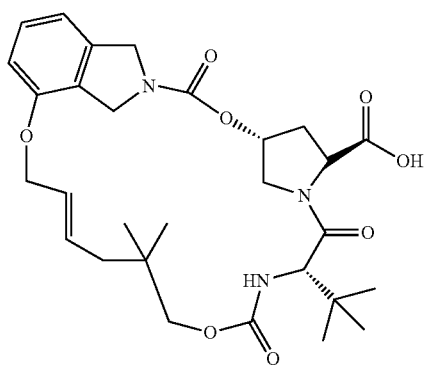
14u
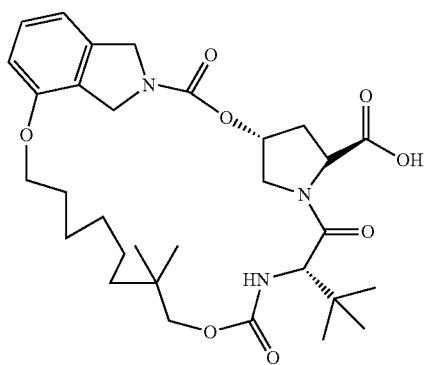
13z
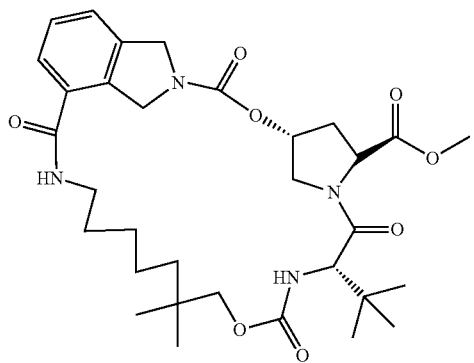
14ah-2
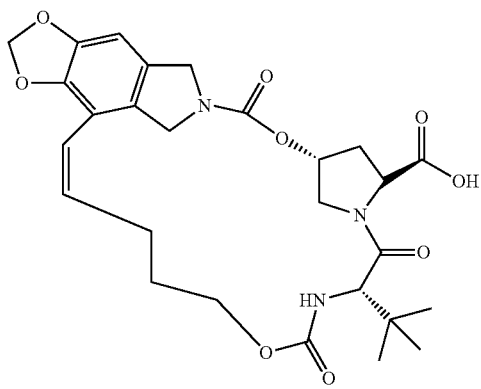
104
-continued
14ak-2
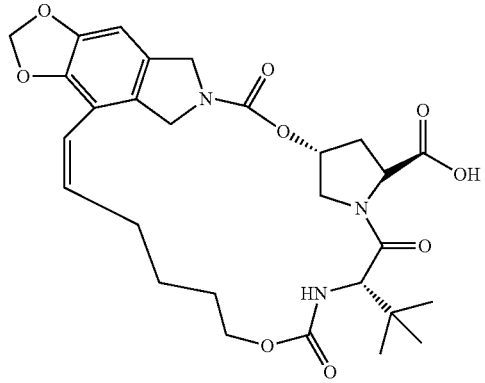
14am-2
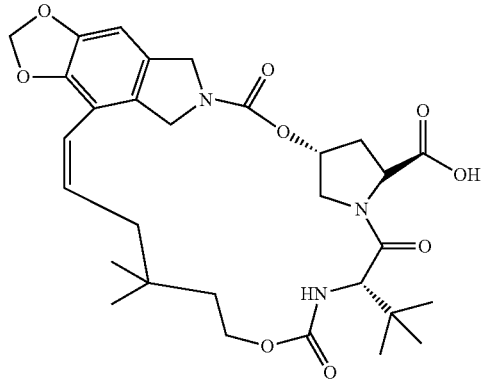
14ak
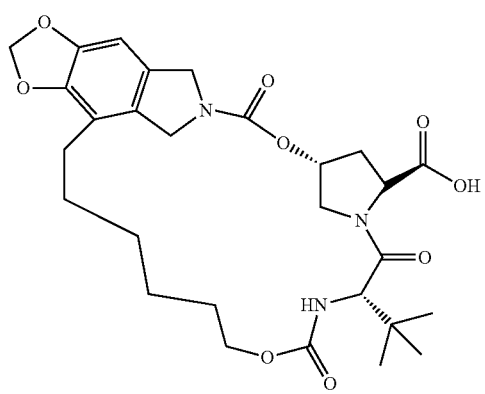
14am
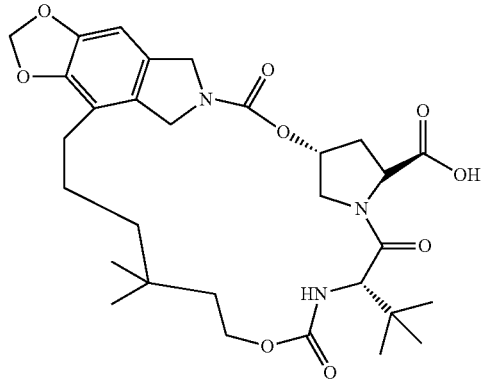

14ax 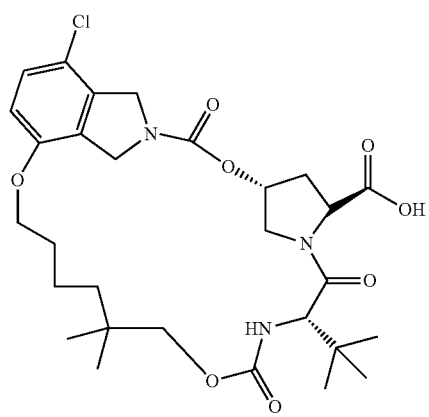
14ba 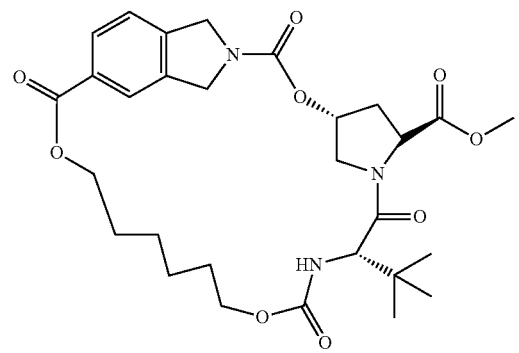
12ac 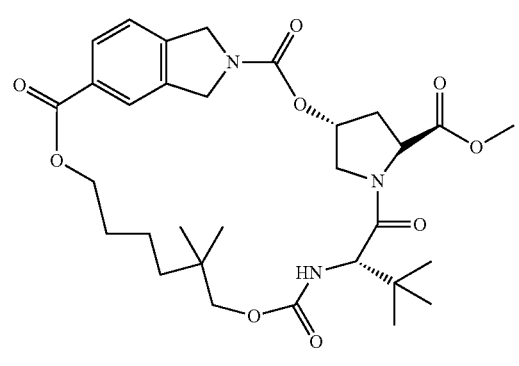
13ad 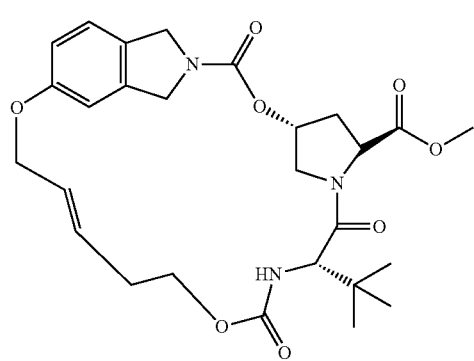
13ae 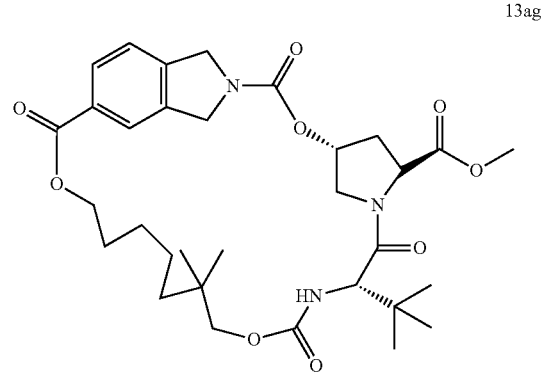
13af 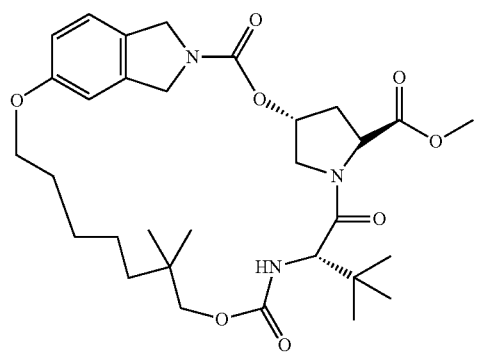
13ag 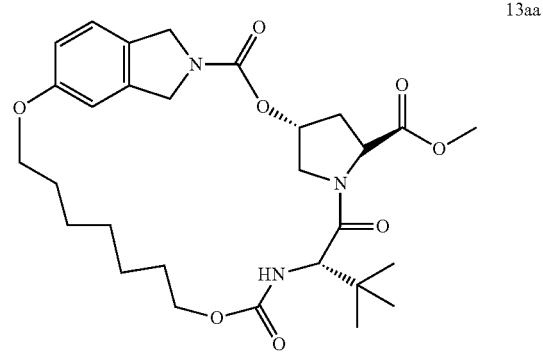
13aa 12aa
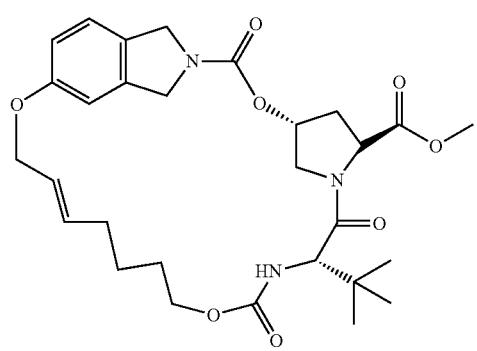
12ab
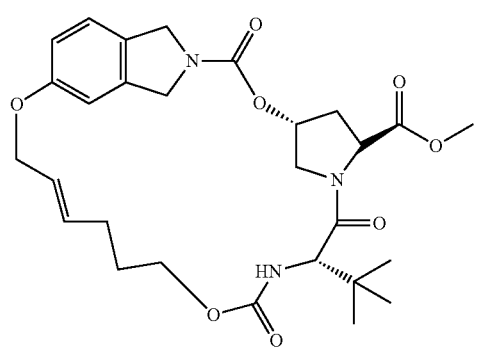
14ae
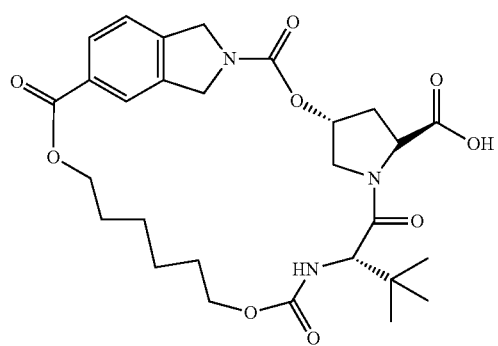
14af
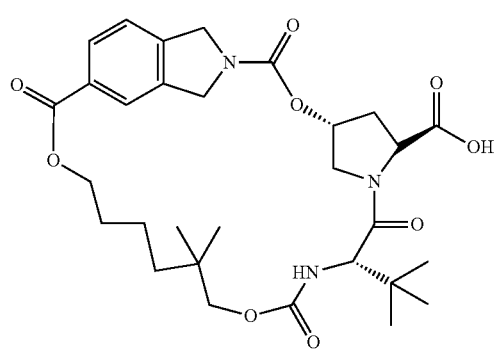
14ag
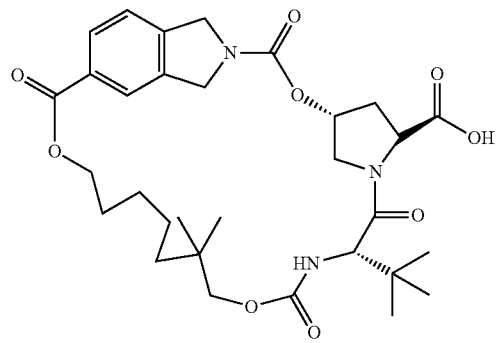
14aa
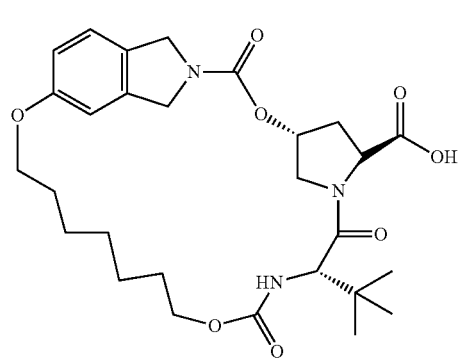
14aa-2
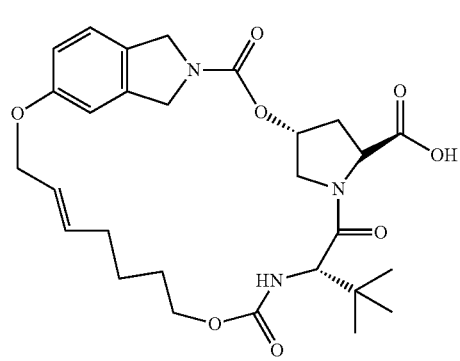
14ab-2
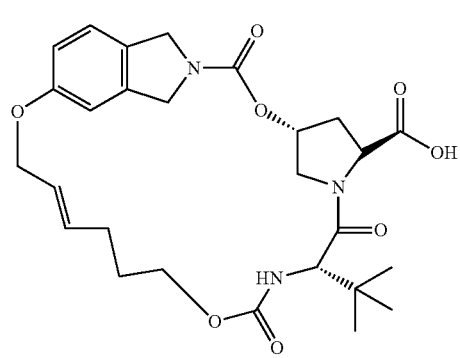

109
-continued
14ac-2
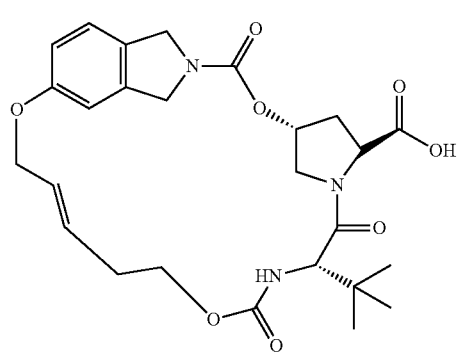
14ad
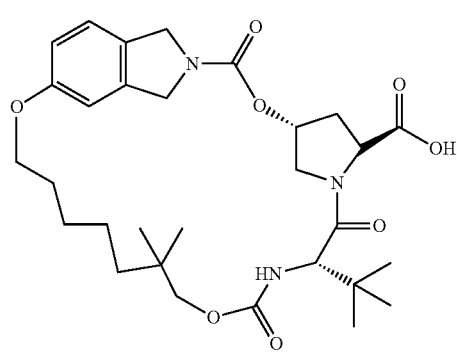
Structural FIG. 9:
15a
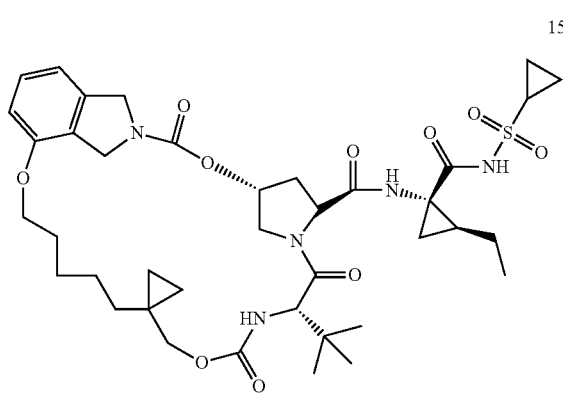
15b
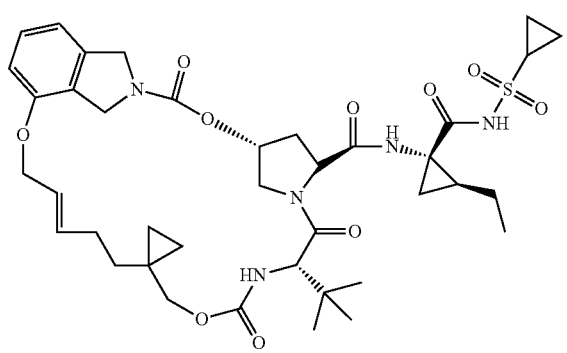
110
-continued
15c
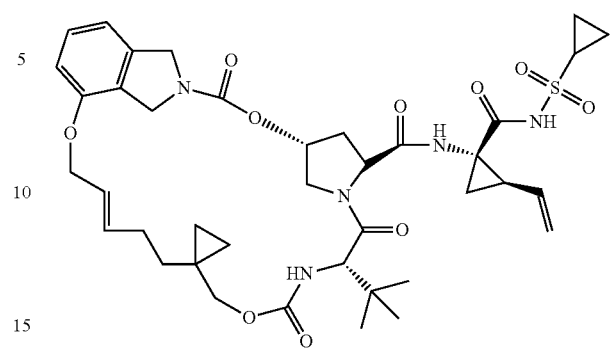
15d
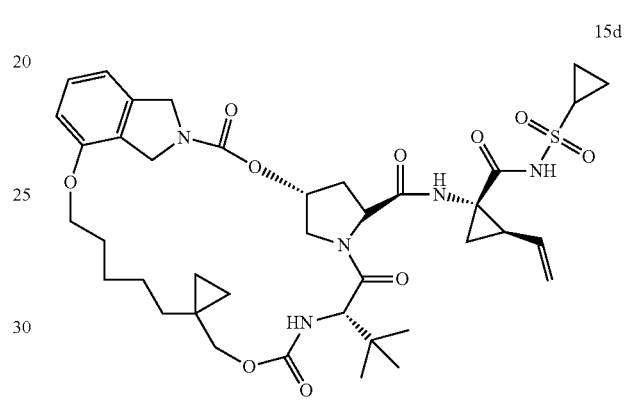
15e
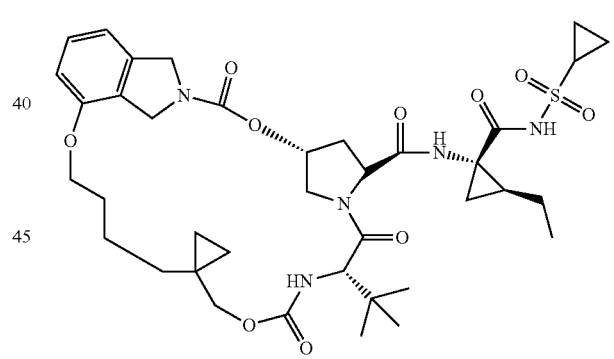
15f
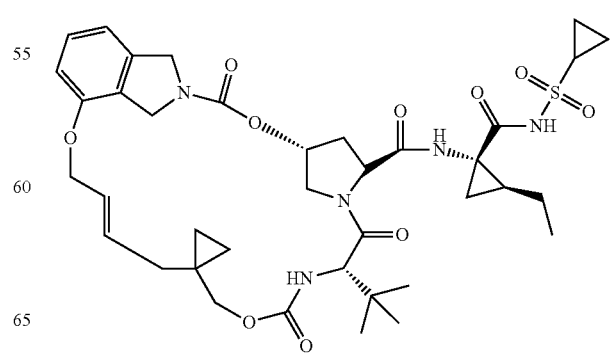

15g
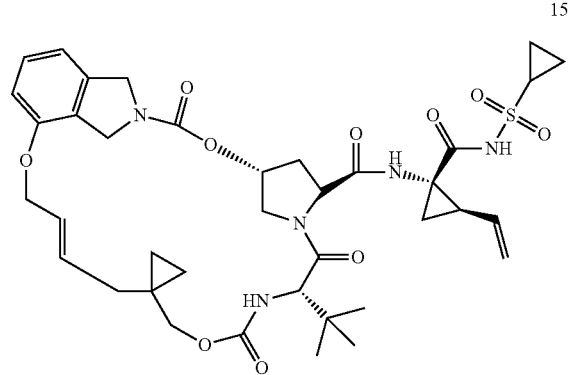
15m
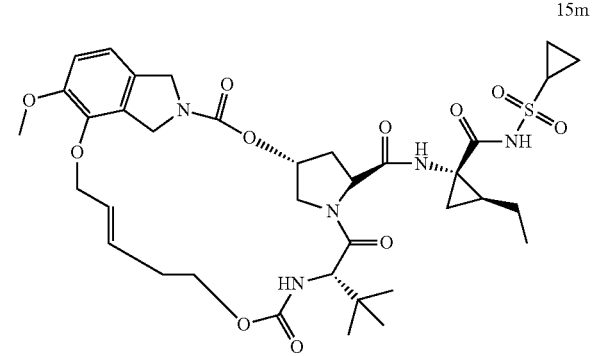
15h
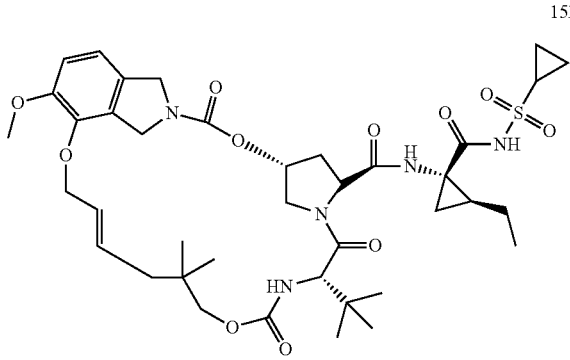
15n
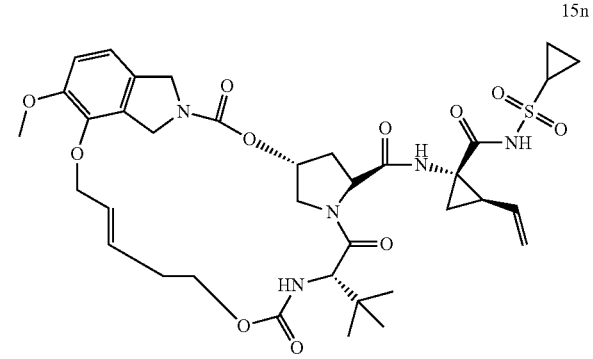
15j
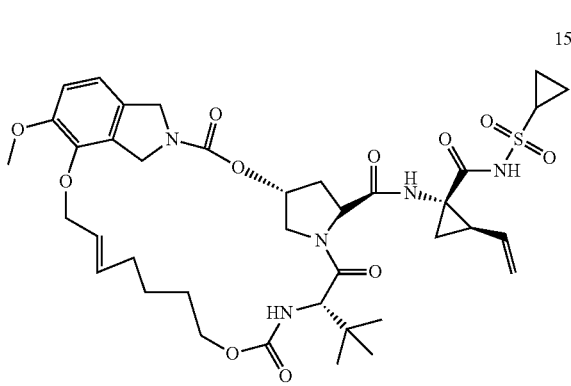
15p
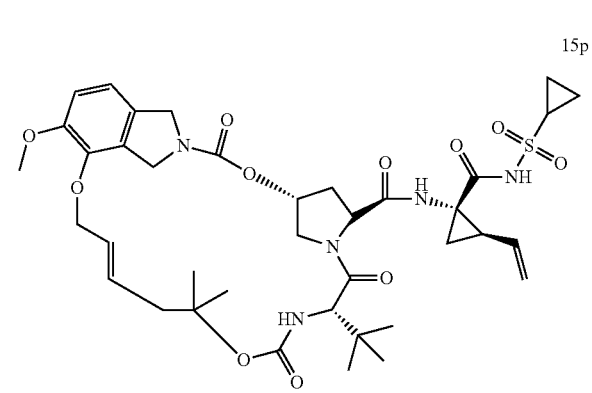
15k
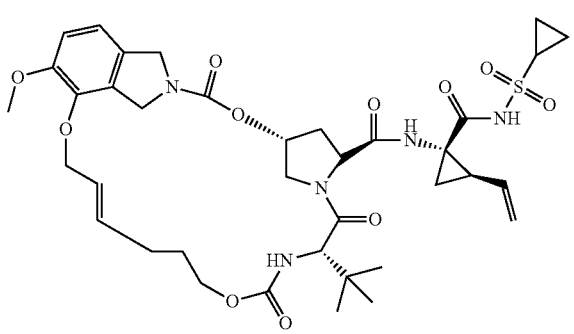
15q
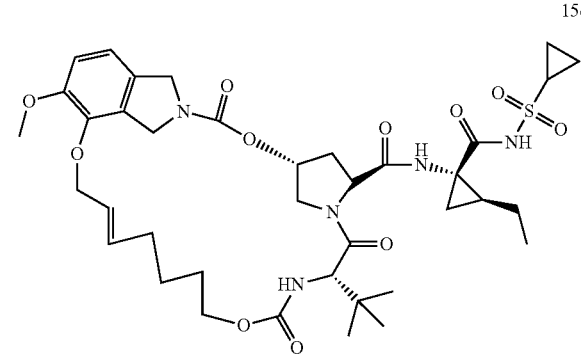

-continued
15r
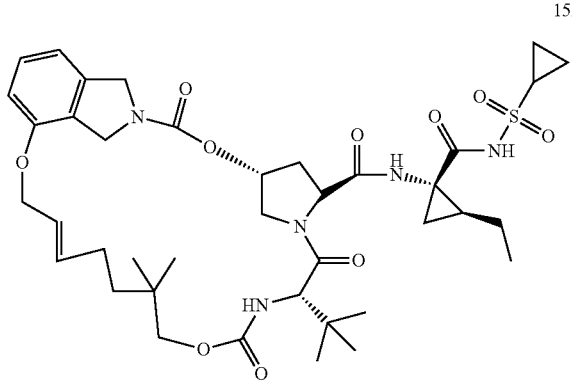
15s
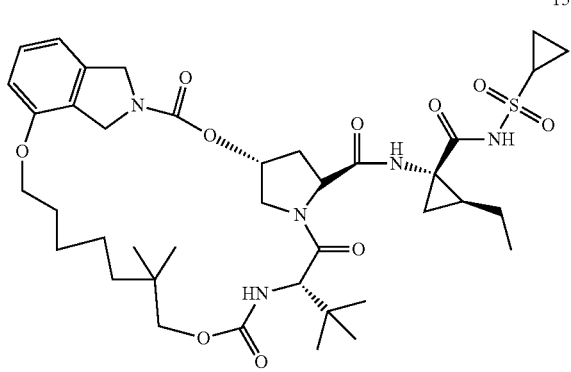
15t
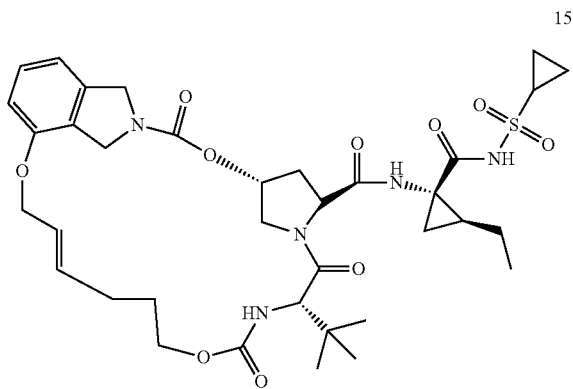
15u
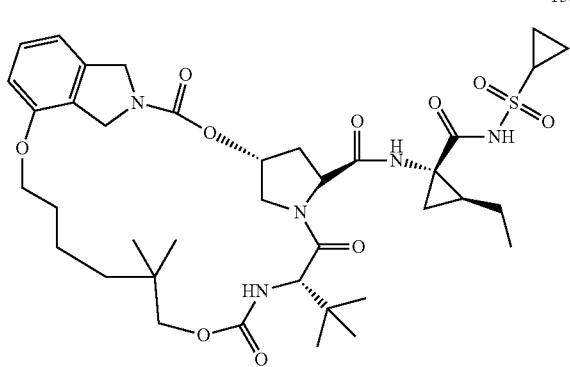
-continued
15v
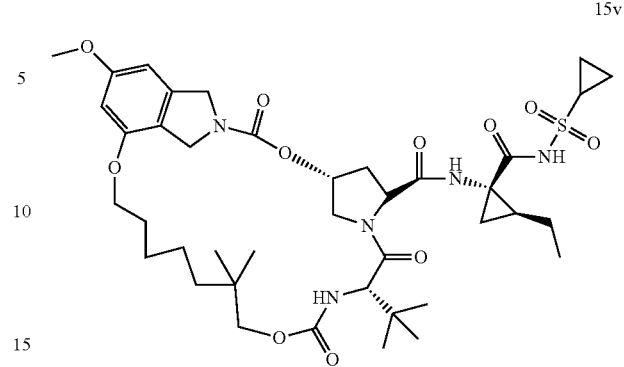
15w
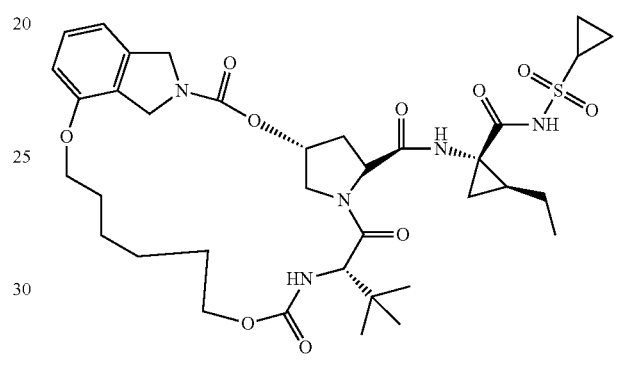
15x
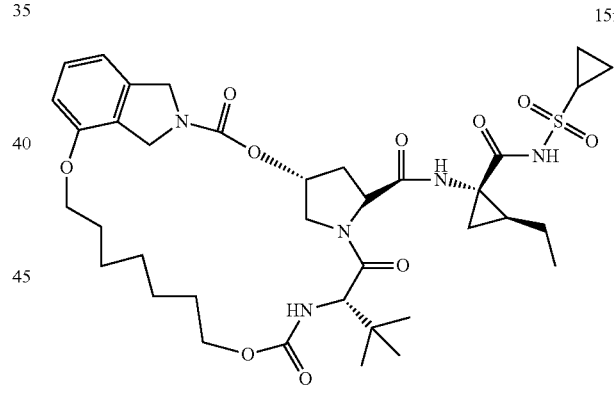
15y
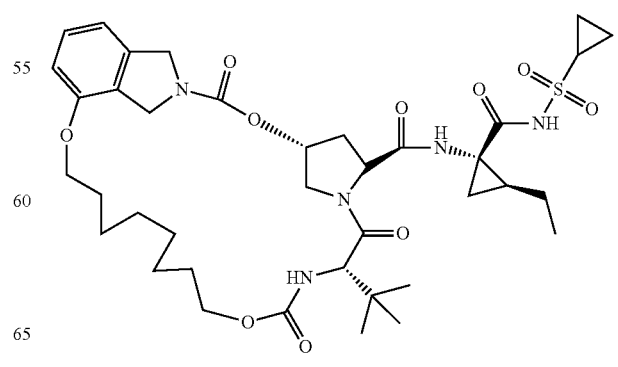

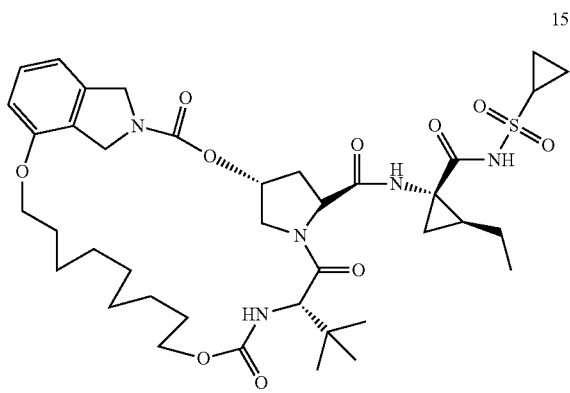
15z
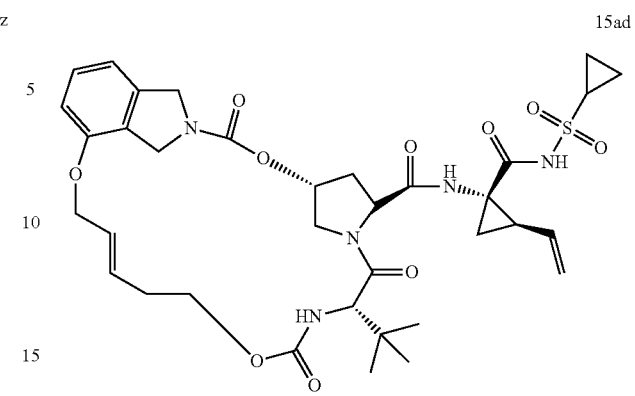
15ad
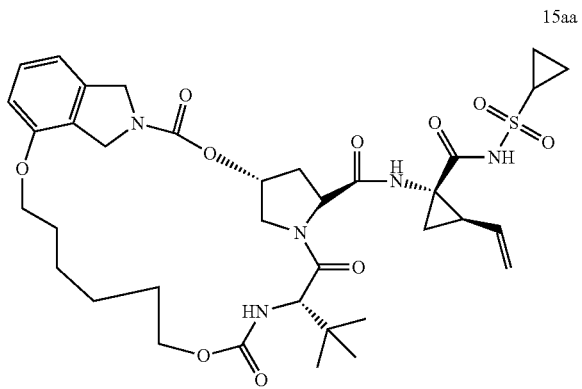
15aa
15ae
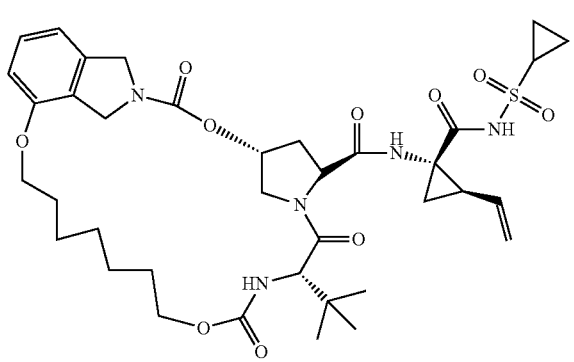
15ab
15af
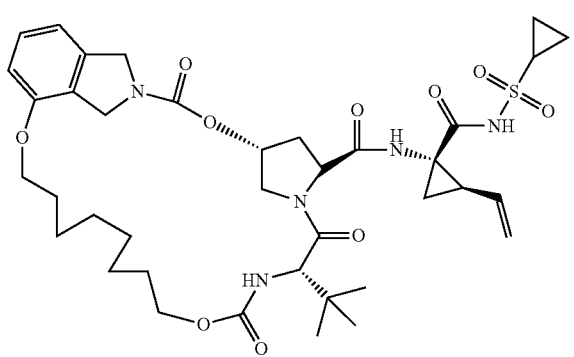
15ac
15ag

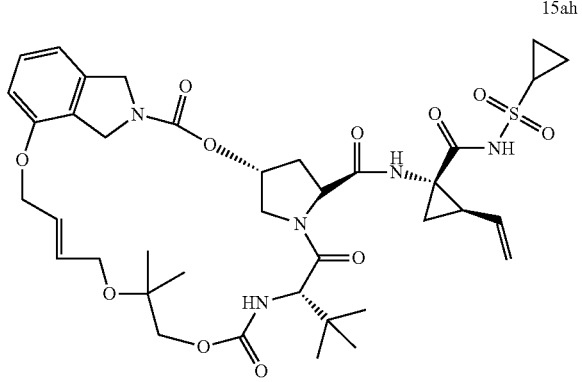
15ah
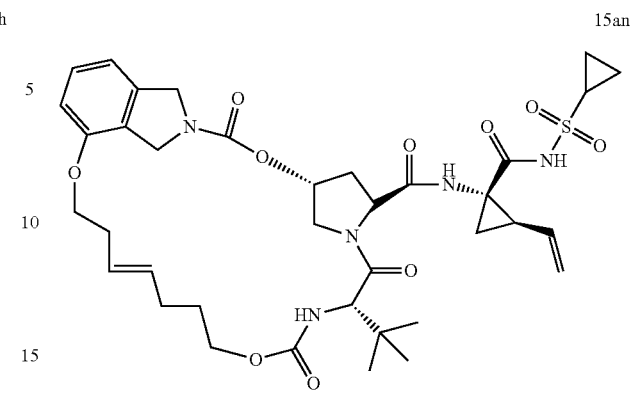
15an
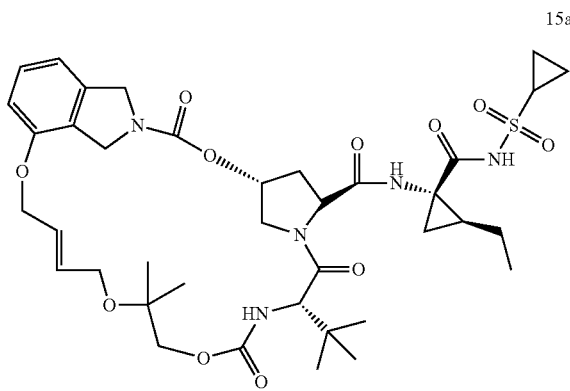
15aj
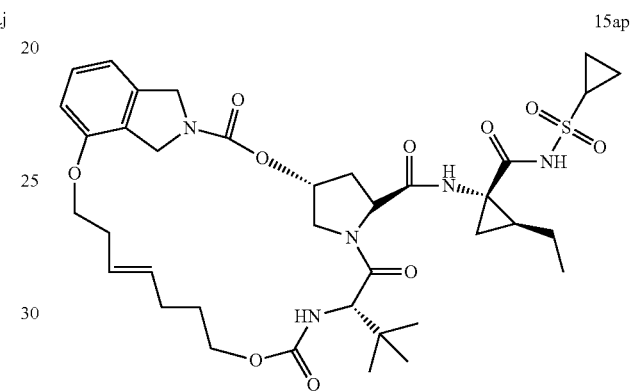
15ap
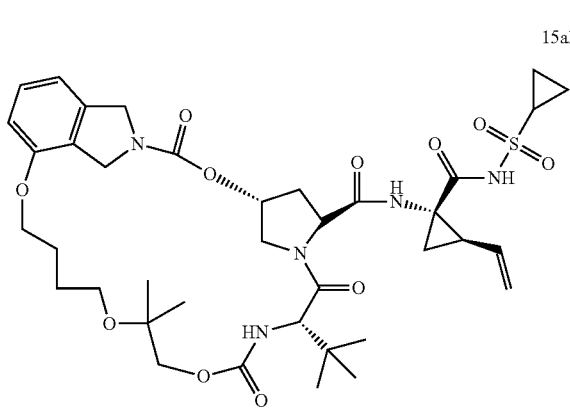
15ak
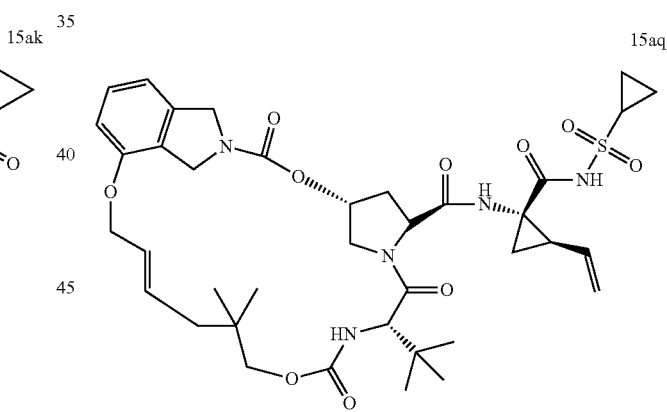
15aq
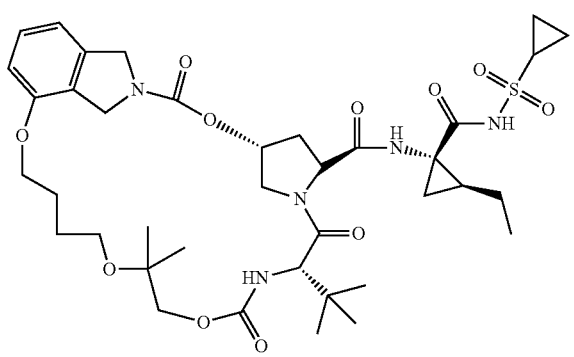
15am
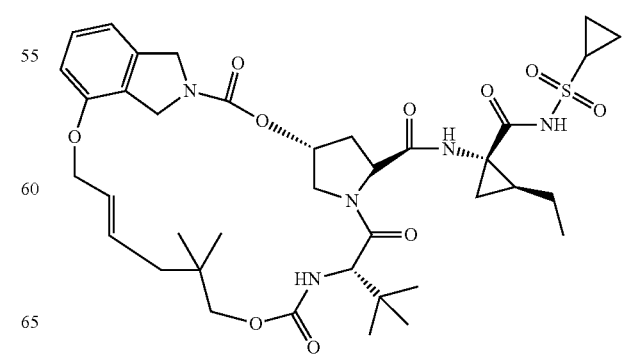
15ar 15as
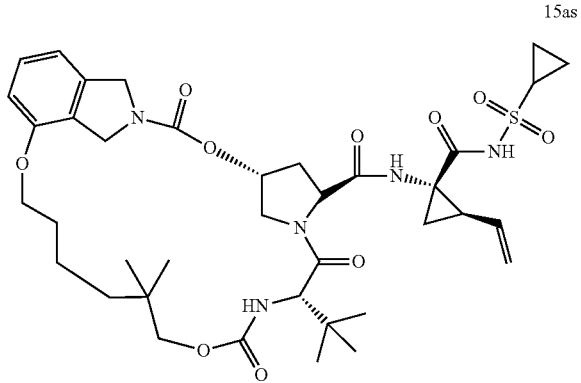
15aw
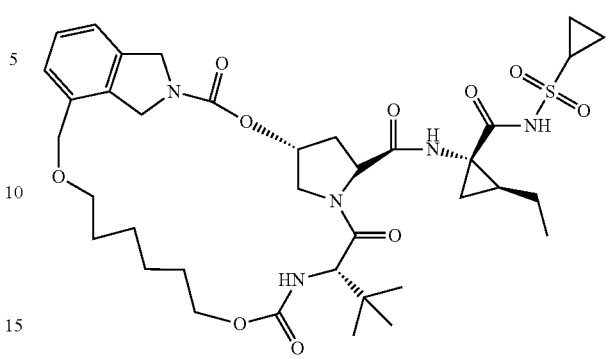
15at
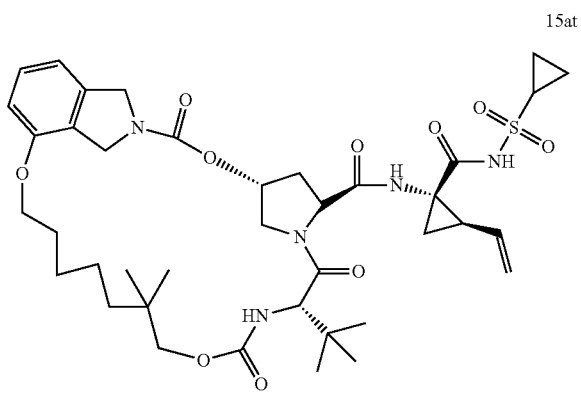
15ax
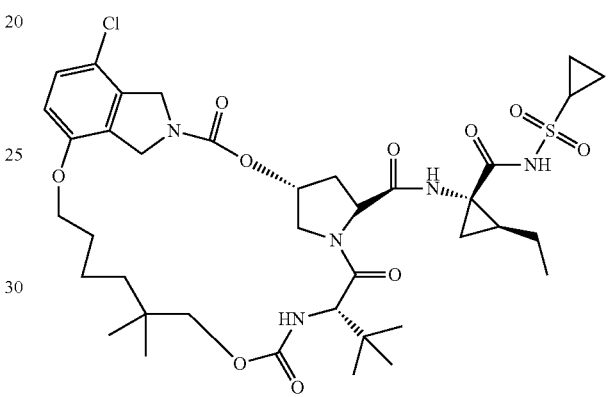
15au
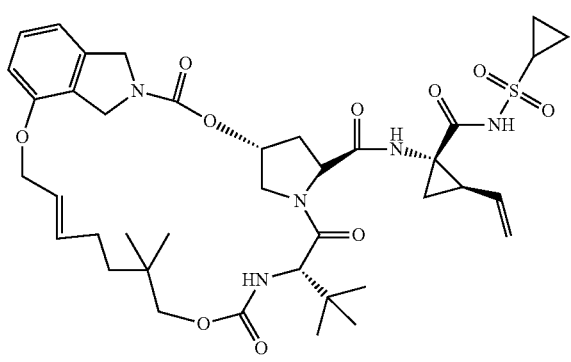
15ba
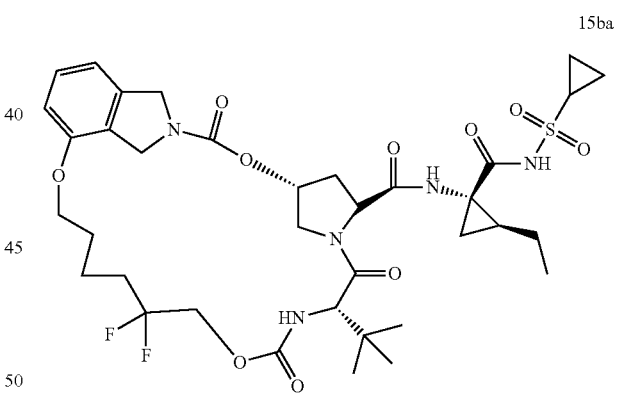
15av
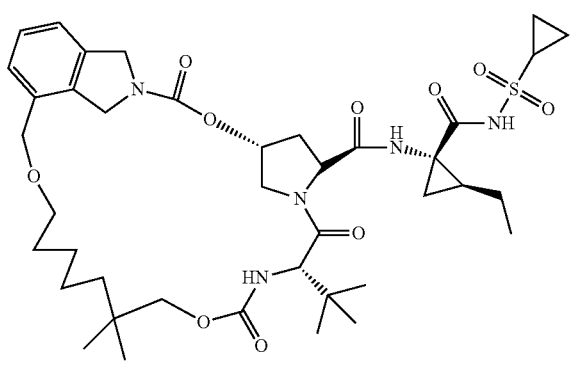
15bb
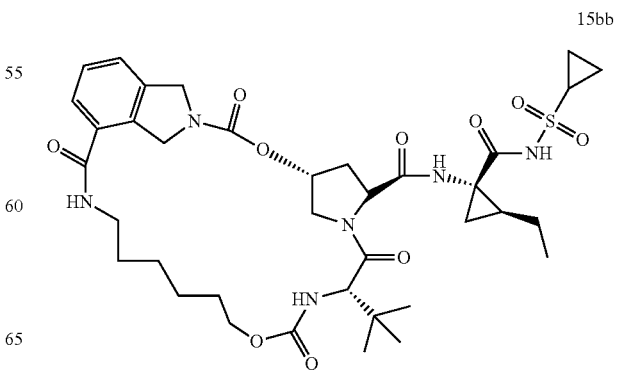

121
-continued
15bc
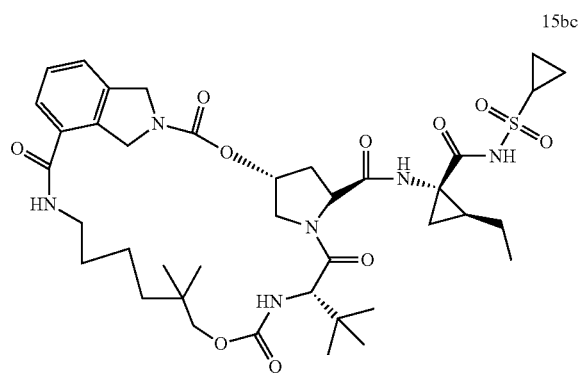
15bd
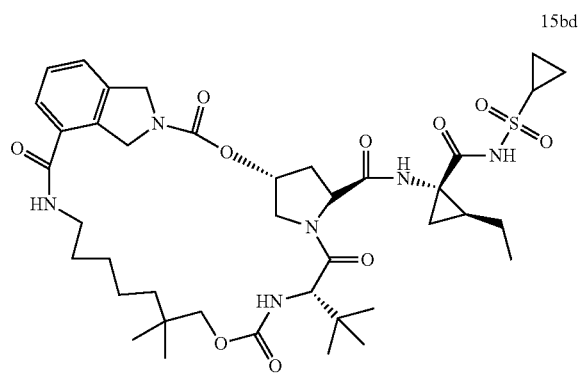
15be
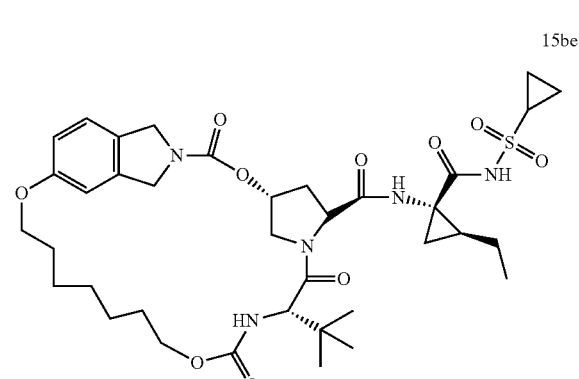
15bf
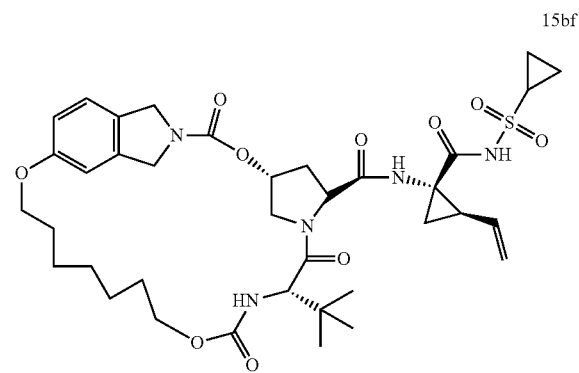
122
-continued
15bg
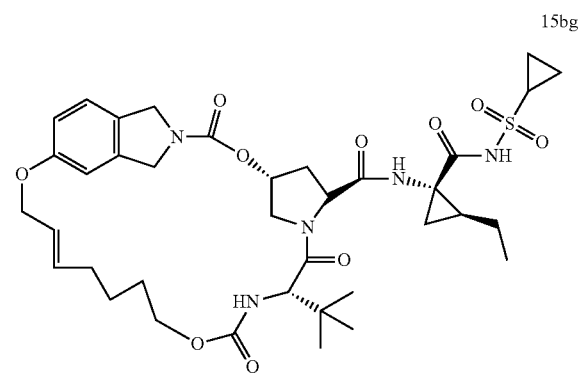
15bh
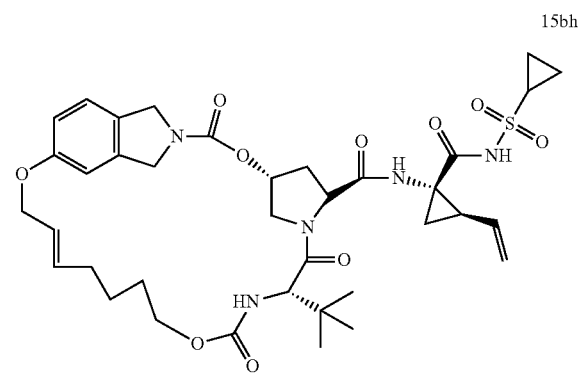
15bj
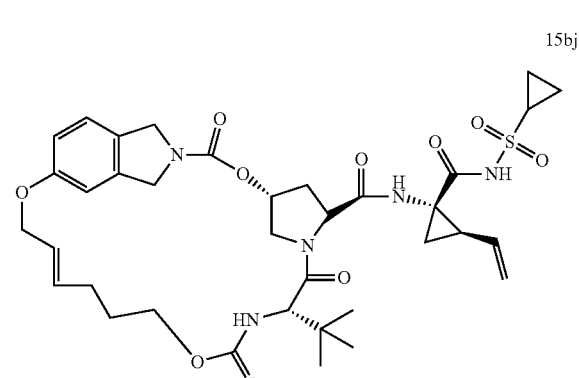
15bk
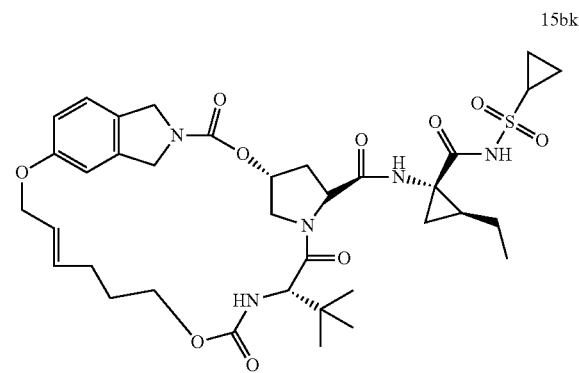

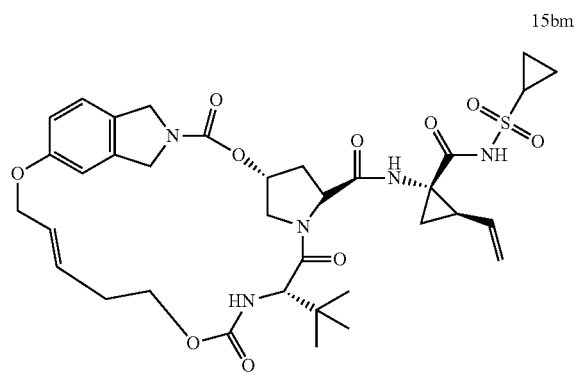
15bm
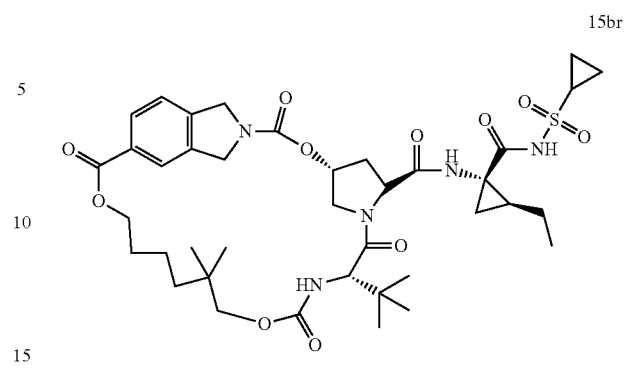
15br
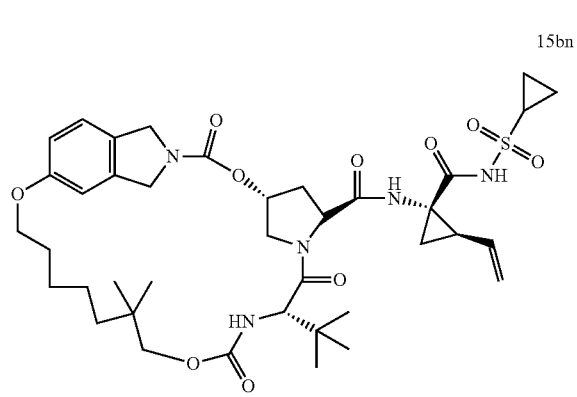
15bn
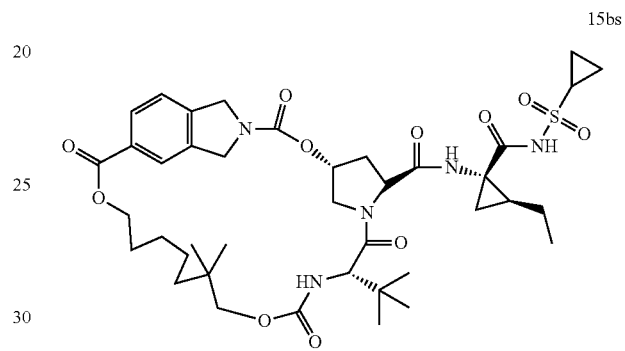
15bs
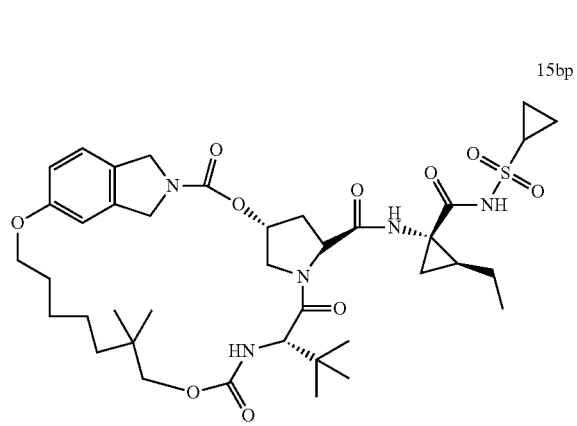
15bp
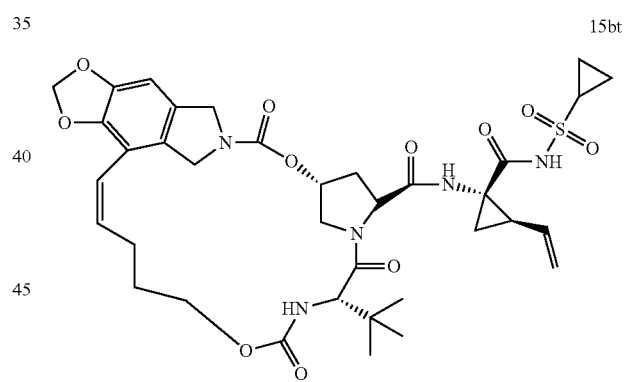
15bt
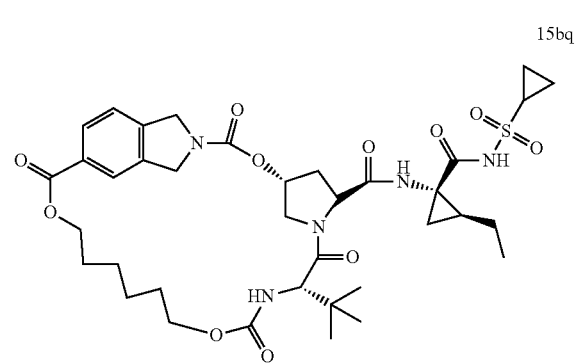
15bq
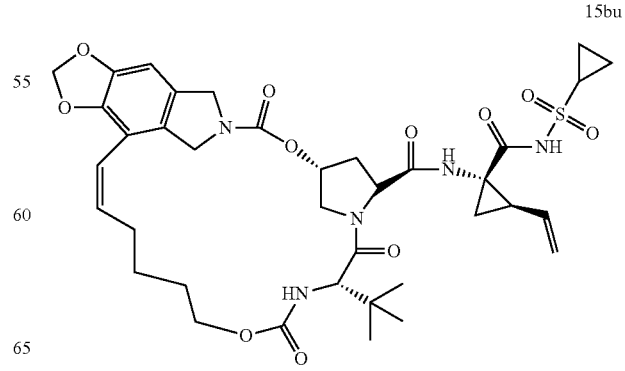
15bu

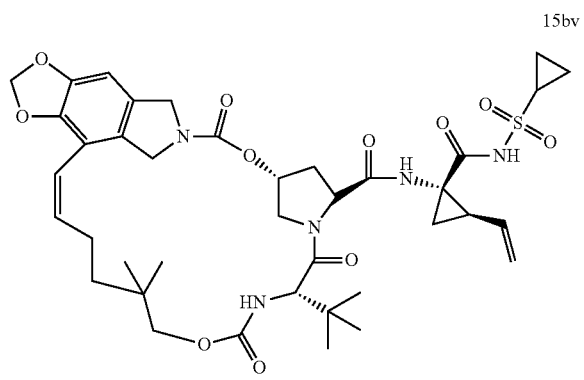
15bv
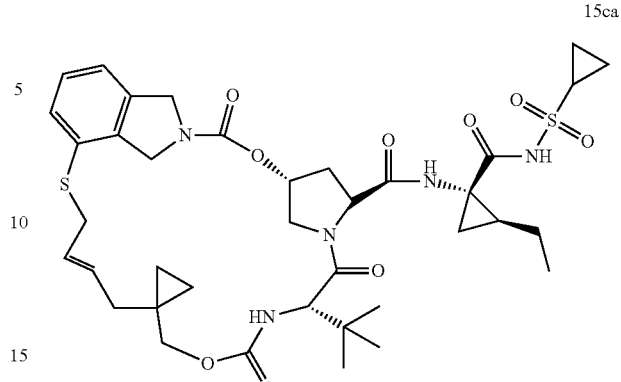
15ca
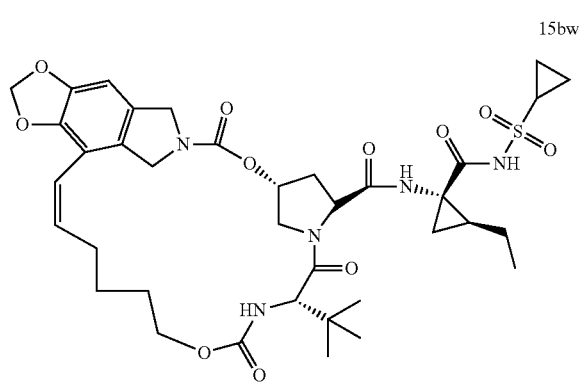
15bw
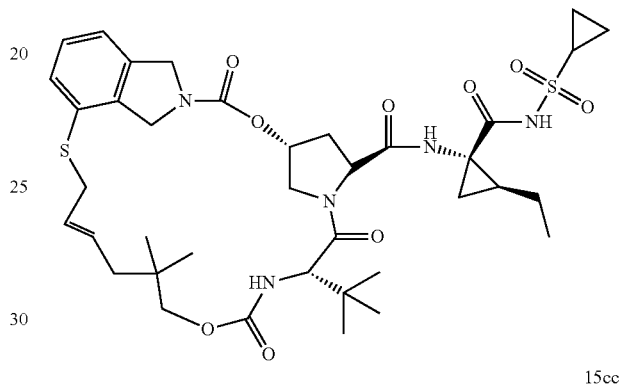
15cb
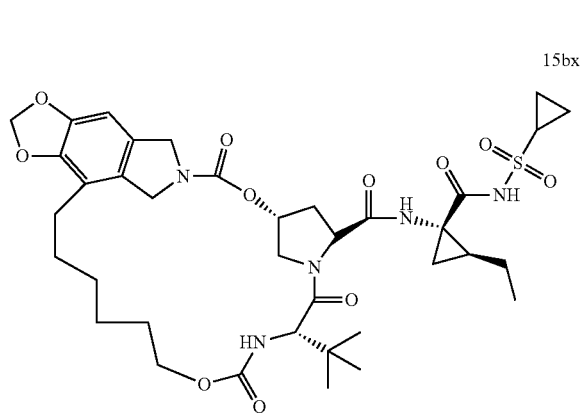
15bx
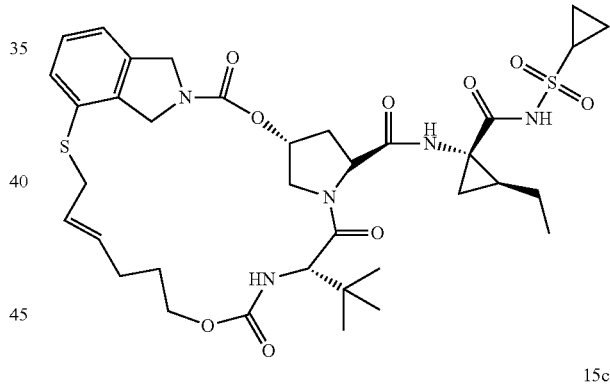
15cc
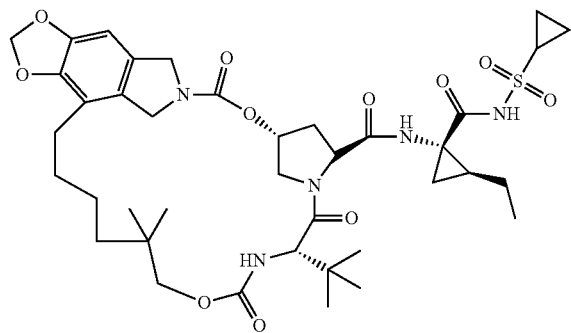
15by
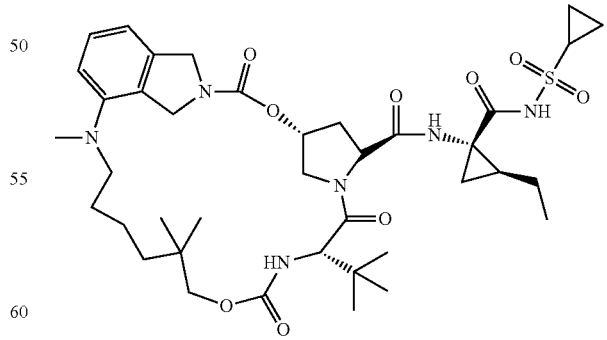
15cd
In the eighth aspect of the invention, an application of compounds Ia or Ib, and/or their stereoisomers, tautomers, esterification or amidation prodrugs, pharmaceutically acceptable salts or their mixtures to the preparation of new drugs inhibiting HCV.

In the ninth aspect of the invention, a pharmaceutical composition, which contains: one or one more kind of compounds Ia or Ib and/or their stereoisomers, tautomers, esterification or amidation prodrugs, pharmaceutically acceptable salts and excipients.

In the tenth aspect of the invention, a pharmaceutical composition, which contains the following one or one more kind of medicaments or one or one more kind of compounds Ia or Ib and/or their stereoisomers, tautomers, esterification or amidation prodrugs, pharmaceutically acceptable salt: (1) immuno-modulators; (2) HCV protease inhibitors; (3) HCV polymerase inhibitors; (4) Nucleosides or their derivatives which do not belong to (2)-(3); (5) HBV inhibitors; (6) HIV inhibitors; (7) anti-cancer drugs; (8) anti-inflammation drugs; or (9) other compounds not belonging to (1)-(8).

Wherein, the immuno-modulator is the interferon or its derivatives, and the interferon is polyethylene glycol.

The HIV inhibitor is Ritonavir, but not limited to it.

The HBV inhibitors comprising one of the following drugs: Lamivudine, Telbivudine, Adefovir, Emtricitabine, Entecavir, Tenofovir, or Clevudine.

In the eleventh aspect, the invention provides the application of a pharmaceutical composition, wherein the uses in preparation of new HCV inhibitors.

Based on common knowledge in this field, each condition mentioned above can be combined randomly as needed, thereof offering the ideal examples in the invention.

The reagents and materials used in the invention were commercially available.

The advantages of the present invention include the following three aspects:

1) The macroheterocyclic compounds in the invention shows not only excellent potent as HCV NS3 inhibitors, but also obviously superior to other kinds of macroheterocyclic compounds used as HCV inhibitors in clinical trials.

2) The structure activity relationship (SAR) of various macroheterocyclic compounds were thoroughly studied in the invention, and some novel macroheterocyclic compounds with highly potent HCV inhibition activities were discovered.

3) Some macroheterocyclic compounds with high potency in the invention have very low toxicity or almost no toxicity, which offers an opportunity to develop a potent and no-toxic anti-HCV drug

DETAILED DESCRIPTION OF THE INVENTION

In the following section, some detailed embodiments were illustrated for the further explanation of the present invention, but the effective coverage of the invention is not limited to the detailed embodiments described in the invention. Some experimental methods in the following embodiments were carried out by the regular conditions or published merchandise specifications.

The key innovation point in the invention is first to prepare the novel heterocyclic building blocks V-1 to V-9, from which several new heterocyclic intermediates IIIa-IIIb were synthesized. Therefore, the macrocyclic compounds IIa-IIb was obtained through three step's synthesis from IIIa-IIIb, followed by the amidation to furnish compounds Ia-Ib.

The abbreviations of the chemical reagents and solvents used in the synthesis of the novel macro-heterocyclic compounds in the invention were summarized in the instrument and material sections.

In scheme 1 below, the starting materials SM-1a, SM-1b, SM-1c, SM-1d, SM-1e, SM-1f, SM-1g, SM-1 h were reacted in the organic solvents (methanol, THF, N,N-dimethylformamide or dimethyl sulfoxide) respectively, of which SM-1a was reacted with $CH_2$=$CHCH_2NH_2$ to form 1-1 using the coupling reagent HBTU; or SM-1b, SM-1c, SM-1d, SM-1e, SM-1g, SM-1 h were reacted with $CH_2$=$CHCH_2Br$ respectively to form 1-1, 1-2, 1-3, 1-4, 1-5, 1-6, 1-8, 1-9, 1-10, 1-11 or 1-12 in the treatment of the inorganic bases (such as sodium hydroxide, sodium methoxide or sodium hydride); or SM-1f was reacted with the ethylene borate reagent SM-1j to form 1-7 using palladium catalyst; Subsequently, the obtained products 1-1 to 1-9 were subjected to hydrogenation to remove the protecting group (Bn) or treated with strong acid (HCl, TFA) as shown in scheme 1 to remove the protecting group Boc to prepare the key products V-1, V-2, V-3, V-4, V-5, V-6, V-7, V-8, V-9, V-10, V-11 or V-12 as shown in Structural Figure 2.

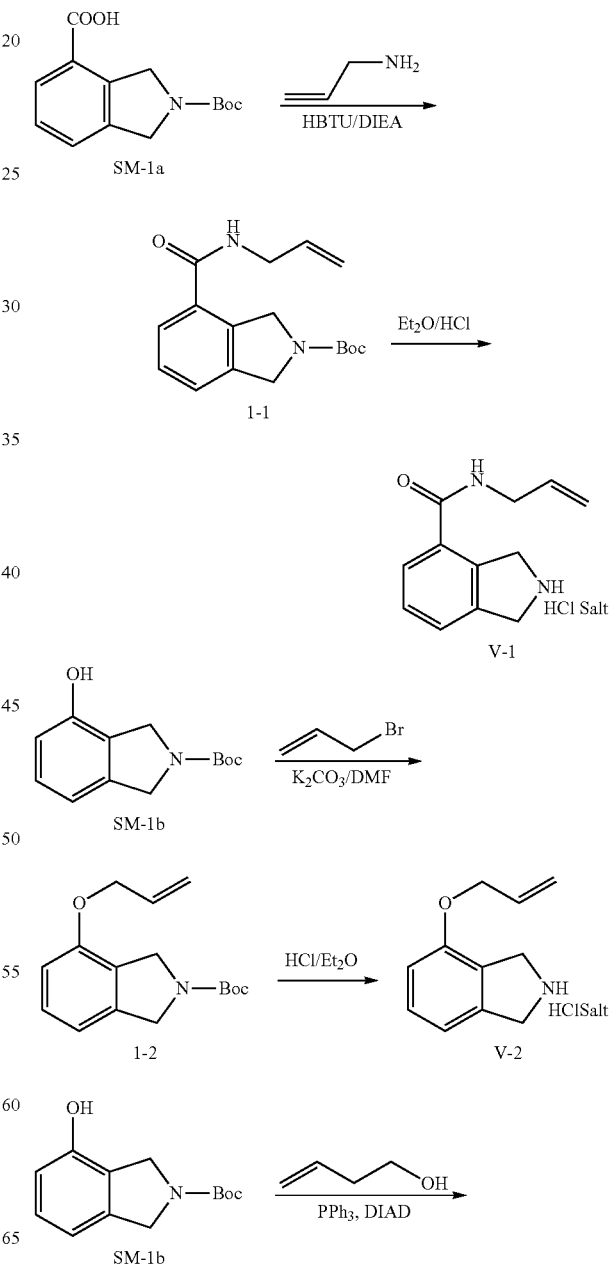

Scheme 1:

-continued
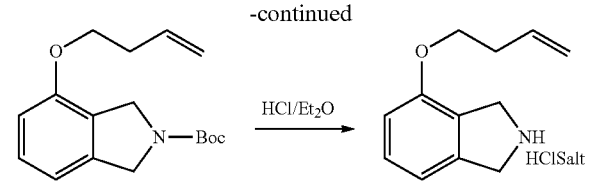
1-3 → V-3 (HCl/Et₂O)
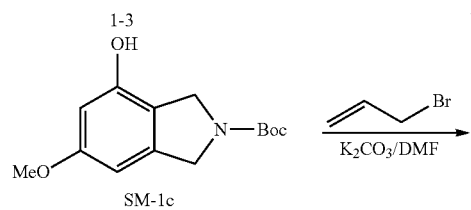
SM-1c → (allyl bromide, K₂CO₃/DMF)
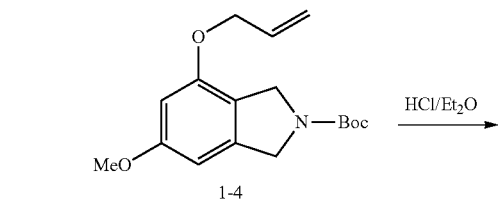
1-4 → V-4 (HCl/Et₂O)
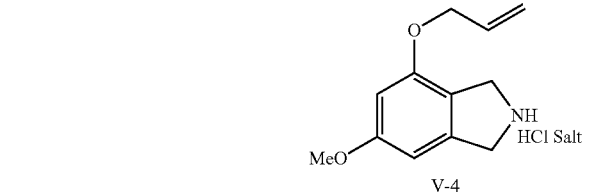
SM-1d → (allyl bromide, K₂CO₃/DMF)
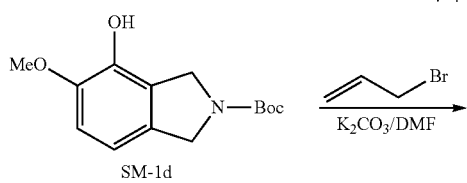
1-5 → V-5 (HCl/Et₂O)
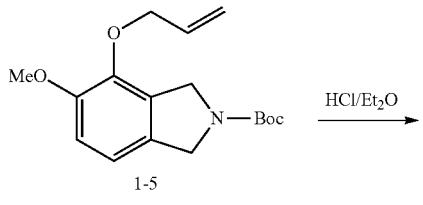
SM-1e → (allyl bromide, NaH/DMF)
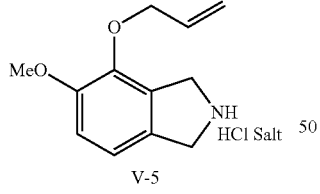
1-6 → 1) Et₂O/HCl 2) Na₂CO₃
-continued
V-6 HCl Salt
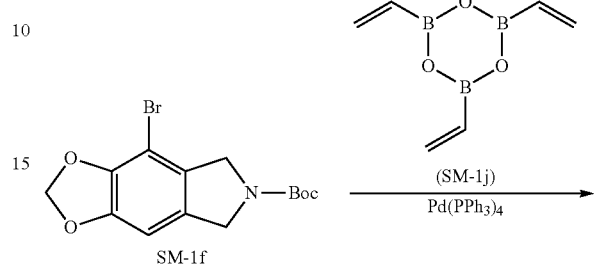
SM-1f → (SM-1j)/Pd(PPh₃)₄
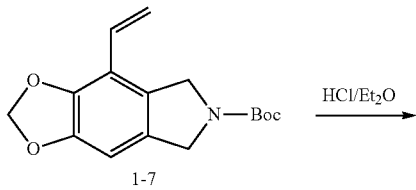
1-7 → (HCl/Et₂O)
V-7 HCl Salt
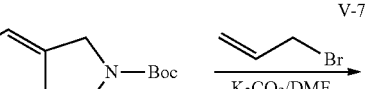
SM-1g → (allyl bromide, K₂CO₃/DMF)
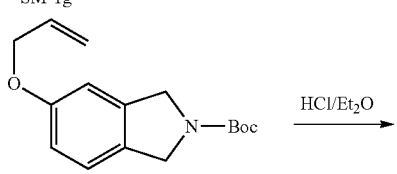
1-8 → (HCl/Et₂O)
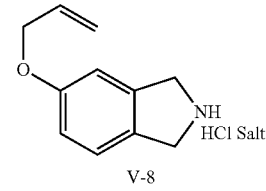
V-8 HCl Salt
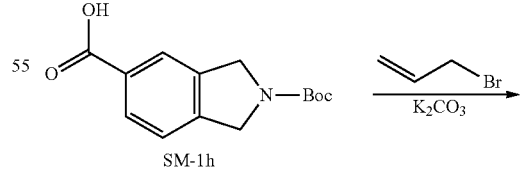
SM-1h → (allyl bromide, K₂CO₃)
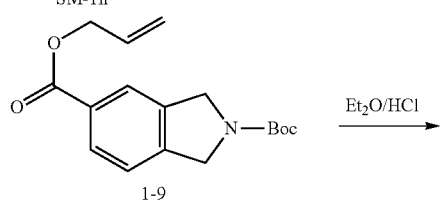
1-9 → (Et₂O/HCl)

131
-continued
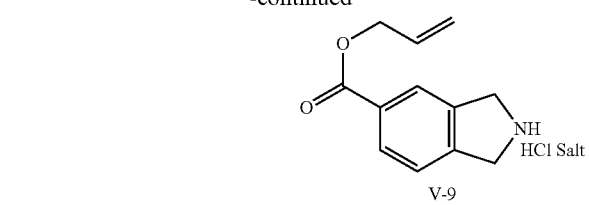
V-9
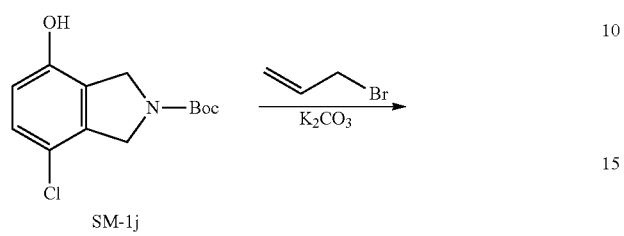
1-10
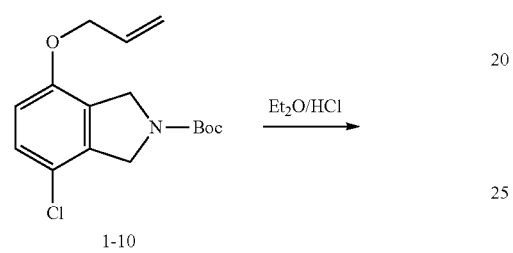
V-10
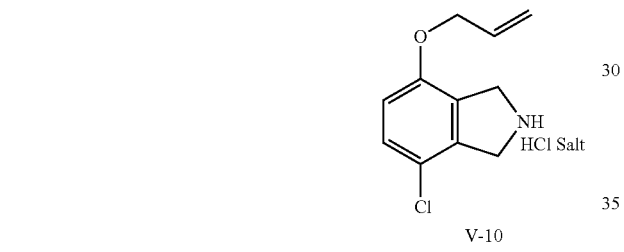
1-11
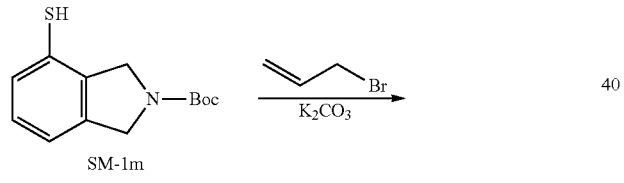
V-11
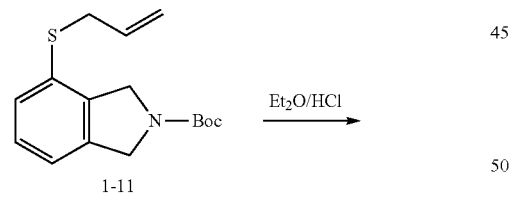
132
-continued
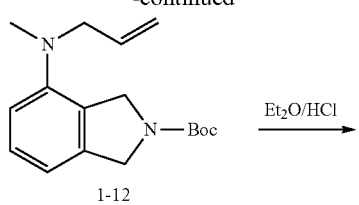
1-12
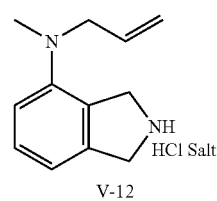
V-12
Structural FIG. 2:
V-1
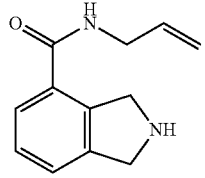
V-2
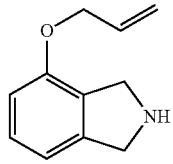
V-3
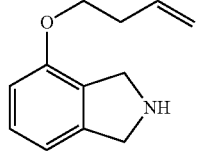
V-4
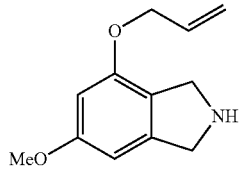
V-5
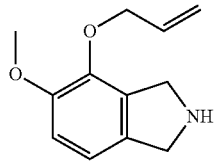
V-6
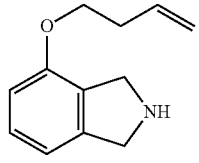

133
-continued

V-7
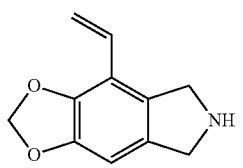

V-8
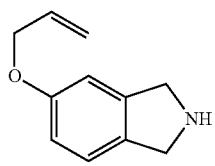

V-9
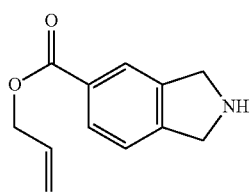

V-10
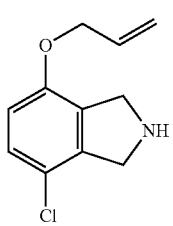

V-11
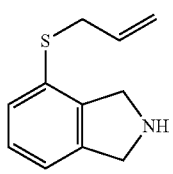

V-12
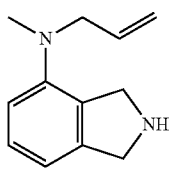

In Scheme 2 shown below, SM-2 was first coupled with SM-3a, SM-3b, SM-3c, SM-3d, SM-3e, SM-3f, SM-3g, SM-3h, SM-3h, SM-3k by amidation in the treatment of CDI or EDCI in organic solvent (dichloromethane, THF or N,N-dimethylformamide) to offer the intermediates 3a, 3b, 3c, 3d, 3e, 3f, 3g, 3b, 3j, 3k, 3m, 3n which was used for the next reaction:

134

Scheme 2:

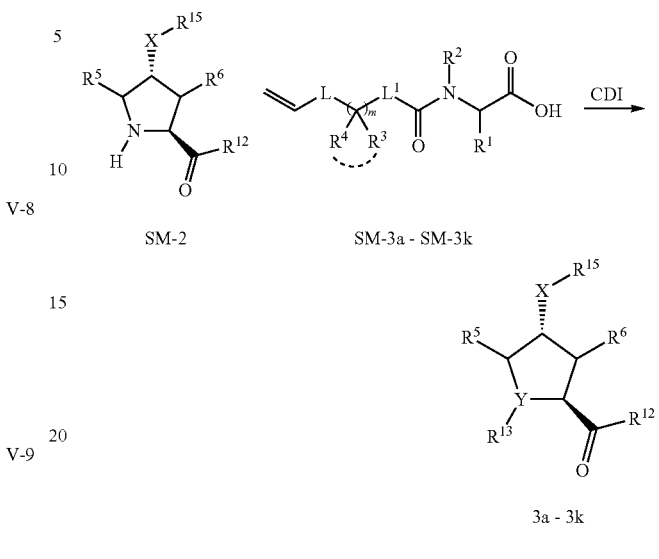

SM-2     SM-3a - SM-3k

3a - 3k

In the product 3a-3k, the definition of m, L, $L^1$ and $R^{13}$ group was the same as that of L, $L^1$ and $R^{13}$ group described above, $R^{15}$ was selected from hydrogen, $C_1$-$C_{15}$ alkylcarbonyl, $C_1$-$C_{15}$ alkoxycarbonyl or $C_1$-$C_{15}$ alkyl aminocarbonyl group; wherein, the amino acid derivative reagents SM-3a-SM-3n ($R^{13}$—OH) were each selected from structural Figure 3 shown as below:

Structural FIG. 3:

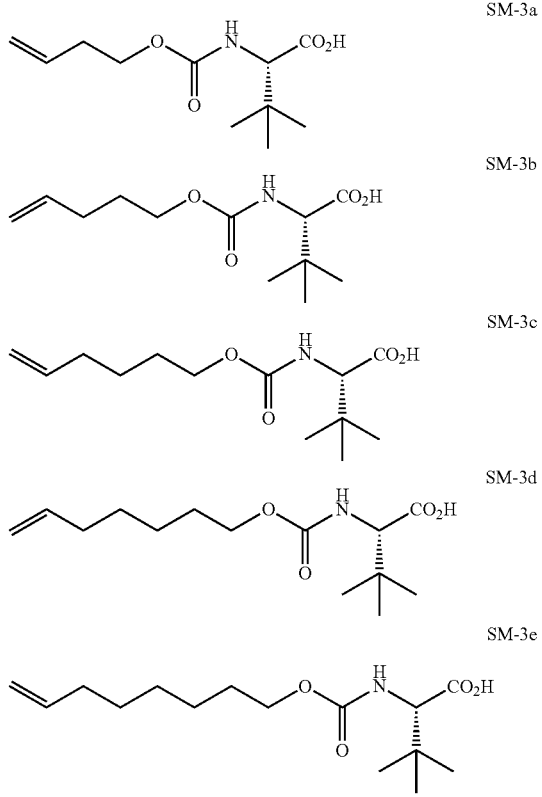

-continued

SM-3f
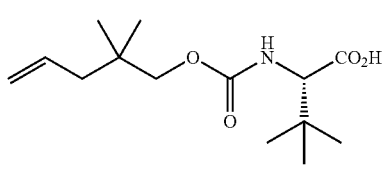

SM-3g
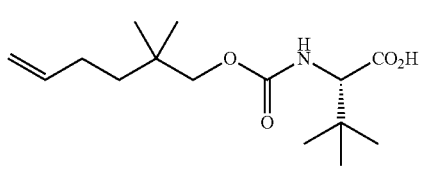

SM-3h
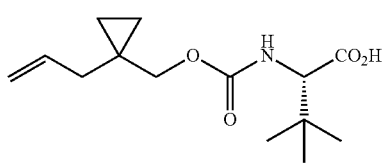

SM-3j
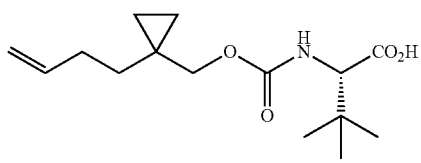

SM-3k
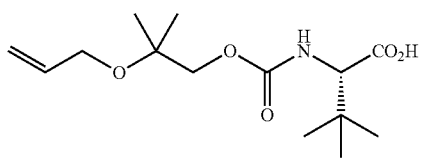

SM-3m
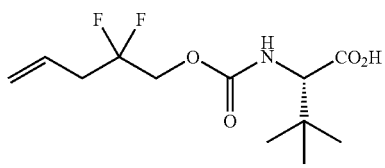

Scheme 3 shown below gives the example of the preparation of the new compounds IIIa-IIIb with novel structures and properties, in which the intermediates IVa-Ivb (V-1 to V-12) together with SM-3a-SM-3m were coupled with the products (3a-3m) from Scheme 2 respectively by an amidation reaction using CDI or EDCI in the organic solvents (dichloromethane, THF or N,N-dimethylformamide), leading to the compounds IIIa-IIIb (4a-4j) with different kinds of heterocycles as shown in Structural Figure 4 in the invention.

Scheme 3:

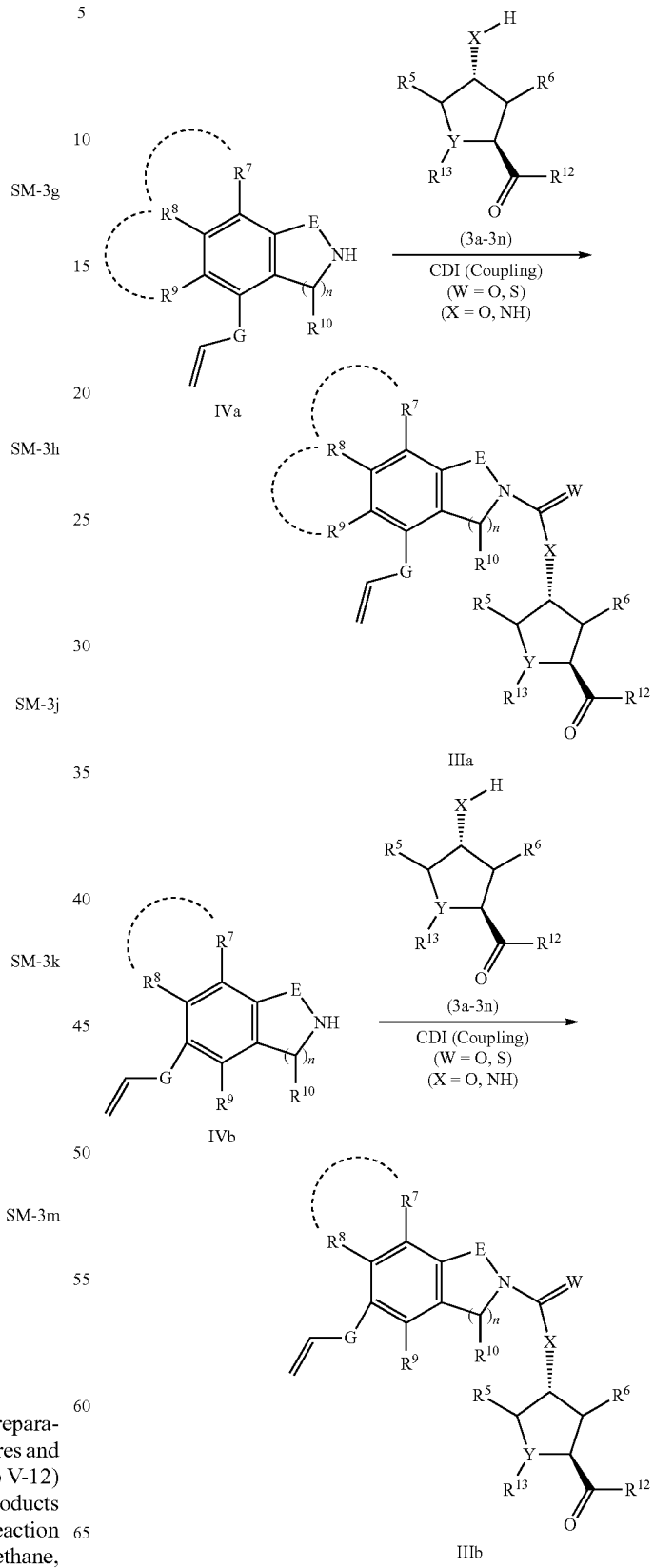

Wherein, $R^{13}$ shown above is the same as the definition of $R^{13}$ in summary of the present invention, n=1 or 2.
Structural Figure 4:
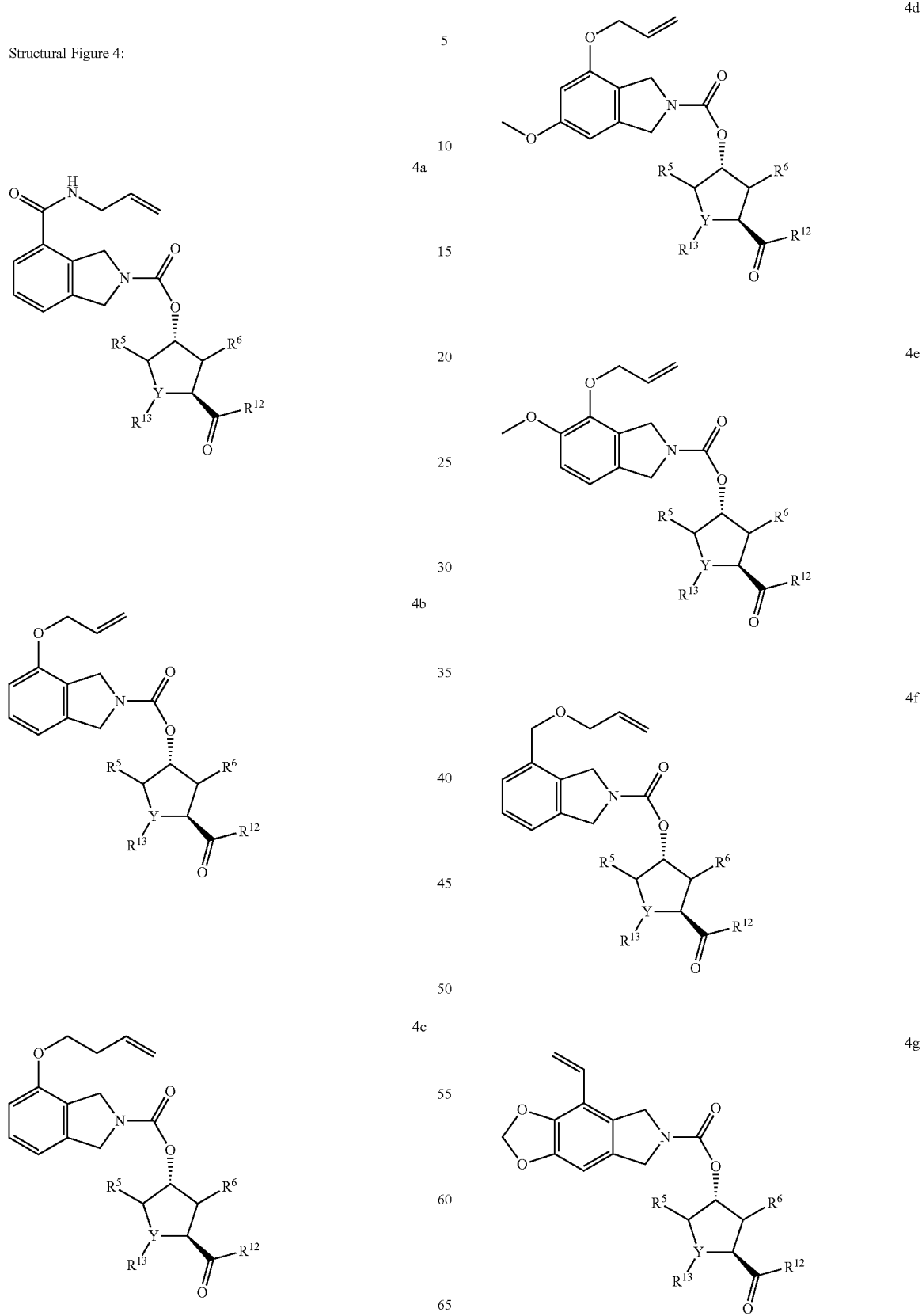

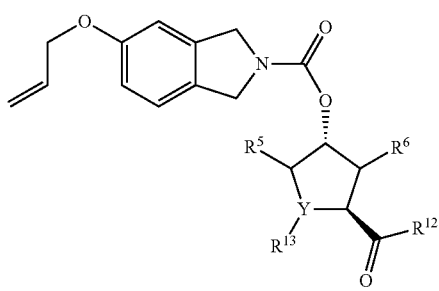
4h

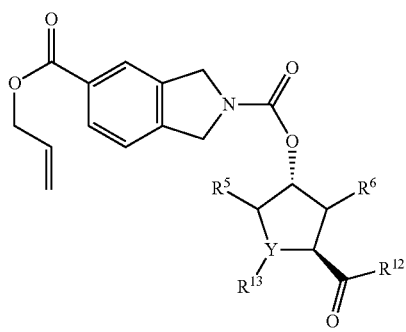
4j

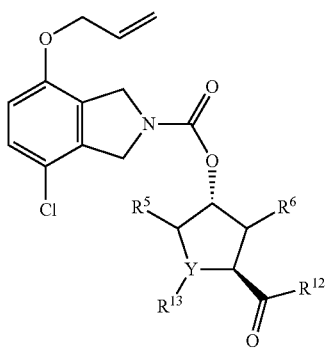
4k

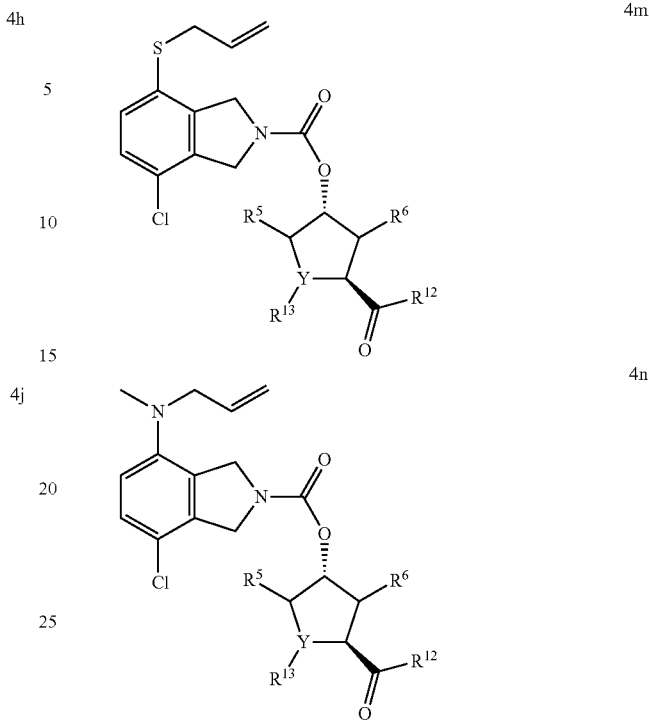
4m

4n

Wherein, $R^{13}$ is selected from H, Boc or amino acid derivative $R^{13}$—OH in Structural Figure 3.

In order to optimize a feasible synthetic method, when "Y" in IIIa-IIIb is the nitrogen atom, we use another synthetic way shown in Schemes 4a and 4b in the invention to synthesize compounds IIIa-IIIb. Therefore, IVa, IVb and SM-4 were first subjected to the coupling reaction by using CDI to obtain the intermediates (4aa-4an) respectively, followed by the cleavage of the protecting group Boc under the acidic treatment (HCl or TFA), to furnish the intermediates 4-A and 4-B (4ba-4bn) respectively. The obtained intermediates 4-A and 4-B were again subjected to an coupling amidation reaction respectively by using CDI or EDCI in the organic solvents (dichloromethane, THF or N,N-dimethyl formamide) to offer compounds IIIa-IIIb (4a-4n) with different kinds of heterocyclic structure as shown in Structural Figure 4 in the invention.

Scheme 4a:

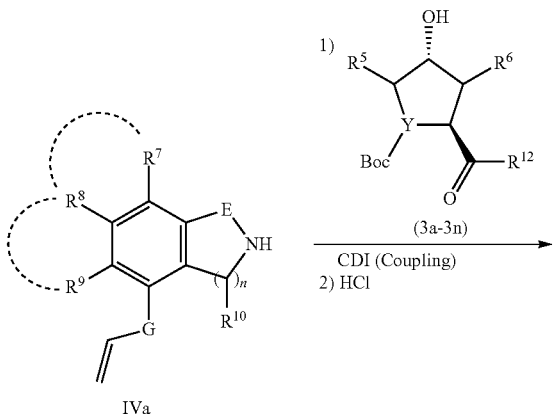

-continued
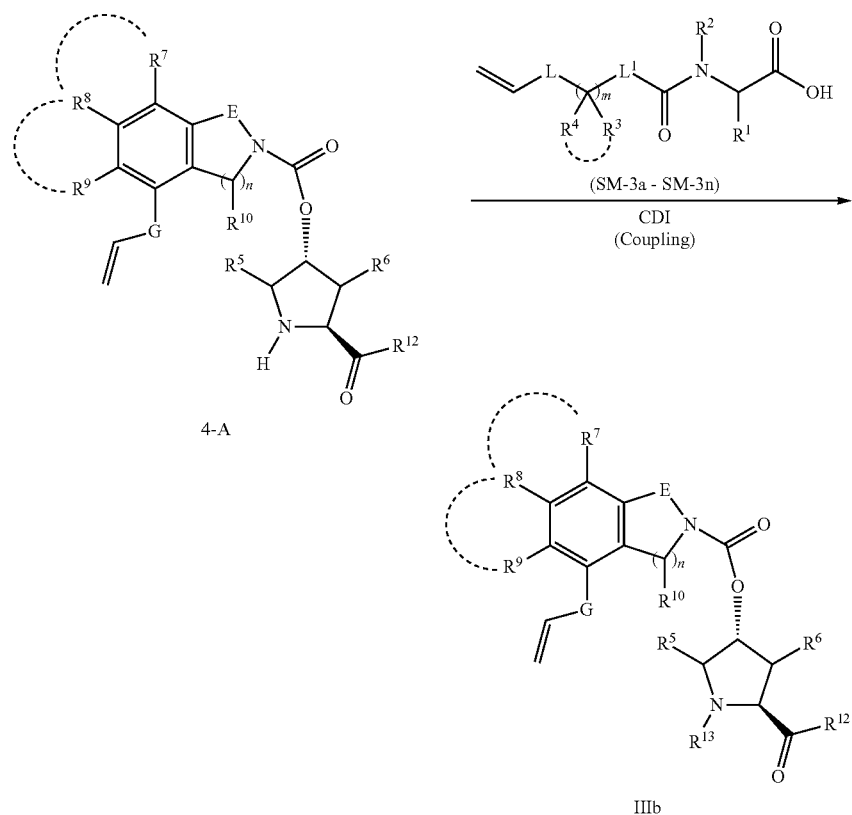
Scheme 4b:
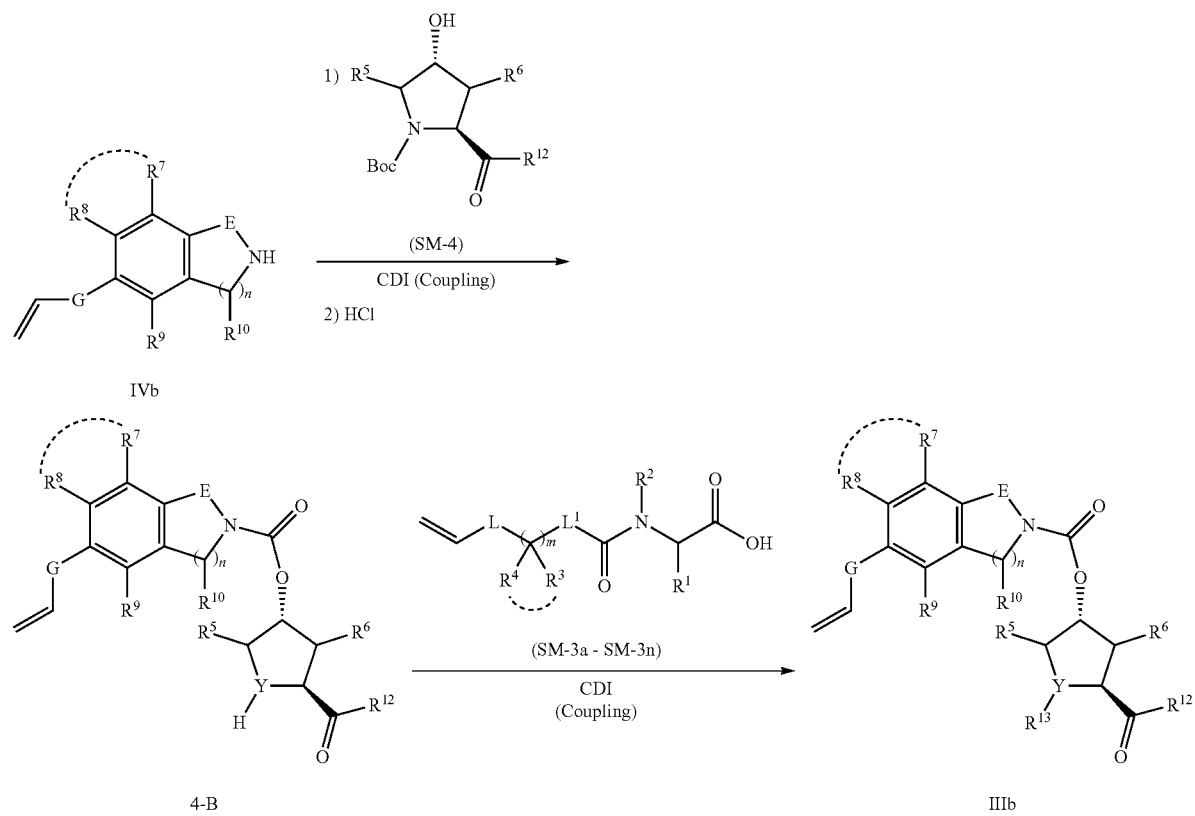

Wherein, $R^{13}$ group is each selected from the amino acid derivatives $R^{13}$—OH shown in Structural Figure 3. According to Scheme 4a and 4b shown above, Compounds V (V-1-V-9) were reacted with the reagents SM-4a ($R^5$, $R^6$=H; $R^{12}$=OMe) to furnish a varieties of heterocyclic intermediates 4A-4B (4aa-4an and 4ba-4bn), which were shown in Structural Figures 5a and 5b as below:
Structural Figure 5a:
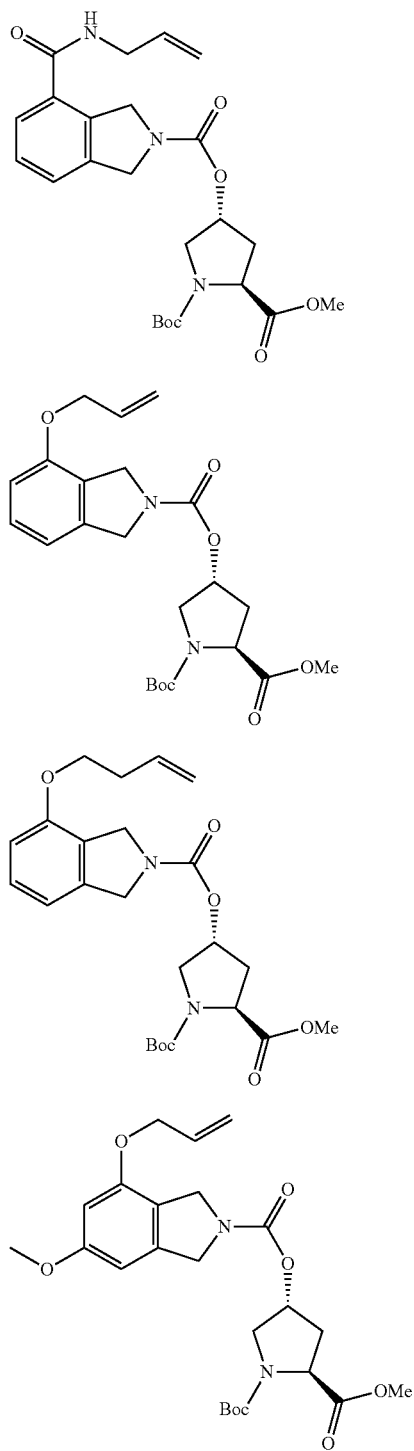
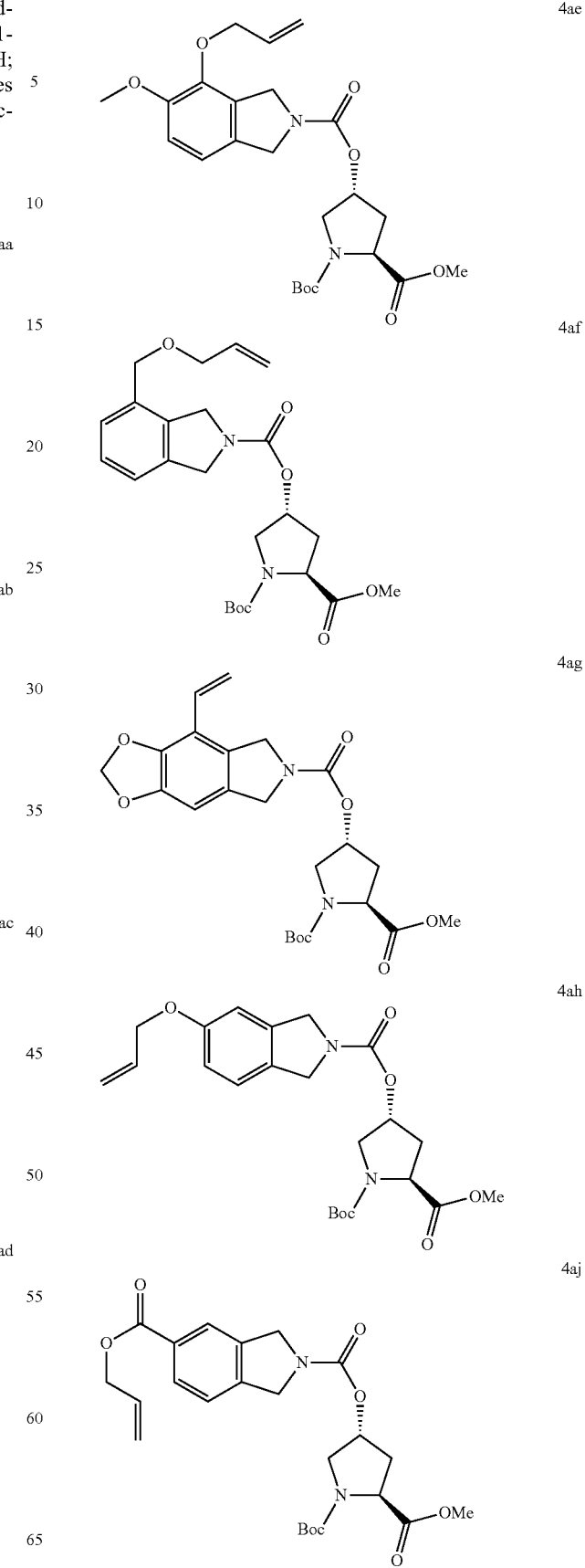

-continued
4ak
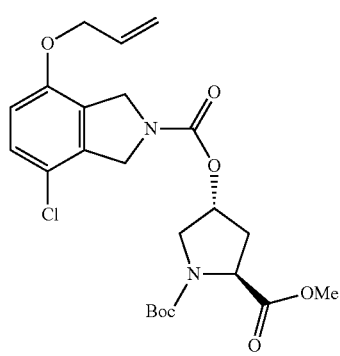
4am
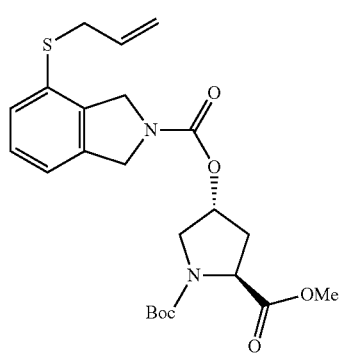
4an
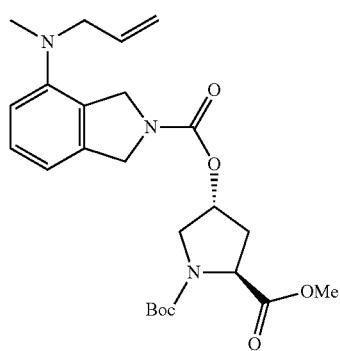
Structural Figure 5b:
4ba
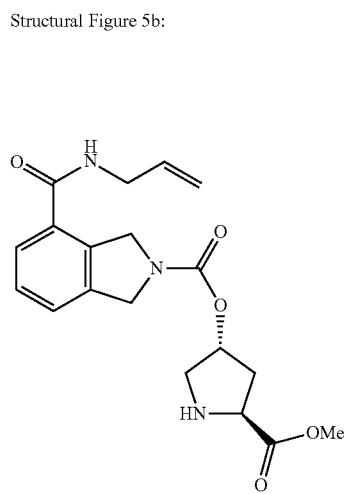
-continued
4bb
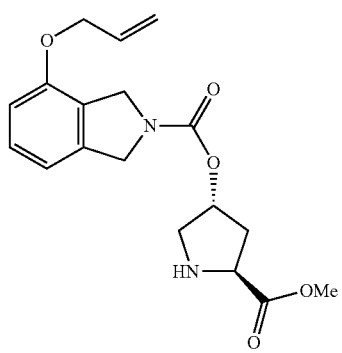
4bc
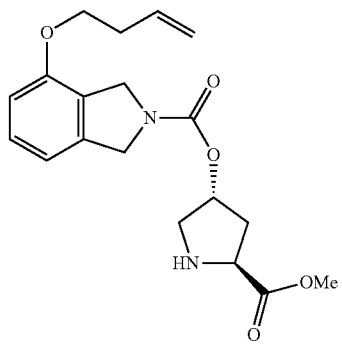
4bd
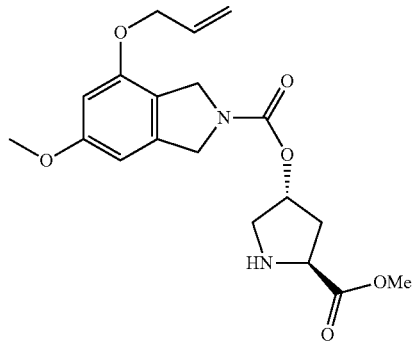
4be
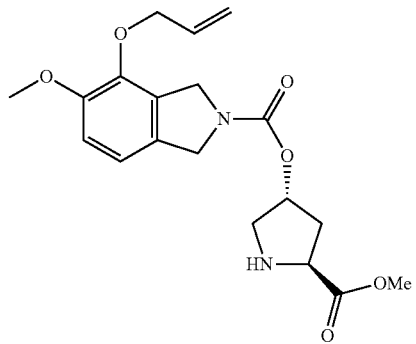

-continued

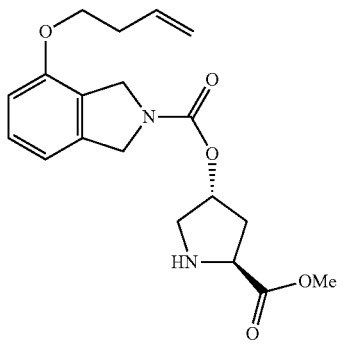
4bf

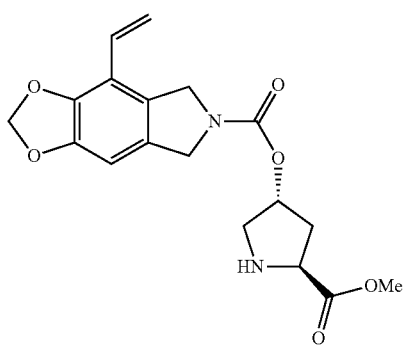
4bg

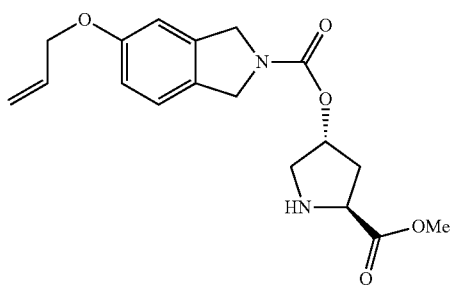
4bh

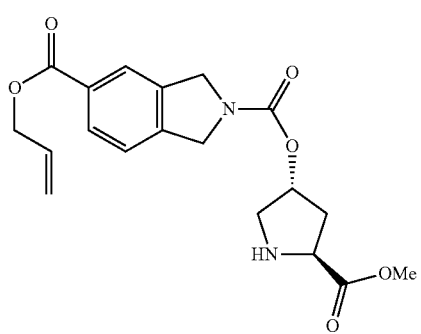
4bj

-continued

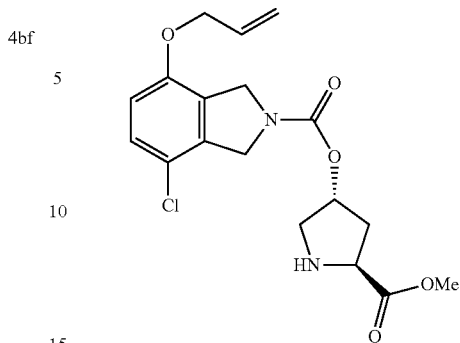
4bj

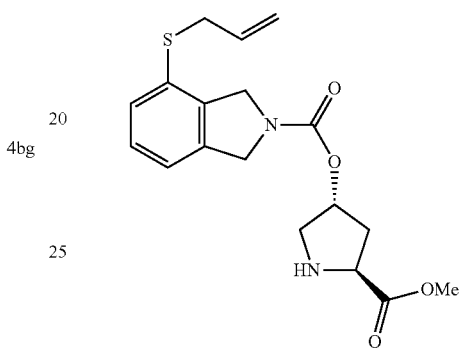
4bj

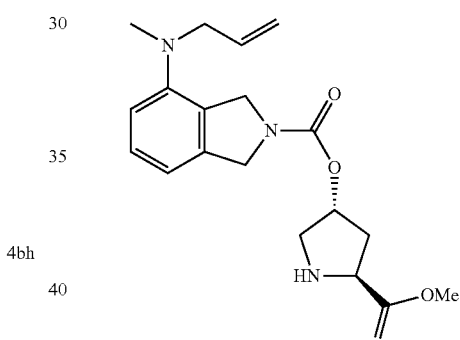
4bn

After the key heterocyclic compounds IIIa-IIIb (i.e., 3a-3n) in the present invention were synthesized according to Scheme 1-4 shown above, the following synthetic schemes (Scheme 5a-5d) were designed for the purpose of structural and functional optimization and innovation. Therefore, the diene compounds (IIIa or IIIb) obtained from Scheme 4a-4b were subjected to the Ring Closure Metathesis reaction (RCM, 0-100) respectively by using RCM catalysts (such as 0.1-5% mol of Zhan catalyst or Grubbs catalyst, etc) in anhydrous organic solvents (such as dichloromethane, dichloroethane or toluene) to afford the 17-25 membered cyclic olefin products 6a-6b (IIa-IIb). The hydrogenation of the olefin bond in 6a-6b (IIa-IIb) with Pd/C catalyst offered products 7a-7b, which was subsequently hydrolysed or methanolized with base (LiOH) followed by acidation to offer the macrocyclic compounds 8a-8b. In the end, the obtained compounds 8a-8b were reacted with various amino acid derivatives SM-5 by amidation with their amino groups in the presence of the coupling reagents (i.e., EDCI or HATU) at 0-80, furnishing the final novel macro-heterocyclic compounds Ia-Ib (such as compounds 15a-15cd in Structural Figure 9). The details of reaction procedure and structural characterization for each compound were shown in the experimental examples, respectively.

Scheme 5a:
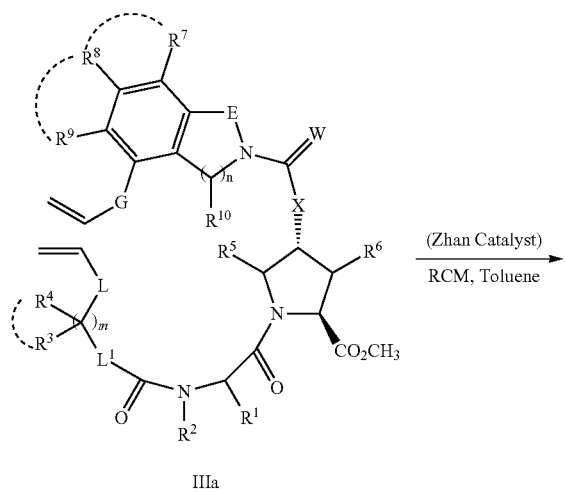
IIIa
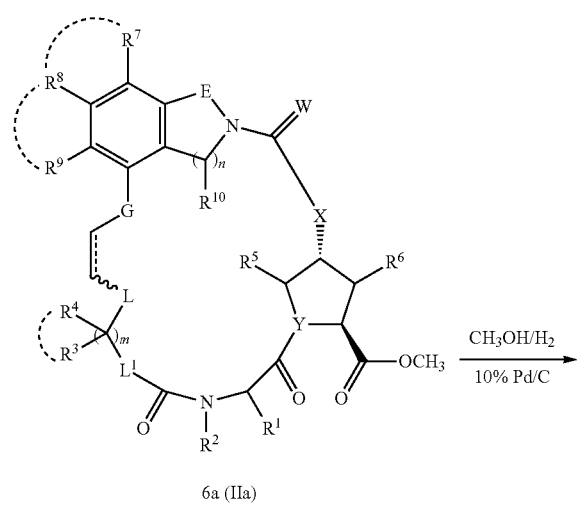
6a (IIa)
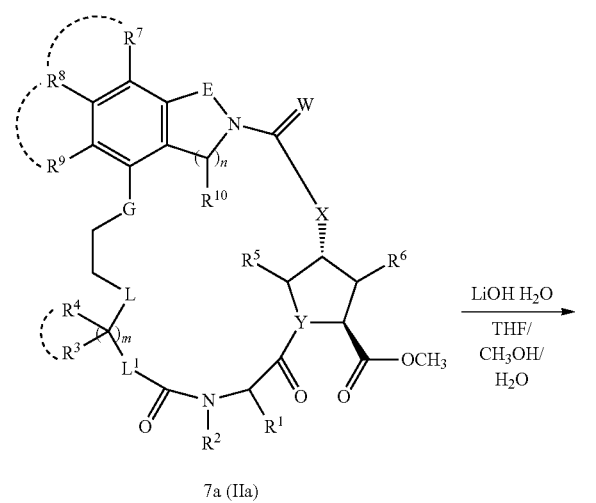
7a (IIa)
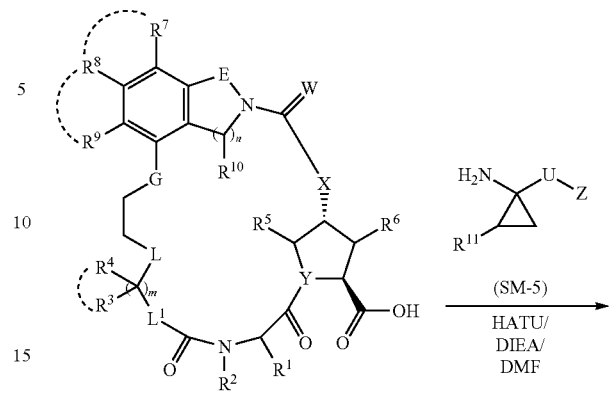
8a (IIa)
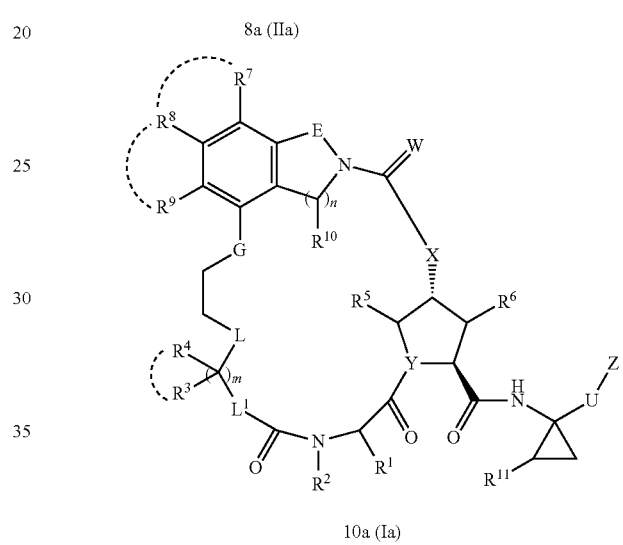
10a (Ia)
Scheme 5b:
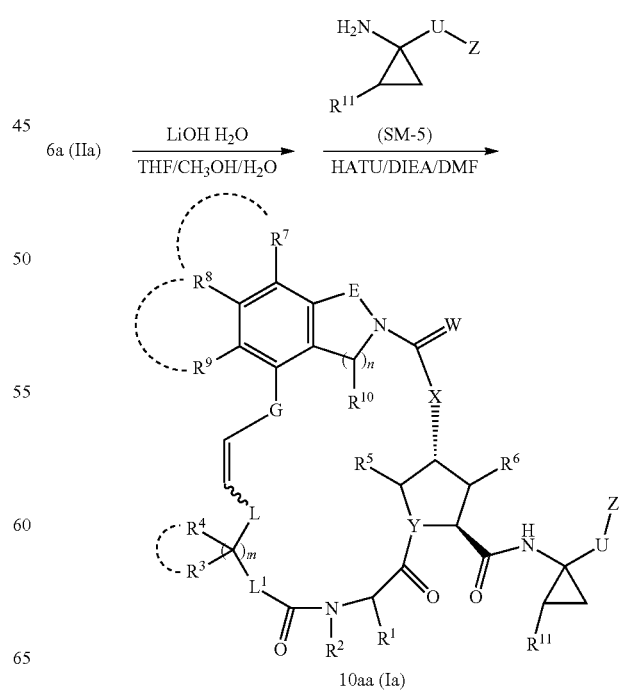
10aa (Ia)

Scheme 5c:
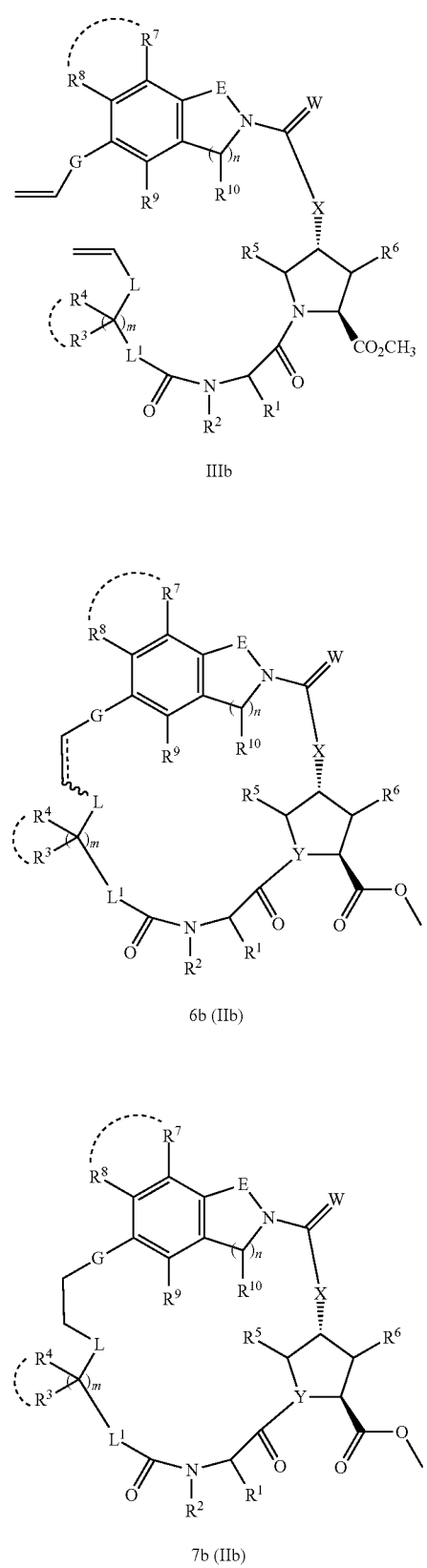
Scheme 5d:
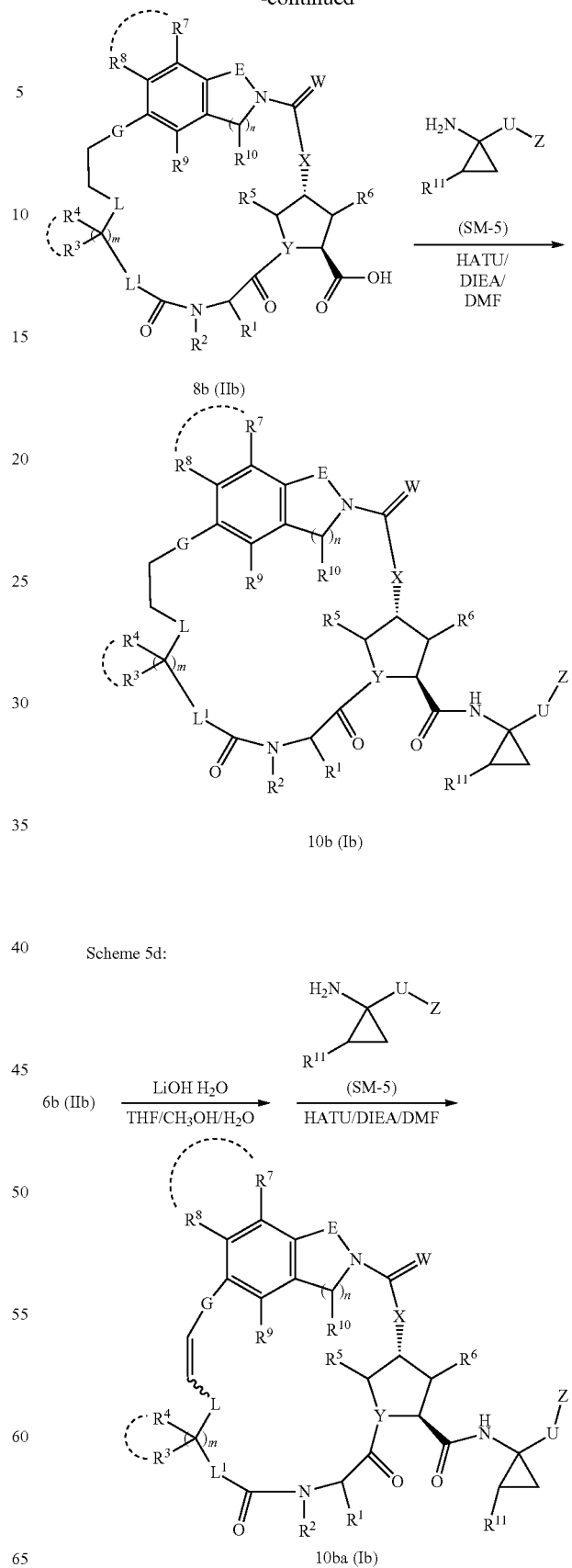

In Scheme 5a-5d, the desired amino acid derivatives SM-5 were optimally selected from Structural Figure 6 (i.e., SM-5a, SM-5b) as below:

Structural FIG. 6

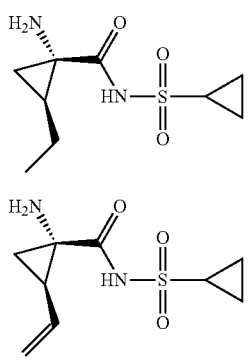

Other than the synthetic scheme described above, in the following synthetic way as shown in Scheme 6a in the invention, compound 4bb (V) is reacted with SM-3j through the amidation reaction in the presence of CDI or EDCI in the organic solvents (dichloromethane, tetrahydrofuran or N,N-dimethylformamide) to give the diene compound IIa, which is then subjected to ring closure metathesis (RCM, 0-100) using RCM catalyst (such as 0.1-10% mol of Zhan catalyst or Grubbs catalyst, etc) in anhydrous organic solvents (such as dichloromethane, dichloroethane or toluene) to afford the macro-heterocyclic compounds 12a (IIa). Hydrogenation of the olefin bond in macrocycle of 12a gives compound 13a, which was subsequently hydrolysed or methanolized with base (LiOH) followed by acidation to give the macrocyclic compound 14a. In the end, the obtained compound 14a were reacted with various amino acid derivatives SM-5a through amidation in the presence of the coupling reagents (i.e., EDCI or HATU) at 0-80 to furnish the final novel macro-heterocyclic compounds 15a (Ia). In Scheme 6b, the obtained intermediate 12a from Scheme 6a is directly subjected to hydrolization with base (LiOH) followed by acidation to afford compound 14b, neglecting the hydrogenation forementioned. Subsequently, the obtained compound 14b were reacted with various amino acid derivatives SM-5a and SM-5b respectively through amidation in the presence of the coupling reagents (i.e., EDCI or HATU) at 0-80 to furnish the final novel macro-heterocyclic compounds 15b and 15c. The details of reaction procedure and structural characterization for each compound were shown in the experimental examples, respectively.

Scheme 6a:

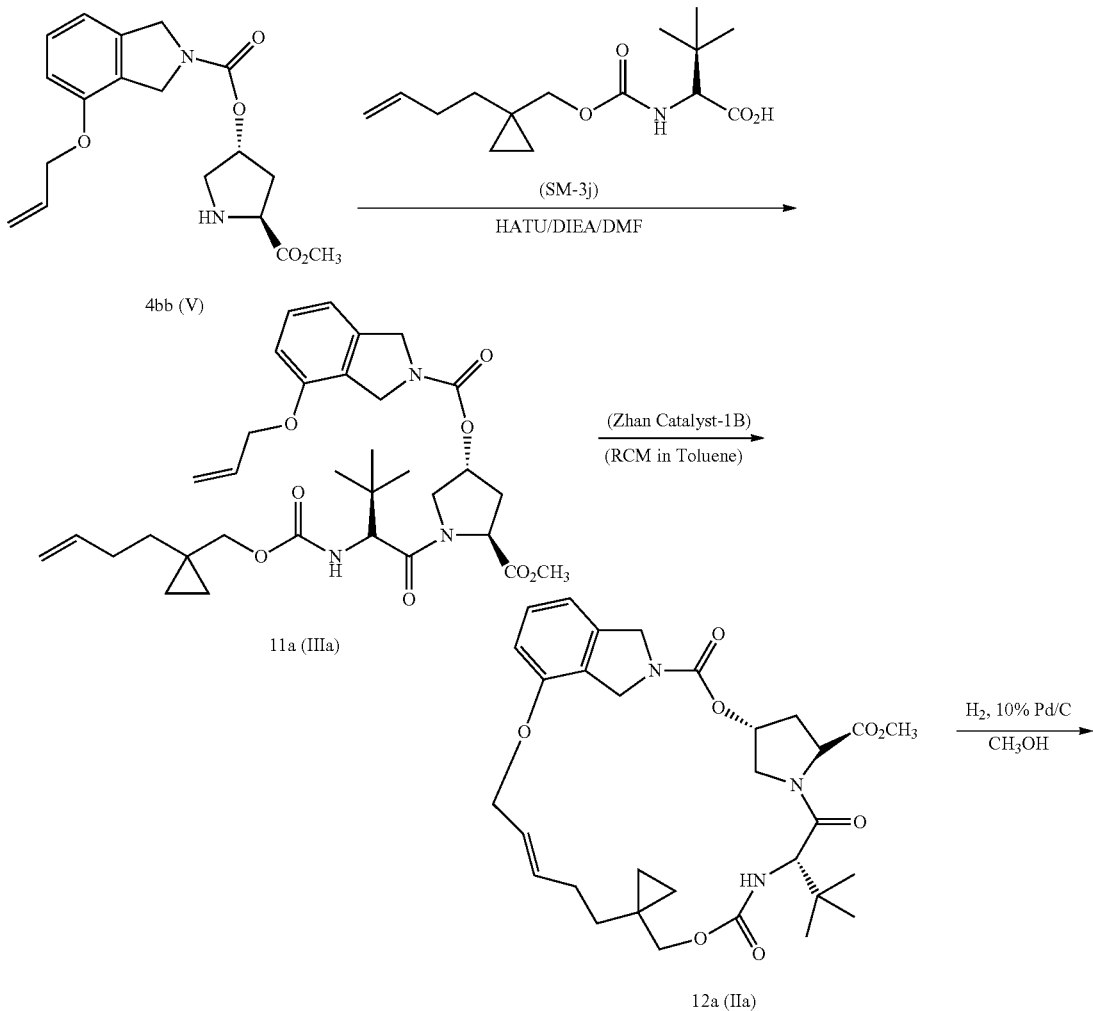

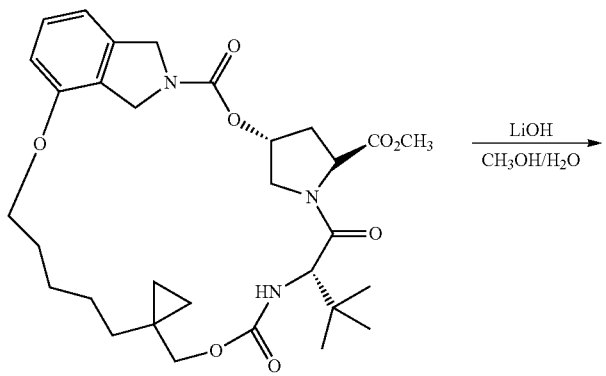
13a (IIa)
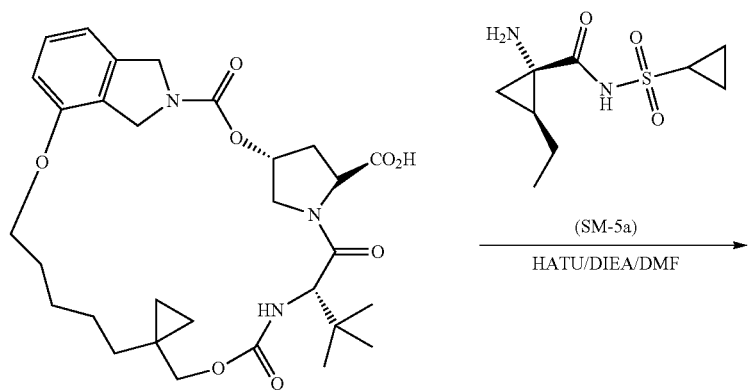
14a (IIa)
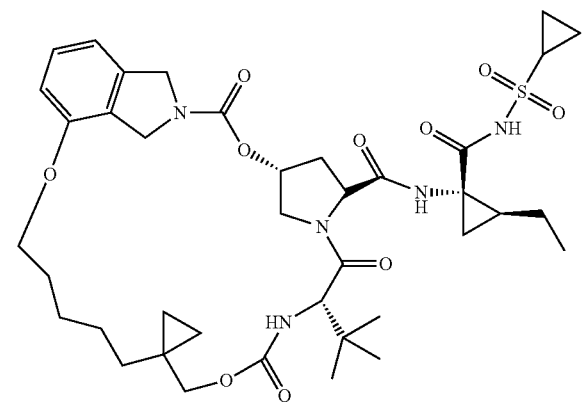
15a (Ia)

Scheme 6b:
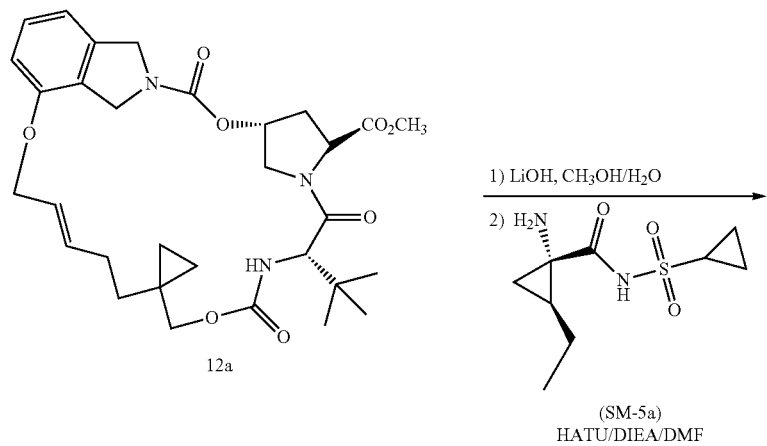
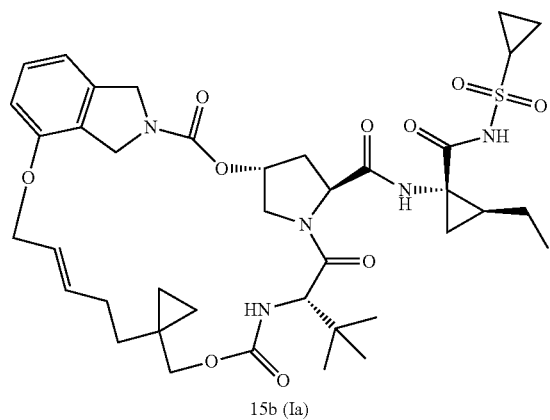
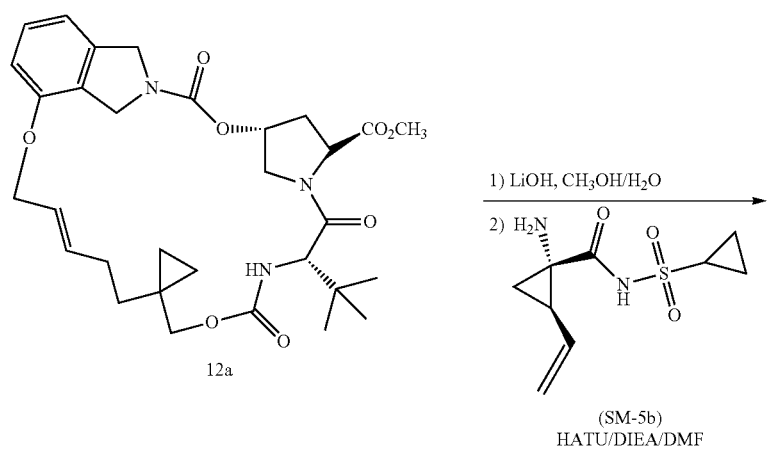

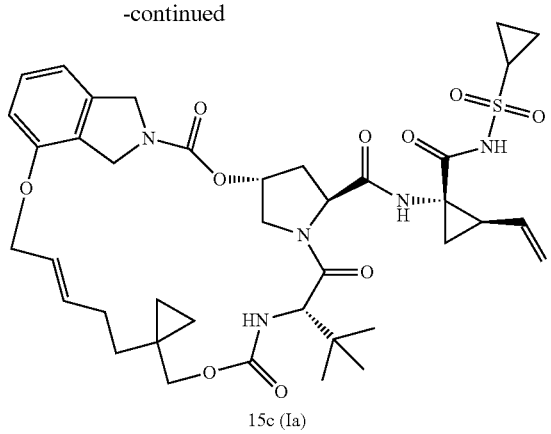

15c (Ia)

Zhan Catalyst-1B used in Ring Closure Metathesis of diene intermediates IIIa-IIIb in Scheme 6 is shown as below:

Structural FIG. 7

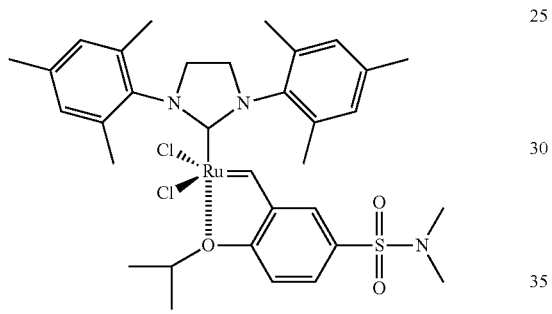

Zhan Catalyst-1B, the patented product of Zannan; Catalogue No. RC-303

Above all, a varieties of macro heterocyclic based intermediates IIa-IIb and final compounds Ia-Ib with different new functional groups were synthesized by multi-step reactions shown in Scheme 5 and 6. In Structural Figures 8 and 9, it is shown that the structure of the novel macro-heterocyclic intermediates IIa-IIb and the final compounds Ia-Ib, which corresponds to compounds 12a-14ba (IIa-IIb) in Structural Figure 8 and compounds 15a-15cd (Ia-Ib) in Structural Figure 9:

Structural Figure 8:

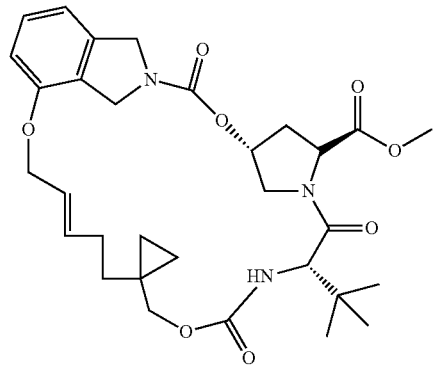

12a

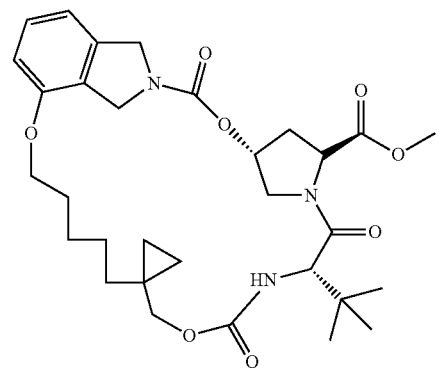

13a

12b

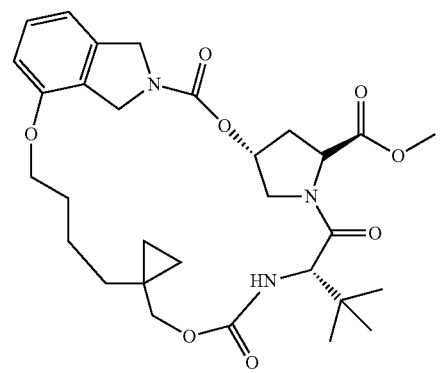

13b

12c
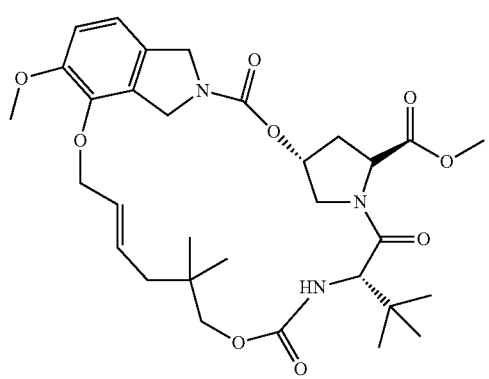
12d
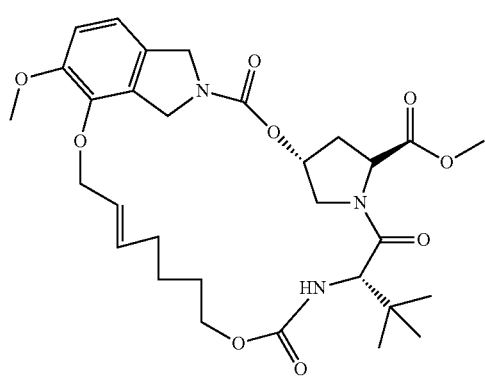
12e
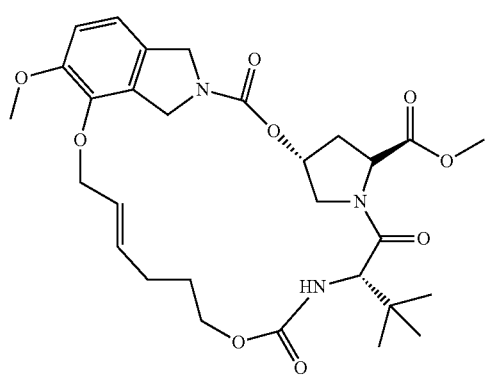
12f
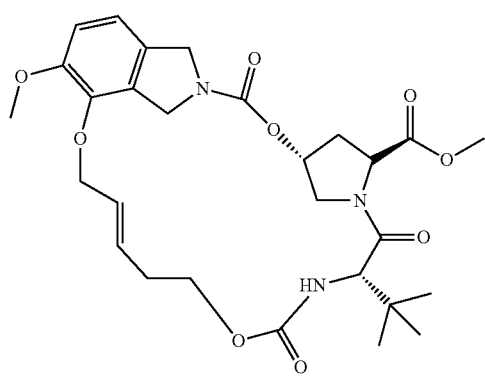
12g
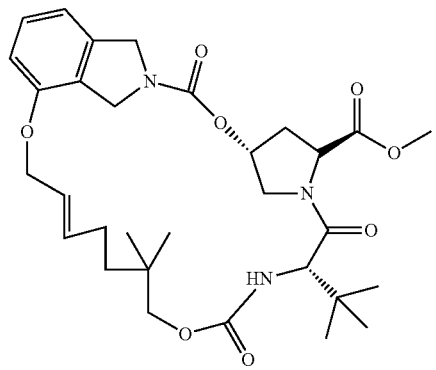
13g
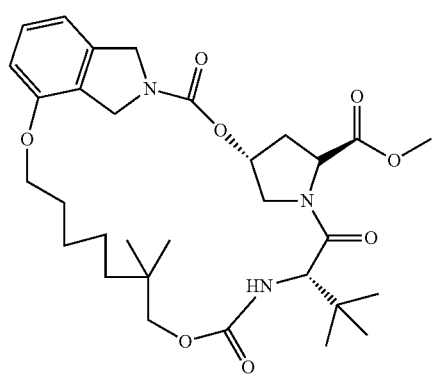
12h
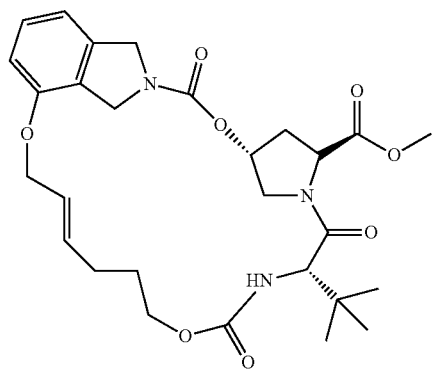
13k
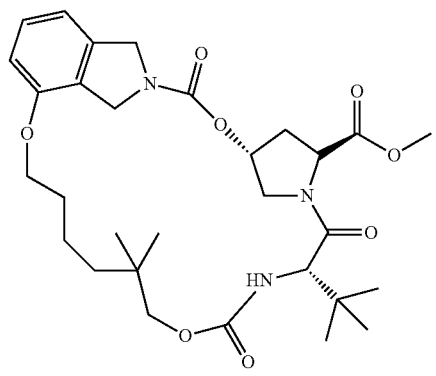

| 163 -continued | 164 -continued |
|---|---|
| 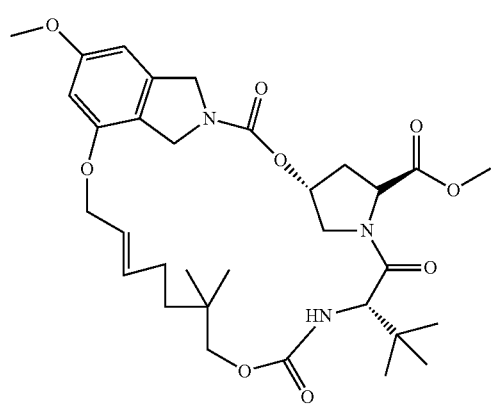 13m | 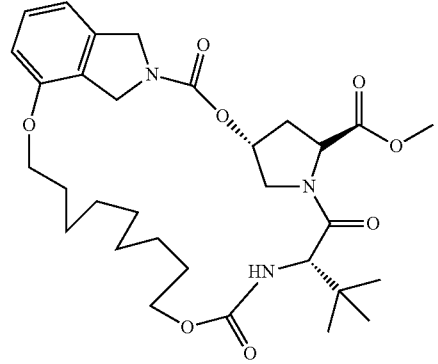 13q |
| 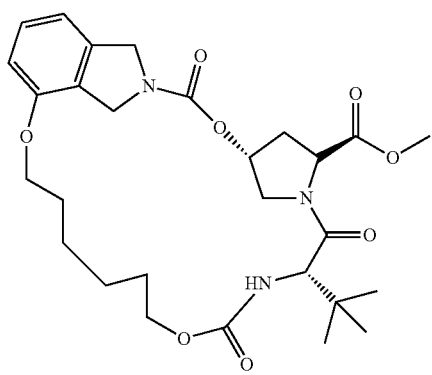 13h | 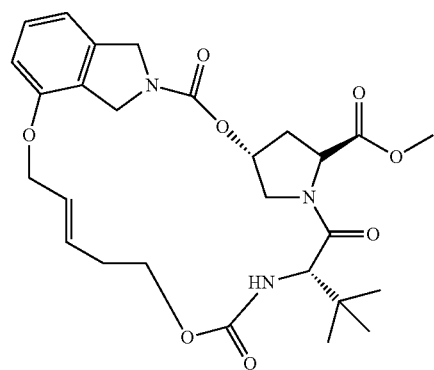 12r |
| 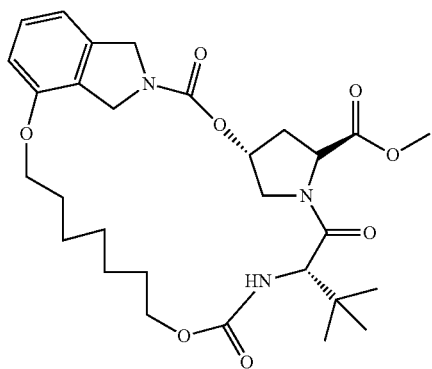 13n | 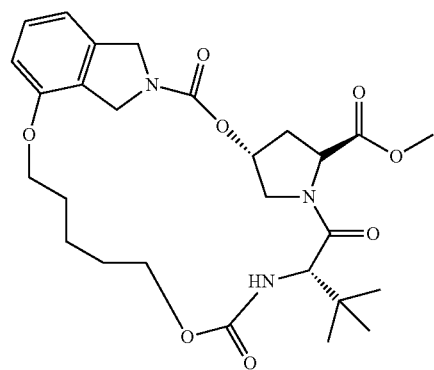 13r |
| 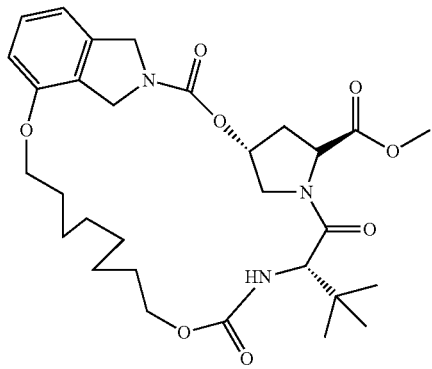 13p | 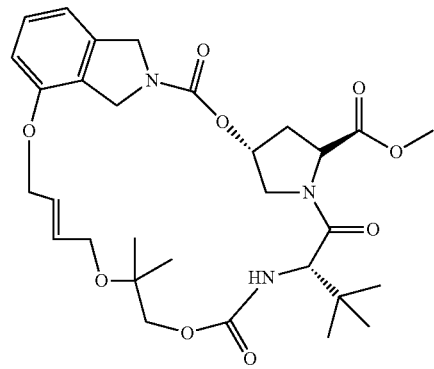 12s |

13s
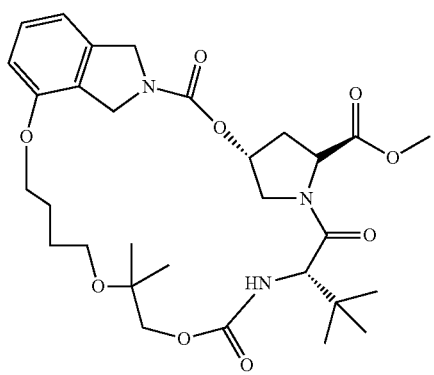
12t
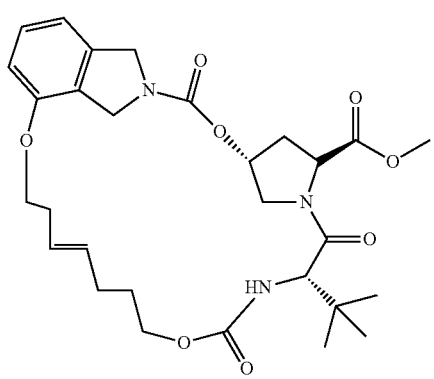
12k
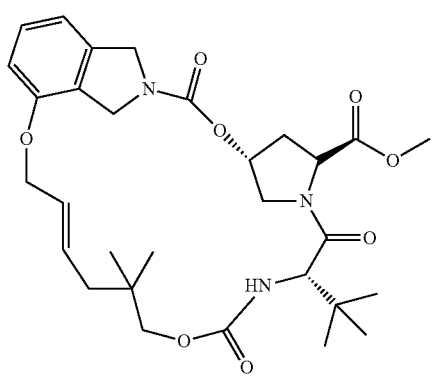
13u
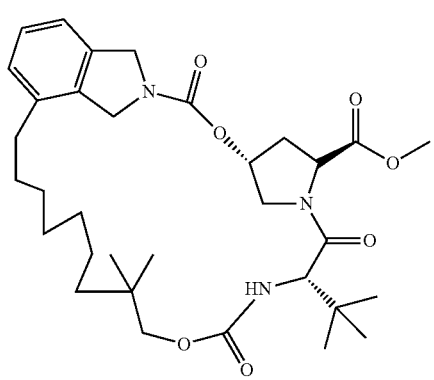
13v
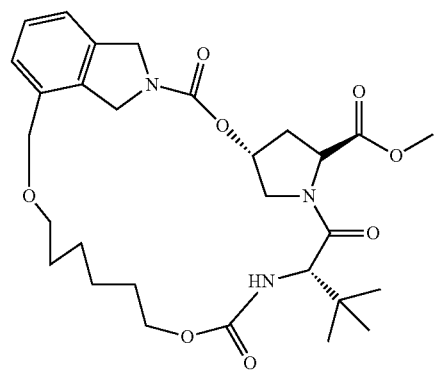
13w
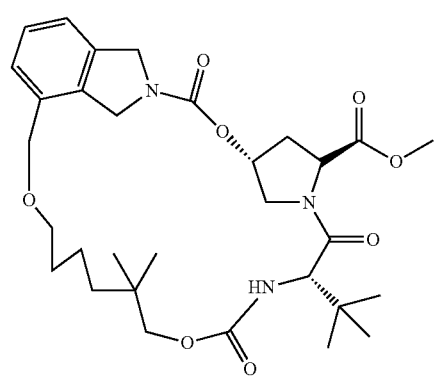
13x
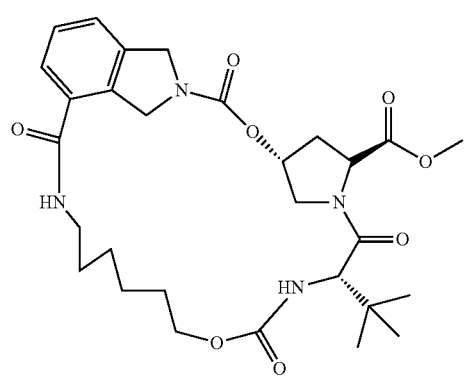
13y
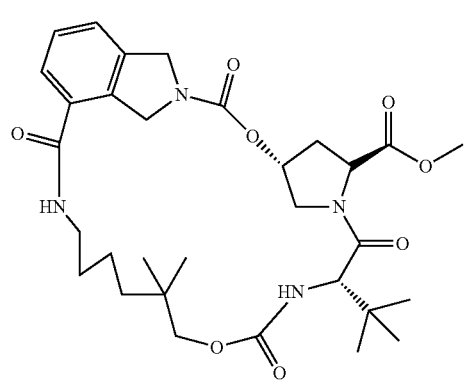

13z
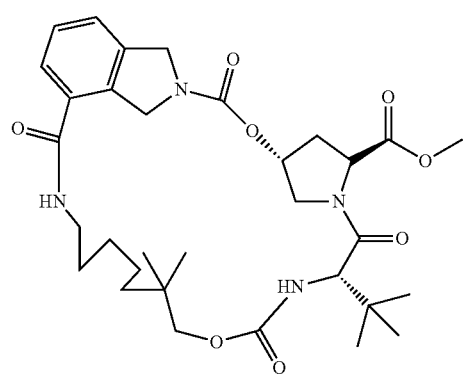
13aa
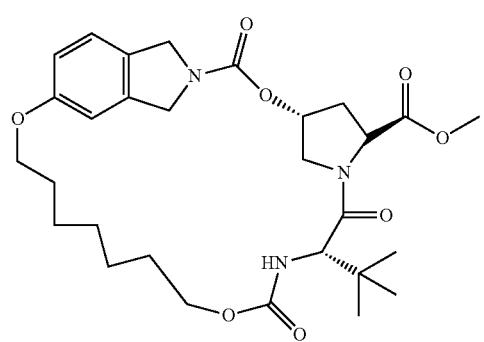
12aa
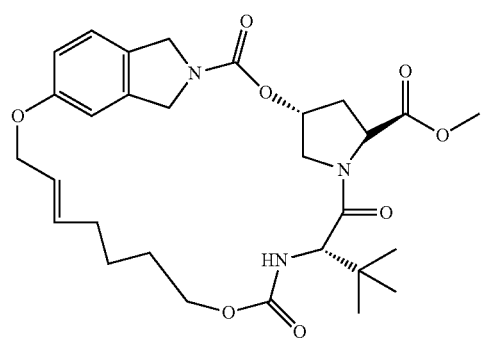
12ab
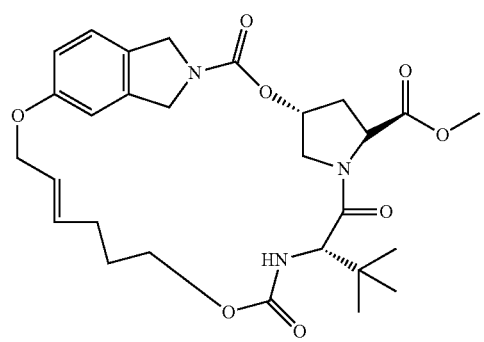
12ac
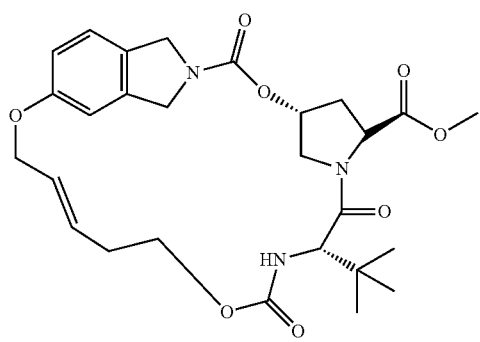
13ad
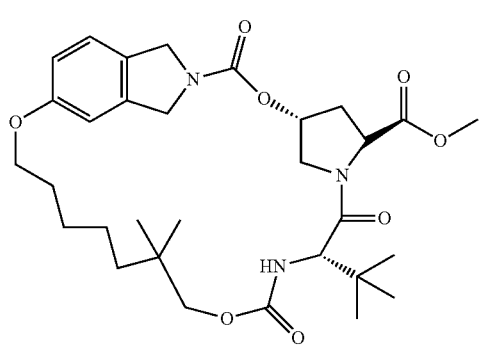
13ae
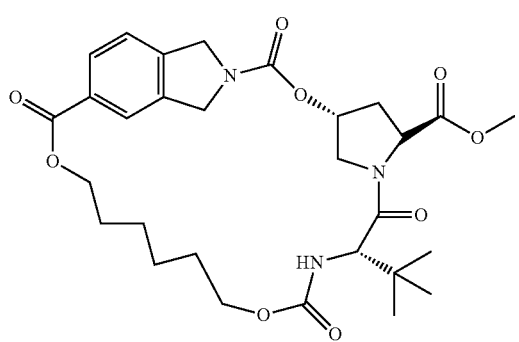
13af
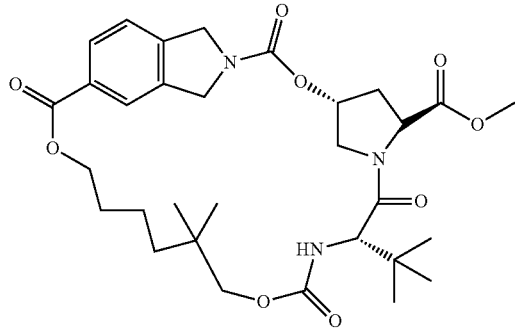

13ag
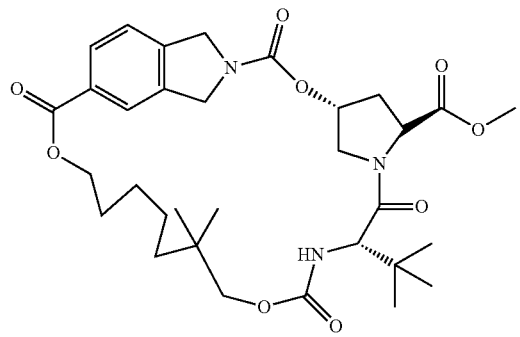
12ah
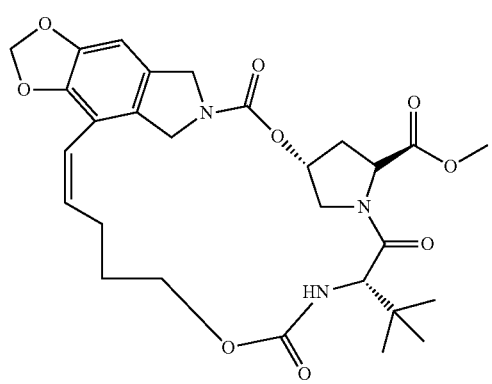
12ak
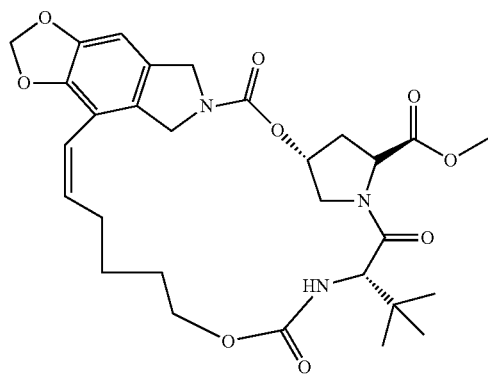
12am
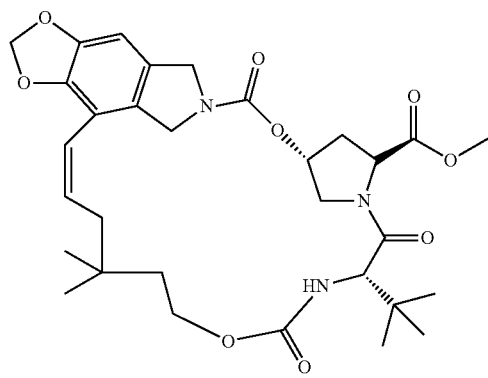
13ak
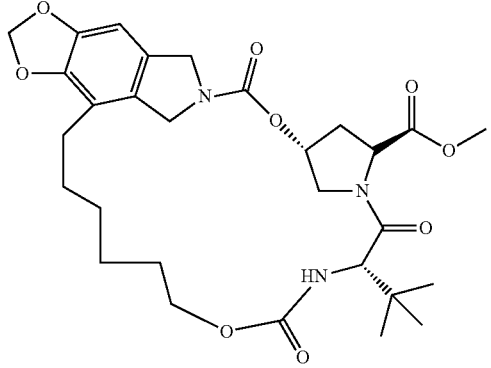
13am
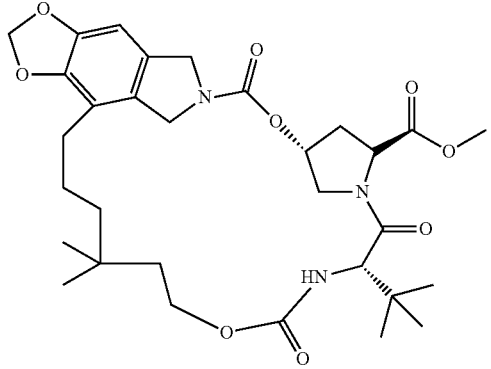
14a-2
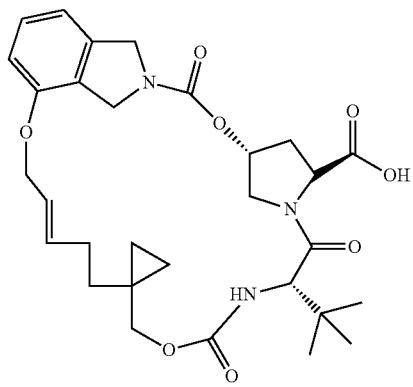
14a
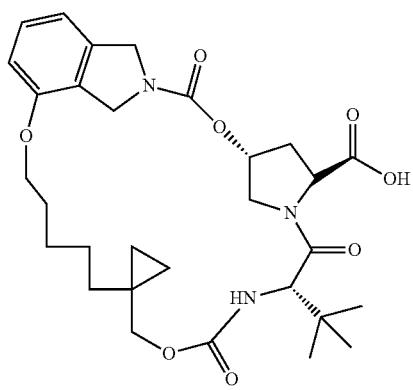

14b-2
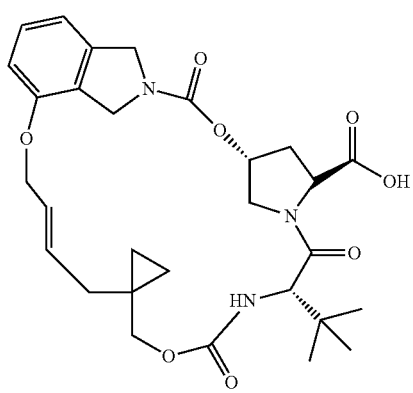
14b
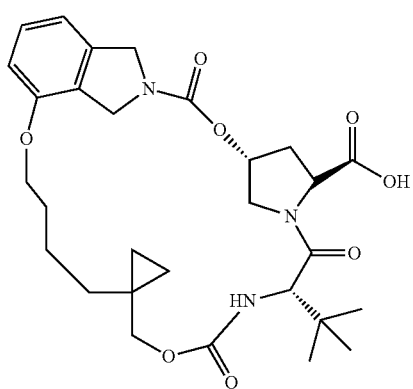
14c-2
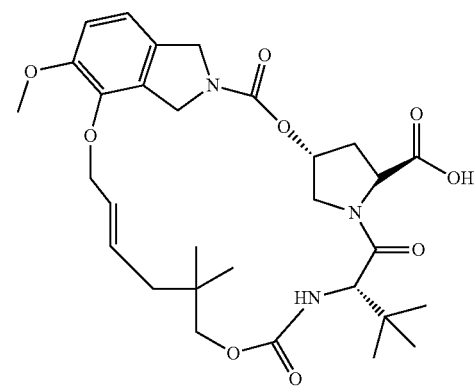
14d-2
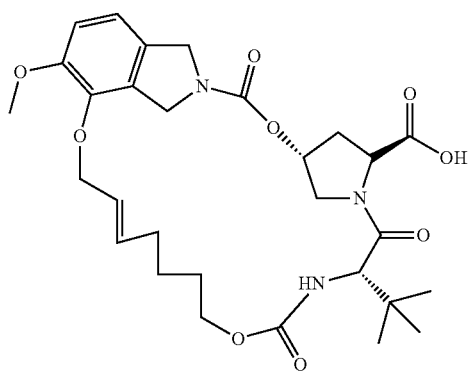
14e-2
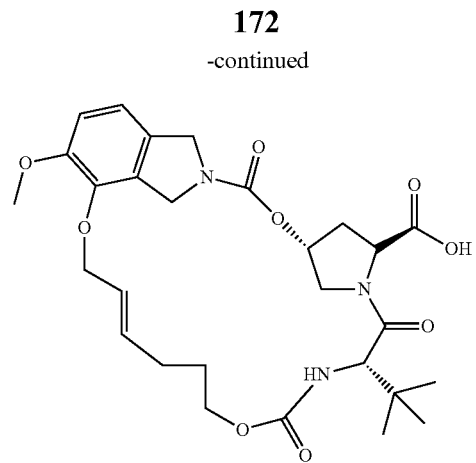
14f-2
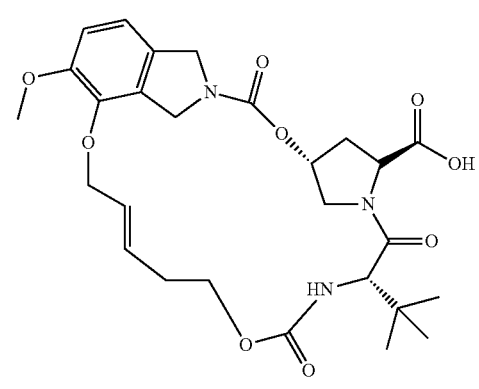
14g-2
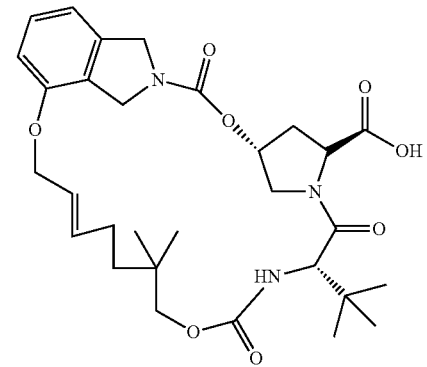
14g
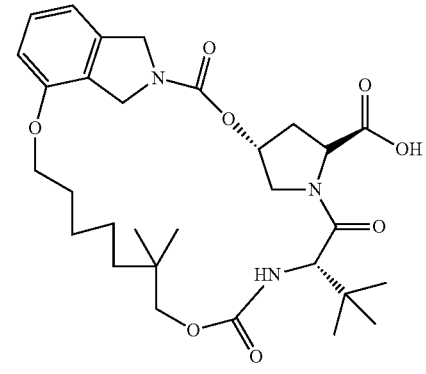

| 14h-2 | 14n |
|---|---|
| 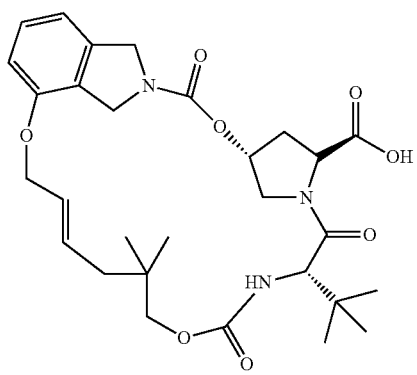 | 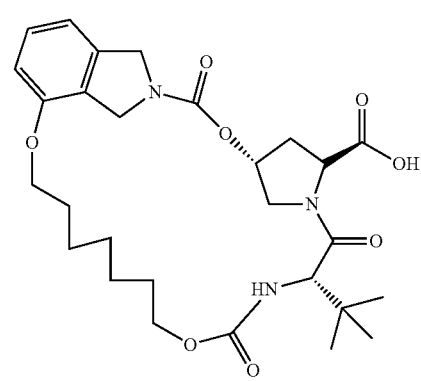 |
| 14k | 14p |
| 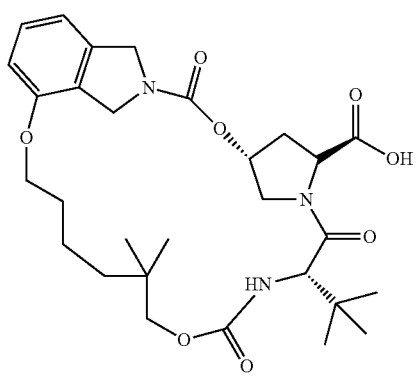 | 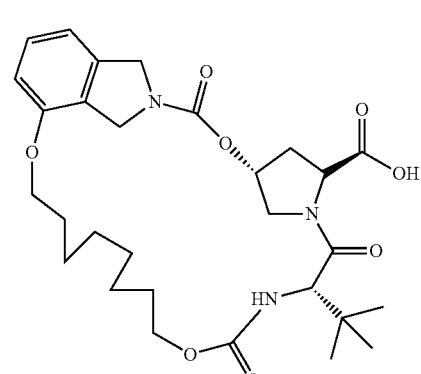 |
| 14m | 14q |
| 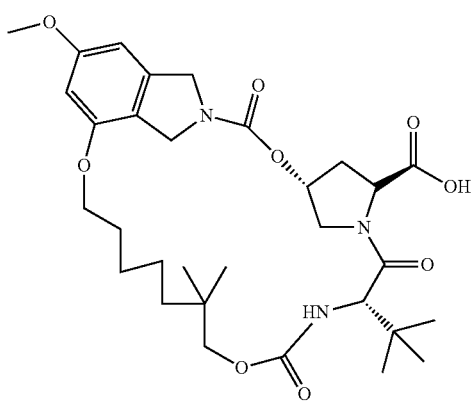 | 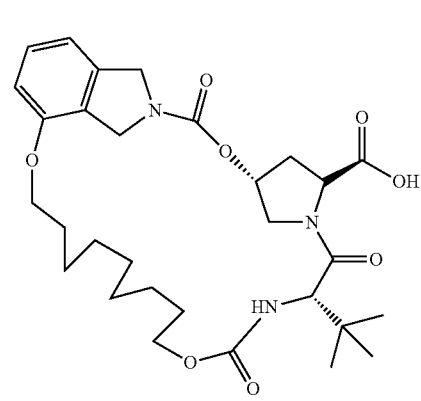 |
| 14h | 14r2 |
| 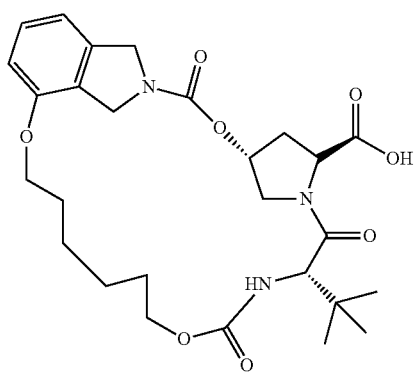 | 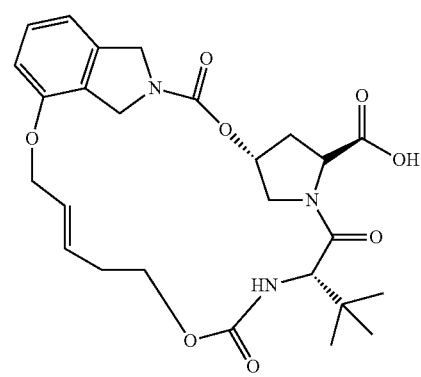 |

14r
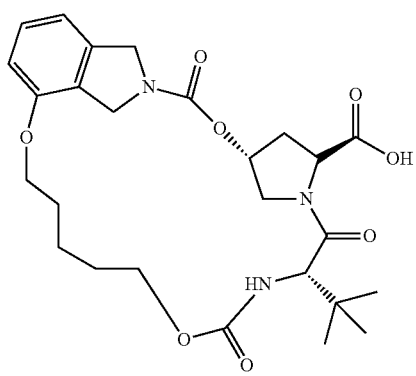
14s-2
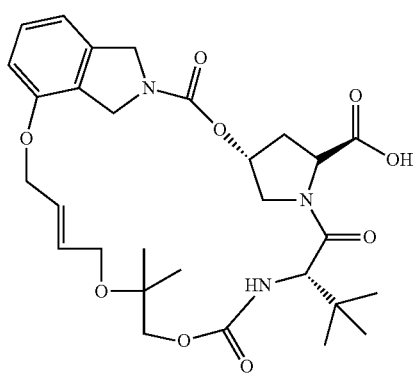
14s
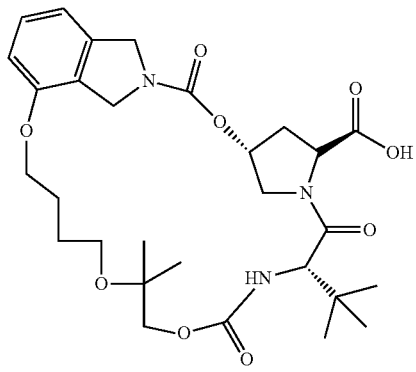
14t-2
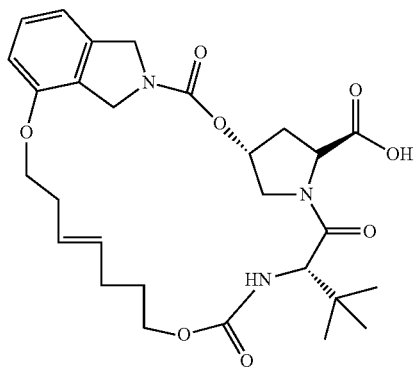
14k-2
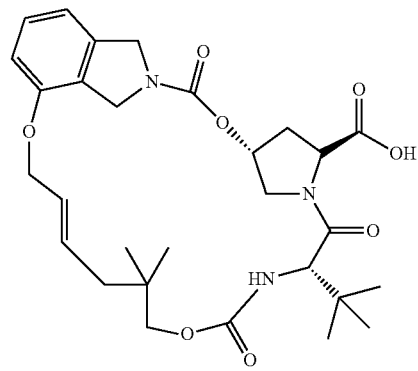
14u
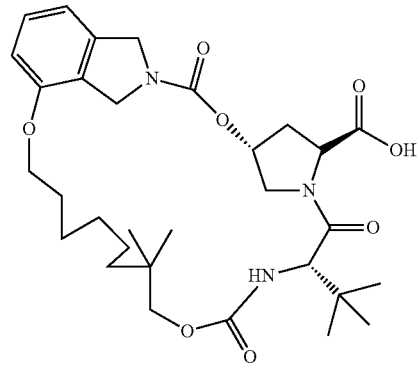
13z
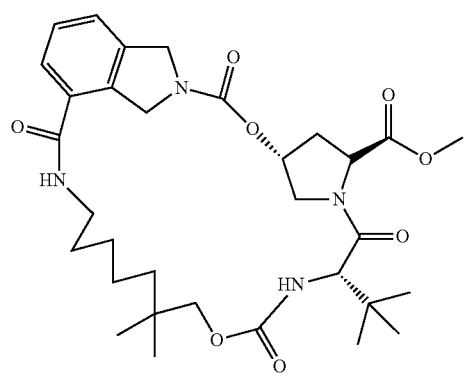
14ah-2
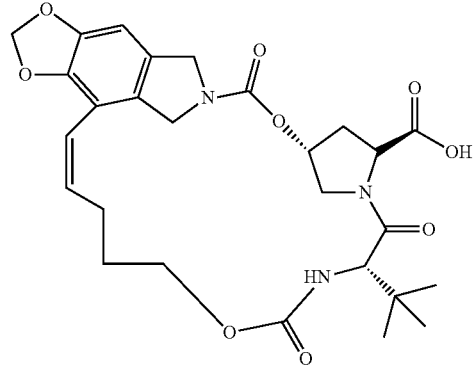

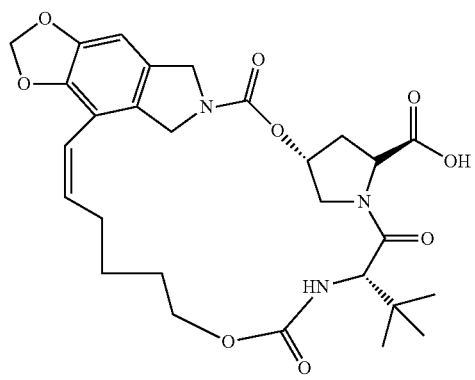
14ak-2
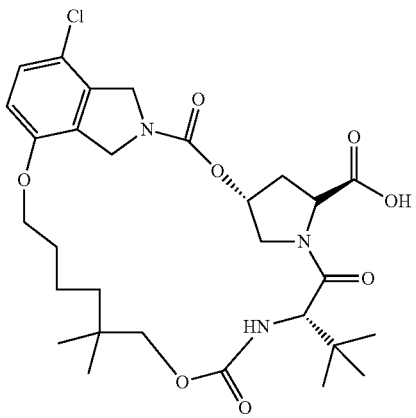
14ax
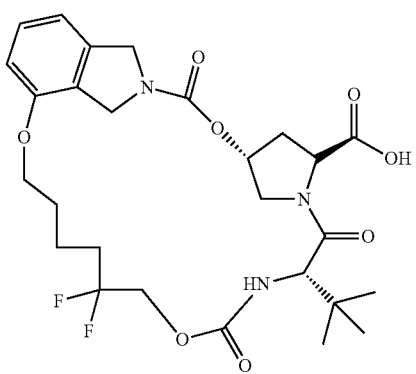
14ba
14am-2
14ac-2
14ak
14am
14ad
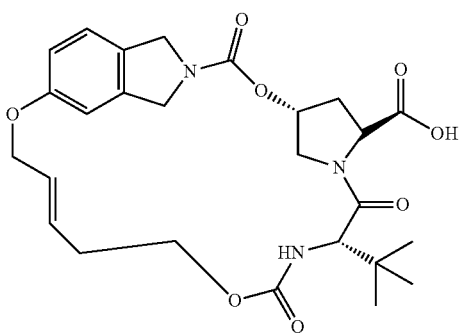
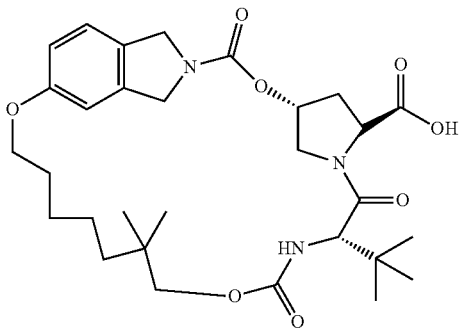

14ae
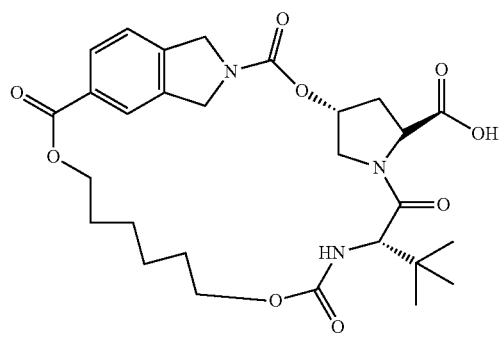
14af
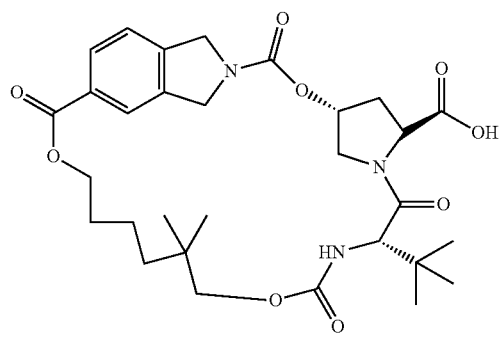
14ag
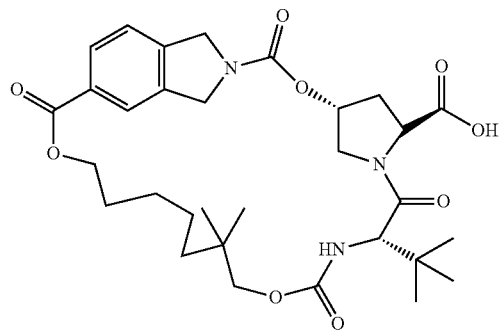
14ah-2
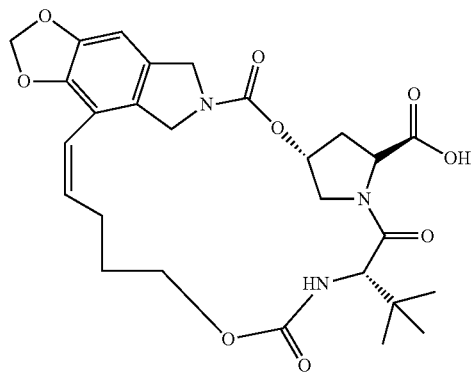
14ak-2
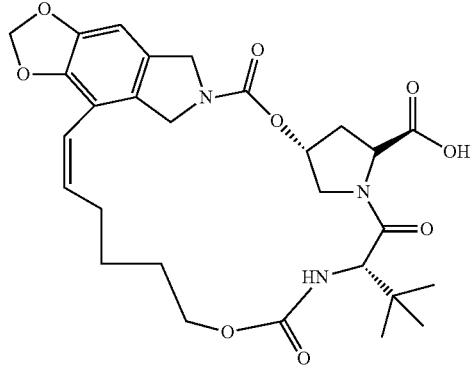
14am-2
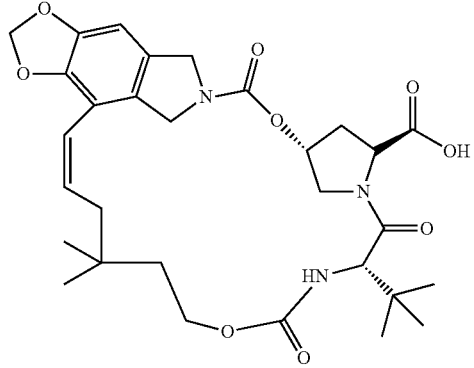
14ak
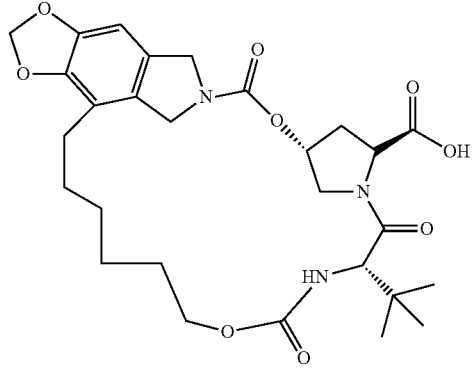
14am
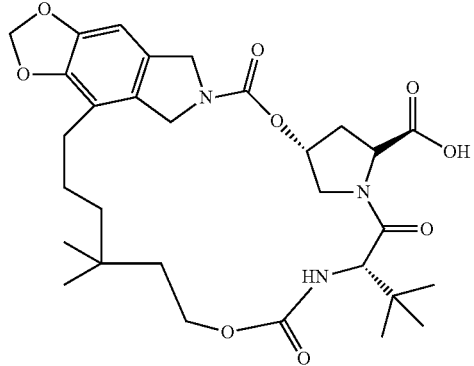

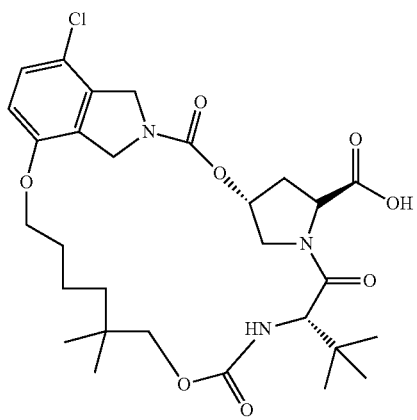
14ax
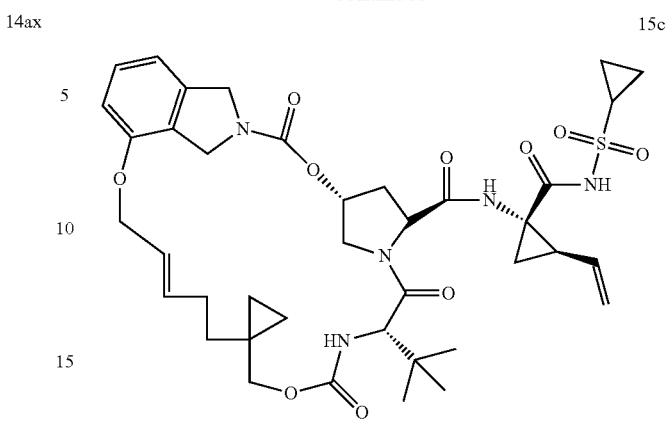
15c
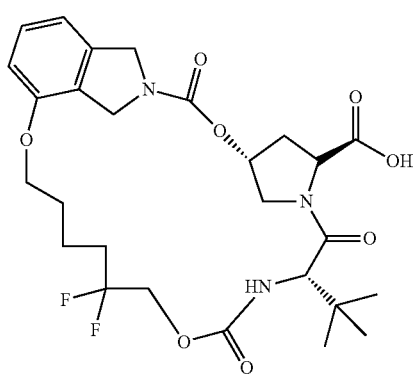
14ba
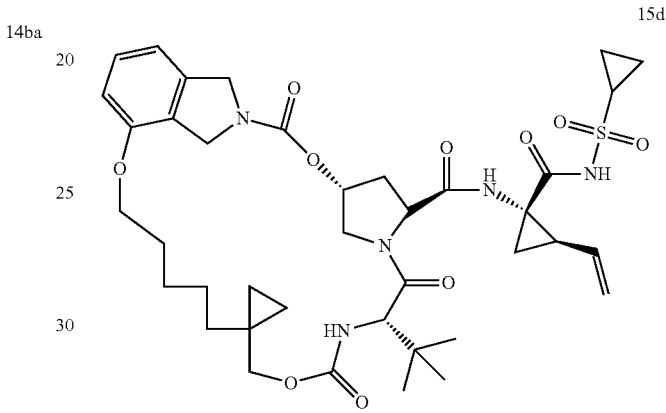
15d
Structural Figure 9:
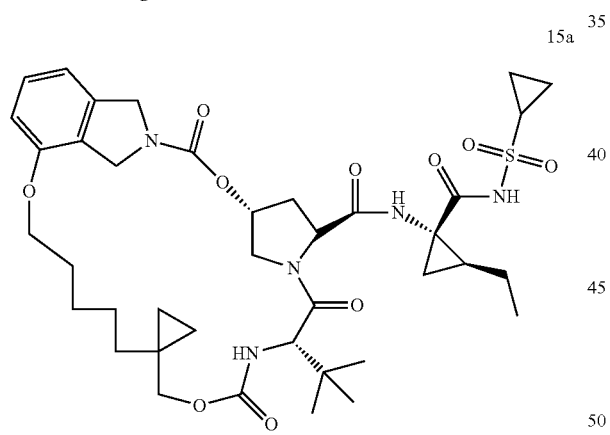
15a
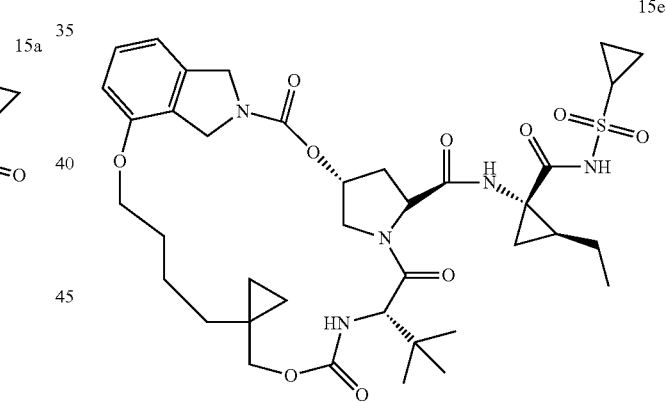
15e
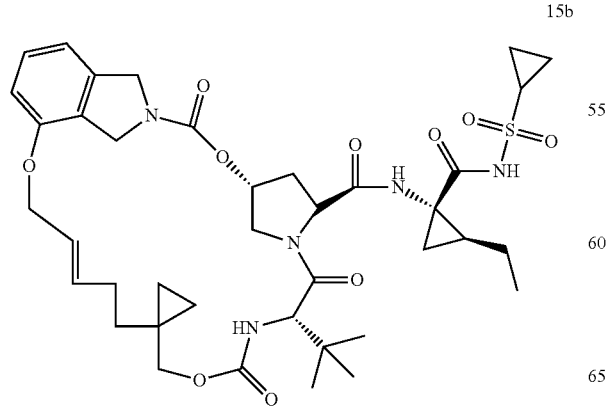
15b
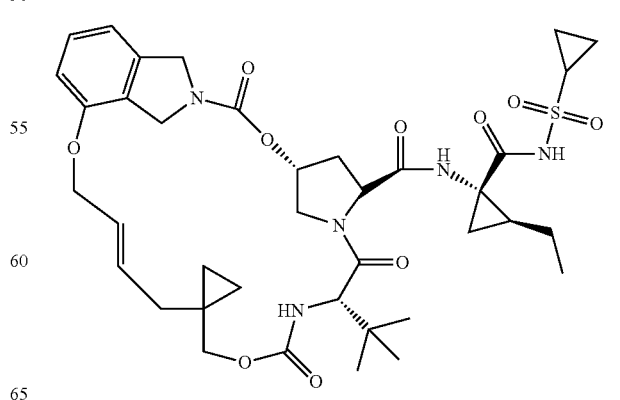
15f 183
-continued
15g
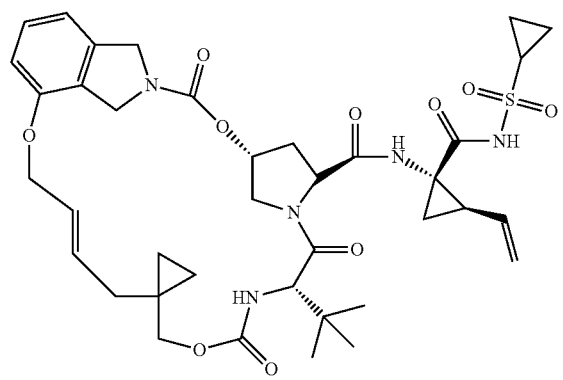
15h
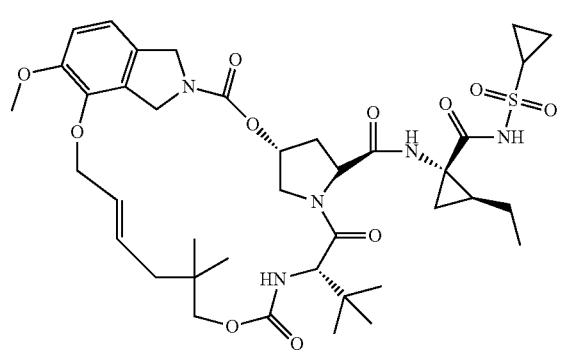
15j
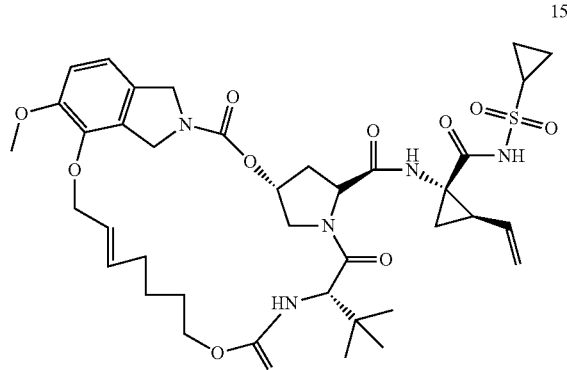
15k
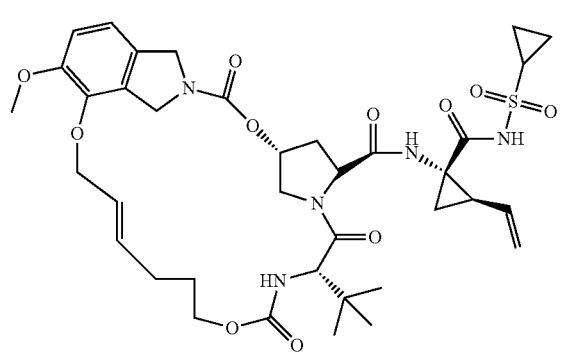
184
-continued
15m
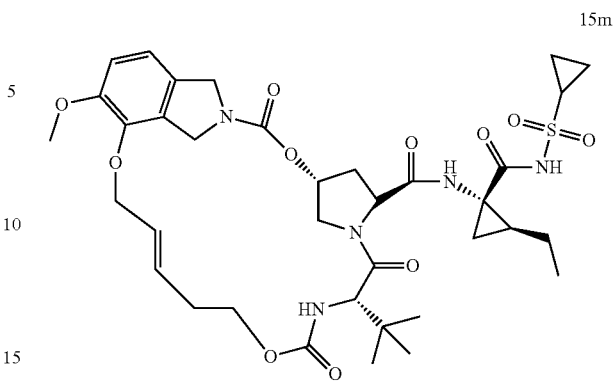
15n
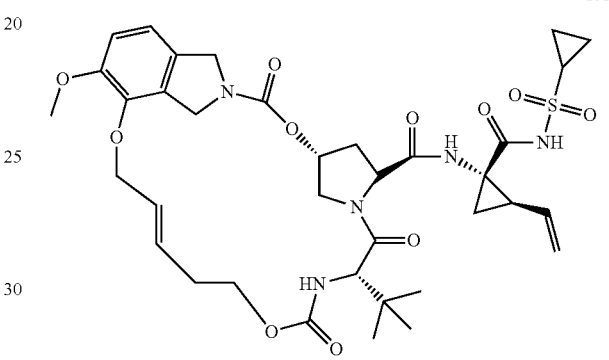
15p
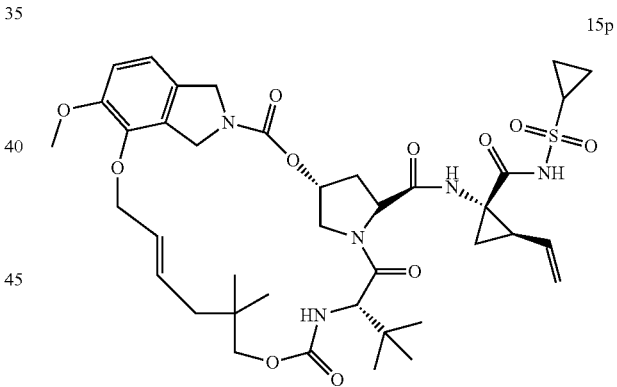
15q
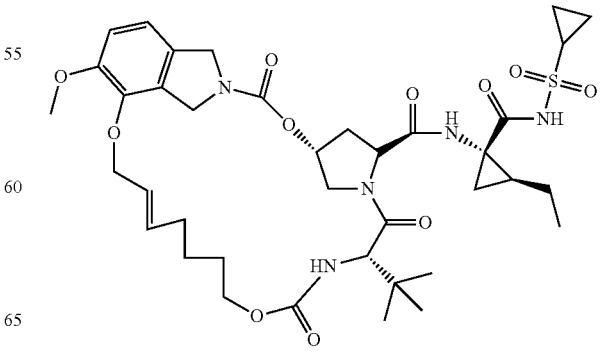

15r
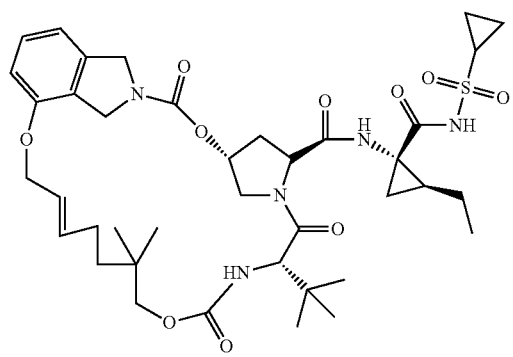
15s
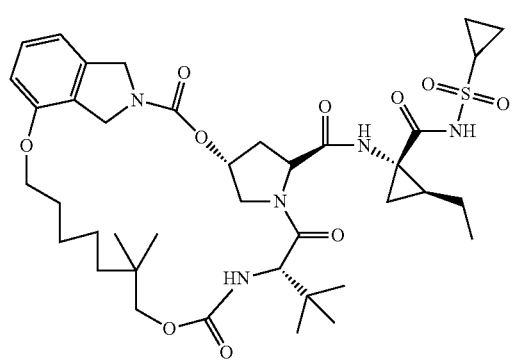
15t
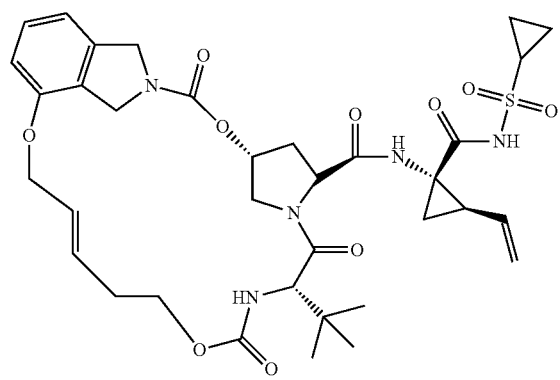
15u
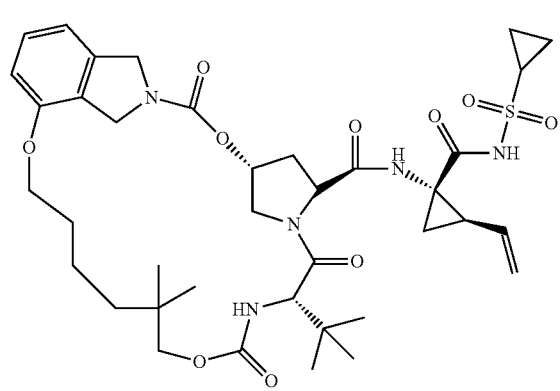
15v
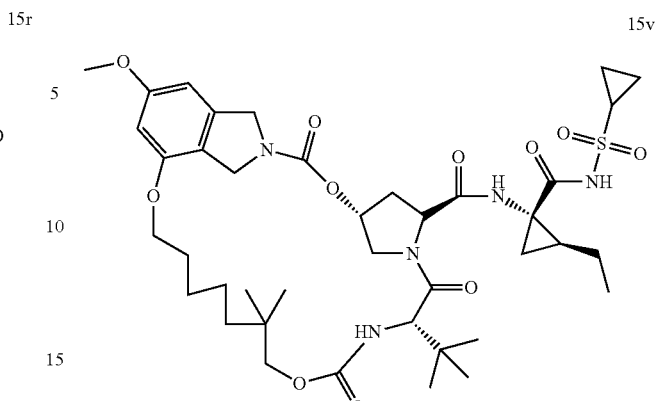
15w
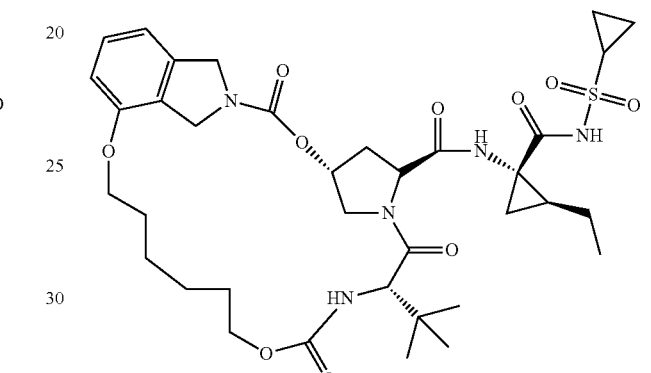
15x
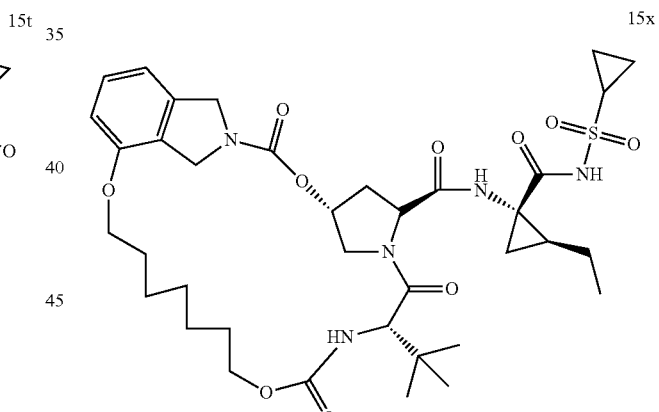
15y
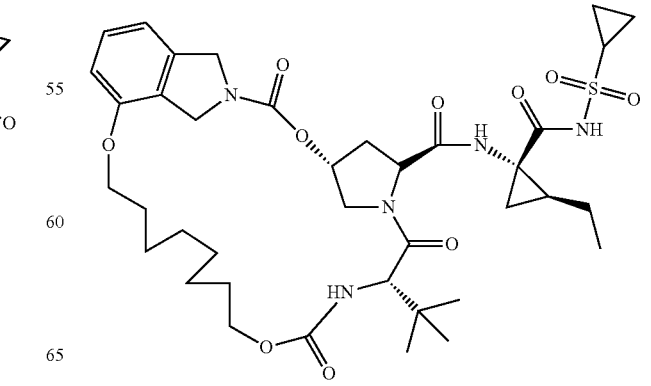

187
-continued
15z
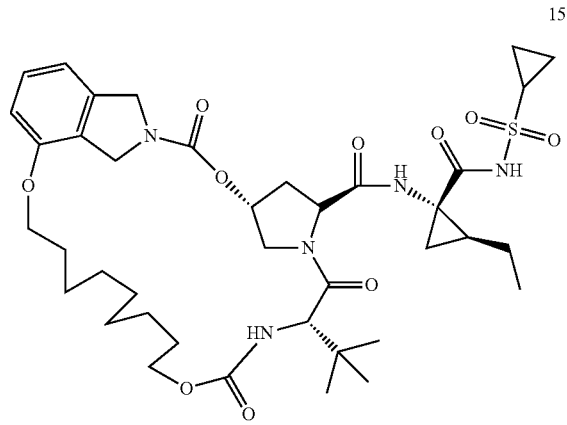
15aa
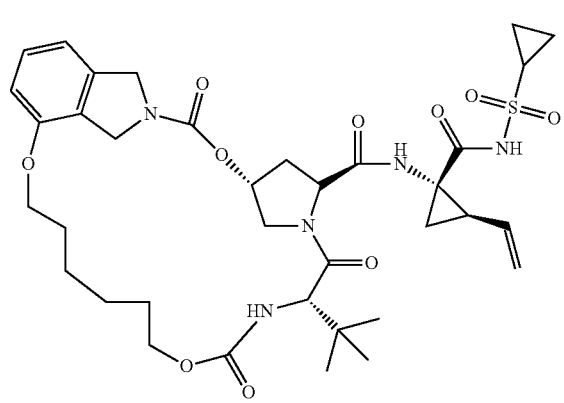
15ab
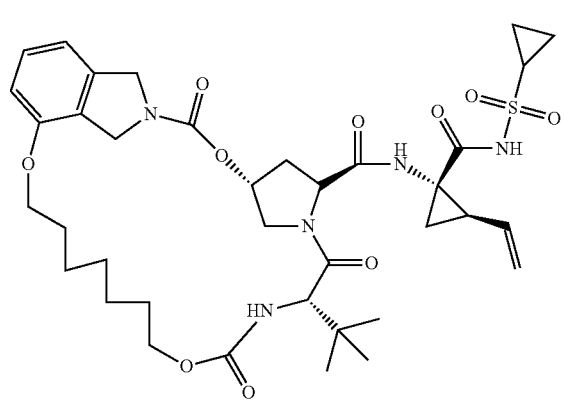
15ac
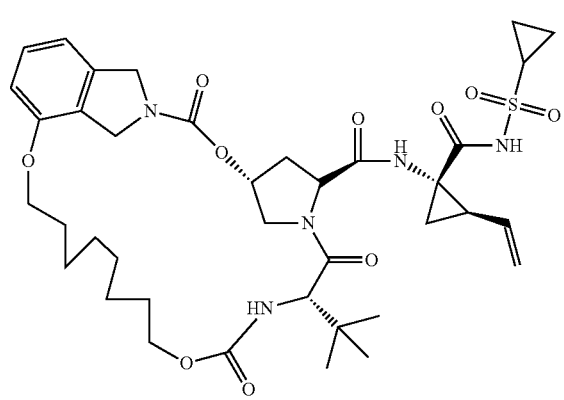
188
-continued
15ad
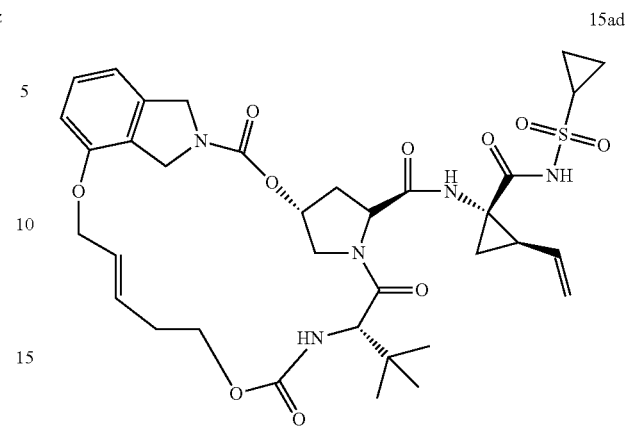
15ae
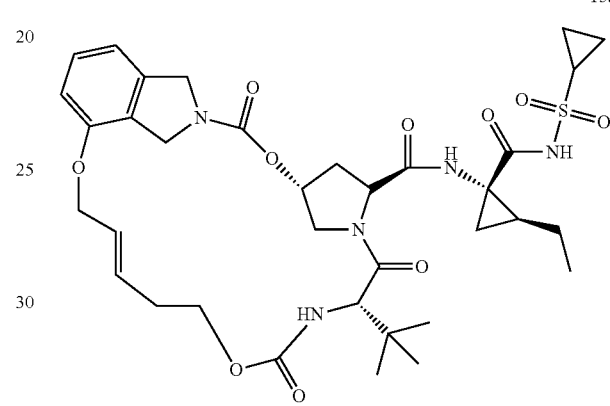
15af
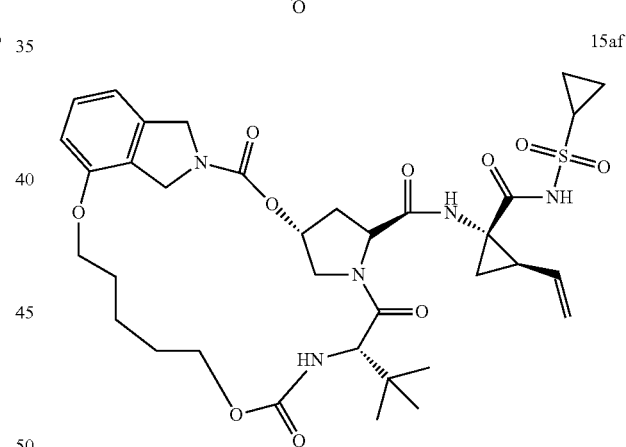
15ag
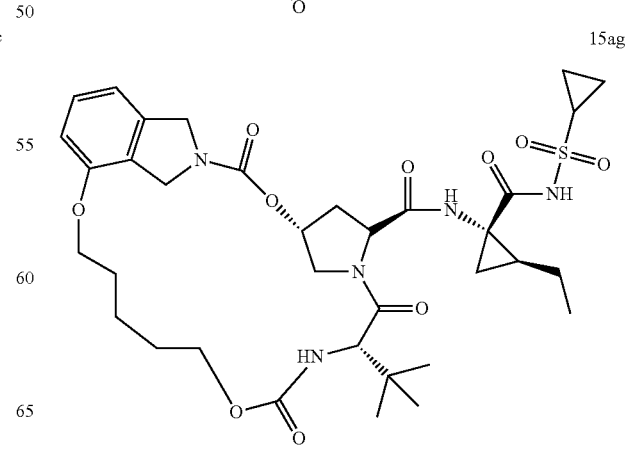

189
-continued
15ah
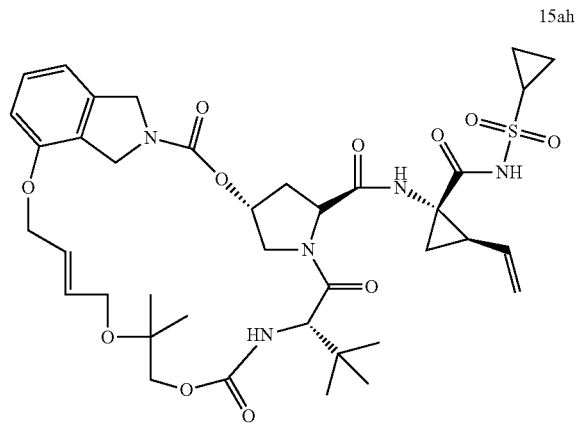
15aj
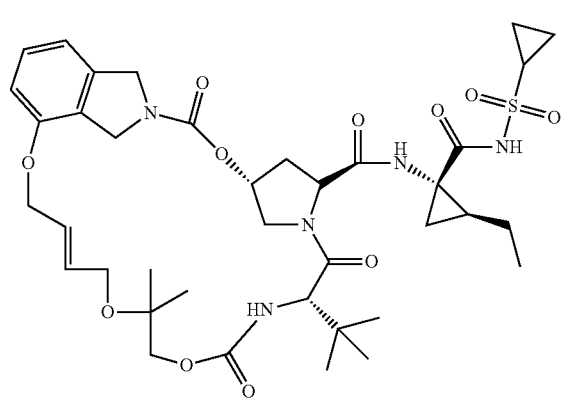
15ak
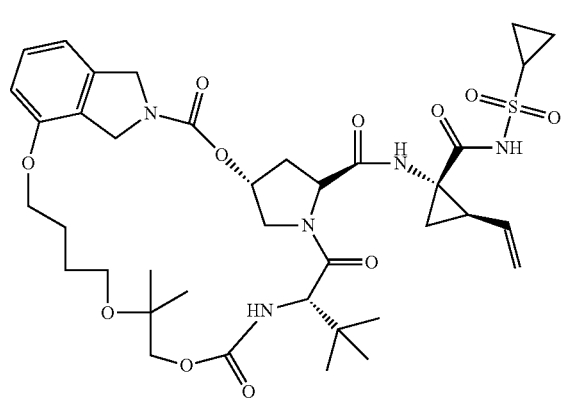
15am
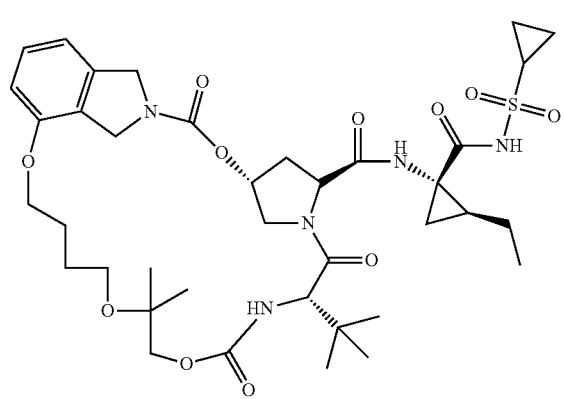
190
-continued
15an
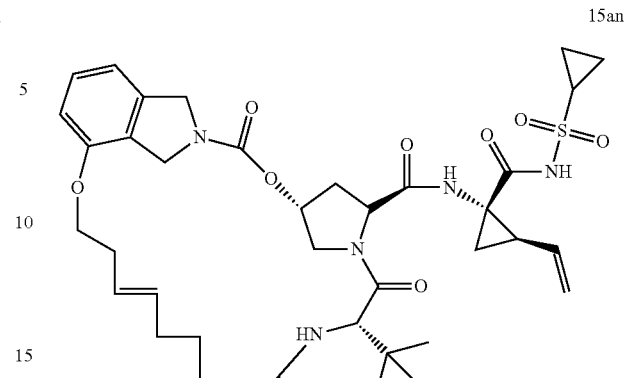
15ap
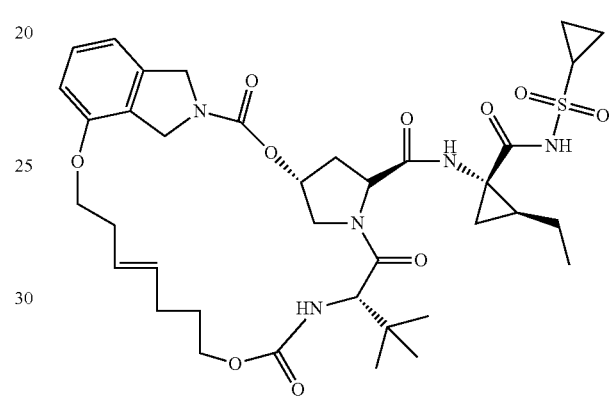
15aq
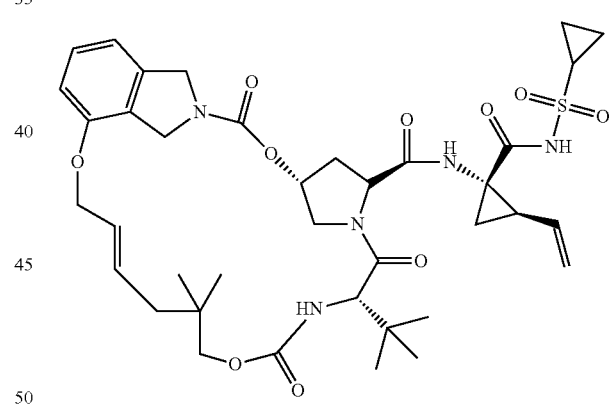
15ar
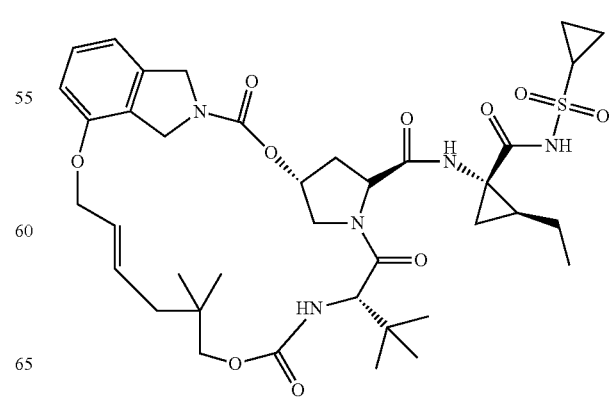

| 191 -continued | 192 -continued |
|---|---|
| 15as 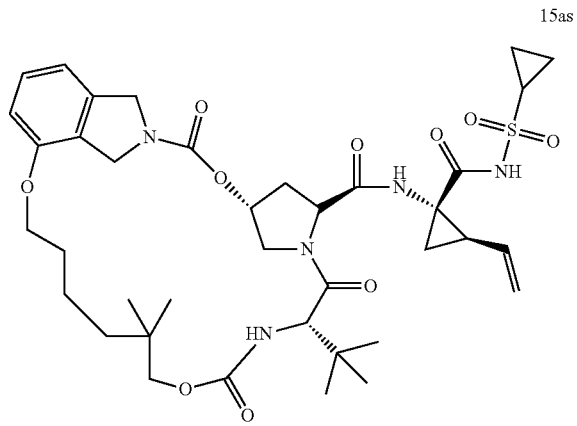 | 15aw 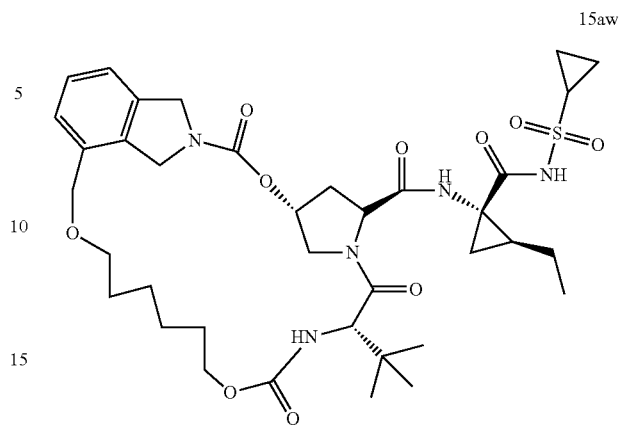 |
| 15at 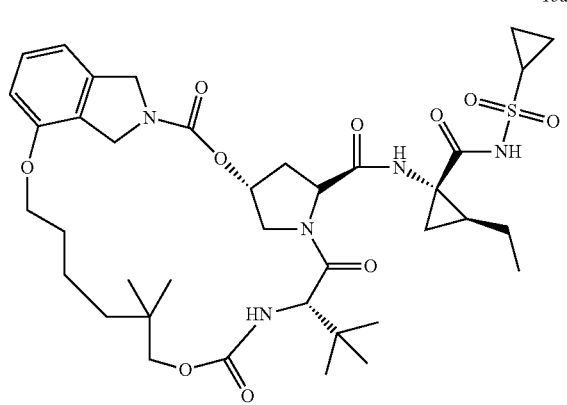 | 15ax 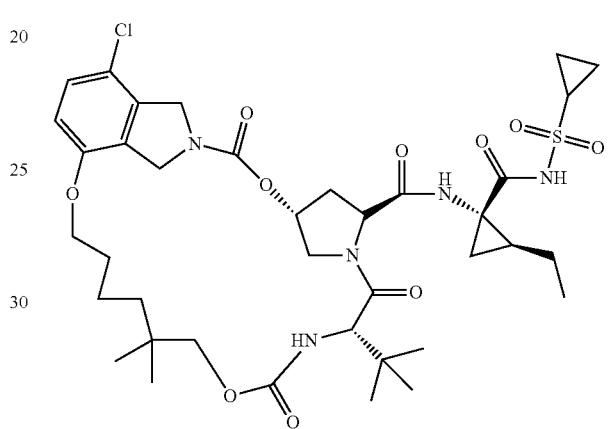 |
| 15au 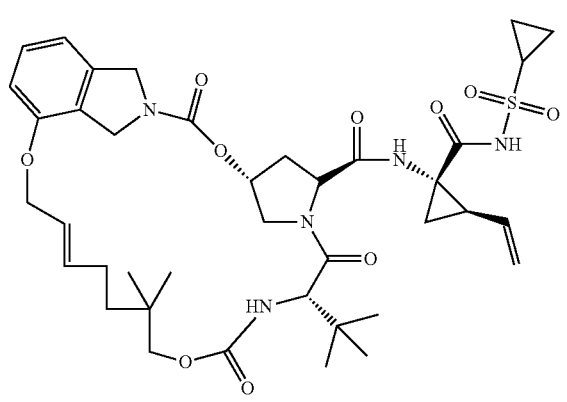 | 15ba 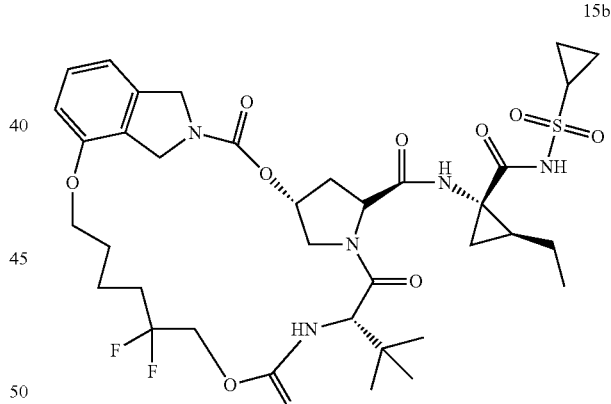 |
| 15av 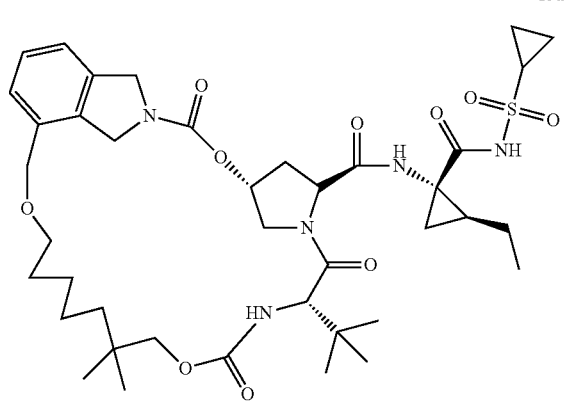 | 15bb 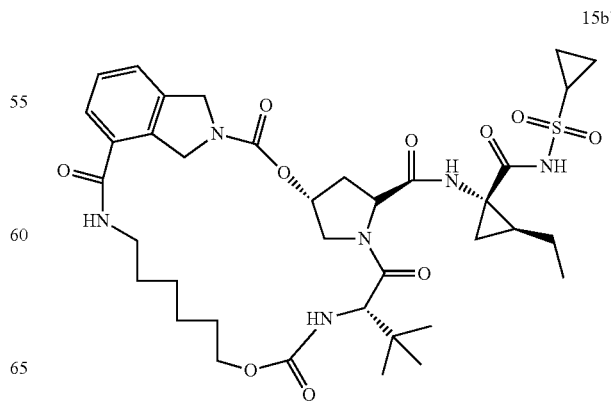 |

193
-continued
15bc
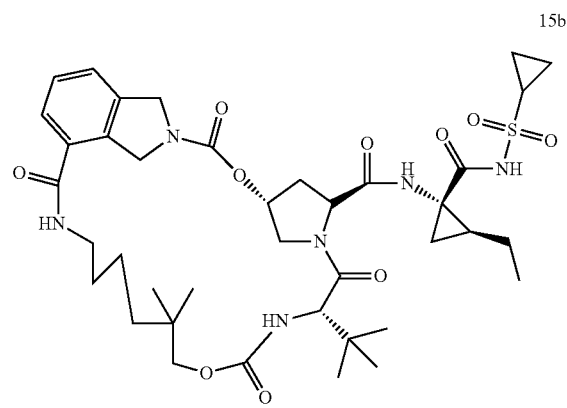
15bd
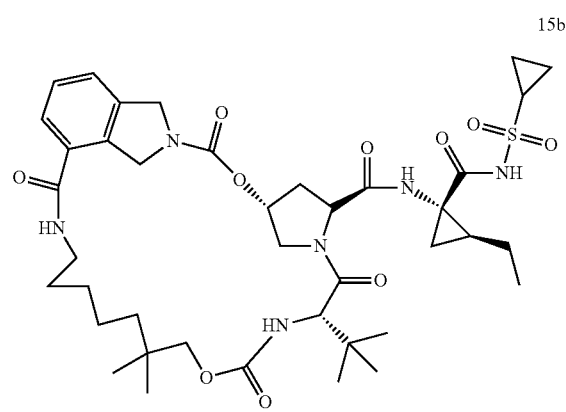
15be
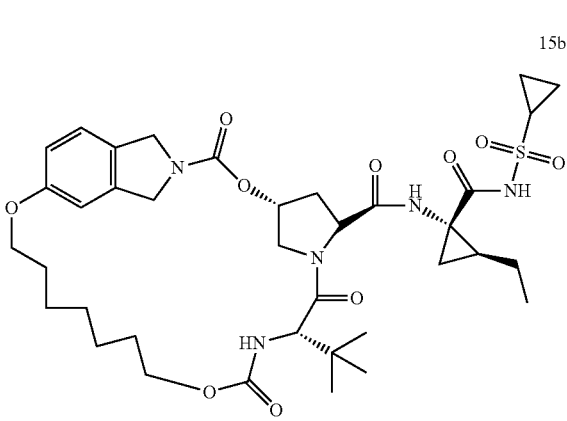
15bf
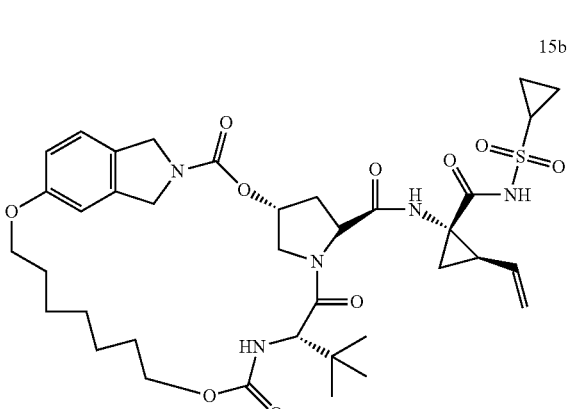
194
-continued
15bg
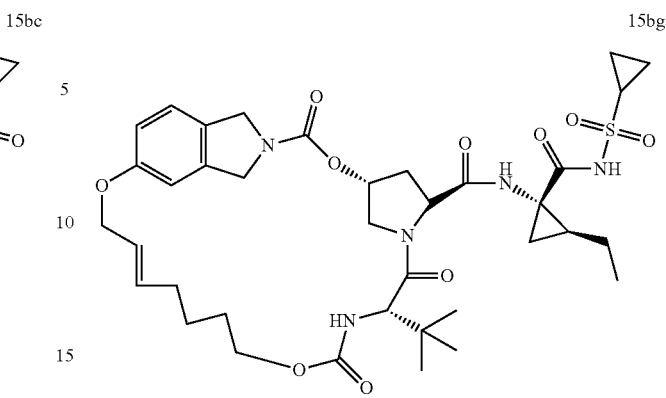
15bh
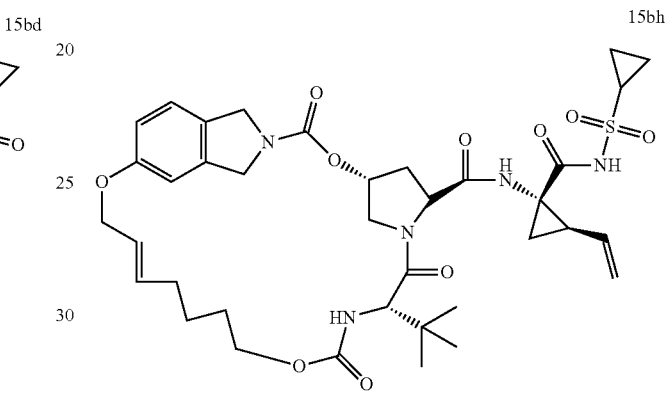
15bj
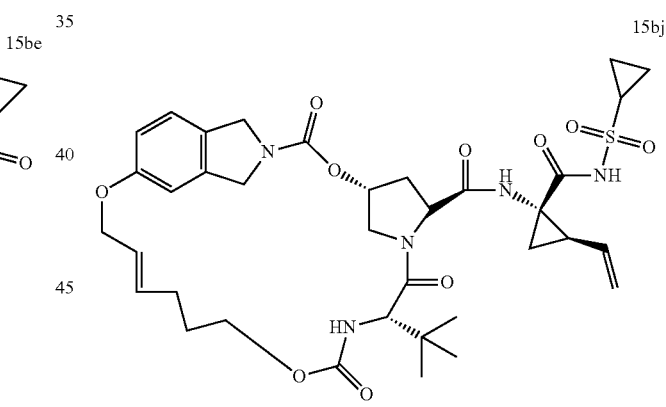
15bk
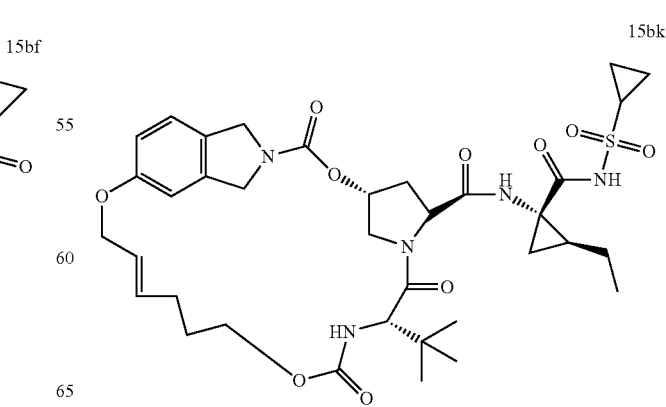

195
-continued
15bm
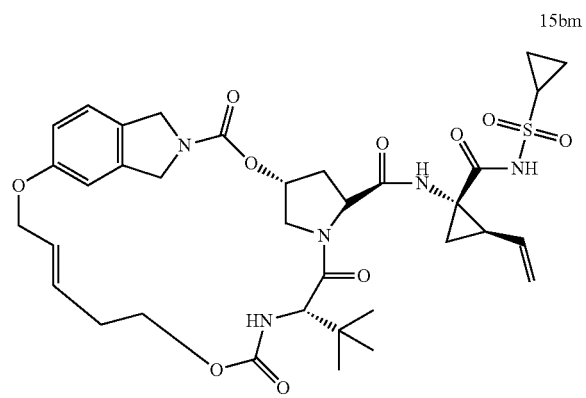
15bn
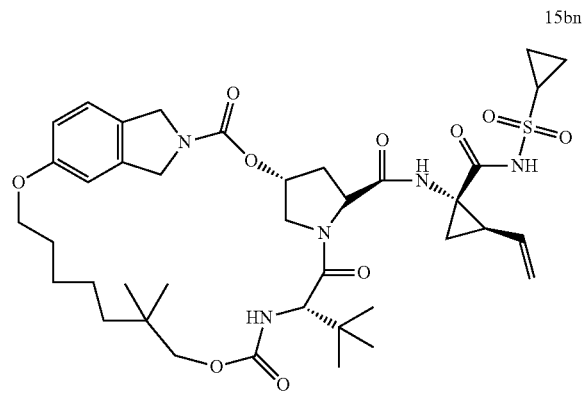
15bp
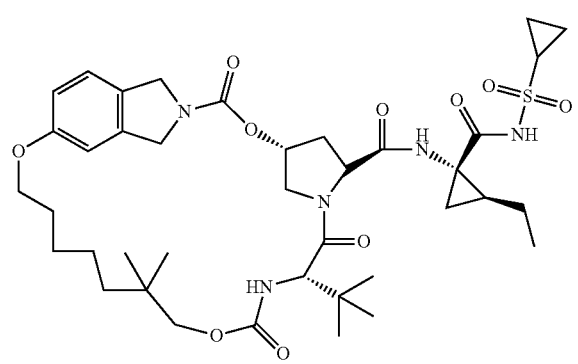
15bq
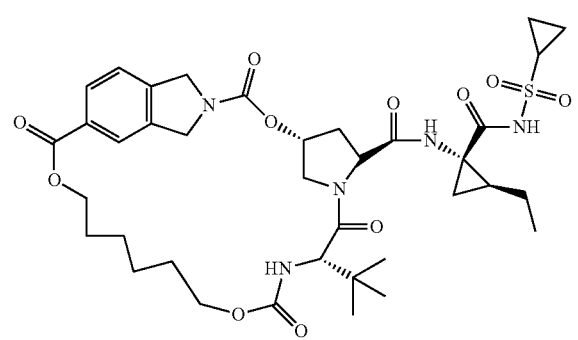
196
-continued
15br
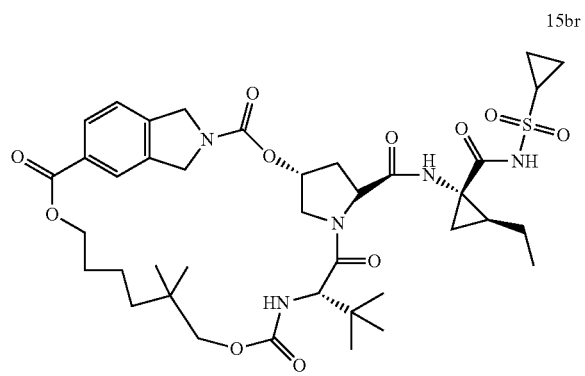
15bs
15bt
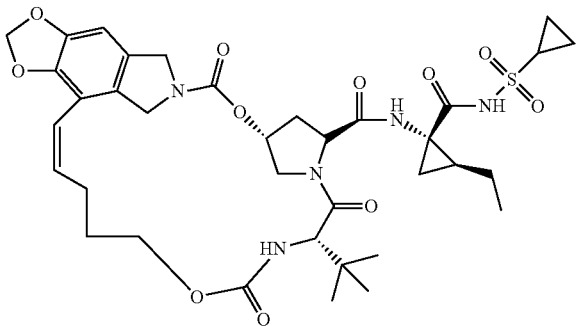
15bu
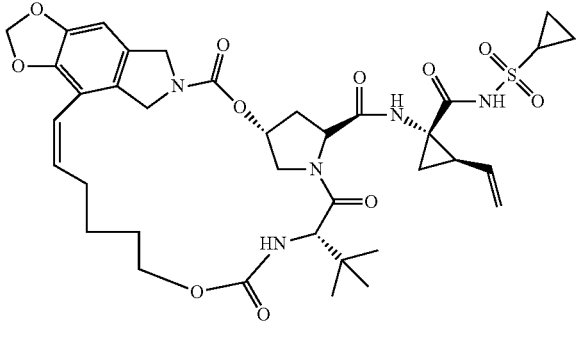

197
-continued
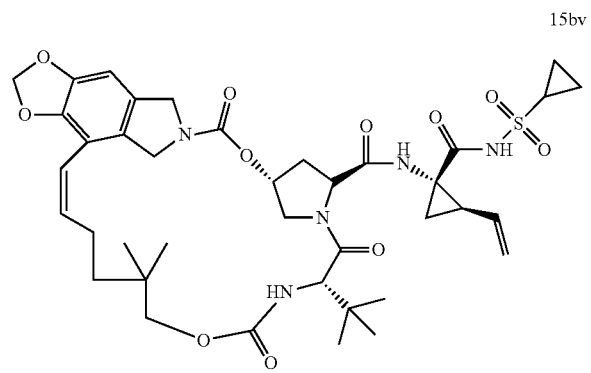
15bv
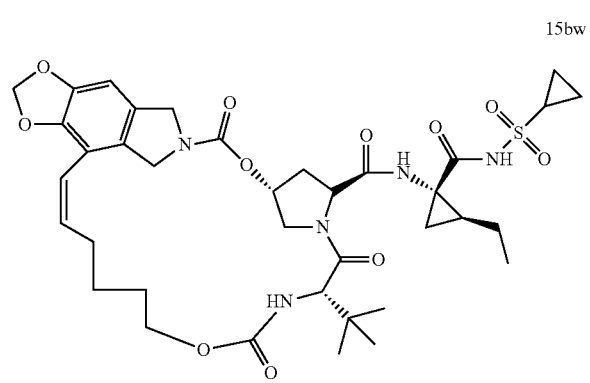
15bw
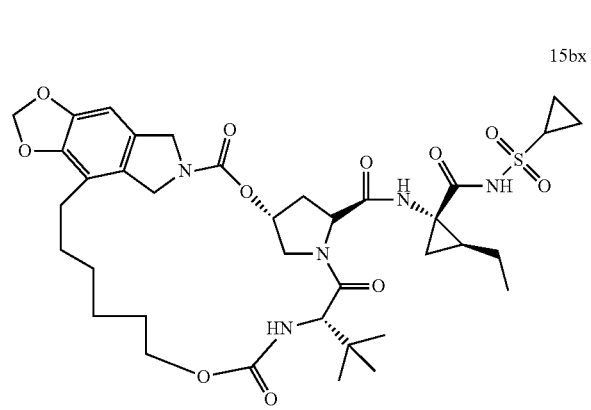
15bx
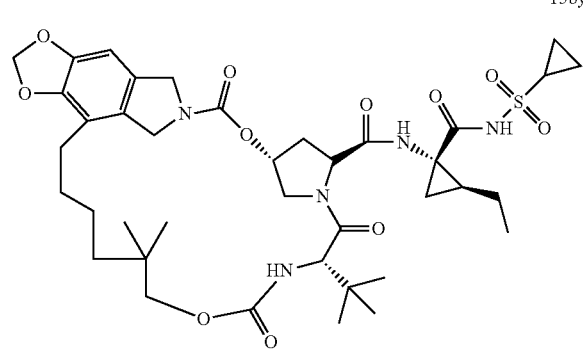
15by
198
-continued
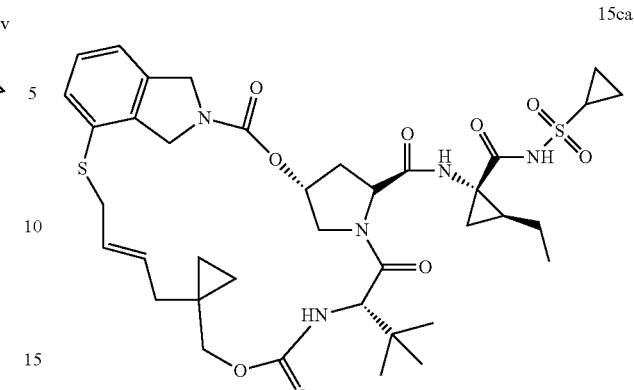
15ca
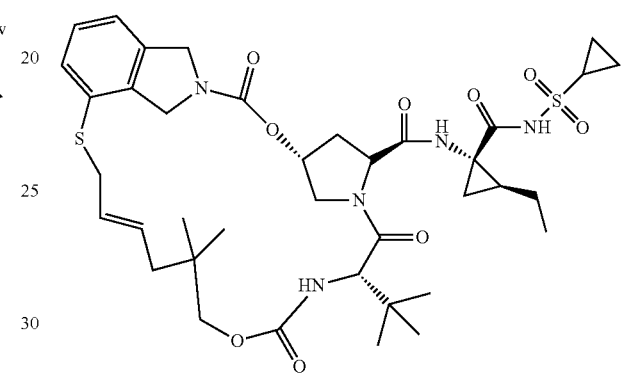
15cb
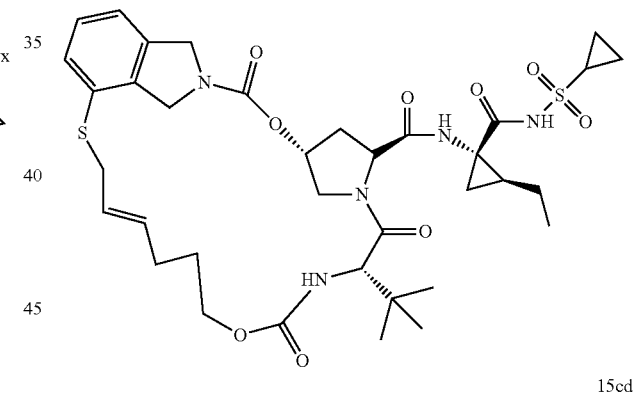
15cc
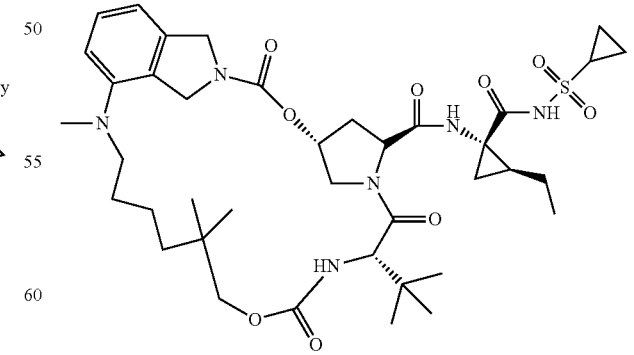
15cd
The compounds in the present invention may contain a non-aromatic double bond and one or more asymmetric centers. Thus, they can occur as racemates and racemic mixtures, single enantiomers, individual diastereomers, diastereomeric mixtures, tautomers, and cis- or trans-isomeric forms. The prepared compounds Ia-Ib of the invention is a chiral macroheterocyclic compound with purity of 95-99%, and the natural amino acids and non-natural amino acids in products Ia-Ib were determined by the optical purity of rotation and chiral HPLC columns, the structural characterization for each of the final product (15a-15cd) was conformed by LC-MS and $^1$H nuclear magnetic resonance ($^1$H-NMR).

HCV has low self-replication in normal liver cells in vitro, and the only animal that is possible to be infected is chimpanzee, so that there were still no suitable animal models for pre-clinical pharmacodynamic study. Some researchers tried to transplant HCV infected human liver tissue into immunodeficient mice to establish mice model in vivo, but it's difficult to feed this kind of mice and the model is instable. There's a lack of normal immunication effects, and there is big difference of hepatitis C Pathogenesis. It is not used as a suitable animal model to evaluate HCV drugs pharmacodynamic research. There was no effective HCV Cell culture system until 1999, the R&D of anti-virus drugs were developed slowly because of the unknown HCV Pathogenic mechanisms and the viral life cycle. The researchers made a lot of efforts and had breakthrough progress, they established an effective cell culture models—replicon system which was based on subgenomic HCV RNA constructed by genetic engineering, the self-replication was presented in infected human liver cancer cell Huh-7.

The in vitro studies were taken in effective cell culture models—replicon system as above which was accepted in the present area. According to the results, the drugs were evaluated as HCV NS3 inhibitors by the principal data as follows:

1) The inhibition effects against HCV NS3 activities ($IC_{50}$);

2) The inhibition effects against HCV Replicons ($EC_{50}$);

The compounds prepared in the present invention were preliminarily screened for their potency in treating HCV infection by evaluating an anti-activity assay in vitro as follows, and then confirmed by animal studies and clinic trials. Other methods were also apparent for scientists in the present area.

After studies, the compounds in the present invention and/or its stereoisomers, tautomers, esterification or amidation prodrugs, pharmaceutically acceptable salts, or mixtures thereof have excellent efficacy in treating HCV infection. Most of compounds 15a-15cd have good inhibition against HCV infection, by studies of compounds 15a-15cd and two control compounds "ITMN-191(RG-7227) and MK-7009" for inhibiting HCV protease (NS3) activity assays, the results show that many compounds of 15a-15cd have better activity inhibition ($EC_{50}$) than both ITMN-191(RG-7227) and MK-7009. The potency results for compounds 15a-15cd to inhibit HCV were presented in Table 1, wherein "A" refers to activity ($IC_{50}$) of 51-300 nM, "B" refers to activity ($IC_{50}$) of 5.1-50 nM, "C" refers to activity ($IC_{50}$) of 0.1-5.0 nM;

TABLE 1

Results of Anti-HCV-NS3 Activity for Novel Macroheterocyclic Based Compounds

| No. | Compund | Activity ($IC_{50}$) |
|---|---|---|
| 1 | 15a | C |
| 2 | 15b | C |
| 3 | 15c | C |
| 4 | 15d | C |
| 5 | 15e | C |
| 6 | 15f | C |
| 7 | 15g | C |
| 8 | 15h | B |
| 9 | 15j | C |
| 10 | 15k | C |
| 11 | 15m | B |
| 12 | 15n | C |
| 13 | 15p | C |
| 14 | 15q | B |
| 15 | 15r | C |
| 16 | 15u | C |
| 17 | 15v | C |
| 18 | 15w | C |
| 19 | 15x | C |
| 20 | 15y | B |
| 21 | 15z | B |
| 22 | 15aa | C |
| 23 | 15ab | C |
| 24 | 15ac | C |
| 25 | 15ad | C |
| 26 | 15ae | C |
| 27 | 15af | C |
| 28 | 15ag | C |
| 29 | 15ah | C |
| 30 | 15aj | C |
| 31 | 15ak | C |
| 32 | 15am | C |
| 33 | 15an | C |
| 34 | 15ap | C |
| 35 | 15aq | C |
| 36 | 15ar | C |
| 37 | 15as | C |
| 38 | 15at | C |
| 39 | 15au | C |
| 40 | 15av | B |
| 41 | 15aw | B |
| 42 | 15ax | C |
| 43 | 15ba | C |
| 44 | 15bb | B |
| 45 | 15bc | A |
| 46 | 15bd | A |
| 47 | 15be | C |
| 48 | 15bf | C |
| 49 | 15bg | C |
| 50 | 15bh | C |
| 51 | 15bj | C |
| 52 | 15bk | B |
| 53 | 15bm | A |
| 54 | 15bn | C |
| 55 | 15bp | C |
| 56 | 15bq | A |
| 57 | 15br | A |
| 58 | 15bs | A |
| 59 | 15bt | C |
| 60 | 15bu | C |
| 61 | 15bv | C |
| 62 | 15bw | C |
| 63 | 15bx | C |
| 64 | 15by | C |
| 65 | 15ca | C |
| 66 | 15cb | C |
| 67 | 15cc | C |
| 68 | 15cd | C |

The results in Table 1. present the new macro-polycyclic compounds as 15a-15k, 15r-15x, 15aa-15au, 15ax-15ba, 15be-15bj, 15bn, 15 bp and 15bu-15cd in the present invention have excellent HCV activity inhibition, several compounds as 15a-15g, 15r-15x, 15aa, 15ab, 15an-15au and 15ax-15ba also have great HCV activity inhibition in HCV NS3 Replicon system ($EC_{50}$: 0.05 nM-30 nM). There are new HCV inhibitors having excellent biological activities in comparison with some referred HCV inhibitors already in clinical Phase II and III, developed by pharmaceutical companies such as InterMune and Merck compounds (RG-7227 and MK-7009). The results of Acute Toxocity Study (MTD) showed that many highly potent compounds had low total toxicity ($LD_{50}$>10,000), and the survival of almost all mice and rats after dosing was 80%-100%, one third of them were 100% survival after dosage of 10,000 mg/kg for the noval compounds ($LD_{50}$>15,000). Several highly potent compounds of the novel macro-heteocyclic compounds Ia-Ib in the present invention were worth further development in the animal tests and clinical trials to promot their applications.

The present invention takes deep studies of relationship with structure of different macro-heterocyclic compounds and potency of inhibition against HCV activities, designs, and synthesizes two kinds of macro-heterocyclic compounds (Ia and Ib) as highly potent HCV inhibitors. Some novel macro-heterocyclic compounds had not only excellent inhibition against HCV NS3 activity, but also better than other different macrocyclic based compounds in clinical trials such as MK-7009 and RG-7227. Some macro-heterocyclic compounds in the present invention had very low or even don't have toxicity or side effects, that made it possible to successfully approve a highly potent and non-toxic HCV drug by further development.

Method of HCV Protease (HCV NS3-4A) Anti-Activity Assay:

HCV Protease (HCV NS3/4A) anti-activity was measured by an inter fluorescence quenching system. EDANS group and DABCYL group were bonded on each side of a peptide. When protein cleavage started, fluorescence quenching of EDANS by DABCYL was detected. We used a high throughput screening model for HCV NS3/4A protease inhibitors, the tested drugs were prepared with 5 different concentrations, positive control and negative control were set in the same time. In the optimized reaction system, fluorescence were determined at ex=355, em=520 by a Polarstar fluorescence detector. Calculate the inhibition rate of each concentration; calculate the half maximal inhibitory concentration (IC50) with the method of Reed-Muench.

Materials: HCV Protease: HCV NS3-4A, self-prepared, stored at −70. HCV Protease substrate (FRET-S): Ac-Asp-Glu-Asp(EDANS)-Glu-Glu-Abu-ψ-[COO]-Ala-Ser-Lys-(DABCYL)-NH2, supplied by AnaSpec USA, prepared of 100 µM by DMSO, distributed and stored at −20 without light. Buffer solution: 30 mM NaCl, 5 mM CaCl2, 10 mM DTT, 50 mM Tris (pH7.8).

Instrument: fluorescence detector Polarstar from Germany Company BMG

Preparation and operation: preparation of 10 mg/mL by DMSO, dilute of 10000, 2000, 400, 80, 16 ng/mL as tested concentrations by buffer solutions, adding 20 µL into each well, the total reaction system is 200 µL, to make the final concentrations of 1000, 200, 40, 8, 1.6 ng/mL. Add 140 µL buffer solution, 20 µL drug solution, 20 µL HCV protease, and 20 µL FRET-S substrate with final concentration of 0.25 µM into 96-well fluorescence microtiterplate, the reaction started at 37, set control wells of protease-substrate reaction and of isolate substrate and isolate protease, fluorescence signals were detected by fluorescence detector (ex=355, em=520). Calculate the inhibition rates of samples for each concentration by comparison of fluorescence value of sample in each well and the fluorescence control value of enzyme, calculate the half maximal inhibitory concentration (IC50) of samples to HCV protease with the method of Reed-Muench.

Method of Inhibition of Virus Activity ($EC_{50}$) Assay in HCV Replicon System:

The study was completed by a new constructed double reporter genes replicon assay system, the capacity of viral replicon in infected cell was determined by detecting the reporter gene *Renilla* luciferase. The relationship of the reporting genes, HCV RNA replicon and viral proteins is well linear. 8 gradient concentrations for 2-fold dilution, 3-wells, 3-times repetition and 1 or 2 control drugs were set to finally determine $EC_{50}$ value of compounds.

Toxicity Screening Studies of Compounds:

To study toxicity of some highly potent ($EC_{50}$<50 nM) compounds such as 15a-15g, 15r-15x, 15aa, 15ab, 15an-15au and 15ax-15ba of all novel compounds 15a-15by, and the Acute Toxocity Study (MTD) in the present invention was established by choosing 18-22 g healthy mices to take single dosage for 10,000 mg/kg by gavage and evaluating toxicity of compounds to body by observing animals toxic effects. The results showed that these kinds of compounds had very low total toxicity ($LD_{50}$>10,000). The survival of almost all mice and rats after dosing was 80%-100%, one third of them were 100% survival after dosage of 10,000 mg/kg for the noval compounds ($LD_{50}$>15,000). After studies, the compounds in the present invention not only had excellent inhibition against HCV activity, but also one third of them had very low total toxicity (the survival of mice is 100%, $LD_{50}$>10,000), that was generally supposed to be non toxicity.

The synthesis and anti-viral effects of each kind of compounds and intermediates in the present invention were explained by the following examples.

Instruments and Materials Related to the Examples were Explained as Follow:

Infrared (IR) spectra were recorded on Thermo Nicolet company Fourier Transform AVATAR™ 360 E.S.P™ spectrophotometer (Unit: $cm^{-1}$).

$^1$H NMR spectra were recorded on a Varian Mercury Plus 400 (400 MHz) spectrometer. Chemical shifts were reported in ppm from tetramethylsilane with the solvent resonance as the internal standard ($CHCl_3$: 7.26 ppm). Data were reported as follows: chemical shift, multiplicity (s: single, d: doublet, t: triplet, q: quartet, br: broad, m: multiplet) and coupling constants.

Unless otherwise noted, mass spectra were obtained at Finnigan LCQ Advantage of liquid chromatography-mass spectrometer analysis, all reactions were conducted in oven and flame-dried glassware with vacuum-line techniques under an inert atmosphere of dry Ar. Solid metal organic compounds were stored in Ar in a drying box.

THF and $Et_2O$ were distilled from sodium metal and benzophenone. DCM, pentane and hexane were distilled form calcium hydride. Special raw materials and intermediates in the invention were supplied by Zannan SciTech Co. for ordered processing, Ltd. in Shanghai, others reagents were purchased from Shanghai reagent company, Aldrich, Acros etc. If intermediates or products of synthesis were not enough for the next step of reaction, the synthesis shall be repeated until it is sufficient. The HCV protease (HCV NS3-4A) inhibitory activity assays in the present invention were performed by relevant cooperation service units of China Institutes for Biological Science in Beijing.

Abbreviations of chemical materials, reagents, and solvents related to the present invention are listed as follows:

SM-4a: N-Boc-trans-4-hydroxy-L-proline methyl ester
Alcalase 2.4 L: Subtilisin-Carlsberg: hydrolysis protease
AIBN: azobisisobutyronitrile
Boc: tert-butoxycarbonyl
$(Boc)_2O$: di-tert-butyl carbonate CDI: N,N'-carbonyldiimidazole imidazole
DBU: 1,8-Diazabicyclo[5.4.0]undec-7-ene
EDCI: N-ethyl-N-(3-dimethyl aminopropyl) carbodiimide hydrochloride
HATU: 2-(7-benzotriazole azo)-N,N,N',N'-tetramethyl urea phosphate hexafluoride
NBS: N-bromosuccinimide
DMAP: 4-dimethylaminopyridine
DIEA: N,N-diisopropyl ethylamine
$SOCl_2$: thionyl chloride
Pd/C: Palladium carbon
HMTA: hexamethylene tetramine
HOAc: acetic acid
HBr: Hydrobromic acid
HCl: hydrochloric acid
TFA: trifluoroacetic acid
TsOH: p-toluenesulfonate
NaOH: sodium hydroxide
ACN: acetonitrile
DCM: dichloromethane
DCE: dichloroethane
DMF: N,N-dimethylformamide
DMSO: dimethyl sulfoxide
Et2O: diethyl ether
EA: ethyl acetate
PE: petroleum ether
THF: tetrahydrofuran
TBME: tert-butyl methyl ether

EXAMPLE 1

Synthesis of Compound V-1

Synthesis of compound V-1 was carried out by the following two steps:

First step: the starting material SM-1a (45 g, 170 mmol) was dissolved in 400 mL dried DMF, then acrylamide (14 mL 187 mmol 1.1 eq.) and HBTU (68 g, 180 mmol, 1.05 eq) were added. After cooling with ice water, DIEA (2.27 g, 17.5 mmol, 4 eq.) was added dropwise. Warmed up to room temperature and stirred overnight. After the reaction was completed, the reaction solution as poured into ice-water then ethyl acetate and 1N hydrochloric acid were added to pH=7-8. Separated, aqueous phase as extracted by ethyl acetate, combined the organic phase, washed with 1N HCl, water saturated $NaHCO_3$ and brine, dried and concentrated to obtain a brown viscous solid product 1-1 (51 g, yield: 82%). Confirmed by MS, ESI-MS [(M+H)$^+$]: m/z calculated 303.1, founded 303.1.

Second step: the above product 1-1 (50 g, 165 mmol) was dissolved in 10 mL methanol and $Et_2O$/HCl solution (4N, 100 mL), then refluxed to complete the reaction. Concentrated and recrystallized from ether to give a pale gray solid product V-1 (25.3 g, yield: 74%).

$^1$H-NMR for the product V-1 (CD3OD, 400 MHz): δ 7.82-7.80 (d, 1H), 7.61-7.59 (d, 1H), 7.55-7.52 (m, 1H), 5.97-5.90 (m, 1H), 5.26-5.22 (m, 1H), 5.16-5.14 (m, 1H), 4.91 (s, 2H), 4.65 (s, 2H), 4.0-3.99 (d, 2H). ESI-MS [(M+H)$^+$]: m/z calculated 203.1, founded 203.1.

EXAMPLE 2

Synthesis of Compound V-2

Synthesis of Compound V-2 was carried out by the following two steps:

First step: after the starting material SM-1b (50g, 0.22 mol) was dissolved in 500 mL DMF, anhydrous $K_2CO_3$ (87 g, 0.66 mol, 3 eq.) and allyl bromide (35.6 g, 0.28 mol, 1.3 eq.) were added under ice-cooling over. The reaction temperature was raised to 65 overnight to complete the reaction. The reaction solution was poured into 2.5 L ice-water, extracted with ethyl (1.0 L×2), washed with saturated brine (500 mL×2), dried over anhydrous sodium sulfate, then concentrated, purified by column chromatography to obtain the product 1-2 (57.6 g, yield: 95%). ESI-MS [(M+H)$^+$]: m/z calculated 276.1, founded 276.2.

Second step: the above product 1-2 (55.1 g, 0.20 mol) was dissolved in HCl/$Et_2O$ (4N, 500 mL), then naturally warmed to room temperature, stirred overnight to complete the reaction. Filtered, washed with ether and dried to give crude product. The crude product was neutralized, and purified by column chromatography, then salted with HCl to obtain the product V-2 (33.2 g, yield: 79%).

$^1$H-NMR for the product V-2 ($CD_3OD$, 400 MHz): δ 7.38-7.34 (m, 1H), 7.00-6.96 (m, 2H), 6.11-6.03 (m, 1H), 5.43-5.39 (m, 1H), 5.29-5.27 (m, 1H), 4.65-4.64 (m, 2H), 4.62 (s, 2H), 4.57 (s, 2H). ESI-MS [(M+H)$^+$]: m/z calculated 176.1, founded 176.2.

EXAMPLE 3

Synthesis of Compound V-3

Synthesis of Compound V-3 was carried out by the following two steps:

First step: the starting material SM-1b (30 g, 127 mmol) and 3-en-1-butanol (10 g, 153 mmol) were dissolved in 200 mL THF, under ice-cooling over triphenylphosphine (43.5 g, 166 mmol) was added, then DIAD (37.5 mL, 190 mmol) was added slowly dropwise. After the addition, the reaction solution was naturally warmed to room temperature overnight to complete the reaction. The reaction solution was poured into 2.0 L ice-water, and extracted with diethyl ether (800 mL×2), washed with saturated brine, dried, and concentrated, purified by column chromatography (eluent: PE: EtOAc=20:1) to obtain the product 1-3 (28.3 g, yield: 72%).

$^1$H-NMR for the product 1-3 ($CDCl_3$, 500 MHz): δ 7.23-7.19 (m, 1H), 6.85-6.89 (m, 1H), 4.71-6.73 (m, 1H), 5.87-5.91 (m, 1H), 5.07-5.19 (m, 2H), 4.57-4.68 (m, 4H), 4.02-4.06 (m, 2H), 2.51-2.57 (m, 2H), 1.52 (s, 5H), 1.51 (s, 4H). ESI-MS [(M+H)$^+$]: m/z calculated 290.1, founded 290.2.

Second step: the above product 1-3 (26.2 g, 0.09 mol) was dissolved in HCl/$Et_2O$ (4N, 300 mL), then naturally warmed to room temperature, stirred overnight to complete the reaction. Filtered, washed with ether and dried to give crude product. The crude product was neutralized, and purified by column chromatography, then salted with HCl to obtain the product V-3 (15.2 g, yield: 76%). Confirmed by MS, ESI-MS (M+H$^+$): m/z calculated 190.1, founded 190.2.

EXAMPLE 4

Synthesis of Compound V-4

Compound V-4 was prepared by two steps identical to that described in example 2, after two-step reaction the product V-4 (31.6 g) was obtained. Using the reagent SM-1c instead of SM-1b in the first-stage reaction, the intermediate product 1-4 was obtained, which was confirmed by MS, ESI-MS (M+H$^+$): m/z calculated 306.1, founded 306.2.

$^1$H-NMR for the product V-4 ($CD_3OD$, 400 MHz): δ 6.37-6.34 (d, 2H), 6.03-5.95 (m, 1H), 5.40-5.36 (m, 1H), 5.30-5.28 (m, 1H), 4.63-4.58 (m, 4H), 4.52-4.51 (m, 2H), 3.77 (s, 3H). ESI-MS [(M+H)$^+$]: m/z calculated 206.1, founded 206.2.

EXAMPLE 5

Synthesis of Compound V-5

Compound V-5 was prepared by two steps identical to that described in example 2, after two-step reaction the product V-5 (30.2 g) was obtained. Using the reagent SM-1d instead of SM-1b in the first-stage reaction, the intermediate product 1-5 was obtained, which was confirmed by MS, ESI-MS (M+H$^+$): m/z calculated 306.1, founded 306.2.

$^1$H-NMR for the product V-5 (DMSO-d6, 500 MHz): δ 6.28-6.27 (m, 2H), 5.29-5.21 (m, 1H), 4.54-4.50 (m, 1H), 4.42-4.39 (m, 1H), 4.06 (s, 3H). 3.82-3.80 (m, 2H), 3.78 (s, 2H), 3.75 (s, 2H), 3.0 (s, 2H). ESI-MS [(M+H)$^+$]: m/z calculated 206.1, founded 206.3.

EXAMPLE 6

Synthesis of Compound V-6

Synthesis of Compound V-6 was carried out by the following two steps:

First step: sodium hydroxide (1.2 g, 60%, 30 mmol, 3.25 eq.) was added to 25 mL dried DMF under the ice water bath, then the starting material SM-1e (2.3 g, 9.23 mmol) was added. After stirred for 10 min, allyl bromide (0.95 mL, 1.33 g, 11.0 mmol, 1.2 eq) was added, then the reaction solution was warmed to 70 overnight to complete the reaction. The reaction was quenched with water, extracted with ethyl acetate. The combined organic phases was washed with saturated sodium carbonate solution and saturated brine, then dried, concentrated, purified by column chromatography to obtain the product 1-6 as a pale yellow viscous oil (1.4 g, yield: 63%).

$^1$H-NMR for the product 1-6 (CDCl$_3$, 400 MHz): δ 7.26-7.25 (d, 1H), 7.23-7.20 (m, 1H), 7.16-7.15 (d, 1H), 5.96-5.92 (m, 1H), 5.34-5.29 (m, 1H), 5.24-5.20 (m, 1H), 4.72-4.66 (m, 4H), 4.50-4.47 (d, 2H), 4.03 (s, 2H), 1.65-1.52 (m, 9H). ESI-MS [(M+H)$^+$]: m/z calculated 290.1, founded 290.2.

Second step: under the ice water bath, the above product 1-6 (3 g, 10.4 mmol) was added to Et$_2$O/HCl solution (4N, 30 mL), then the reaction solution was warmed to 30 for 3 h. After the reaction was completed, concentrated, dissolved in DCM, neutralized by saturated sodium carbonate solution, then extracted with DCM. The combined organic phases was washed with saturated brine, dried, and concentrated to obtain a brown viscous product V-6 (1.7 g, yield: 87%).

ESI-MS for the product V-6 [(M+H)$^+$]: m/z calculated 190.1, founded 190.2.

EXAMPLE 7

Synthesis of Compound V-7

Synthesis of Compound V-7 was carried out by the following two steps:

First step: under protection of argon, the starting material SM-1f (13.8 g, 40.3 mmol), 150 mL DMF, anhydrous potassium carbonate (10.3 g, 74.5 mmol, 1.85 eq.), Vinyl boronic acid (5.52 g, 22.9 mmol, 0.57 eq.), tetrakistriphenylphosphine palladium phosphate (0.46 g, 0.4 mmol, 0.01 eq.) were added successively to a 250 mL flask, then the reaction solution was heated to 90 overnight. Filtered, and the filtrate was concentrated, purified by column chromatography to obtain the product 1-7 (9.7 g, yield: 83%).

$^1$H-NMR for the product 1-7 (CDCl$_3$, 400 MHz): δ 6.59 (m, 2H), 6.04 (s, 2H), 5.97 (d, J=12 Hz, 2H), 5.52 (d, J=8 Hz, 2H), 4.61 (m, 2H), 1.53 (s, 9H). ESI-MS [(M+H)$^+$]: m/z calculated 290.1, founded 290.2.

Second step: under the ice bath, the above product 1-7 (9.7 g, 33.5 mmol) was dissolved in HCl/Et$_2$O (4N, 100 mL), then warmed to room temperature overnight naturally. Filtered, washed with ether and dried to give the product V-7 (7.0 g, yield 93%).

ESI-MS for the product V-7 [(M+H)$^+$]: m/z calculated 190.1, founded 190.2.

EXAMPLE 8

Synthesis of Compound V-8

Compound V-8 was prepared by two steps identical to that described in example 2, after two-step reaction the product V-8 (31.8 g) was obtained. Using the reagent SM-1g instead of SM-1b in the first-stage reaction, the intermediate product 1-8 was obtained, which was confirmed by MS, ESI-MS [(M+H)$^+$]: m/z calculated 276.1, founded 276.2.

$^1$H-NMR for the product V-8 (CD$_3$OD, 400 MHz): δ 7.31-7.30 (d, 1H), 7.00-6.96 (m, 2H), 6.09-6.01 (m, 1H), 5.41-5.37 (m, 1H), 5.27-5.24 (m, 1H), 4.57 (s, 2H), 4.56 (d, 2H), 4.53 (s, 2H). ESI-MS [(M+H)$^+$]: m/z calculated 176.1, founded 176.2.

EXAMPLE 9

Synthesis of Compound V-9

Compound V-9 was prepared by a sequence of two steps identical to that described in example 2, after two-step reaction the product V-9 (32.2 g) was obtained. Using the reagent SM-1 h instead of SM-1b in the first-stage reaction, the intermediate product 1-9 was obtained, which was confirmed by MS, ESI-MS [(M+H)$^+$]: m/z calculated 304.1, founded 304.2.

$^1$H-NMR for the product V-9 (CD$_3$OD, 400 MHz): δ 8.10-8.09 (d, 1H), 8.09-8.07 (s, 1H), 7.57-7.55 (d, 1H), 6.06-6.04 (m, 1H), 5.43-5.40 (m, 1H), 5.30-5.28 (m, 1H), 4.84-4.83 (m, 2H), 4.70-4.69 (d, 4H). ESI-MS [(M+H)$^+$]: m/z calculated 204.1, founded 204.2.

EXAMPLE 10

Synthesis of compound V-10

Compound V-10 was prepared by two steps identical to that described in example 2, after two-step reaction the product V-10 (30.1 g) was obtained. Using the reagent SM-1j instead of SM-1b in the first-stage reaction, the intermediate product 1-10 was obtained, which was confirmed by MS, ESI-MS [(M+H)$^+$]: m/z calculated 310.1, founded 310.2.

$^1$H-NMR for the product V-10 (CD$_3$OD, 400 MHz): δ 7.39-7.37 (d, 1H), 7.03-7.02 (d, 1H), 6.05-5.97 (m, 1H), 5.41-5.37 (m, 1H), 5.28-5.25 (m, 1H), 4.65-4.64 (d, 2H), 4.49 (s, 2H), 4.48 (s, 2H). ESI-MS [(M+H)$^+$]: m/z calculated 210.1, founded 210.2.

EXAMPLE 11

Synthesis of Compound V-11

Compound V-11 was prepared by two steps identical to that described in example 2, after two-step reaction the product V-11 (29.6 g) was obtained. Using the reagent SM-1m instead of SM-1b in the first-stage reaction, the intermediate product 1-11 was obtained, which was confirmed by MS, ESI-MS [(M+H)$^+$]: m/z calculated 292.1, founded 292.2.

$^1$H-NMR for the product V-11 (CD$_3$OD, 400 MHz): δ 7.32-7.28 (m, 2H), 7.13-7.12 (d, 1H), 5.89-5.80 (m, 1H), 5.15-5.10 (t, J=9 Hz, 2H), 4.73 (s, 2H), 4.68-4.67 (d, J=4.5

Hz, 2H), 3.56-3.55 (d, J=7 Hz, 2H). ESI-MS [(M+H)⁺]: m/z calculated 192.1, founded 192.2.

EXAMPLE 12

Synthesis of Compound V-12

Compound V-12 was prepared by two steps identical to that described in example 2, after two-step reaction the product V-12 (16.3 g) was obtained. Using the reagent SM-1n instead of SM-1b in the first-stage reaction, the intermediate product 1-12 was obtained, which was confirmed by MS, ESI-MS [(M+H)⁺]: m/z calculated 289.2, founded 289.3.

ESI-MS for the product V-12 [(M+H)⁺]: m/z calculated 189.2, founded 189.3.

EXAMPLE 13

Synthesis of Compound 4ba

Synthesis of Compound 4ba was carried out by the following two steps:

First Step: Synthesis of compound 4aa

SM-4a (4.9 g, 2.0 mmol) was dissolved in 50 mL of anhydrous DCM, then CDI (4.0 g, 24 mmol, 1.2 eq.) was added. After the reaction solution was warmed to 40 to complete the reaction, the compound V-1 (3.0 mmol, 1.5 eq.) was added. The reaction was continued until the end of the reaction. Cooled, 50 mL DCM was added, washed successively with 1N hydrochloric acid, saturated brine, dried, concentrated and purified by column chromatography to obtain a yellow foamy solid product 4aa (7.2 g; yield: 81%).

$^1$H-NMR for the product 4aa (CDCl$_3$, 500 MHz): δ 7.46-7.48 (m, 1H), 7.35-7.39 (m, 2H), 6.23-6.33 (dbrs, 1H), 5.88-5.95 (m, 1H), 5.19-5.32 (m, 3H), 4.97-5.02 (m, 2H), 4.66-4.72 (ds, 2H), 4.42-4.47 (m, 1H), 4.06-4.08 (m, 2H), 3.57-3.82 (m, 5H), 2.46 (m, 1H), 2.21 (m, 1H), 1.45-1.46 (d, 4H), 1.42 (s, 5H). ESI-MS [(M+H)⁺]: m/z calculated 474.2, founded 474.3.

Second Step: Synthesis of compound 4ba

The above product 4aa (7.0 g) was dissolved in 10 mL methanol, and Et$_2$O/HCl solution (4N, 20 mL) was added. The mixture was refluxed for 3 h. Concentrated, a white foamy solid hydrochloride product 4ba (5.8 g; yield: 87%) was obtained.

$^1$H-NMR for the product 4ba (CD$_3$OD, 500 MHz): δ 7.65-7.68 (m, 1H), 7.42-7.50 (m, 2H), 5.93-5.94 (m, 1H), 5.44 (brs, 1H), 5.22-5.25 (d, J=17.0 Hz, 1H), 5.13-5.15 (d, J=10.0 Hz, 1H), 4.96-5.00 (m, 3H), 4.72-4.79 (m, 3H), 3.98 (s, 2H), 3.89 (s, 3H), 3.71 (m, 1H), 3.63-3.64 (m, 1H), 2.70-2.72 (m, 1H), 2.47 (m, 1H). ESI-MS [(M+H)⁺]: m/z calculated 374.2, founded 374.3.

EXAMPLE 14

Synthesis of Compound 4bb

Compound 4bb was prepared by two steps identical to that described in example 13, after two-step reaction the product 4bb (5.1 g) was obtained using the reagent V-2 instead of V-1 in the first-stage reaction.

$^1$H-NMR for the product 4ab (CDCl$_3$, 500 MHz): δ 7.19-7.22 (m, 1H), 6.78-6.84 (dd, J=7.5, 20 Hz, 1H), 6.71-6.72 (d, J=8.0 Hz, 1H), 6.01 (m, 1H), 5.36-5.39 (d, J=16.5 Hz, 1H), 5.24-5.29 (m, 2H), 4.53-4.69 (m, 6H), 4.34-4.48 (m, 1H), 3.60-3.73 (m, 5H), 2.41-2.49 (m, 1H), 2.21 (m, 1H), 1.41-1.44 (m, 9H). ESI-MS [(M+H)⁺]: m/z calculated 447.2, founded 447.3.

$^1$H-NMR for the product 4bb (CD$_3$OD, 500 MHz): δ 7.24 (m, 1H), 6.84-6.89 (m, 2H), 6.05 (m, 1H), 5.37-5.41 (m, 2H), 5.24-5.26 (m, 1H), 4.58-4.76 (m, 7H), 3.88 (s, 3H), 3.59-3.68 (m, 2H), 2.70 (m, 1H), 2.45 (m, 1H). ESI-MS [(M+H)⁺]: m/z calculated 347.2, founded 347.3.

EXAMPLE 15

Synthesis of Compound 4bc

Compound 4bc was prepared by two steps identical to that described in example 13, after two-step reaction the product 4bc (4.8 g) was obtained. Using the reagent V-3 instead of V-1 in the first-stage reaction, the intermediate product 4ac was obtained, which was confirmed by MS, ESI-MS [(M+H)⁺]: m/z calculated 461.1, founded 461.2.

$^1$H-NMR for the product 4bc (CD$_3$OD, 500 MHz): δ 7.25-7.28 (t, J=7.1 Hz, 1H), 6.85-6.90 (m, 2H), 5.93 (m, 1H), 5.43 (m, 1H), 5.08-5.18 (m, 2H), 4.70-4.78 (m, 4H), 4.61 (m, 1H), 4.07-4.10 (m, 2H), 3.86-3.89 (m, 3H), 3.64-3.71 (m, 2H), 2.71 (m, 1H), 2.47-2.53 (m, 3H). ESI-MS [(M+H)⁺]: m/z calculated 361.2, founded 361.3.

EXAMPLE 16

Synthesis of Compound 4bd

Compound 4bd was prepared by two steps identical to that described in example 13, after two-step reaction the product 4bd (4.8 g) was obtained using the reagent V-4 instead of V-1 in the first-stage reaction.

$^1$H-NMR for the product 4ad (CDCl$_3$, 500 MHz): δ 6.33-6.38 (ds, 2H), 5.97-6.07 (m, 1H), 5.38-5.41 (d, J=16.5 Hz, 1H), 5.26-5.31 (m, 2H), 4.67 (m, 1H), 4.54-4.67 (m, 5H), 4.35-4.49 (m, 1H), 3.78 (s, 3H), 3.61-3.75 (m, 5H), 2.46 (m, 1H), 2.22 (m, 1H), 1.46 (s, 4H), 4.43 (s, 5H). ESI-MS [(M+H)⁺]: m/z calculated 477.2, founded 477.3.

$^1$H-NMR for the product 4bd (CD$_3$OD, 500 MHz): δ 6.42-6.48 (m, 2H), 6.04 (m, 1H), 5.41 (m, 2H), 5.25-5.27 (m, 1H), 4.71 (m, 2H), 4.63-4.64 (m, 2H), 4.55 (m, 3H), 3.88 (s, 3H), 3.77 (s, 3H), 3.64-3.71 (m, 2H), 2.69 (m, 1H), 2.46 (m, 1H). ESI-MS [(M+H)⁺]: m/z calculated 377.2, founded 377.4.

EXAMPLE 17

Synthesis of Compound 4be

Compound 4be was prepared by two steps identical to that described in example 13, after two-step reaction the product 4be (5.2 g) was obtained using the reagent V-5 instead of V-1 in the first-stage reaction.

$^1$H-NMR for the product 4ae (CDCl$_3$, 500 MHz): δ 6.85-6.91 (m, 2H), 6.04 (m, 1H), 5.29-5.34 (m, 2H), 5.21-5.24 (m, 2H), 4.55-4.72 (m, 6H), 4.40-4.48 (m, 1H), 3.85 (s, 3H), 3.62-3.76 (m, 5H), 2.47 (m, 1H), 2.23 (m, 1H), 1.43-1.46 (m, 9H). ESI-MS [(M+H)⁺]: m/z calculated 477.2, founded 477.3.

$^1$H-NMR for the product 4be (CD$_3$OD, 500 MHz): δ 6.70-6.95 (m, 2H), 6.01 (m, 1H), 5.41 (m, 1H), 5.32 (m, 1H), 5.17-5.19 (d, J=10 Hz, 1H), 4.54-4.70 (m, 6H), 3.88-4.08 (m, 2H), 3.83 (s, 3H), 3.71 (m, 1H), 3.64 (m, 1H), 3.31-3.35 (m, 2H), 2.69 (m, 1H), 2.46 (m, 1H). ESI-MS [(M+H)⁺]: m/z calculated 377.2, founded 377.4.

EXAMPLE 18

Synthesis of Compound 4bf

Compound 4bf was prepared by two steps identical to that described in example 13, after two-step reaction the product 4bf (4.6 g) was obtained. Using the reagent V-6 instead of V-1 in the first-stage reaction, the intermediate product 4af was obtained, which was confirmed by MS, ESI-MS [(M+H)⁺]: m/z calculated 461.2, founded 461.4.

¹H-NMR for the product 4bf (CD₃OD, 500 MHz): δ 7.24-7.30 (m, 3H), 5.96 (m, 1H), 5.44 (m, 1H), 5.28-5.32 (m, 1H), 5.18-5.20 (m, 1H), 4.72-4.82 (m, 5H), 4.53 (m, 2H), 4.02-4.03 (m, 2H), 3.86-3.89 (m, 3H), 3.70 (m, 1H), 3.63 (m, 1H), 2.72 (m, 1H), 2.47 (m, 1H). ESI-MS [(M+H)⁺]: m/z calculated 361.2, founded 361.4.

EXAMPLE 19

Synthesis of Compound 4bg

Compound 4bg was prepared by two steps identical to that described in Example 13, after two-step reaction the product 4bg (4.9 g) was obtained using the reagent V-7 instead of V-1 in the first-stage reaction.

¹H-NMR for the product 4ag (CDCl₃, 500 MHz): δ 6.58-6.70 (m, 1H), 6.47-6.54 (m, 1H), 6.04 (m, 2H), 5.93-5.96 (m, 2H), 5.51-5.54 (m, 1H), 5.32 (brs, 1H), 4.56-4.70 (m, 4H), 4.39-4.48 (m, 1H), 3.62-3.75 (m, 5H), 2.48 (m, 1H), 2.23 (m, 1H), 1.43-1.46 (d, 9H). ESI-MS [(M+H)⁺]: m/z calculated 461.2, founded 461.4.

¹H-NMR for the product 4bg (CD₃OD, 500 MHz): δ 6.53-6.77 (m, 2H), 6.02-6.03 (m, 2H), 5.94-5.96 (m, 1H), 5.24-5.43 (m, 2H), 4.60-4.83 (m, 5H), 3.89 (s, 3H), 3.69 (m, 1H), 3.61-3.64 (m, 1H), 3.35 (brs, 1H), 2.70 (m, 1H), 2.47 (m, 1H). ESI-MS [(M+H)⁺]: m/z calculated 361.2, founded 361.4.

EXAMPLE 20

Synthesis of Compound 4bh

Compound 4bh was prepared by two steps identical to that described in example 13, after two-step reaction the product 4bh (5.0 g) was obtained using the reagent V-8 instead of V-1 in the first-stage reaction.

¹H-NMR for the product 4ah (CDCl₃, 500 MHz): δ 7.11-7.17 (dd, J=9.0, 11.3 Hz, 1H), 6.84-6.86 (d, J=8.5 Hz, 1H), 6.77-6.81 (d, J=20.5 Hz, 1H), 6.05 (m, 1H), 5.40-5.43 (d, J=17.5 Hz, 1H), 5.28-5.32 (m, 2H), 4.52-4.69 (m, 6H), 4.38-4.47 (m, 1H), 3.62-3.76 (m, 5H), 2.44-2.51 (m, 1H), 2.24 (m, 1H), 1.46 (s, 4H), 1.43 (s, 5H). ESI-MS [(M+H)⁺]: m/z calculated 447.2, founded 447.4.

¹H-NMR for the product 4bh (CD₃OD, 500 MHz): δ 7.18 (m, 1H), 6.87 (m, 2H), 6.05 (m, 1H), 5.37-5.42 (m, 2H), 5.23-5.25 (d, J=10.5 Hz, 1H), 4.61-4.73 (m, 5H), 4.53 (m, 2H), 3.89 (s, 3H), 3.64-3.70 (m, 2H), 2.68 (m, 1H), 2.47 (m, 1H). ESI-MS [(M+H)⁺]: m/z calculated 347.2, founded 347.4.

EXAMPLE 21

Synthesis of Compound 4bj

Compound 4bj was prepared by two steps identical to that described in example 13, after two-step reaction the product 4bj (5.0 g) was obtained using the reagent V-9 instead of V-1 in the first-stage reaction.

¹H-NMR for the product 4aj (CDCl₃, 500 MHz): δ 8.00-8.01 (d, J=8.0 Hz, 1H), 7.94-7.97 (d, J=18.0 Hz, 1H), 7.30-7.35 (dd, J=8.0, 10.8 Hz, 1H), 6.03 (m, 1H), 5.39-5.43 (d, J=17.0 Hz, 1H), 5.29-5.33 (m, 2H), 4.70-4.83 (m, 6H), 4.38-4.47 (m, 1H), 3.62-3.75 (m, 5H), 2.48 (m, 1H), 2.24 (m, 1H), 1.46 (s, 4H), 1.43 (s, 5H). ESI-MS [(M+H)⁺]: m/z calculated 475.2, founded 475.3.

¹H-NMR for the product 4bj (CD₃OD, 500 MHz): δ 7.95-7.97 (m, 2H), 7.43 (m, 1H), 5.45 (m, 1H), 4.69-4.82 (m, 8H), 3.91 (s, 3H), 3.89 (s, 2H), 3.64-3.70 (m, 2H), 2.72 (m, 1H), 2.47 (m, 1H). ESI-MS [(M+H)⁺]: m/z calculated 375.2, founded 375.3.

EXAMPLE 22

Synthesis of Compound 4bk

Compound 4bk was prepared by two steps identical to that described in example 13, after two-step reaction the product 4bk (4.2 g) was obtained using the reagent V-10 instead of V-1 in the first-stage reaction.

The product 4ak was confirmed by MS, ESI-MS [(M+H)⁺]: m/z calculated 481.2, founded 481.3. The product 4bk was confirmed by MS, ESI-MS [(M+H)⁺]: m/z calculated 381.2, founded 381.3.

EXAMPLE 23

Synthesis of Compound 4bm

Compound 4bm was prepared by two steps identical to that described in example 13, after two-step reaction the product 4bm (3.6 g) was obtained using the reagent V-11 instead of V-1 in the first-stage reaction.

The product 4ak was confirmed by MS, ESI-MS [(M+H)⁺]: m/z calculated 463.1, founded 463.3. The product 4bk was confirmed by MS, ESI-MS [(M+H)⁺]: m/z calculated 363.1, founded 363.2.

EXAMPLE 24

Synthesis of Compound 4bn

Compound 4bn was prepared by two steps identical to that described in example 13, after two-step reaction the product 4bn (2.4 g) was obtained using the reagent V-12 instead of V-1 in the first-stage reaction.

The product 4an was confirmed by MS, ESI-MS [(M+H)⁺]: m/z calculated 460.2, founded 460.3. The product 4bn was confirmed by MS, ESI-MS [(M+H)⁺]: m/z calculated 360.2, founded 360.3.

EXAMPLE 25

Synthesis of Compound 15a

Synthesis of Compound 15a was carried out by the following five steps:

First Step: Synthesis of compound 11a

Compound 4bb (1.91 g, 5.0 mmol), SM-3j (1.05 eq.), HATU (1.1 eq.) were dissolved in DMF (50 mL), then DIEA (4 eq.) was added dropwise under the ice bath. Naturally returned to room temperature, stirred overnight to complete the reaction. After concentrated, 200 mL ethyl acetate wased added, successively washed with water, 1N hydrochloric acid, saturated brine, dried, concentrated and purified by column chromatography to obtain a pale yellow viscous oily product 11a (2.63 g, yield: 87%). The product 11a was confirmed by MS, ESI-MS [(M+H)⁺]: m/z calculated 612.3, founded 612.4.

Second Step: Synthesis of compound 12a

The above product 11a (0.62 g, 1.0 mmol) was dissolved in 180 mL of anhydrous DCE, after deoxygenation Zhan Catalyst-1B (18 mg) was added under an argon atmosphere in a 80 oil bath until the end of the reaction. After cooling, concentrated, and purified by column chromatography to obtain a white foamy solid product 12a (0.46 g, yield: 81%). The product 12a was confirmed by MS, ESI-MS [(M+H)⁺]: m/z calculated 584.3, founded 584.4.

Third Step: Synthesis of compound 13a

The above product 12a (0.22 g) was dissolved in 20 mL of anhydrous methanol, then 10% Pd/C (20 mg, 10% w) was added, hydrogenated overnight to complete the reaction. Filtered, the filtrate was concentrated to obtain a white foamy solid product 13a (0.22 g, yield: 100%). The product 13a was confirmed by MS, ESI-MS [(M+H)$^+$]: m/z calculated 586.3, founded 586.4.

Forth Step: Synthesis of compound 14a

The above product 13a (0.2 g) was dissolved in the mixture of 10 mL THF, 5 mL CH$_3$OH and 5 mL water, and lithium hydroxide monohydrate (90.0 mg, 2.14 mmol, 3 eq.) was added. The reaction solution was stirred in a 45 oil bath until the reaction was completed. Concentrated and dissolved in 50 mL water, aqueous phase was adjusted to pH=2-3 using 1N HCl, extracted with ethyl acetate. The combined organic phase was washed with saturated brine, dried, and concentrated to obtain a white foamy solid product 14a (0.18 g, yield: 92%). The product 14a was confirmed by MS, ESI-MS [(M+H)$^+$]: m/z calculated 572.3, founded 572.4.

Fifth Step: Synthesis of compound 15a

The above product 14a (57 mg, 0.12 mmol), SM-5a (38 mg, 1.05 eq.), HATU (54 mg, 1.1 eq.) were dissolved in 5.0 mL DMF, DIEA (66 mg, 4 eq.) was added dropwise under the ice bath. Naturally returned to room temperature, stirred overnight to complete the reaction. Concentrated, 30 mL ethyl acetate was added, successively washed with water, 1N hydrochloric acid, saturated brine, dried, concentrated and purified by column chromatography to obtain a pale yellow foamy solid 15a (55 mg, yield: 71%).

$^1$H-NMR for the product 15a (CDCl$_3$, 500 MHz): δ 10.12 (s, 1H), 7.22-7.25 (t, J=8.3 Hz, 1H), 6.83-6.85 (d, J=7.1 Hz, 1H), 6.71-6.72 (d, J=8.2 Hz, 1H), 6.59 (s, 1H), 5.54-5.56 (d, J=9.1 Hz, 1H), 5.41 (m, 1H), 4.85-4.87 (d, J=11.2 Hz, 1H), 4.70-4.74 (m, 2H), 4.54-4.57 (m, 1H), 4.44-4.47 (m, 1H), 4.36-4.38 (d, J=9.0 Hz, 1H), 4.28-4.31 (m, 1H), 4.16-4.18 (m, 1H), 3.99-4.01 (m, 2H), 3.90-3.93 (m, 1H), 2.88-2.93 (m, 2H), 2.52 (m, 1H), 2.30 (m, 1H), 1.88 (m, 1H), 1.58-1.77 (m, 7H), 1.25-1.44 (m, 7H), 1.04-1.06 (m, 11H), 0.92-0.95 (t, J=7.3 Hz, 3H), 0.53 (m, 1H), 0.40 (m, 1H), 0.31 (m, 2H). ESI-MS [(M+H)$^+$]: m/z calculated 786.4, founded 786.6

EXAMPLE 26

Synthesis of Compound 15b

Compound 15b was prepared by a sequence of five steps identical to that described in example 25. The product 12a of the second step was directly hydrolysised in the fourth step without passing through the third hydrogenation reaction. In the fifth-stage the reagent SM-5a was amidated to obtain product 15b (57 mg).

$^1$H-NMR for the product 15b (CDCl$_3$, 500 MHz): δ 10.13 (s, 1H), 7.22-7.26 (t, J=8.5 Hz, 1H), 6.85-6.86 (d, J=7.2 Hz, 1H), 6.73-6.75 (d, J=8.4 Hz, 1H), 6.70 (s, 1H), 5.84-5.89 (m, 1H), 5.67-5.72 (m, 1H), 5.40 (m, 1H), 5.51-5.53 (d, J=9.7 Hz, 1H), 5.39 (m, 1H), 4.68-4.75 (m, 3H), 4.58-4.60 (m, 1H), 4.47-4.50 (m, 2H), 4.38-4.42 (m, 1H), 431-4.35 (m, 2H), 4.15-4.18 (m, 1H), 3.88-3.91 (m, 1H), 2.83-2.96 (m, 2H), 2.52 (m, 1H), 2.31 (m, 1H), 1.96 (m, 1H), 1.72 (m, 1H), 1.59-1.71 (m, 3H), 1.32-1.44 (m, 5H), 1.02-1.05 (m, 11H), 0.93-0.96 (t, J=7.2 Hz, 3H), 0.53 (m, 1H), 0.39 (m, 1H), 0.36 (m, 2H), 0.28 (m, 1H). ESI-MS [(M+H)$^+$]: m/z calculated 784.4, founded 784.5.

EXAMPLE 27

Synthesis of Compound 15c

Compound 15c was prepared by a sequence of five steps identical to that described in example 25. The product 12a of the second step was directly hydrolysised in the fourth step without passing through the third hydrogenation reaction. In the fifth-stage the reagent SM-5b instead of SM-5a was amidated to obtain product 15c (51 mg).

$^1$H-NMR for the product 15c (CDCl$_3$, 500 MHz): δ 10.14 (s, 1H), 7.23-7.26 (t, J=7.8 Hz, 1H), 6.85-6.87 (d, J=7.6 Hz, 1H), 6.74-6.75 (m, 2H), 5.83-5.89 (m, 2H), 5.68-5.71 (m, 1H), 5.52-5.53 (m, 1H), 5.39 (m, 1H), 5.24-5.28 (d, J=16.9 Hz, 1H), 5.14-5.16 (d, J=10.0 Hz, 1H), 4.69-4.79 (m, 3H), 4.59-4.62 (d, J=14.7 Hz, 1H), 4.49-4.52 (m, 2H), 4.39-4.43 (m, 1H), 432-4.34 (m, 2H), 4.17-4.19 (d, J=11.0 Hz, 1H), 3.89-3.92 (m, 1H), 3.04 (m, 1H), 2.89-2.91 (m, 1H), 2.52-2.57 (m, 2H), 2.30-2.35 (m, 1H), 2.05-2.15 (m, 3H), 1.96-1.99 (m, 1H), 1.55-1.58 (m, 1H), 1.31-1.43 (m, 3H), 1.01-1.06 (m, 11H), 0.53 (m, 1H), 0.41 (m, 1H), 0.35 (m, 1H), 0.26 (m, 1H). ESI-MS [(M+H)$^+$]: m/z calculated 782.3, founded 782.5.

EXAMPLE 28

Synthesis of Compound 15d

Compound 15d was prepared by a sequence of five steps identical to that described in example 25. In the fifth-stage the reagent SM-5b instead of SM-5a was amidated to obtain product 15d (48 mg).

$^1$H-NMR for the product 15d (CDCl$_3$, 500 MHz): δ 10.14 (s, 1H), 7.22-7.25 (t, J=7.6 Hz, 1H), 6.83-6.84 (d, J=7.6 Hz, 1H), 6.77 (s, 1H), 6.70-6.72 (d, J=7.6 Hz, 1H), 5.80-5.87 (d, J=8.6 Hz, 1H), 5.56-5.58 (d, J=9.2 Hz, 1H), 5.40 (m, 1H), 5.23-5.26 (d, J=17.4 Hz, 1H), 5.13-5.15 (d, J=10.4 Hz, 1H), 4.86-4.88 (d, J=11.1 Hz, 1H), 4.67-4.77 (q, J=14.7 Hz, 2H), 4.55-4.58 (m, 1H), 4.46-4.49 (m, 1H), 4.36-4.38 (d, J=9.7 Hz, 1H), 4.29-4.33 (m, 1H), 4.15-4.17 m, 1H), 3.99-4.01 (m, 2H), 3.90-3.93 (m, 1H), 2.81-2.91 (m, 2H), 2.55 (m, 1H), 2.30 (m, 1H), 2.08-2.14 (m, 1H), 1.96-1.99 (m, 1H), 1.84-1.89 (m, 1H), 1.69-1.76 (m, 4H), 1.54-1.59 (m, 3H), 1.39-1.42 (m, 2H), 1.28-1.35 (m, 1H), 1.02-1.04 (m, 11H), 0.53 (m, 1H), 0.40 (m, 1H), 0.31 (m, 2H). ESI-MS [(M+H)$^+$]: m/z calculated 784.4, founded 784.6.

EXAMPLE 29

Synthesis of Compound 15e

Compound 15e was prepared by a sequence of five steps identical to that described in example 25. In the first-stage the reagent SM-3h instead of SM-3j was amidated to obtain product 15e (49 mg).

$^1$H-NMR for the product 15e (CDCl$_3$, 500 MHz): δ 10.04 (s, 1H), 7.23-7.26 (t, J=7.9 Hz, 1H), 6.83-6.85 (d, J=7.6 Hz, 1H), 6.70-6.72 (d, J=7.7 Hz, 1H), 6.79 (s, 1H), 5.49 (m, 1H), 5.45-5.47 (d, J=10.1 Hz, 1H), 4.72 (m, 2H), 4.63-4.65 (d, J=10.2 Hz, 1H), 4.42-4.51 (m, 3H), 4.28-4.32 (m, 2H), 4.09 (m, 1H), 3.87-3.89 (m, 2H), 2.95-2.98 (m, 2H), 2.42 (m, 1H), 2.31 (m, 1H), 2.12 (m, 1H), 1.84 (m, 3H), 1.59-1.73 (m, 4H), 1.32-1.42 (m, 5H), 1.04-1.06 (m, 11H), 0.92-0.95 (t, J=7.3 Hz, 3H), 0.57 (m, 1H), 0.43 (m, 1H), 0.31 (m, 2H). ESI-MS [(M+H)$^+$]: m/z calculated 772.4, founded 772.6.

EXAMPLE 30

Synthesis of Compound 15f

Compound 15f was prepared by a sequence of five steps identical to that described in example 25. In the first-stage using the reagent SM-3h instead of SM-3j, the product of the second step was directly hydrolysised in the fourth step without passing through the third hydrogenation reaction. In the fifth-stage the reagent SM-5a was amidated to obtain product 15f (44 mg).

$^1$H-NMR for the product 15f (CDCl$_3$, 500 MHz): δ 10.01 (s, 1H), 7.21-7.24 (t, J=7.5 Hz, 1H), 6.83-6.85 (d, J=8.2 Hz, 1H), 6.79 (s, 1H), 6.71-6.72 (d, J=7.9 Hz, 1H), 5.78-5.80 (m, 2H), 5.43-5.45 (d, J=10.1 Hz, 1H), 5.40 (m, 1H), 4.71 (m, 2H), 4.28-4.49 (m, 8H), 3.80-3.83 (m, 1H), 3.02-3.04 (d, J=11.0 Hz, 1H), 2.94 (m, 1H), 2.85 (m, 1H), 2.71 (m, 1H), 2.43 (m, 1H), 2.32 (m, 1H), 1.83 (m, 1H), 1.70 (m, 1H), 1.57-1.64 (m, 2H), 1.34-1.41 (m, 3H), 1.05 (m, 11H), 0.93-0.96 (t, J=7.5 Hz, 3H), 0.61 (m, 1H), 0.47 (m, 1H), 0.38 (m, 1H), 0.32 (m, 1H). ESI-MS [(M+H)$^+$]: m/z calculated 770.3, founded 770.4.

EXAMPLE 31

Synthesis of Compound 15g

Compound 15g was prepared by a sequence of five steps identical to that described in example 25. In the first-stage using the reagent SM-3h instead of SM-3j, the product of the second step was directly hydrolysised in the fourth step without passing through the third hydrogenation reaction. In the fifth-stage the reagent SM-5b instead of SM-5a was amidated to obtain product 15g (41 mg).

$^1$H-NMR for the product 15g (CDCl$_3$, 500 MHz): δ 10.03 (s, 1H), 7.21-7.24 (t, J=8.3 Hz, 1H), 7.04 (s, 1H), 6.83-6.85 (d, J=7.8 Hz, 1H), 6.70-6.72 (d, J=7.9 Hz, 1H), 5.75-5.81 (m, 3H), 5.45-5.47 (d, J=10.1 Hz, 1H), 5.40 (m, 1H), 5.22-5.26 (d, J=17.0 Hz, 1H), 5.12-5.14 (d, J=10.3 Hz, 1H), 4.71 (m, 2H), 4.28-4.49 (m, 8H), 3.80-3.83 (m, 1H), 3.03-3.05 (d, J=10.1 Hz, 1H), 2.93 (m, 1H), 2.73 (m, 1H), 2.47 (m, 1H), 2.31 (m, 1H), 2.11 (m, 1H), 1.98 (m, 1H), 1.79 (s, 1H), 1.54 (m, 1H), 1.31-1.41 (m, 2H), 0.99-1.03 (m, 11H), 0.61 (m, 1H), 0.46 (m, 1H), 0.38 (m, 1H), 0.31 (m, 1H).

ESI-MS [(M+H)$^+$]: m/z calculated 768.3, founded 768.5.

EXAMPLE 32

Synthesis of Compound 15h

Compound 15h was prepared by a sequence of five steps identical to that described in example 25. In the first-stage using the reagent SM-3h instead of SM-3j and the reagent 4be instead of 4bb, the product of the second step was directly hydrolysised in the fourth step without passing through the third hydrogenation reaction. In the fifth-stage the reagent SM-5a was amidated to obtain product 15h (52 mg).

$^1$H-NMR for the product 15h (CDCl$_3$, 500 MHz): δ 6.87-6.89 (m, 1H), 6.81-6.82 (m, 1H), 5.40-5.50 (m, 2H), 5.30 (m, 2H), 4.83 (m, 2H), 4.72-4.83 (m, 2H), 4.66 (m, 2H), 4.47-4.57 (m, 2H), 4.27-4.29 (m, 2H), 3.85 (s, 3H), 3.65 (m, 1H), 3.11 (m, 1H), 2.96 (m, 1H), 2.35-2.51 (m, 2H), 2.15 (m, 1H), 1.85 (m, 1H), 1.56-1.75 (m, 5H), 1.37 (m, 2H), 1.26 (s, 6H), 1.17 (m, 2H), 1.04 (m, 2H), 1.01 (s, 9H), 0.87-0.88 (m, 3H). ESI-MS [(M+H)$^+$]: m/z calculated 802.4, founded 802.5.

EXAMPLE 33

Synthesis of Compound 15j

Compound 15j was prepared by a sequence of five steps identical to that described in example 25. In the first-stage using the reagent SM-3h instead of SM-3j and the reagent 4be instead of 4bb, the product of the second step was directly hydrolysised in the fourth step without passing through the third hydrogenation reaction. In the fifth-stage the reagent SM-5b instead of SM-5a was amidated to obtain product 15j (39 mg).

$^1$H-NMR for the product 15j (CDCl$_3$, 500 MHz): δ 10.16 (s, 1H), 7.49 (s, 1H), 6.94-6.99 (m, 1H), 6.78-6.85 (m, 1H), 5.44-5.85 (m, 4H), 5.11-5.34 (m, 3H), 4.69 (m, 4H), 4.58 (m, 2H), 4.17-4.22 (m, 2H), 4.04-3.92 (m, 1H), 3.85 (m, 3H), 3.59-3.71 (m, 1H), 2.87 (m, 1H), 2.20-2.50 (m, 2H), 1.94-2.14 (m, 4H), 1.60-1.86 (m, 2H), 1.46-1.55 (m, 2H), 1.26-1.46 (m, 4H), 0.95-1.09 (m, 10H), 0.84 (m, 1H). ESI-MS [(M+H)$^+$]: m/z calculated 786.3, founded 786.4.

EXAMPLE 34

Synthesis of Compound 15k

Compound 15k was prepared by a sequence of five steps identical to that described in example 25. In the first-stage using the reagent SM-3b instead of SM-3j and the reagent 4be instead of 4bb, the product of the second step was directly hydrolysised in the fourth step without passing through the third hydrogenation reaction. In the fifth-stage the reagent SM-5b instead of SM-5a was amidated to obtain product 15k (39 mg).

$^1$H-NMR for the product 15j (CDCl$_3$, 500 MHz): δ 9.86-9.96 (m, 1H), 7.23 (s, 1H), 6.82-6.89 (m, 2H), 5.73 (m, 1H), 5.35-5.50 (m, 3H), 5.15-5.26 (m, 3H), 4.65-4.88 (m, 3H), 4.47-4.55 (m, 3H), 4.27-4.36 (m, 2H), 3.86 (s, 3H), 3.73 (m, 1H), 3.64-3.67 (m, 3H), 2.93 (m, 1H), 2.35-2.49 (m, 2H), 1.98-2.09 (m, 2H), 1.61-1.73 (m, 2H), 1.36-1.46 (m, 2H), 1.26-1.34 (m, 4H), 1.03 (s, 9H), 0.88 (m, 2H). ESI-MS [(M+H)$^+$]: m/z calculated 772.3, founded 772.4.

EXAMPLE 35

Synthesis of Compound 15m

Compound 15m was prepared by a sequence of five steps identical to that described in example 25. In the first-stage using the reagent SM-3a instead of SM-3j and the reagent 4be instead of 4bb, the product of the second step was directly hydrolysised in the fourth step without passing through the third hydrogenation reaction. In the fifth-stage the reagent SM-5a was amidated to obtain product 15m (47 mg).

The product 15m was confirmed by MS, ESI-MS [(M+H)$^+$]: m/z calculated 760.3, founded 760.4.

EXAMPLE 36

Synthesis of Compound 15n

Compound 15n was prepared by a sequence of five steps identical to that described in example 25. In the first-stage using the reagent SM-3a instead of SM-3j and the reagent 4be instead of 4bb, the product of the second step was directly hydrolysised in the fourth step without passing through the third hydrogenation reaction. In the fifth-stage the reagent SM-5b instead of SM-5a was amidated to obtain product 15n (36 mg).

$^1$H-NMR for the product 15n (CDCl$_3$, 500 MHz): δ 9.85-9.95 (m, 1H), 7.13-7.21 (m, 1H), 6.92-6.94 (m, 1H), 6.83-6.86 (m, 1H), 5.40-5.83 (m, 4H), 5.13-5.30 (m, 3H), 4.91 (m, 1H), 4.67 (m, 2H), 4.37-4.59 (m, 4H), 4.10-4.22 (m, 2H), 3.85 (m, 3H), 3.81 (m, 1H), 3.65 (m, 1H), 2.91 (m, 1H), 2.27-2.49 (m, 2H), 2.08 (m, 1H), 1.95 (m, 1H), 1.47 (m, 2H), 1.29-1.35 (m, 4H), 1.00-1.01 (m, 9H), 0.88 (m, 2H). ESI-MS [(M+H)$^+$]: m/z calculated 758.3, founded 758.4.

EXAMPLE 37

Synthesis of Compound 15p

Compound 15p was prepared by a sequence of five steps identical to that described in example 25. In the first-stage using the reagent SM-3f instead of SM-3j and the reagent 4be instead of 4bb, the product of the second step was directly hydrolysised in the fourth step without passing through the third hydrogenation reaction. In the fifth-stage the reagent SM-5b instead of SM-5a was amidated to obtain product 15p (43 mg).

The product 15p was confirmed by MS, ESI-MS [(M+H)$^+$]: m/z calculated 800.4, founded 800.6.

EXAMPLE 38

Synthesis of Compound 15q

Compound 15q was prepared by a sequence of five steps identical to that described in example 25. In the first-stage using the reagent SM-3c instead of SM-3j and the reagent 4be instead of 4bb, the product of the second step was directly hydrolysised in the fourth step without passing through the third hydrogenation reaction. In the fifth-stage the reagent SM-5a was amidated to obtain product 15q (49 mg).

$^1$H-NMR for the product 15q (CDCl$_3$, 500 MHz): δ 9.86-10.16 (s, 1H), 7.32 (m, 1H), 6.87-6.92 (m, 1H), 6.68-6.79 (m, 1H), 5.61-5.77 (m, 1H), 5.26-5.45 (m, 2H), 4.69-4.72 (m, 2H), 4.55-4.64 (m, 3H), 4.41-4.52 (m, 2H), 4.19-4.36 (m, 2H), 3.90-4.05 (m, 1H), 3.86 (s, 3H), 3.58-3.69 (m, 1H), 2.95 (m, 1H), 2.32-2.67 (m, 4H), 2.05-2.18 (m, 2H), 1.68-1.73 (m, 2H), 1.54-1.60 (m, 2H), 1.44-1.51 (m, 2H), 1.32-1.40 (m, 4H), 1.01-1.05 (m, 9H), 0.93-0.96 (m, 3H), 0.88 (m, 1H). ESI-MS [(M+H)$^+$]: m/z calculated 788.4, founded 788.4.

EXAMPLE 39

Synthesis of Compound 15r

Compound 15r was prepared by a sequence of five steps identical to that described in example 25. In the first-stage using the reagent SM-3g instead of SM-3j, the product of the second step was directly hydrolysised in the fourth step without passing through the third hydrogenation reaction. In the fifth-stage the reagent SM-5a was amidated to obtain product 15q (49 mg).

$^1$H-NMR for the product 15r (CDCl$_3$, 500 MHz): δ 10.20 (s, 1H), 7.22-7.26 (t, J=7.4 Hz, 1H), 6.85-6.86 (d, J=7.4 Hz, 1H), 6.72-6.74 (d, J=8.2 Hz, 1H), 6.61 (s, 1H), 5.82-5.86 (m, 1H), 5.67-5.70 (m, 1H), 5.58-5.60 (d, J=9.4 Hz, 1H), 5.40 (m, 1H), 4.71-4.77 (m, 2H), 4.60 (m, 1H), 4.84 (m, 2H), 4.39 (m, 2H), 4.33 (m, 1H), 4.26 (m, 1H), 4.06 (m, 1H), 3.96 (m, 1H), 3.38 (m, 1H), 2.90 (m, 1H), 2.49 (m, 1H), 2.26 (m, 1H), 2.04 (m, 2H), 1.61-1.72 (m, 4H), 1.42 (m, 1H), 1.34-1.36 (m, 2H), 1.26 (m, 3H), 1.06 (s, 9H), 1.02-1.04 (m, 4H), 0.98 (s, 3H), 0.84 (m, 3H). ESI-MS [(M+H)$^+$]: m/z calculated 786.4, founded 786.5.

EXAMPLE 40

Synthesis of Compound 15s

Compound 15s was prepared by a sequence of five steps identical to that described in example 25. In the first-stage using the reagent SM-3g instead of SM-3j, product 15s (53 mg) was obtained.

$^1$H-NMR for the product 15s (CDCl$_3$, 500 MHz): δ 10.18 (s, 1H), 7.23-7.25 (t, J=6.9 Hz, 1H), 6.84-6.86 (d, J=7.1 Hz, 1H), 6.72-6.74 (d, J=8.9 Hz, 1H), 6.54 (s, 1H), 5.55-5.56 (d, J=9.4 Hz, 1H), 5.42 (m, 1H), 4.69-4.77 (m, 2H), 4.40-4.56 (m, 4H), 4.27 (m, 2H), 3.96-4.04 (m, 3H), 3.28-3.30 (d, J=9.7 Hz, 1H), 2.91 (m, 1H), 2.52 (m, 1H), 2.29 (m, 1H), 2.21 (m, 1H), 2.06 (m, 1H), 1.75 (m, 2H), 1.61-1.68 (m, 3H), 1.40-1.43 (m, 2H), 1.31-1.35 (m, 2H), 1.19-1.22 (m, 6H), 1.07 (s, 9H), 0.94-0.96 (m, 4H), 0.87-0.89 (m, 2H), 0.78-0.81 (m, 3H). ESI-MS [(M+H)$^+$]: m/z calculated 788.4, founded 788.4.

EXAMPLE 41

Synthesis of Compound 15t

Compound 15t was prepared by a sequence of five steps identical to that described in example 25. In the first-stage using the reagent SM-3b instead of SM-3j and the reagent 4be instead of 4bb, the product of the second step was directly hydrolysised in the fourth step without passing through the third hydrogenation reaction. In the fifth-stage the reagent SM-5a was amidated to obtain product 15t (37 mg).

The product 15t was confirmed by MS, ESI-MS [(M+H)$^+$]: m/z calculated 744.3, founded 744.4.

EXAMPLE 42

Synthesis of Compound 15u

Compound 15u was prepared by a sequence of five steps identical to that described in example 25, using the reagent SM-3f instead of SM-3j in the first-stage reaction. After purification, 50 mg of product 15u was obtained.

$^1$H-NMR for the product 15u (CHCl$_3$, 500 MHz): δ 9.99 (s, 1H), 7.22-7.25 (t, J=7.7 Hz, 1H), 6.83-6.84 (d, J=7.2 Hz, 1H), 6.69-6.71 (d, J=7.8 Hz, 1H), 6.64 (s, 1H), 5.49 (m, 1H), 5.40-5.42 (d, J=9.9 Hz, 1H), 4.71 (s, 2H), 4.42-4.49 (m, 3H), 4.24-4.30 (m, 2H), 4.14-4.16 (m, 1H), 4.04-4.06 (d, J=10.8 Hz, 1H), 3.80-3.89 (m, 2H), 3.39-3.41 (d, J=10.6 Hz, 1H), 2.93-2.95 (m, 1H), 2.39-2.43 (m, 1H), 2.26-2.30 (m, 1H), 1.92-1.99 (m, 1H), 1.71-1.73 (m, 1H), 1.55-1.66 (m, 4H), 1.40-1.43 (m, 2H), 1.31-1.34 (m, 2H), 1.12-1.17 (m, 1H), 1.07 (s, 9H), 1.01 (s, 3H), 0.92-0.95 (t, J=7.4 Hz, 3H), 0.84-0.87 (m, 4H), 0.84 (s, 3H). ESI-MS [(M+H)$^+$]: m/z calculated 774.4, founded 774.5.

EXAMPLE 43

Synthesis of Compound 15v

Compound 15v was prepared by a sequence of five steps identical to that described in example 25, using the reagent SM-3g instead of SM-3j and compound 4 db instead of compound 4bb in the first-stage reaction. After purification, 42 mg of product 15v was obtained.

$^1$H-NMR for the product 15v (CHCl$_3$, 500 MHz): δ 10.17 (s, 1H), 6.60 (s, 1H), 6.31 (s, 1H), 6.36 (s, 1H), 5.54-5.56 (d, J=9.6 Hz, 1H), 5.41 (m, 1H), 4.62-4.71 (m, 2H), 4.46-4.47 (m, 1H), 4.35-4.47 (m, 3H), 4.26-4.29 (m, 1H), 4.09-4.11 (m, 1H), 3.99 (m, 1H), 3.91-3.94 (m, 2H), 3.80 (s, 3H), 3.29-3.31 (m, 1H), 2.88-2.93 (m, 1H), 2.45-2.52 (m, 2H), 2.26-2.31 (m, 1H), 1.71-1.73 (m, 3H), 1.57-1.68 (m, 2H), 1.39-1.44 (m, 4H), 1.32-1.36 (m, 3H), 1.25-1.27 (m, 2H), 1.18-1.20 (m, 1H), 1.06 (s, 9H), 0.99-1.04 (m, 3H), 0.92-0.95 (m, 6H), 0.80 (s, 3H). ESI-MS [(M+H)$^+$]: m/z calculated 818.4, founded 818.5.

EXAMPLE 44

Synthesis of Compound 15w

Compound 15w was prepared by a sequence of five steps identical to that described in example 25, using the reagent SM-3b instead of SM-3j in the first-stage reaction. After purification, 46 mg of product 15w was obtained.

$^1$H-NMR for the product 15w (CHCl$_3$, 500 MHz): δ 10.03 (s, 1H), 7.22-7.27 (t, J=8.6 Hz, 1H), 6.83-6.85 (d, J=7.1 Hz, 1H), 6.70-6.72 (d, J=8.2 Hz, 1H), 6.66 (s, 1H), 5.55 (m, 1H), 5.38-5.40 (d, J=10.2 Hz, 1H), 4.72 (s, 2H), 4.47-4.53 (m, 2H), 4.39-4.41 (m, 1H), 4.26-4.33 (m, 3H), 4.11 (m, 1H), 3.88-3.91 (m, 2H), 3.81 (m, 1H), 2.94 (m, 1H), 2.41 (m, 1H), 2.27-2.32 (m, 1H), 1.58-1.90 (m, 2H), 1.70-1.73 (m, 2H), 1.65-1.66 (m, 2H), 1.58 (m, 2H), 1.41 (m, 2H), 1.33 (m, 2H), 1.26 (m, 2H), 1.06 (s, 9H), 0.99 (m, 2H), 0.93-0.96 (t, J=7.2 Hz, 3H). ESI-MS [(M+H)$^+$]: m/z calculated 746.3, founded 746.4.

EXAMPLE 45

Synthesis of Compound 15x

Compound 15x was prepared by a sequence of five steps identical to that described in example 25, using the reagent SM-3c instead of SM-3j in the first-stage reaction. After purification, 49 mg of product 15x was obtained.

$^1$H-NMR for the product 15x (CHCl$_3$, 500 MHz): δ 10.20 (s, 1H), 7.23-7.26 (t, J=7.7 Hz, 1H), 6.84-6.85 (d, J=7.0 Hz, 1H), 6.72-6.74 (d, J=7.8 Hz, 1H), 6.69 (s, 1H), 5.49-5.51 (d, J=10.1 Hz, 1H), 5.47 (m, 1H), 4.68-4.77 (m, 2H), 4.53-4.57 (m, 2H), 4.46-4.49 (m, 1H), 4.35-4.38 (m, 1H), 4.26-4.29 (m, 1H), 4.14 (m, 1H), 4.10 (m, 1H), 3.94-3.97 (m, 2H), 3.69-3.73 (m, 1H), 2.91 (m, 1H), 2.50 (m, 1H), 2.27-2.33 (m, 1H), 1.73 (m, 4H), 1.62 (m, 2H), 1.50 (m, 3H), 1.41 (m, 4H), 1.35 (m, 4H), 1.06 (s, 9H), 1.03-1.04 (m, 2H), 0.92-0.95 (t, J=7.2 Hz, 3H). ESI-MS [(M+H)$^+$]: m/z calculated 760.4, founded 760.5.

EXAMPLE 46

Synthesis of Compound 15y

Compound 15y was prepared by a sequence of five steps identical to that described in example 25, using the reagent SM-3d instead of SM-3j in the first-stage reaction. After purification, 46 mg of product 15y was obtained.

$^1$H-NMR for the product 15y (CHCl$_3$, 500 MHz): δ 10.10 (s, 1H), 7.23-7.26 (t, J=8.0 Hz, 1H), 6.84-6.85 (d, J=7.1 Hz, 1H), 6.73-6.75 (d, J=8.2 Hz, 1H), 6.59 (s, 1H), 5.59 (m, 1H), 5.44-5.45 (d, J=9.6 Hz, 1H), 4.47 (s, 2H), 4.50-4.57 (m, 2H), 4.37-4.38 (m, 1H), 4.28-4.30 (m, 2H), 4.06-4.13 (m, 2H), 3.96-4.01 (m, 2H), 3.77-3.81 (m, 1H), 2.92 (m, 1H), 2.30-2.35 (m, 2H), 1.79 (m, 2H), 1.71-1.74 (m, 2H), 1.64-1.68 (m, 2H), 1.53 (m, 2H), 1.45 (m, 3H), 1.39 (m, 4H), 1.36 (m, 4H), 1.06 (s, 9H), 1.02-1.06 (m, 2H), 0.94-0.95 (t, J=7.4 Hz, 3H). ESI-MS [(M+H)$^+$]: m/z calculated 774.4, founded 774.5.

EXAMPLE 47

Synthesis of Compound 15z

Compound 15z was prepared by a sequence of five steps identical to that described in example 25, using the reagent SM-3e instead of SM-3j in the first-stage reaction. After purification, 49 mg of product 15z was obtained.

$^1$H-NMR for the product 15z (CHCl$_3$, 500 MHz): δ 10.19 (s, 1H), 7.23-7.25 (d, J=7.7 Hz, 1H), 6.74-6.76 (d, J=8.3 Hz, 1H), 6.66 (s, 1H), 5.51-5.55 (m, 2H), 4.74 (s, 2H), 4.53-4.62 (m, 2H), 4.31-4.36 (m, 3H), 3.98-4.09 (m, 4H), 3.73-3.77 (m, 1H), 2.91 (m, 1H), 2.34-2.37 (m, 2H), 1.78-1.82 (m, 2H), 1.70-1.72 (m, 2H), 1.63-1.65 (m, 3H), 1.55 (m, 2H), 1.47 (m, 2H), 1.39-1.42 (m, 4H), 1.29-1.36 (m, 6H), 1.06 (s, 9H), 0.99 (m, 2H), 0.93-0.96 (t, J=7.2 Hz, 3H). ESI-MS [(M+H)$^+$]: m/z calculated 788.4, founded 788.4.

EXAMPLE 48

Synthesis of Compound 15aa

Compound 15aa was prepared by a sequence of five steps identical to that described in example 25, using the reagent SM-3b instead of SM-3j in the first-stage reaction and the reagent SM-5b instead of SM-5a in the fifth-stage reaction. After purification, 39 mg of product 15aa was obtained.

ESI-MS for the product 15aa [(M+H)$^+$]: m/z calculated 744.3, founded 744.4.

EXAMPLE 49

Synthesis of Compound 15ab

Compound 15ab was prepared by a sequence of five steps identical to that described in example 25, using the reagent SM-3c instead of SM-3j in the first-stage reaction and the reagent SM-5b instead of SM-5a in the fifth-stage reaction. After purification, 45 mg of product 15ab was obtained.

ESI-MS for the product 15ab [(M+H)$^+$]: m/z calculated 758.3, founded 758.4.

EXAMPLE 50

Synthesis of Compound 15ac

Compound 15ac was prepared by a sequence of five steps identical to that described in example 25, using the reagent SM-3d instead of SM-3j in the first-stage reaction and the reagent SM-5b instead of SM-5a in the fifth-stage reaction. After purification, 31 mg of product 15ac was obtained.

ESI-MS for the product 15ac [(M+H)$^+$]: m/z calculated 772.4, founded 772.4.

EXAMPLE 51

Synthesis of Compound 15ad

Compound 15ad was prepared by a sequence of five steps identical to that described in example 25, using the reagent SM-3a instead of SM-3j in the first-stage reaction, the product of the second step directly to hydrolysis of the fourth step without passing through the third hydrogenation reaction step and the reagent SM-5b instead of SM-5a in the fifth-stage amidation reaction. After purification, 47 mg of product 15ad was obtained.

$^1$H-NMR for the product 15ad (CHCl$_3$, 500 MHz): δ 9.98 (s, 1H), 7.21-7.24 (t, J=8.0 Hz, 1H), 7.08 (brs, 1H), 6.84-6.86 (d, J=8.0 Hz, 1H), 6.72-6.74 (d, J=8.0 Hz, 1H), 5.87 (m, 1H), 5.77 (m, 1H), 5.68 (m, 2H), 5.33 (m, 1H), 5.22-5.25 (d, J=11.5 Hz, 1H), 5.11-5.13 (d, J=11.0 Hz, 1H), 4.63-4.71 (m, 3H), 4.47-4.53 (m, 2H), 4.42-4.44 (m, 1H), 4.36 (m, 2H), 4.09-4.14 (m, 2H), 3.83 (m, 2H), 2.89 (m, 1H), 2.47-2.56 (m, 2H), 2.25-2.33 (m, 2H), 1.50-1.53 (m, 1H), 1.24-1.28 (m, 4H), 0.99-1.03 (m, 11H). ESI-MS [(M+H)$^+$]: m/z calculated 728.3, founded 728.3.

EXAMPLE 52

Synthesis of Compound 15ae

Compound 15ae was prepared by a sequence of five steps identical to that described in example 25, using the reagent SM-3a instead of SM-3j in the first-stage reaction, the product of the second step directly to hydrolysis of the fourth step without passing through the third hydrogenation reaction and the reagent SM-5a in the fifth-stage amidation reaction. After purification, 39 mg of product 15ae was obtained.

$^1$H-NMR for the product 15ae (CHCl$_3$, 500 MHz): δ 9.94-10.00 (ds, 1H), 7.21-7.25 (m, 1H), 6.92 (brs, 1H), 6.84-6.87 (m, 1H), 6.72-6.74 (m, 1H), 5.70-6.02 (m, 2H), 5.61 (m, 1H), 5.34-5.40 (m, 1H), 4.67-4.76 (m, 2H), 4.53-4.65 (m, 2H), 4.23-4.42 (m, 5H), 4.10-4.14 (m, 1H), 3.73-3.86 (m, 2H), 2.94 (m, 1H), 2.45-2.60 (m, 2H), 2.28-2.37 (m, 2H), 1.67-1.70 (m, 1H), 1.53-1.64 (m, 2H), 1.35-1.41 (m, 3H), 1.24-1.28 (m, 2H), 1.00-1.04 (m, 11H), 0.92-0.97 (m, 3H). ESI-MS [(M+H)$^+$]: m/z calculated 730.3, founded 730.4.

EXAMPLE 53

Synthesis of Compound 15af

Compound 15ae was prepared by a sequence of five steps identical to that described in example 25, using the reagent SM-3a instead of SM-3j in the first-stage reaction and the reagent SM-5b instead of SM-5a in the fifth-stage amidation reaction. After purification, 38 mg of product 15af was obtained.

$^1$H-NMR for the product 15af (CHCl$_3$, 500 MHz): δ 10.01 (s, 1H), 7.21-7.24 (t, J=8.0 Hz, 1H), 6.99 (brs, 1H), 6.83-6.85 (d, J=8.0 Hz, 1H), 6.71-6.72 (d, J=8.5 Hz, 1H), 5.76-5.83 (m, 1H), 5.60-5.62 (d, J=10.5 Hz, 1H), 5.42 (m, 1H), 5.23-5.26 (d, J=17.0 Hz, 1H), 5.12-5.14 (d, J=10.5 Hz, 1H), 4.65-4.75 (m, 2H), 4.55-4.59 (m, 2H), 4.36-4.45 (m, 3H), 4.21-4.23 (d, J=11.5 Hz, 1H), 4.10-4.14 (m, 1H), 3.82-3.89 (m, 2H), 3.73-3.76 (m, 1H), 2.90 (m, 1H), 2.50-2.54 (m, 1H), 2.28-2.32 (m, 1H), 1.76 (m, 5H), 1.59-1.60 (m, 2H), 1.51-1.54 (m, 1H), 1.44 (m, 1H), 1.31-1.37 (m, 2H), 0.99-1.04 (m, 11H). ESI-MS [(M+H)$^+$]: m/z calculated 730.3, founded 730.5.

EXAMPLE 54

Synthesis of Compound 15ag

Compound 15ag was prepared by a sequence of five steps identical to that described in example 25, using the reagent SM-3a instead of SM-3j in the first-stage reaction. After purification, 56 mg of product 15ag was obtained.

$^1$H-NMR for the product 15ag (CHCl$_3$, 500 MHz): δ 10.03 (s, 1H), 7.21-7.24 (t, J=7.5 Hz, 1H), 6.83-6.85 (d, J=7.5 Hz, 1H), 6.82 (brs, 1H), 6.71-6.72 (d, J=8.5 Hz, 1H), 5.54-5.56 (d, J=10.0 Hz, 1H), 5.43 (m, 1H), 4.65-4.75 (m, 2H), 4.55-4.58 (m, 2H), 4.38-4.43 (m, 2H), 4.32-4.35 (m, 1H), 4.20-4.22 (d, J=10.5 Hz, 1H), 4.12 (m, 1H), 3.81-3.89 (m, 2H), 3.74 (m, 1H), 2.93 (m, 1H), 2.47-2.51 (m, 1H), 2.28-2.33 (m, 1H), 1.68-1.78 (m, 4H), 1.57-1.63 (m, 4H), 1.39-1.48 (m, 3H), 1.31-1.32 (m, 2H), 1.03-1.04 (m, 11H), 0.92-0.95 (t, J=7.5 Hz, 3H). ESI-MS [(M+H)$^+$]: m/z calculated 732.3, founded 732.5.

EXAMPLE 55

Synthesis of Compound 15ah

Compound 15ah was prepared by a sequence of five steps identical to that described in example 25, using the reagent SM-3k instead of SM-3j in the first-stage reaction, the product of the second step directly to hydrolysis of the fourth step without passing through the third hydrogenation reaction and the reagent SM-5b instead of SM-5a in the fifth-stage amidation reaction. After purification, 57 mg of product 15ah was obtained.

$^1$H-NMR for the product 15ah (CHCl$_3$, 500 MHz): δ 10.14-10.21 (ds, 1H), 7.23-7.26 (t, J=7.5 Hz, 1H), 6.84-6.86 (d, J=8.0 Hz, 1H), 6.72-6.73 (d, J=7.5 Hz, 1H), 6.62 (brs, 1H), 5.83-5.91 (m, 1H), 5.58-5.61 (m, 2H), 5.41 (m, 2H), 5.25-5.29 (d, J=17.0 Hz, 1H), 5.14-5.16 (d, J=10.5 Hz, 1H), 4.68-4.77 (m, 2H), 4.51-4.60 (m, 3H), 4.35-4.37 (m, 1H), 4.29 (m, 1H), 4.12-4.14 (m, 1H), 401-4.02 (m, 2H), 3.89-3.91 (m, 1H), 3.38-3.44 (m, 3H), 2.93 (m, 1H), 2.50 (m, 1H), 2.32 (m, 1H), 1.64 (m, 2H), 1.31-1.43 (m, 3H), 1.28 (m, 3H), 1.12 (m, 3H), 1.00-1.06 (m, 11H). ESI-MS [(M+H)$^+$]: m/z calculated 786.3, founded 786.5.

EXAMPLE 56

Synthesis of Compound 15aj

Compound 15aj was prepared by a sequence of five steps identical to that described in example 25, using the reagent SM-3k instead of SM-3j in the first-stage reaction, the product of the second step directly to hydrolysis of the fourth step without passing through the third hydrogenation reaction and the reagent SM-5a in the fifth-stage amidation reaction. After purification, 53 mg of product 15aj was obtained.

$^1$H-NMR for the product 15aj (CHCl$_3$, 500 MHz): δ 10.16 (s, 1H), 7.23-7.26 (t, J=8.0 Hz, 1H), 6.86-6.87 (d, J=7.5 Hz, 1H), 6.71-6.73 (d, J=8.0 Hz, 1H), 6.63 (brs, 1H), 5.94 (m, 2H), 5.59-5.61 (d, J=9.5 Hz, 1H), 5.37 (m, 1H), 4.71-4.74 (m, 2H), 4.42-4.59 (m, 5H), 4.33-4.35 (m, 1H), 3.97-4.11 (m, 3H), 3.90-3.92 (m, 1H), 3.54-3.56 (m, 1H), 2.93 (m, 1H), 2.50 (m, 1H), 2.28 (m, 1H), 1.61-1.69 (m, 3H), 1.39-1.42 (m, 2H), 1.32 (m, 3H), 1.26 (m, 2H), 1.19 (m, 3H), 1.04-1.06 (m, 11H), 0.93-0.96 (t, J=7.5 Hz, 4H). ESI-MS [(M+H)$^+$]: m/z calculated 788.4, founded 788.6.

EXAMPLE 57

Synthesis of Compound 15ak

Compound 15ak was prepared by a sequence of five steps identical to that described in example 25, using the reagent SM-3k instead of SM-3j in the first-stage reaction and the reagent SM-5b instead of SM-5a in the fifth-stage amidation reaction. After purification, 46 mg of product 15ak was obtained.

$^1$H-NMR for the product 15ak (CHCl$_3$, 500 MHz): δ 10.21 (s, 1H), 7.22-7.26 (t, J=8.3 Hz, 1H), 6.84-6.85 (d, J=7.5 Hz, 1H), 6.80 (brs, 1H), 6.71-6.73 (d, J=8.0 Hz, 1H), 5.83-5.90 (m, 1H), 5.61-5.63 (d, J=9.5 Hz, 1H), 5.40 (m, 1H), 5.25-5.29 (d, J=17.0 Hz, 1H), 5.14-5.16 (d, J=10.0 Hz, 1H), 4.68-4.77 (m, 2H), 4.49-4.60 (m, 3H), 4.34-4.36 (d, J=9.5 Hz, 1H), 4.29 (m, 1H), 4.11-4.13 (d, J=6.5 Hz, 1H), 4.01-4.02 (m, 2H), 3.90-3.92 (m, 1H), 3.39-3.42 (m, 3H), 2.90-2.93 (m, 1H), 2.51 (m, 1H), 2.31-2.34 (m, 1H), 1.65-1.80 (m, 6H), 1.33-1.40 (m, 3H), 1.28 (s, 3H), 1.12 (s, 3H), 1.00-1.05 (m, 11H). ESI-MS [(M+H)$^+$]: m/z calculated 788.4, founded 788.6.

EXAMPLE 58

Synthesis of Compound 15am

Compound 15am was prepared by a sequence of five steps identical to that described in example 25, using the reagent SM-3k instead of SM-3j in the first-stage reaction. After purification, 55 mg of product 15am was obtained.

$^1$H-NMR for the product 15am (CHCl$_3$, 500 MHz): δ 10.17-10.25 (ds, 1H), 7.23-7.26 (t, J=8.0 Hz, 1H), 6.86-6.87

(d, J=7.0 Hz, 1H), 6.71-6.72 (d, J=7.5 Hz, 1H), 6.60 (brs, 1H), 5.93-5.95 (m, 1H), 5.37 (m, 1H), 4.51-4.83 (m, 6H), 4.24-4.45 (m, 3H), 3.63-4.02 (m, 4H), 3.41-3.56 (m, 1H), 2.91 (m, 1H), 2.50 (m, 1H), 2.31 (m, 1H), 1.58-1.72 (m, 6H), 1.29-1.43 (m, 6H), 1.12-1.26 (m, 5H), 1.03-1.05 (m, 11H), 0.93-0.96 (t, J=7.5 Hz, 3H). ESI-MS [(M+H)$^+$]: m/z calculated 790.4, founded 790.5.

EXAMPLE 59

Synthesis of Compound 15an
Compound 15an was prepared by a sequence of five steps identical to that described in example 25, using the reagent SM-3b instead of SM-3j in the first-stage reaction, the product of the second step directly to hydrolysis of the fourth step without passing through the third hydrogenation reaction and the reagent SM-5b instead of SM-5a in the fifth-stage amidation reaction. After purification, 41 mg of product 15an was obtained.
$^1$H-NMR for the product 15an (CHCl$_3$, 500 MHz): δ 10.06 (s, 1H), 7.21-7.24 (t, J=7.5 Hz, 1H), 7.04 (brs, 1H), 6.83-6.84 (d, J=7.5 Hz, 1H), 6.72-6.73 (d, J=8.5 Hz, 1H), 5.77-5.84 (m, 1H), 5.48-5.55 (m, 3H), 5.24-5.30 (m, 2H), 5.13-5.15 (d, J=10.5 Hz, 1H), 4.47-4.76 (m, 5H), 4.39-4.43 (m, 1H), 4.25-4.31 (m, 2H), 4.09-4.16 (m, 3H), 3.86-3.88 (m, 1H), 3.76-3.79 (m, 1H), 2.91 (m, 1H), 2.32-2.44 (m, 4H), 2.11-2.13 (m, 1H), 1.96-1.98 (m, 1H), 1.85 (m, 1H), 1.74 (m, 1H), 1.50-1.53 (m, 2H), 1.28-1.37 (m, 3H), 0.96-1.04 (m, 11H). ESI-MS [(M+H)$^+$]: m/z calculated 756.3, founded 756.5.

EXAMPLE 60

Synthesis of Compound 15ap
Compound 15ap was prepared by a sequence of five steps identical to that described in example 25, using the reagent SM-3b instead of SM-3j in the first-stage reaction, the product of the second step directly to hydrolysis of the fourth step without passing through the third hydrogenation reaction and the reagent SM-5a in the fifth-stage amidation reaction. After purification, 46 mg of product 15ap was obtained.
$^1$H-NMR for the product 15ap (CHCl$_3$, 500 MHz): δ 10.06 (s, 1H), 7.22-7.25 (t, J=8.0 Hz, 1H), 6.83-6.85 (d, J=7.5 Hz, 1H), 6.80 (brs, 1H), 6.72-6.74 (d, J=7.5 Hz, 1H), 5.56 (m, 2H), 5.48 (m, 1H), 5.40-5.41 (d, J=9.5 Hz, 1H), 4.50-4.73 (m, 5H), 4.39 (m, 1H), 4.26-4.31 (m, 2H), 4.11-4.15 (m, 3H), 3.84-3.86 (m, 1H), 3.76 (m, 1H), 2.94 (m, 1H), 2.41-2.50 (m, 4H), 2.13 (m, 1H), 2.01 (m, 1H), 1.52-1.71 (m, 4H), 1.27-1.42 (m, 5H), 1.00-1.05 (m, 11H), 0.94-0.97 (t, J=7.5 Hz, 1H). ESI-MS [(M+H)$^+$]: m/z calculated 758.3, founded 758.4.

EXAMPLE 61

Synthesis of Compound 15aq
Compound 15aq was prepared by a sequence of five steps identical to that described in example 25, using the reagent SM-3f instead of SM-3j in the first-stage reaction, the product of the second step directly to hydrolysis of the fourth step without passing through the third hydrogenation reaction and the reagent SM-5b instead of SM-5a in the fifth-stage amidation reaction. After purification, 49 mg of product 15aq was obtained.
$^1$H-NMR for the product 15aq (CHCl$_3$, 500 MHz): δ 9.98 (s, 1H), 7.21-7.27 (t, J=7.3 Hz, 1H), 7.01 (s, 1H), 6.84-6.86 (d, J=7.2 Hz, 1H), 6.72-6.73 (d, J=8.6 Hz, 1H), 5.70-5.80 (m, 2H), 5.63 (m, 1H), 5.36-5.39 (m, 2H), 5.24-5.27 (d, J=17.3 Hz, 1H), 5.13-5.15 (d, J=10.8 Hz, 1H), 4.68-4.77 (q, J=14.5 Hz, 2H), 4.45-4.55 (m, 4H), 4.34-4.40 (m, 3H), 3.81-3.83 (m, 1H), 3.65-3.67 (d, J=10.2 Hz, 1H), 3.41-3.43 (d, J=9.4 Hz, 1H), 2.93 (m, 1H), 2.46 (m, 1H), 2.37 (m, 1H), 2.28 (m, 1H), 1.99 (m, 1H), 1.80 (m, 1H), 1.50 (m, 1H), 1.36 (m, 2H), 1.05 (s, 9H), 1.00 (m, 3H), 0.97 (s, 3H), 0.75 (m, 3H). ESI-MS [(M+H)$^+$]: m/z calculated 770.3, founded 770.5.

EXAMPLE 62

Synthesis of Compound 15ar
Compound 15ar was prepared by a sequence of five steps identical to that described in example 25, using the reagent SM-3f instead of SM-3j in the first-stage reaction, the product of the second step directly to hydrolysis of the fourth step without passing through the third hydrogenation reaction and the reagent SM-5a in the fifth-stage amidation reaction. After purification, 49 mg of product 15ar was obtained.
$^1$H-NMR for the product 15ar (CHCl$_3$, 500 MHz): δ 9.96 (s, 1H), 7.22-7.25 (t, J=8.4 Hz, 1H), 6.85-6.86 (d, J=7.0 Hz, 1H), 6.77 (s, 1H), 6.73-6.74 (d, J=7.8 Hz, 1H), 5.70 (m, 1H), 5.62 (m, 1H), 5.39 (m, 1H), 5.34-5.36 (d, J=9.3 Hz, 1H), 4.69-4.78 (q, J=12.0 Hz, 2H), 4.50 (m, 4H), 4.36 (m, 3H), 3.82 (m, 1H), 3.64 (m, 1H), 3.41 (m, 1H), 2.95 (m, 1H), 2.44 (m, 1H), 2.37 (m, 1H), 2.28 (m, 1H), 1.79 (m, 1H), 1.70 (m, 1H), 1.61 (m, 4H), 1.37 (m, 4H), 1.06 (s, 9H), 1.00 (s, 3H), 0.96-0.97 (t, J=7.4 Hz, 3H), 0.75 (s, 3H). ESI-MS [(M+H)$^+$]: m/z calculated 772.4, founded 772.6.

EXAMPLE 63

Synthesis of Compound 15as
Compound 15as was prepared by a sequence of five steps identical to that described in example 25, using the reagent SM-3f instead of SM-3j in the first-stage reaction and the reagent SM-5b instead of SM-5a in the fifth-stage amidation reaction. After purification, 43 mg of product 15as was obtained.
$^1$H-NMR for the product 15as (CHCl$_3$, 500 MHz): δ 10.01 (s, 1H), 7.22-7.25 (t, J=8.3 Hz, 1H), 6.83-6.84 (d, J=8.0 Hz, 1H), 6.79 (s, 1H), 6.69-6.71 (d, J=8.7 Hz, 1H), 5.85 (m, 1H), 5.50 (m, 1H), 5.41-5.43 (d, J=9.4 Hz, 1H), 5.23-5.27 (d, J=16.6 Hz, 1H), 5.13-5.27 (d, J=10.3 Hz, 1H), 4.71 (m, 2H), 4.42-4.50 (m, 3H), 4.25-4.31 (m, 2H), 4.14 (m, 1H), 4.04-4.06 (d, J=11.3 Hz, 1H), 3.89 (m, 2H), 3.39-3.41 (d, J=10.7 Hz, 1H), 2.92 (m, 1H), 2.83 (s, 2H), 2.41 (m, 1H), 2.29 (m, 1H), 1.91-2.00 (m, 2H), 1.54-1.64 (m, 4H), 1.36 (m, 2H), 1.07 (s, 9H), 1.04-1.05 (m, 3H), 1.02 (s, 3H), 0.84 (s, 3H). ESI-MS [(M+H)$^+$]: m/z calculated 772.4, founded 772.5.

EXAMPLE 64

Synthesis of Compound 15at
Compound 15at was prepared by a sequence of five steps identical to that described in example 25, using the reagent SM-3g instead of SM-3j in the first-stage reaction and the reagent SM-5b instead of SM-5a in the fifth-stage amidation reaction. After purification, 45 mg of product 15at was obtained.
$^1$H-NMR for the product 15at (CHCl$_3$, 500 MHz): δ 10.20 (s, 1H), 7.22-7.25 (t, J=7.6 Hz, 1H), 6.83-6.85 (d, J=7.2 Hz, 1H), 6.71-6.73 (d, J=7.8 Hz, 1H), 6.64 (s, 1H), 5.82-5.89 (m, 1H), 5.55-5.57 (d, J=7.2 Hz, 1H), 5.42 (m, 1H), 5.22-5.26 (d, J=7.2 Hz, 1H), 5.13-5.15 (d, J=7.2 Hz, 1H), 4.68-4.77 (q, J=14.7 Hz, 2H), 4.53-4.56 (d, J=15.1 Hz, 1H), 4.45-4.48 (d, J=14.0 Hz, 1H), 4.37-4.39 (d, J=9.7 Hz, 2H), 4.27-4.30 (m, 1H), 4.09-4.12 (d, J=12.2 Hz, 1H), 4.04 (m, 1H), 3.93-3.95 (m, 2H), 3.28-3.30 (d, J=10.1 Hz, 1H), 2.88 (m, 1H), 2.52 (m, 1H), 2.29 (m, 1H), 2.08-2.14 (m, 1H), 1.97-1.99 (m, 1H), 1.75

(m, 3H), 1.58 (m, 1H), 1.34-1.36 (m, 1H), 1.26 (m, 3H), 1.12 (m, 2H), 1.06 (s, 9H), 1.02-1.04 (m, 3H), 0.98 (s, 3H), 0.84 (m, 3H). ESI-MS [(M+H)$^+$]: m/z calculated 786.4, founded 786.5.

EXAMPLE 65

Synthesis of Compound 15au

Compound 15au was prepared by a sequence of five steps identical to that described in example 25, using the reagent SM-3g instead of SM-3j in the first-stage reaction, the product of the second step directly to hydrolysis of the fourth step without passing through the third hydrogenation reaction and the reagent SM-5b instead of SM-5a in the fifth-stage amidation reaction. After purification, 41 mg of product 15au was obtained.

$^1$H-NMR for the product 15au (CHCl$_3$, 500 MHz): δ 10.25 (s, 1H), 7.23-7.26 (t, J=8.6 Hz, 1H), 6.85-6.87 (d, J=7.5 Hz, 1H), 6.73-6.74 (d, J=8.9 Hz, 1H), 6.59 (s, 1H), 5.84-5.88 (m, 2H), 5.72 (m, 1H), 5.55-5.57 (d, J=8.8 Hz, 1H), 5.41 (m, 1H), 5.23-5.26 (d, J=17.2 Hz, 1H), 5.13-5.15 (d, J=9.8 Hz, 1H), 4.68-4.78 (m, 2H), 4.55-4.63 (m, 1H), 4.48-4.51 (m, 2H), 4.34-4.39 (m, 2H), 4.25-4.28 (m, 1H), 4.05-4.07 (m, 1H), 3.93-3.95 (m, 1H), 3.67 (m, 1H), 3.36-3.38 (d, J=10.6 Hz, 1H), 2.88 (m, 1H), 2.50 (m, 1H), 2.29 (m, 1H), 2.11 (m, 1H), 1.99 (m, 1H), 1.61 (m, 1H), 1.33-1.43 (m, 5H), 1.05 (s, 9H), 1.03 (m, 3H), 0.98 (s, 3H), 0.82 (m, 3H). ESI-MS [(M+H)$^+$]: m/z calculated 784.4, founded 784.6.

EXAMPLE 66

Synthesis of Compound 15av

Compound 15av was prepared by a sequence of five steps identical to that described in example 25, using the reagent SM-3g instead of SM-3j and 4bf instead of 4bb in the first-stage reaction. After purification, 43 mg of product 15av was obtained.

$^1$H-NMR for the product 15av (CHCl$_3$, 500 MHz): δ 10.12 (s, 1H), 7.17-7.25 (m, 3H), 6.94 (s, 1H), 5.57 (m, 2H), 4.77 (m, 2H), 4.62-4.66 (m, 3H), 4.40-4.43 (m, 1H), 4.31-4.33 (m, 2H), 4.10-4.12 (m, 2H), 3.93-3.95 (m, 1H), 3.36-3.39 (m, 2H), 3.29-3.31 (d, J=11.0 Hz, 1H), 2.93 (m, 1H), 2.32 (m, 2H), 1.52-1.59 (m, 6H), 1.34-1.39 (m, 5H), 2.06 (m, 1H), 1.75 (m, 2H), 1.61-1.68 (m, 3H), 1.40-1.43 (m, 2H), 1.31-1.35 (m, 2H), 1.18-1.22 (m, 3H), 1.03 (s, 9H), 0.95-1.01 (m, 6H), 0.92 (s, 3H), 0.70 (s, 3H). ESI-MS [(M+H)$^+$]: m/z calculated 802.4, founded 802.6.

EXAMPLE 67

Synthesis of Compound 15aw

Compound 15aw was prepared by a sequence of five steps identical to that described in example 25, using the reagent SM-3b instead of SM-3j and 4bf instead of 4bb in the first-stage reaction. After purification, 41 mg of product 15an was obtained.

ESI-MS for the product 15aw [(M+H)$^+$]: m/z calculated 760.4, founded 760.5.

EXAMPLE 68

Synthesis of Compound 15ax

Compound 15ax was prepared by a sequence of five steps identical to that described in example 25, using the reagent SM-3f instead of SM-3j and 4bk instead of 4bb in the first-stage reaction. After purification, 49 mg of product 15ax was obtained.

ESI-MS for the product 15ax [(M+H)$^+$]: m/z calculated 808.3, founded 808.4.

EXAMPLE 69

Synthesis of Compound 15ba

Compound 15ba was prepared by a sequence of five steps identical to that described in example 25, using the reagent SM-3m instead of SM-3j in the first-stage reaction. After purification, 55 mg of product 15ba was obtained.

ESI-MS for the product 15ba [(M+H)$^+$]: m/z calculated 781.3, founded 781.4.

EXAMPLE 70

Synthesis of Compound 15bb

Compound 15bb was prepared by a sequence of five steps identical to that described in example 25, using the reagent SM-3b instead of SM-3j and 4ba instead of 4bb in the first-stage reaction. After purification, 43 mg of product 15bb was obtained.

ESI-MS for the product 15bb [(M+H)$^+$]: m/z calculated 773.4, founded 773.5.

EXAMPLE 71

Synthesis of Compound 15bc

Compound 15bc was prepared by a sequence of five steps identical to that described in example 25, using the reagent SM-3f instead of SM-3j and 4ba instead of 4bb in the first-stage reaction. After purification, 52 mg of product 15bc was obtained.

ESI-MS for the product 15bc [(M+H)$^+$]: m/z calculated 801.4, founded 801.3.

EXAMPLE 72

Synthesis of Compound 15bd

Compound 15bd was prepared by a sequence of five steps identical to that described in example 25, using the reagent SM-3g instead of SM-3j and 4ba instead of 4bb in the first-stage reaction. After purification, 41 mg of product 15bd was obtained.

ESI-MS for the product 15bd [(M+H)$^+$]: m/z calculated 815.4, founded 815.7.

EXAMPLE 73

Synthesis of Compound 15be

Compound 15be was prepared by a sequence of five steps identical to that described in example 25, using the reagent SM-3c instead of SM-3j and 4bh instead of 4bb in the first-stage reaction. After purification, 37 mg of product 15be was obtained.

$^1$H-NMR for the product 15be (CHCl$_3$, 500 MHz): δ 9.98 (s, 1H), 7.27 (m, 1H), 7.15 (m, 1H), 6.82 (m, 1H), 6.66 (m, 1H), 5.46-5.47 (m, 2H), 4.71 (m, 1H), 4.55-4.61 (m, 5H), 4.23-4.26 (m, 2H), 4.13-4.14 (m, 2H), 3.70-3.73 (m, 3H), 2.94 (m, 1H), 2.37-2.38 (m, 2H), 2.08 (s, 2H), 1.66 (m, 1H), 1.64-1.67 (m, 2H), 1.50-1.59 (m, 4H), 1.39-1.43 (m, 3H), 1.32-1.35 (m, 2H), 1.21-1.24 (m, 2H), 1.01 (s, 9H), 0.94-0.97 (m, 5H). ESI-MS [(M+H)$^+$]: m/z calculated 760.4, founded 760.5.

EXAMPLE 74

Synthesis of Compound 15bf

Compound 15bf was prepared by a sequence of five steps identical to that described in example 25, using the reagent SM-3c instead of SM-3j and 4bh instead of 4bb in the first-stage reaction, and the reagent SM-5b instead of SM-5a in the fifth-stage amidation reaction. After purification, 42 mg of product 15bf was obtained.

$^1$H-NMR for the product 15bf (CHCl$_3$, 500 MHz): δ 9.93 (s, 1H), 7.42 (m, 1H), 7.14 (m, 1H), 6.82 (m, 1H), 6.68 (s, 1H), 5.74 (m, 1H), 5.48 (m, 2H), 5.26-5.29 (m, 1H), 5.14 (m, H), 4.72 (m, 1H), 4.48-4.59 (m, 4H), 4.24 (m, 2H), 4.15 (m, 2H), 3.66-3.74 (m, 3H), 2.91 (m, 1H), 2.39 (m, 2H), 2.11 (m, 1H), 1.95 (m, 1H), 1.75 (m, 1H), 1.63 (m, 1H), 1.52 (m, 1H), 1.44 (m, 3H), 1.32 (m, 3H), 1.26 (m, 6H), 1.02 (s, 9H). ESI-MS [(M+H)$^+$]: m/z calculated 758.3, founded 758.4.

EXAMPLE 75

Synthesis of Compound 15bg

Compound 15bg was prepared by a sequence of five steps identical to that described in Example 25, using the reagent SM-3c instead of SM-3j and 4bh instead of 4bb in the first-stage reaction, the product of the second step directly to hydrolysis of the fourth step without passing through the third hydrogenation reaction and the reagent SM-5a in the fifth-stage amidation reaction. After purification, 41 mg of product 15bg was obtained.

$^1$H-NMR for the product 15bg (CHCl$_3$, 500 MHz): δ 9.91 (s, 1H), 7.12-7.14 (d, J=7.8 Hz, 1H), 7.05 (m, 1H), 6.83 (m, 1H), 6.69 (m, 1H), 5.62-5.66 (m, 1H), 5.56 (m, 2H), 5.32-5.34 (m, 1H), 4.61-4.73 (m, 3H), 4.49-4.57 (m, 2H), 4.46 (m, 2H), 4.31-4.35 (m, 2H), 4.03 (m, 1H), 3.61-3.72 (m, 2H), 2.97 (m, 1H), 2.35-2.44 (m, 2H), 2.23 (m, 1H), 2.07 (m, 2H), 1.67-1.69 (m, 2H), 1.55-1.62 (m, 2H), 1.38-1.39 (m, 3H), 1.32-1.34 (m, 2H), 1.26 (m, 2H), 1.07 (m, 2H), 1.03 (s, 9H), 0.98 (m, 4H). ESI-MS [(M+H)$^+$]: m/z calculated 758.3, founded 758.4.

EXAMPLE 76

Synthesis of Compound 15bh

Compound 15bh was prepared by a sequence of five steps identical to that described in example 25, using the reagent SM-3c instead of SM-3j and 4bh instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 39 mg of product 15bh was obtained.

$^1$H-NMR for the product 15bh (CHCl$_3$, 500 MHz): δ 9.91 (s, 1H), 7.19 (s, 1H), 7.13-7.14 (d, J=8.0 Hz, 1H), 6.84-6.85 (m, 1H), 6.70 (m, 1H), 5.74-5.79 (m, 1H), 5.60-5.65 (m, 1H), 5.49 (m, 2H), 5.36-5.38 (m, 1H), 5.27-5.30 (m, 1H), 5.16-5.18 (m, 1H), 4.60-4.72 (m, 4H), 4.47-4.50 (m, 2H), 4.32-4.39 (m, 2H), 4.06 (m, 1H), 3.71-3.73 (m, 1H), 3.62 (m, 1H), 2.91 (m, 1H), 2.26-2.43 (m, 2H), 2.01-2.09 (m, 2H), 1.98 (m, 1H), 1.68 (m, 2H), 1.44-1.47 (m, 2H), 1.32-1.39 (m, 5H), 1.26 (s, 1H), 1.03 (s, 9H), 0.98 (s, 1H). ESI-MS [(M+H)$^+$]: m/z calculated 756.3, founded 756.4.

EXAMPLE 77

Synthesis of Compound 15bj

Compound 15bj was prepared by a sequence of five steps identical to that described in example 25, using the reagent SM-3b instead of SM-3j and 4bh instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 43 mg of product 15bj was obtained.

$^1$H-NMR for the product 15bj (CHCl$_3$, 500 MHz): δ 9.98 (s, 1H), 7.12-7.14 (d, J=8.0 Hz, 1H), 7.09 (s, 1H), 6.82-6.84 (m, 1H), 6.68 (m, 1H), 5.73-5.79 (m, 1H), 5.51 (m, 1H), 5.49 (m, 2H), 5.29 (m, 1H), 5.23-5.26 (m, 1H), 5.16-5.18 (m, 1H), 4.70-4.75 (m, 2H), 4.58-4.61 (m, 2H), 4.43-4.49 (m, 2H), 4.19-4.25 (m, 2H), 3.75-3.80 (m, 1H), 3.63-3.70 (m, 1H), 2.92 (m, 1H), 2.50 (m, 1H), 2.37 (m, 1H), 2.24 (m, 1H), 2.04-2.09 (m, 2H), 1.97-1.99 (m, 1H), 1.74-1.78 (m, 1H), 1.62 (m, 3H), 1.46-1.49 (m, 1H), 1.35-1.39 (m, 2H), 1.26 (s, 1H), 1.03 (s, 9H), 0.98 (s, 1H). ESI-MS [(M+H)$^+$]: m/z calculated 742.3, founded 742.4.

EXAMPLE 78

Synthesis of Compound 15bk

Compound 15bk was prepared by a sequence of five steps identical to that described in example 25, using the reagent SM-3b instead of SM-3j and 4bh instead of 4bb in the first-stage reaction, the product of the second step directly to hydrolysis of the fourth step without passing through the third hydrogenation reaction and the reagent SM-5a in the fifth-stage amidation reaction. After purification, 36 mg of product 15bk was obtained.

$^1$H-NMR for the product 15bk (CHCl$_3$, 500 MHz): δ 9.92 (s, 1H), 7.27 (s, 1H), 7.12 (m, 1H), 6.81 (m, 1H), 6.67 (m, 1H), 5.55 (m, 3H), 5.33 (m, 1H), 4.69 (m, 2H), 4.60 (m, 2H), 4.44-4.48 (m, 2H), 4.21 (m, 2H), 3.66-3.76 (m, 3H), 2.95 (m, 1H), 2.39 (m, 1H), 2.23 (m, 1H), 1.90-2.04 (m, 2H), 1.74 (m, 3H), 1.59 (m, 3H), 1.37 (m, 2H), 1.25 (m, 3H), 1.03 (s, 9H), 0.88-0.97 (m, 4H). ESI-MS [(M+H)$^+$]: m/z calculated 744.3, founded 744.4.

EXAMPLE 79

Synthesis of Compound 15bm

Compound 15bm was prepared by a sequence of five steps identical to that described in example 25, using the reagent SM-3a instead of SM-3j and 4bh instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 48 mg of product 15bm was obtained.

$^1$H-NMR for the product 15bm (CHCl$_3$, 500 MHz): δ 9.86 (s, 1H), 7.47 (s, 1H), 7.48 (s, 1H), 7.09-7.14 (m, 1H), 6.81-6.83 (m, 1H), 6.70 (m, 1H), 5.67-5.75 (m, 2H), 5.46-5.51 (m, 2H), 5.27-5.31 (m, 1H), 5.16-5.18 (m, 1H), 4.71-4.75 (m, 1H), 4.57-4.60 (m, 2H), 4.40 (m, 1H), 4.34 (m, 1H), 4.26 (m, 1H), 3.72 (m, 1H), 3.65 (m, 1H), 3.61 (m, 1H), 2.92 (m, 1H), 2.47 (m, 1H), 2.23-2.40 (m, 2H), 2.18 (m, 2H), 2.08 (m, 1H), 1.64 (m, 1H), 1.98 (m, 1H), 1.41-1.45 (m, 2H), 1.34-1.42 (m, 4H), 1.29 (s, 9H). ESI-MS [(M+H)$^+$]: m/z calculated 728.3, founded 728.3.

EXAMPLE 80

Synthesis of Compound 15bn

Compound 15bn was prepared by a sequence of five steps identical to that described in example 25, using the reagent SM-3g instead of SM-3j and 4bh instead of 4bb in the first-stage reaction, and the reagent SM-5b instead of SM-5a in the fifth-stage amidation reaction. After purification, 32 mg of product 15bn was obtained.

$^1$H-NMR for the product 15bn (CHCl$_3$, 500 MHz): δ 9.96 (s, 1H), 7.16 (m, 1H), 6.99 (s, 1H), 6.83 (m, 1H), 6.69 (m, 1H), 5.50 (s, 1H), 5.28 (m, 1H), 4.62-4.75 (m, 3H), 4.48-4.59 (m, 2H), 4.11-4.28 (m, 4H), 3.71-3.74 (m, 1H), 3.59 (m, 2H), 2.98 (m, 1H), 2.37-2.51 (m, 2H), 1.68-1.78 (m, 6H), 1.57 (m, 2H), 1.38-1.42 (m, 6H), 1.24-1.26 (m, 3H), 1.11 (m, 1H), 1.04 (s, 9H), 0.96-1.01 (m, 5H), 0.92 (s, 3H), 0.83 (s, 3H). ESI-MS [(M+H)$^+$]: m/z calculated 786.4, founded 786.4.

EXAMPLE 81

Synthesis of Compound 15bp

Compound 15bp was prepared by a sequence of five steps identical to that described in example 25, using the reagent SM-3g instead of SM-3j and 4bh instead of 4bb in the first-stage reaction. After purification, 48 mg of product 15bp was obtained.

$^1$H-NMR for the product 15bp (CHCl$_3$, 500 MHz): δ 9.96 (s, 1H), 7.16 (m, 1H), 6.99 (m, 1H), 6.83 (m, 1H), 6.69 (m, 1H), 5.50 (s, 1H), 5.28 (m, 1H), 4.62-4.75 (m, 3H), 4.48-4.59 (m, 2H), 4.11-4.28 (m, 4H), 3.71-3.74 (m, 1H), 3.59 (m, 2H), 2.98 (m, 1H), 2.37-2.51 (m, 2H), 1.68-1.78 (m, 6H), 1.57 (m, 2H), 1.38-1.42 (m, 6H), 1.24-1.26 (m, 3H), 1.11 (m, 1H), 1.04 (s, 9H), 0.96-1.01 (m, 5H), 0.92 (s, 3H), 0.83 (s, 3H). ESI-MS [(M+H)$^+$]: m/z calculated 788.4, founded 788.5.

EXAMPLE 82

Synthesis of Compound 15bq

Compound 15bq was prepared by a sequence of five steps identical to that described in example 25, using the reagent SM-3b instead of SM-3j and 4bj instead of 4bb in the first-stage reaction. After purification, 46 mg of product 15bq was obtained.

ESI-MS for the product 15bq [(M+H)$^+$]: m/z calculated 774.3 founded 774.5.

EXAMPLE 83

Synthesis of Compound 15br

Compound 15br was prepared by a sequence of five steps identical to that described in example 25, using the reagent SM-3f instead of SM-3j and 4bj instead of 4bb in the first-stage reaction. After purification, 31 mg of product 15br was obtained.

ESI-MS for the product 15br [(M+H)$^+$]: m/z calculated 802.4 founded 802.5.

EXAMPLE 84

Synthesis of Compound 15bs

Compound 15bs was prepared by a sequence of five steps identical to that described in example 25, using the reagent SM-3g instead of SM-3j and 4bj instead of 4bb in the first-stage reaction. After purification, 47 mg of product 15bs was obtained.

ESI-MS for the product 15bs [(M+H)$^+$]: m/z calculated 816.4 founded 816.5.

EXAMPLE 85

Synthesis of Compound 15bt

Compound 15bt was prepared by a sequence of five steps identical to that described in example 25, using the reagent SM-3b instead of SM-3j and 4bg instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 56 mg of product 15bt was obtained.

$^1$H-NMR for the product 15bt (CHCl$_3$, 500 MHz): δ 9.91 (s, 1H), 7.34 (s, 1H), 6.56 (s, 1H), 6.31-6.34 (m, 1H), 6.08-6.11 (m, 1H), 5.99-6.01 (m, 2H), 5.71-5.78 (m, 1H), 5.45-5.47 (m, 1H), 5.43 (m, 1H), 5.24-5.28 (m, 1H), 5.14-5.16 (m, 1H), 4.57-4.60 (m, 2H), 4.46-4.48 (m, 1H), 4.39-4.42 (m, 1H), 4.34-4.36 (m, 1H), 4.30-4.33 (m, 1H), 4.22-4.27 (m, 1H), 3.90-3.94 (m, 1H), 3.74-3.77 (m, 1H), 2.91-2.94 (m, 1H), 2.43-2.47 (m, 1H), 2.30-2.40 (m, 3H), 2.07-2.08 (m, 1H), 1.95-1.98 (m, 2H), 1.72 (m, 1H), 1.45-1.49 (m, 1H), 1.35 (m, 2H), 1.26 (m, 3H), 1.06 (s, 9H). ESI-MS [(M+H)$^+$]: m/z calculated 756.3, founded 756.4.

EXAMPLE 86

Synthesis of Compound 15bu

Compound 15bu was prepared by a sequence of five steps identical to that described in example 25, using the reagent SM-3c instead of SM-3j and 4bg instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 51 mg of product 15bu was obtained.

$^1$H-NMR for the product 15bu (CHCl$_3$, 500 MHz): δ 10.08 (s, 1H), 7.06 (s, 1H), 6.55 (s, 1H), 6.21 (m, 1H), 6.15-6.18 (m, 1H), 5.99-6.00 (m, 2H), 5.79-5.86 (m, 1H), 5.59-5.61 (m, 1H), 5.38 (m, 1H), 5.26 (m, 1H), 5.12-5.18 (m, 1H), 4.69 (m, 1H), 4.59-4.61 (m, 2H), 4.45-4.47 (m, 1H), 4.39-4.41 (m, 1H), 4.27-4.38 (m, 1H), 4.14-4.19 (m, 1H), 3.89-3.91 (m, 1H), 3.74-3.77 (m, 1H), 2.89 (m, 1H), 2.54-2.58 (m, 1H), 2.30-2.31 (m, 3H), 2.23-2.24 (m, 3H), 2.00-2.02 (m, 1H), 1.96 (m, 1H), 1.68 (m, 1H), 1.62 (m, 4H), 1.51-1.55 (m, 3H), 1.05 (s, 9H). ESI-MS [(M+H)$^+$]: m/z calculated 770.3, founded 770.4.

EXAMPLE 87

Synthesis of Compound 15bv

Compound 15bv was prepared by a sequence of five steps identical to that described in example 25, using the reagent SM-3g instead of SM-3j and 4bg instead of 4bb in the first-stage reaction, the product of the second step directly to hydrolysis of the fourth step without passing through the third hydrogenation reaction and the reagent SM-5b instead of SM-5a in the fifth-stage amidation reaction. After purification, 43 mg of product 15by was obtained.

$^1$H-NMR for the product 15by (CHCl$_3$, 500 MHz): δ 10.11 (s, 1H), 6.91 (s, 1H), 6.53 (s, 1H), 6.12-6.20 (m, 2H), 5.98-6.00 (m, 2H), 5.78-5.85 (m, 1H), 5.57-5.59 (m, 1H), 5.31 (m, 1H), 5.23-5.26 (m, 1H), 5.12-5.15 (m, 1H), 4.57-4.61 (m, 4H), 4.42-4.46 (m, 2H), 4.30-4.33 (m, 1H), 4.10-4.13 (m, 1H), 3.88-3.91 (m, 1H), 3.29-3.32 (m, 1H), 2.88 (m, 1H), 2.59-2.61 (m, 1H), 2.24-2.32 (m, 4H), 2.09-2.15 (m, 3H), 1.96-1.97 (m, 1H), 1.61 (m, 1H), 1.55-1.57 (m, 1H), 1.36-1.40 (m, 1H), 1.05 (s, 9H), 0.99-1.02 (m, 6H). ESI-MS [(M+H)$^+$]: m/z calculated 798.3, founded 798.4.

EXAMPLE 88

Synthesis of Compound 15bw

Compound 15bw was prepared by a sequence of five steps identical to that described in example 25, using the reagent SM-3c instead of SM-3j and 4bg instead of 4bb in the first-stage reaction, the product of the second step directly to hydrolysis of the fourth step without passing through the third hydrogenation reaction and the reagent SM-5a in the fifth-stage amidation reaction. After purification, 52 mg of product 15bw was obtained.

$^1$H-NMR for the product 15bw (CHCl$_3$, 500 MHz): δ 10.05 (s, 1H), 6.83 (s, 1H), 6.55 (s, 1H), 6.20-6.25 (m, 1H), 6.13-6.16 (m, 1H), 5.98-6.00 (m, 2H), 5.56-5.58 (m, 1H), 5.37 (m, 1H), 4.67 (m, 1H), 4.58-4.60 (m, 3H), 4.39-4.44 (m, 2H), 4.30-4.33 (m, 1H), 4.16-4.19 (m, 1H), 3.87-3.90 (m, 1H), 3.75-3.77 (m, 1H), 2.91 (m, 1H), 2.52-2.57 (m, 1H), 2.21-2.29 (m, 4H), 2.01 (m, 1H), 1.87 (m, 1H), 1.68-1.70 (m, 2H), 1.59-1.63 (m, 3H), 1.50 (m, 2H), 1.30-1.32 (m, 3H), 1.02-1.06 (m, 12H). ESI-MS [(M+H)$^+$]: m/z calculated 772.3, founded 772.4.

EXAMPLE 89

Synthesis of Compound 15bx

Compound 15bx was prepared by a sequence of five steps identical to that described in example 25, using the reagent SM-3c instead of SM-3j and 4bg instead of 4bb in the first-stage reaction. After purification, 57 mg of product 15bx was obtained.

$^1$H-NMR for the product 15bx (CHCl$_3$, 500 MHz): δ 10.00 (s, 1H), 6.84 (s, 1H), 6.56 (s, 1H), 5.94-5.96 (m, 2H), 5.48-5.50 (m, 1H), 5.37 (m, 1H), 4.57-4.66 (m, 3H), 4.49-4.52 (m, 1H), 4.37-4.40 (m, 2H), 4.31-4.33 (m, 1H), 4.02-4.23 (m, 1H), 3.85-3.88 (m, 1H), 3.72 (m, 1H), 2.92 (m, 1H), 2.51-2.56 (m, 2H), 2.29-2.35 (m, 2H), 2.21 (m, 1H), 2.03 (m, 1H), 1.68-1.71 (m, 2H), 1.59-1.64 (m, 4H), 1.51-1.55 (m, 3H), 1.41-1.43 (m, 2H), 1.03-1.06 (m, 12H), 0.93-0.96 (m, 3H). ESI-MS [(M+H)$^+$]: m/z calculated 774.3, founded 774.4.

EXAMPLE 90

Synthesis of Compound 15by

Compound 15by was prepared by a sequence of five steps identical to that described in example 25, using the reagent SM-3g instead of SM-3j and 4bg instead of 4bb in the first-stage reaction. After purification, 50 mg of product 15by was obtained.

$^1$H-NMR for the product 15by (CHCl$_3$, 500 MHz): δ 9.99 (s, 1H), 6.71 (s, 1H), 6.54 (s, 1H), 5.93-5.97 (m, 2H), 5.52-5.54 (m, 1H), 5.30 (m, 1H), 4.54-4.63 (m, 2H), 4.45-4.47 (m, 3H), 4.33-4.40 (m, 2H), 4.18-4.16 (m, 1H), 3.82-3.88 (m, 1H), 3.24-3.30 (m, 1H), 2.95 (m, 1H), 2.59-2.64 (m, 1H), 2.42-2.49 (m, 2H), 2.31-2.36 (m, 1H), 1.84 (br, 1H), 1.72-1.74 (m, 1H), 1.59-1.67 (m, 2H), 1.50 (m, 2H), 1.41-1.44 (m, 2H), 1.38 (m, 1H), 1.32 (m, 4H), 1.17 (m, 1H), 1.07 (s, 9H), 0.98 (m, 6H), 0.82 (s, 3H). ESI-MS [(M+H)$^+$]: m/z calculated 802.4, founded 802.4.

EXAMPLE 91

Synthesis of Compound 15ca

Compound 15ca was prepared by a sequence of five steps identical to that described in example 25, using the reagent SM-3h instead of SM-3j and 4bm instead of 4bb in the first-stage reaction. After purification, 53 mg of product 15ca was obtained.

ESI-MS for the product 15ca [(M+H)$^+$]: m/z calculated 786.3 founded 786.4.

EXAMPLE 92

Synthesis of Compound 15cb

Compound 15cb was prepared by a sequence of five steps identical to that described in example 25, using the reagent SM-3f instead of SM-3j and 4bm instead of 4bb in the first-stage reaction. After purification, 49 mg of product 15cb was obtained.

ESI-MS for the product 15cb [(M+H)$^+$]: m/z calculated 788.3 founded 788.4.

EXAMPLE 93

Synthesis of Compound 15cc

Compound 15cc was prepared by a sequence of five steps identical to that described in example 25, using the reagent SM-3b instead of SM-3j and 4bm instead of 4bb in the first-stage reaction. After purification, 61 mg of product 15cc was obtained.

ESI-MS for the product 15cc [(M+H)$^+$]: m/z calculated 760.3 founded 760.4.

EXAMPLE 94

Synthesis of Compound 15cd

Compound 15cd was prepared by a sequence of five steps identical to that described in example 25, using the reagent SM-3h instead of SM-3j and 4bn instead of 4bb in the first-stage reaction. After purification, 33 mg of product 15cd was obtained.

ESI-MS for the product 15cd [(M+H)$^+$]: m/z calculated 787.4, founded 787.5.

The invention claimed is:

1. A macro-heterocyclic compound of formula Ia or Ib, or its stereoisomer, tautomer, esterification or amidation pro-drug, pharmaceutically acceptable salt or a mixture thereof:

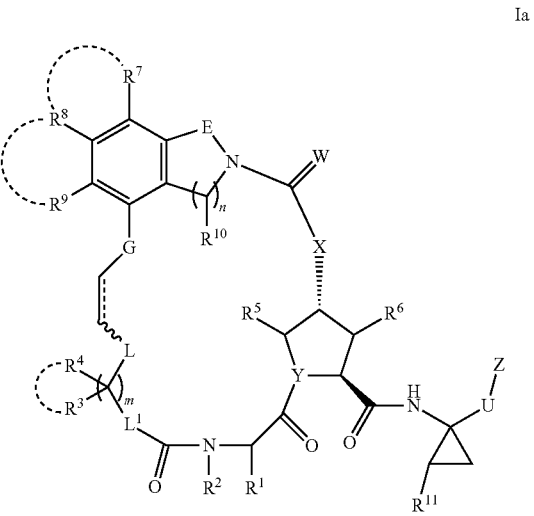

Ia

-continued

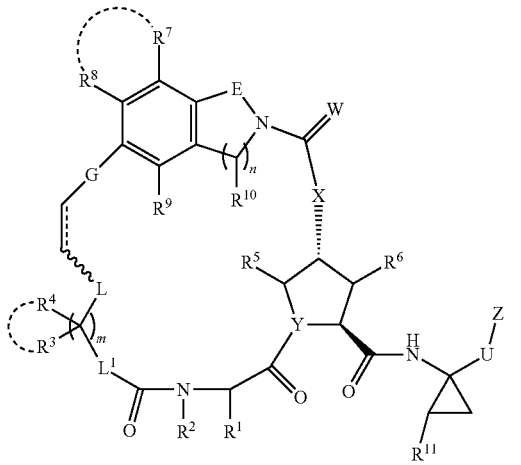

Ib wherein:
m=1 or 2; n=0, 1 or 2;
" ⋯ " is a single bond or double bond;
E is oxygen, —NRa—, —CRbRc-, ethylidene, propylidene, $C_1$-$C_6$ alkoxyl, carbonyl, amino carbonyl or carbonyl amino group;
Ra is selected from hydrogen, $C_1$-$C_{20}$ alkyl, $C_3$-$C_{20}$ cycloalkyl, $C_6$-$C_{20}$ aryl, $C_2$-$C_{20}$ heterocyclic aryl, $C_1$-$C_{20}$ alkylcarbonyl, $C_1$-$C_{20}$ alkoxycarbonyl, $C_6$-$C_{20}$ aryloxycarbonyl, $C_2$-$C_{20}$ heterocyclic oxycarbonyl, aminocarbonyl, $C_1$-$C_{20}$ alkylaminocarbonyl, $C_1$-$C_{20}$ alkylaminosulfonyl, $C_2$-$C_{20}$ heterocyclic aminosulfonyl, or $C_6$-$C_{20}$ aryl-aminosulfonyl group;
Rb and Rc are each independently selected from hydrogen, halogen atom, cyano, nitro, $C_1$-$C_{20}$ alkyl, $C_3$-$C_{20}$ cycloalkyl, $C_6$-$C_{20}$ aryl, $C_1$-$C_{20}$ alkoxyl, $C_1$-$C_{20}$ alkylthio, $C_1$-$C_{20}$ alkoxycarbonyl, $C_6$-$C_{20}$ aryloxy, $C_6$-$C_{20}$ aryloxycarbonyl, $C_2$-$C_{20}$ heterocyclic-oxycarbonyl, $C_2$-$C_{20}$ heterocyclic aryl, $C_1$-$C_{20}$ alkylamino, $C_2$-$C_{20}$ heterocyclic amino, $C_6$-$C_{20}$ arylamino, aminocarbonyl, $C_1$-$C_{20}$ alkylaminocarbonyl, carbonylamino, $C_1$-$C_{20}$ alkylcarbonylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ alkylamino-sulfonamido group;
G is selected from oxygen, sulfur, sulfone, —NRa—, —OC(Rb)(Rc)-, —SC(Rb)(Rc)-, —N(Ra)C(Rb)(Rc)-, $C_1$-$C_{20}$ alkoxyl, $C_1$-$C_{20}$ alkylamino, $C_1$-$C_{20}$ alkyl-oxygen, $C_1$-$C_{20}$ alkyl, $C_1$-$C_{20}$ alkoxycarbonyl, carbonyl, carbonylamino or $C_1$-$C_{20}$ alkylcarbonylamino group; when $R^7$ and $R^8$ or $R^8$ and $R^9$ are connected each other as a cyclic structure, G is methylene or does not exist (i.e., " ⋯ " connected directly with the phenyl group of polyheterocyclic group); wherein the definition of the Ra, Rb and Rc are the same as that in E;
L and $L^1$ are each independently selected from oxygen, sulfur, $C_2$-$C_{20}$ alkenyl, $C_1$-$C_{20}$ alkyl, $C_3$-$C_{20}$ cycloalkyl, $C_2$-$C_{20}$ heterocyclic, $C_6$-$C_{20}$ aryl, $C_3$-$C_{20}$ heterocyclic aryl, $C_1$-$C_{20}$ alkylthio, $C_1$-$C_{20}$ alkoxyl, $C_3$-$C_{20}$ cycloalkoxyl, $C_2$-$C_{20}$ heterocyclic oxyl, $C_1$-$C_{20}$ alkylamino, $C_1$-$C_{20}$ alkoxycarbonyl, $C_6$-$C_{20}$ aryl, or $C_6$-$C_{20}$ aryloxy group;
U is selected from carbonyl, sulfoxide (—SO—), sulfone (—$SO_2$—), —P(O)(ORd)- or —B(ORe)-; Wherein Rd and Re are independently selected from hydrogen (H), $C_1$-$C_{20}$ alkyl, $C_3$-$C_{20}$ cycloalkyl, $C_2$-$C_{20}$ heterocyclic, $C_6$-$C_{20}$ aryl, or $C_3$-$C_{20}$ heterocyclic alkyl group;
W is selected from oxygen or sulfur;
X is selected from oxygen, sulfur, nitrogen or —NRa—; wherein the definition of Ra is the same as that in E and G;
Y is selected from nitrogen or CH;
Z is selected from hydrogen (H), hydroxyl (OH), amino ($NH_2$), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ arylamino, $C_3$-$C_{20}$ heterocyclic arylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkylaminosulfonamido, $C_3$-$C_{20}$ cycloalkylaminosulfonamido, $C_6$-$C_{20}$ aryloxysulfonamido, $C_1$-$C_{20}$ alkylaminosulfonamido, $C_3$-$C_{20}$ cycloalkylaminosulfonamido, $C_6$-$C_{20}$ arylaminosulfonamido, uramido, $C_1$-$C_{20}$ alkyluramido, or $C_1$-$C_{20}$ alkylthiouramido group;
$R^1$ is selected from hydrogen (H), $C_1$-$C_{20}$ alkyl, $C_3$-$C_{20}$ cycloalkyl, $C_6$-$C_{20}$ aryl, $C_3$-$C_{20}$ heterocyclic aryl, $C_1$-$C_{20}$ alkylsulfonamido, $C_2$-$C_{20}$ heterocyclic sulfonamido, or $C_1$-$C_{20}$ alkoxylcarbonylamino group;
$R^2$ is selected from hydrogen (H), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_6$-$C_{20}$ aryl, $C_3$-$C_{20}$ heterocyclic aryl, $C_6$-$C_{20}$ aryloxycarbonyl, $C_1$-$C_{20}$ alkylsulfonyl, $C_3$-$C_{20}$ cycloalkylsulfonyl, $C_1$-$C_{20}$ alkoxysulfonyl, $C_3$-$C_{20}$ cycloalkoxysulfonyl, $C_6$-$C_{20}$ arylsulfonyl, $C_6$-$C_{20}$ aryloxysulfonyl, $C_1$-$C_{20}$ alkylaminosulfonyl, $C_3$-$C_{20}$ cycloalkylaminosulfonyl, or $C_6$-$C_{20}$ arylaminosulfonyl group;
$R^3$, $R^4$, $R^5$ and $R^6$ are each independently selected from hydrogen, halogen atom, hydroxyl, cyano, nitro, $C_1$-$C_{20}$ alkyl, $C_3$-$C_{20}$ cycloalkyl, $C_1$-$C_{20}$ alkoxyl, $C_1$-$C_{20}$ alkylamino, $C_2$-$C_{20}$ heterocyclic amino, $C_6$-$C_{20}$ aryl, $C_6$-$C_{20}$ arylamino, $C_1$-$C_{20}$ alkylsulfonamido, $C_2$-$C_{20}$ heterocyclic sulfonamido, $C_6$-$C_{20}$ arylsulfonamido or $C_1$-$C_{20}$ aminosulfonamido group; wherein the $R^3$ and $R^4$ can be connected as a cyclic structure;
$R^7$, $R^8$ and $R^9$ are each independently selected from hydrogen, halogen atom, cyano, nitro, trifluoromethyl, $C_1$-$C_{20}$ alkyl, $C_1$-$C_{20}$ alkoxyl, $C_1$-$C_{20}$ alkylthio, $C_1$-$C_{20}$ alkoxylcarbonyl, aminocarbonyl, $C_1$-$C_{20}$ alkylaminocarbonyl, carbonylamino, $C_1$-$C_{20}$ alkylcarbonylamino, $C_2$-$C_{20}$ heterocyclicoxyl carbonyl, $C_6$-$C_{20}$ aryl, $C_6$-$C_{20}$ aryloxy, $C_6$-$C_{20}$ aryloxycarbonyl or $C_2$-$C_{20}$ heterocyclic group; wherein $R^7$ and $R^8$ or $R^8$ and $R^9$ can be connected each other as a cyclic structure;
$R^{10}$ is selected from hydrogen, halogen atom, cyano, nitro, trifluoromethyl, $C_1$-$C_{20}$ alkyl, $C_3$-$C_{20}$ cycloalkyl, $C_1$-$C_{20}$ alkoxyl, $C_1$-$C_{20}$ alkylthio, $C_1$-$C_{20}$ alkoxylcarbonyl, $C_1$-$C_{20}$ alkylaminocarbonyl, $C_1$-$C_{20}$ alkylcarbonylamino, $C_6$-$C_{20}$ aryl, $C_6$-$C_{20}$ aryloxy, $C_6$-$C_{20}$ aryloxycarbonyl or $C_2$-$C_{20}$ heterocyclic group; and
$R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group.

2. The compound according to claim 1, or its stereoisomer, tautomer, esterification or amidation prodrug, pharmaceutically acceptable salt or a mixture thereof, wherein in formula Ia or Ib:
m=1 or 2; n=0, 1 or 2;
" ⋯ " is a single bond or double bond;
E is oxygen, —NRa—, —CRbRc-, ethylidene, propylidene, $C_1$-$C_6$ alkoxyl, carbonyl, amino carbonyl or carbonyl amino group;

233

Ra is selected from hydrogen, $C_1$-$C_{15}$ alkyl, $C_3$-$C_{15}$ cycloalkyl, $C_6$-$C_{15}$ aryl, $C_2$-$C_{15}$ heterocyclic aryl, $C_1$-$C_{15}$ alkylcarbonyl, $C_1$-$C_{15}$ alkoxycarbonyl, $C_6$-$C_{15}$ aryloxycarbonyl, $C_2$-$C_{15}$ heterocyclic oxycarbonyl, aminocarbonyl, $C_1$-$C_{15}$ alkylaminocarbonyl, $C_1$-$C_{15}$ alkylaminosulfonyl, $C_2$-$C_{15}$ heterocyclic aminosulfonyl, or $C_6$-$C_{15}$ arylamino aminosulfonyl group;

Rb and Rc are each independently selected from hydrogen, halogen atom, cyano, nitro, $C_1$-$C_{15}$ alkyl, $C_3$-$C_{15}$ cycloalkyl, $C_6$-$C_{15}$ aryl, $C_1$-$C_{15}$ alkoxyl, $C_1$-$C_{15}$ alkylthio, $C_1$-$C_{15}$ alkoxycarbonyl, $C_6$-$C_{15}$ aryloxy, $C_6$-$C_{15}$ aryloxycarbonyl, $C_2$-$C_{15}$ heterocyclic-oxycarbonyl, $C_2$-$C_{15}$ heterocyclic aryl, $C_1$-$C_{15}$ alkylamino, $C_2$-$C_{15}$ heterocyclic amino, $C_6$-$C_{15}$ arylamino, aminocarbonyl, $C_1$-$C_{15}$ alkylaminocarbonyl, carbonylamino, $C_1$-$C_{15}$ alkylcarbonylamino, $C_1$-$C_{15}$ alkylsulfonamido, $C_2$-$C_{15}$ heterocyclic sulfonamido, $C_6$-$C_{15}$ arylsulfonamido or $C_1$-$C_{15}$ alkyl aminosulfonamido group;

G is selected from oxygen, sulfur, sulfone, —NRa—, —OC(Rb)(Rc)-, —SC(Rb)(Rc)-, —N(Ra)C(Rb)(Rc)-, $C_1$-$C_{15}$ alkoxyl, $C_1$-$C_{15}$ alkylamino, $C_1$-$C_{15}$ alkyl-oxygen, $C_1$-$C_{15}$ alkyl, $C_1$-$C_{15}$ alkoxycarbonyl, carbonyl, carbonylamino or $C_1$-$C_{15}$ alkylcarbonylamino group; when $R^7$ and $R^8$ or $R^8$ and $R^9$ are connected each other as a cyclic structure, G is methylene or does not exist (i.e., "═" connected directly with the phenyl group of polyheterocyclic group);

L and $L^1$ are each independently selected from oxygen, sulfur, $C_2$-$C_{15}$ alkenyl, $C_1$-$C_{15}$ alkyl, $C_3$-$C_{15}$ cycloalkyl, $C_2$-$C_{15}$ heterocyclic, $C_6$-$C_{15}$ aryl, $C_3$-$C_{15}$ heterocyclic aryl, $C_1$-$C_{15}$ alkylthio, $C_1$-$C_{15}$ alkoxyl, $C_3$-$C_{15}$ cycloalkoxyl, $C_2$-$C_{15}$ heterocyclic oxyl, $C_1$-$C_{15}$ alkylamino, $C_1$-$C_{15}$ alkoxycarbonyl, $C_6$-$C_{15}$ aryl, or $C_6$-$C_{15}$ aryloxy group;

U is selected from carbonyl, sulfoxide (—SO—), sulfone (—$SO_2$—), —P(O)(ORd)- or —B(ORe)-; Wherein Rd and Re are independently selected from hydrogen (H), $C_1$-$C_{15}$ alkyl, $C_3$-$C_{15}$ cycloalkyl, $C_2$-$C_{15}$ heterocyclic, $C_6$-$C_{15}$ aryl, or $C_3$-$C_{15}$ heterocyclic alkyl group;

W is selected from oxygen or sulfur;

X is selected from oxygen, sulfur, nitrogen or —NRa—; wherein the definition of Ra is the same as that in E and G;

Y is selected from nitrogen or CH;

Z is selected from hydrogen (H), hydroxyl (OH), amino ($NH_2$), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_1$-$C_{15}$ alkylamino, $C_3$-$C_{15}$ cycloalkylamino, $C_2$-$C_{15}$ heterocyclic amino, $C_6$-$C_{15}$ aryl, $C_6$-$C_{15}$ arylamino, $C_3$-$C_{15}$ heterocyclic arylamino, $C_1$-$C_{15}$ alkylsulfonamido, $C_3$-$C_{15}$ cycloalkylsulfonamido, $C_6$-$C_{15}$ arylsulfonamido, $C_1$-$C_{15}$ alkylaminosulfonamido, $C_3$-$C_{15}$ cycloalkylaminosulfonamido, $C_6$-$C_{15}$ aryloxysulfonamido, $C_1$-$C_{15}$ alkylaminosulfonamido, $C_3$-$C_{15}$ cycloalkylaminosulfonamido, $C_6$-$C_{15}$ arylaminosulfonamido, uramido, $C_1$-$C_{15}$ alkyluramido, or $C_1$-$C_{15}$ alkylthiouramido group;

$R^1$ is selected from hydrogen (H), $C_1$-$C_{15}$ alkyl, $C_3$-$C_{15}$ cycloalkyl, $C_6$-$C_{15}$ aryl, $C_3$-$C_{15}$ heterocyclic aryl, $C_1$-$C_{15}$ alkylsulfonamido, $C_2$-$C_{15}$ heterocyclic sulfonamido, or $C_1$-$C_{15}$ alkoxylcarbonylamino group;

$R^2$ is selected from hydrogen (H), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_6$-$C_{15}$ aryl, $C_3$-$C_{15}$ heterocyclic aryl, $C_6$-$C_{15}$ aryloxycarbonyl, $C_1$-$C_{15}$ alkylsulfonyl, $C_3$-$C_{15}$ cycloalkylsulfonyl, $C_1$-$C_{15}$ alkoxysulfonyl, $C_3$-$C_{15}$ cycloalkoxysulfonyl, $C_6$-$C_{15}$ arylsulfonyl, $C_6$-$C_{15}$ aryloxysulfonyl,

234

$C_1$-$C_{15}$ alkylaminosulfonyl, $C_3$-$C_{15}$ cycloalkylaminosulfonyl, or $C_6$-$C_{15}$ arylaminosulfonyl group;

$R^3$, $R^4$, $R^5$ and $R^6$ are each independently selected from hydrogen, halogen atom, hydroxyl, cyano, nitro, $C_1$-$C_{15}$ alkyl, $C_3$-$C_{15}$ cycloalkyl, $C_1$-$C_{15}$ alkoxyl, $C_1$-$C_{15}$ alkylamino, $C_2$-$C_{15}$ heterocyclic amino, $C_6$-$C_{15}$ aryl, $C_6$-$C_{15}$ arylamino, $C_1$-$C_{15}$ alkylsulfonamido, $C_2$-$C_{15}$ heterocyclic sulfonamido, $C_6$-$C_{15}$ arylsulfonamido or $C_1$-$C_{1s}$ aminosulfonamido group; wherein the $R^3$ and $R^4$ can be connected as a cyclic structure;

$R^7$, $R^8$ and $R^9$ are each independently selected from hydrogen, halogen atom, cyano, nitro, trifluoromethyl, $C_1$-$C_{15}$ alkyl, $C_1$-$C_{15}$ alkoxyl, $C_1$-$C_{15}$ alkylthio, $C_1$-$C_{15}$ alkoxylcarbonyl, aminocarbonyl, $C_1$-$C_{15}$ alkylaminocarbonyl, carbonylamino, $C_1$-$C_{15}$ alkylcarbonylamino, $C_2$-$C_{15}$ heterocyclicoxyl carbonyl, $C_6$-$C_{15}$ aryl, $C_6$-$C_{15}$ aryloxy, $C_6$-$C_{15}$ aryloxycarbonyl or $C_2$-$C_{15}$ heterocyclic group; wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_{15}$ alkyl, $C_3$-$C_{15}$ cycloalkyl, $C_1$-$C_{15}$ alkoxyl, $C_1$-$C_{15}$ alkylthio, $C_1$-$C_{15}$ alkoxylcarbonyl, $C_1$-$C_{15}$ alkylaminocarbonyl, $C_1$-$C_{15}$ alkylcarbonylamino, $C_6$-$C_{15}$ aryl, $C_6$-$C_{15}$ aryloxy, $C_6$-$C_{15}$ aryloxycarbonyl or $C_2$-$C_{15}$ heterocyclic group; and $R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group.

3. The compound according to claim 2, or its stereoisomer, tautomer, esterification or amidation prodrug, pharmaceutically acceptable salt or a mixture thereof, wherein in formula Ia or Ib:

m=1 or 2; n=0, 1 or 2;

"═" is a single bond or double bond;

E is oxygen, —NRa—, —CRbRc-, ethylidene, propylidene, $C_1$-$C_6$ alkoxyl, carbonyl, amino carbonyl or carbonyl amino group;

Ra is selected from hydrogen, $C_1$-$C_8$ alkyl, $C_3$-$C_8$ cycloalkyl, $C_6$-$C_{12}$ aryl, $C_2$-$C_8$ heterocyclic aryl, $C_1$-$C_8$ alkylcarbonyl, $C_1$-$C_8$ alkoxycarbonyl, $C_6$-$C_{12}$ aryloxycarbonyl, $C_2$-$C_8$ heterocyclic oxycarbonyl, aminocarbonyl, $C_1$-$C_8$ alkylaminocarbonyl, $C_1$-$C_8$ alkylaminosulfonyl, $C_2$-$C_8$ heterocyclic aminosulfonyl, or $C_6$-$C_{12}$ arylamino aminosulfonyl group;

Rb and Rc are each independently selected from hydrogen, halogen atom, cyano, nitro, $C_1$-$C_8$ alkyl, $C_3$-$C_8$ cycloalkyl, $C_6$-$C_{12}$ aryl, $C_1$-$C_8$ alkoxyl, $C_1$-$C_8$ alkylthio, $C_1$-$C_8$ alkoxycarbonyl, $C_6$-$C_{12}$ aryloxy, $C_6$-$C_{12}$ aryloxycarbonyl, $C_2$-$C_8$ heterocyclic-oxycarbonyl, $C_2$-$C_{12}$ heterocyclic aryl, $C_1$-$C_8$ alkylamino, $C_2$-$C_8$ heterocyclic amino, $C_6$-$C_{12}$ arylamino, aminocarbonyl, $C_1$-$C_8$ alkylaminocarbonyl, carbonylamino, $C_1$-$C_8$ alkylcarbonylamino, $C_1$-$C_8$ alkylsulfonamido, $C_2$-$C_8$ heterocyclic sulfonamido, $C_6$-$C_{12}$ arylsulfonamido or $C_1$-$C_8$ alkyl aminosulfonamido group;

G is selected from oxygen, sulfur, sulfone, —NRa—, —OC(Rb)(Rc)-, —SC(Rb)(Rc)-, —N(Ra)C(Rb)(Rc)-, $C_1$-$C_8$ alkoxyl, $C_1$-$C_8$ alkylamino, $C_1$-$C_8$ alkyl-oxygen, $C_1$-$C_8$ alkyl, $C_1$-$C_8$ alkoxycarbonyl, carbonyl, carbonylamino or $C_1$-$C_8$ alkylcarbonylamino group; when $R^7$ and $R^8$ or $R^8$ and $R^9$ are connected each other as a cyclic structure, G is methylene or does not exist (i.e., "═" connected directly with the phenyl group of polyheterocyclic group);

L and $L^1$ are each independently selected from oxygen, sulfur, $C_2$-$C_8$ alkenyl, $C_1$-$C_8$ alkyl, $C_3$-$C_8$ cycloalkyl, $C_2$-$C_8$ heterocyclic, $C_6$-$C_{12}$ aryl, $C_3$-$C_8$ heterocyclic aryl, $C_1$-$C_8$ alkylthio, $C_1$-$C_8$ alkoxyl, $C_3$-$C_8$ cycloalkoxyl, $C_2$-$C_8$ heterocyclic oxyl, $C_1$-$C_8$ alkylamino, $C_1$-$C_8$ alkoxycarbonyl, $C_6$-$C_{12}$ aryl, or $C_6$-$C_{12}$ aryloxy group;

U is selected from carbonyl, sulfoxide (—SO—), sulfone (—$SO_2$—), —P(O)(ORd)- or —B(ORe)-; Wherein Rd and Re are independently selected from hydrogen (H), $C_1$-$C_8$ alkyl, $C_3$-$C_8$ cycloalkyl, $C_2$-$C_8$ heterocyclic, $C_6$-$C_{12}$ aryl, or $C_3$-$C_{12}$ heterocyclic alkyl group;

W is selected from oxygen or sulfur;

X is selected from oxygen, sulfur, nitrogen or —NRa—; wherein the definition of Ra is the same as that in E and G;

Y is selected from nitrogen or CH;

Z is selected from hydrogen (H), hydroxyl (OH), amino ($NH_2$), $C_1$-$C_8$ alkyl, $C_3$-$C_8$ cycloalkyl, $C_1$-$C_8$ alkoxyl, $C_3$-$C_8$ cycloalkoxyl, $C_1$-$C_8$ alkylamino, $C_3$-$C_8$ cycloalkylamino, $C_2$-$C_8$ heterocyclic amino, $C_6$-$C_{12}$ aryl, $C_6$-$C_{12}$ arylamino, $C_3$-$C_{12}$ heterocyclic arylamino, $C_1$-$C_8$ alkylsulfonamido, $C_3$-$C_8$ cycloalkylsulfonamido, $C_6$-$C_{12}$ arylsulfonamido, $C_1$-$C_8$ alkylaminosulfonamido, $C_3$-$C_8$ cycloalkylaminosulfonamido, $C_6$-$C_{12}$ aryloxysulfonamido, $C_1$-$C_8$ alkylaminosulfonamido, $C_3$-$C_8$ cycloalkylaminosulfonamido, $C_6$-$C_{12}$ arylaminosulfonamido, uramido, $C_1$-$C_8$ alkyluramido, or $C_1$-$C_8$ alkylthiouramido group;

$R^1$ is selected from hydrogen (H), $C_1$-$C_8$ alkyl, $C_3$-$C_8$ cycloalkyl, $C_6$-$C_{12}$ aryl, $C_3$-$C_{12}$ heterocyclic aryl, $C_1$-$C_8$ alkylsulfonamido, $C_2$-$C_{12}$ heterocyclic sulfonamido, or $C_1$-$C_8$ alkoxylcarbonylamino group;

$R^2$ is selected from hydrogen (H), $C_1$-$C_8$ alkyl, $C_3$-$C_8$ cycloalkyl, $C_1$-$C_8$ alkoxyl, $C_3$-$C_8$ cycloalkoxyl, $C_6$-$C_{12}$ aryl, $C_3$-$C_{12}$ heterocyclic aryl, $C_6$-$C_{12}$ aryloxycarbonyl, $C_1$-$C_8$ alkylsulfonyl, $C_3$-$C_8$ cycloalkylsulfonyl, $C_1$-$C_8$ alkoxysulfonyl, $C_3$-$C_8$ cycloalkoxysulfonyl, $C_6$-$C_{12}$ arylsulfonyl, $C_6$-$C_{12}$ aryloxysulfonyl, $C_1$-$C_8$ alkylaminosulfonyl, $C_3$-$C_8$ cycloalkylaminosulfonyl, or $C_6$-$C_{12}$ arylaminosulfonyl group;

$R^3$, $R^4$, $R^5$ and $R^6$ are each independently selected from hydrogen, halogen atom, hydroxyl, cyano, nitro, $C_1$-$C_8$ alkyl, $C_3$-$C_8$ cycloalkyl, $C_1$-$C_8$ alkoxyl, $C_1$-$C_8$ alkylamino, $C_2$-$C_8$ heterocyclic amino, $C_6$-$C_{12}$ aryl, $C_6$-$C_{12}$ arylamino, $C_1$-$C_8$ alkylsulfonamido, $C_2$-$C_8$ heterocyclic sulfonamido, $C_6$-$C_{12}$ arylsulfonamido or $C_1$-$C_8$ aminosulfonamido group; wherein $R^3$ and $R^4$ can be connected as a cyclic structure group;

$R^7$, $R^8$ and $R^9$ are each independently selected from hydrogen, halogen atom, cyano, nitro, trifluoromethyl, $C_1$-$C_8$ alkyl, $C_1$-$C_8$ alkoxyl, $C_1$-$C_8$ alkylthio, $C_1$-$C_8$ alkoxylcarbonyl, aminocarbonyl, $C_1$-$C_8$ alkylaminocarbonyl, carbonylamino, $C_1$-$C_8$ alkylcarbonylamino, $C_2$-$C_8$ heterocyclicoxyl carbonyl, $C_6$-$C_{12}$ aryl, $C_6$-$C_{12}$ aryloxy, $C_6$-$C_{12}$ aryloxycarbonyl or $C_2$-$C_8$ heterocyclic group; wherein $R^7$ and $R^8$ or $R^8$ and $R^9$ can be connected each other as a cyclic structure;

$R^{10}$ is selected from hydrogen, halogen atom, cyano, nitro, trifluoromethyl, $C_1$-$C_8$ alkyl, $C_3$-$C_8$ cycloalkyl, $C_1$-$C_8$ alkoxyl, $C_1$-$C_8$ alkylthio, $C_1$-$C_8$ alkoxylcarbonyl, $C_1$-$C_8$ alkylaminocarbonyl, $C_1$-$C_8$ alkylcarbonylamino, $C_6$-$C_{12}$ aryl, $C_6$-$C_{12}$ aryloxy, $C_6$-$C_{12}$ aryloxycarbonyl or $C_2$-$C_8$ heterocyclic group; and $R^{11}$ is selected from hydrogen (H), $C_1$-$C_8$ alkyl, $C_3$-$C_8$ cycloalkyl, $C_2$-$C_8$ alkenyl, $C_6$-$C_{12}$ aryl, $C_3$-$C_{12}$ heterocyclic aryl group.

4. The compound according to claim 3, or its stereoisomer, tautomer, esterification or amidation prodrug, pharmaceutically acceptable salt or a mixture thereof, wherein in formula Ia or Ib:

m=1; n=1;

p=0, 1 or 2; q=0, 1 or 2; r=0, 1 or 2;

"⋯" is a single bond or double bond;

E is methylene (—$CH_2$—);

G is selected from oxygen, sulfur, —$SCH_2$—, —N(Ra)$CH_2$—, —NRa—, methylene (—$CH_2$—), —$OCH_2$—, —$CH_2OCH_2$—, $C_1$-$C_3$ alkoxycarbonyl, carbonylamino, or $C_1$-$C_3$ alkylcarbonylamino group; when $R^7$ and $R^8$ or $R^8$ and $R^9$ are connected each other as a cyclic structure, G is methylene or does not exist (i.e., "⋯" connected directly with the phenyl group of polyheterocyclic group); wherein the Ra is selected from hydrogen, $C_1$-$C_6$ alkyl, $C_1$-$C_6$ alkylcarbonyl, or $C_1$-$C_6$ alkoxycarbonyl group;

L is methylene (—$CH_2$—);

$L^1$ is $C_1$-$C_6$ alkyl, $C_1$-$C_6$ alkoxyl, or $C_1$-$C_6$ alkylamino group;

U is carbonyl;

W and X are both oxygen (O);

Y is nitrogen (N);

Z is selected from hydroxyl, $C_1$-$C_6$ alkoxyl, $C_1$-$C_6$ alkylsulfonamido, $C_3$-$C_6$ cycloalkylsulfonamido, or $C_6$-$C_{10}$ arylsulfonamido group;

$R^1$ is selected from $C_1$-$C_6$ alkyl, $C_6$-$C_{10}$ aryl, $C_1$-$C_6$ alkylsulfonamido, $C_2$-$C_6$ heterocyclic sulfonamido, or $C_1$-$C_6$ alkoxylcarbonylamino group;

$R^2$, $R^5$ and $R^6$ are each independently hydrogen;

$R^3$ and $R^4$ are each independently selected from hydrogen, methyl, fluorine, or $R^3$ and $R^4$ connect each other to be cyclopropyl group;

$R^7$, $R^8$ and $R^9$ are each independently selected from hydrogen, halogen, $C_1$-$C_3$ alkyl, or $C_1$-$C_3$ alkoxyl group;

$R^{10}$ is hydrogen; and $R^{11}$ is selected from $C_1$-$C_3$ alkyl or vinyl group.

5. The compound according to claim 4, or its stereoisomer, tautomer, esterification or amidation prodrug, pharmaceutically acceptable salt or a mixture thereof, wherein the compound of formula Ia is selected from the following structures:

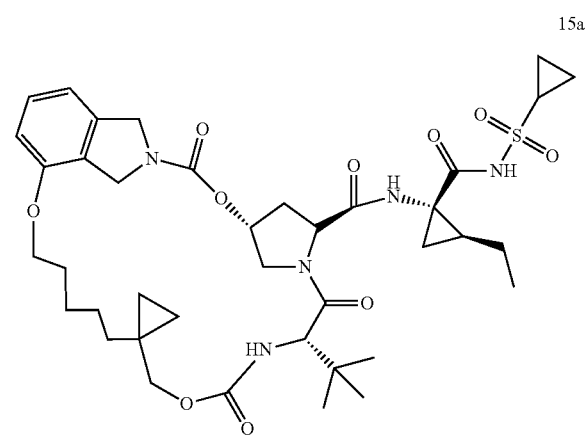

15a

| 15b | 15f |
|---|---|
| 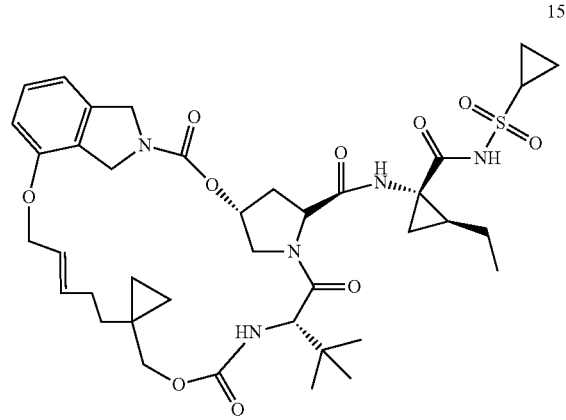 | 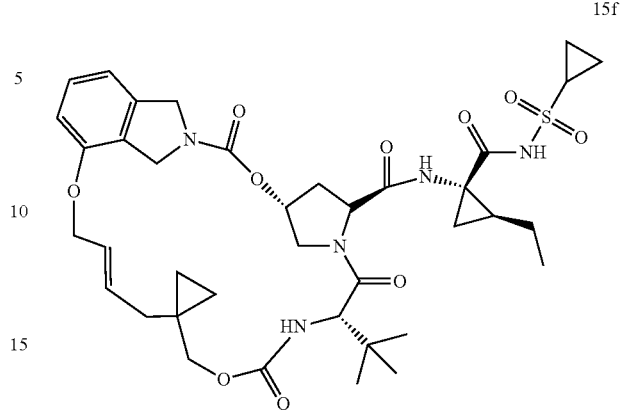 |
| 15c | 15g |
| 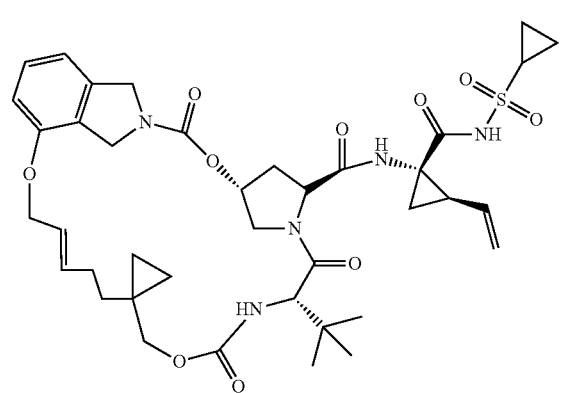 | 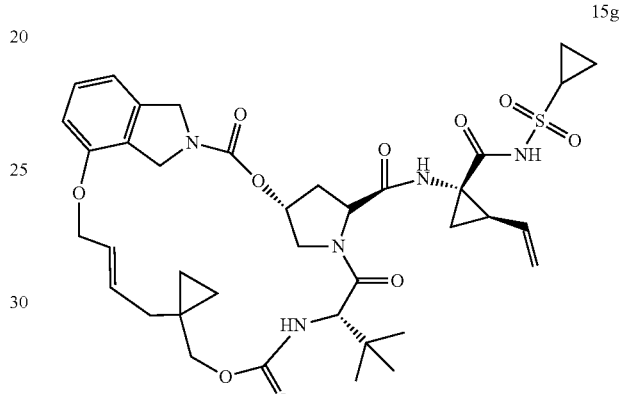 |
| 15d | 15h |
| 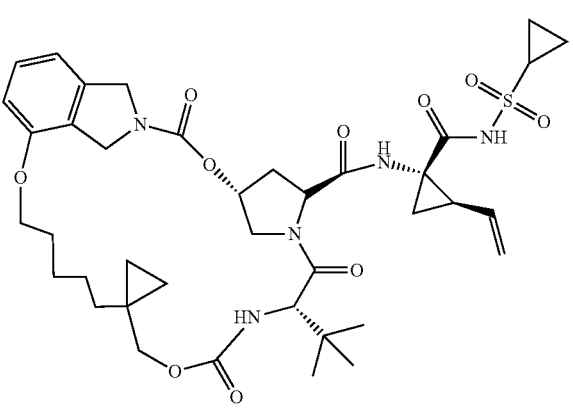 | 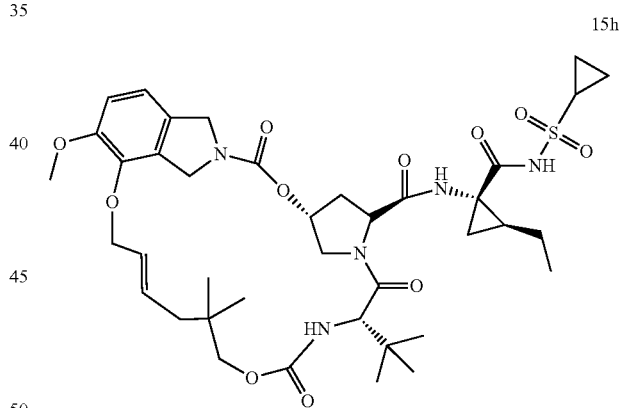 |
| 15e | 15j |
| 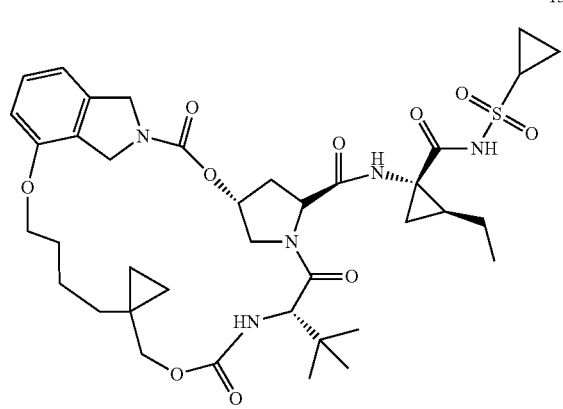 | 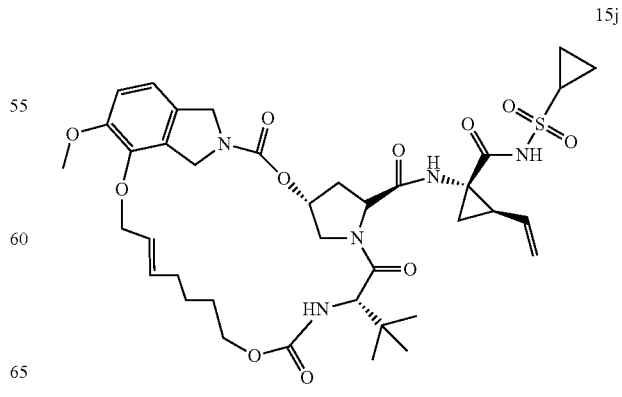 |

239
-continued
15k
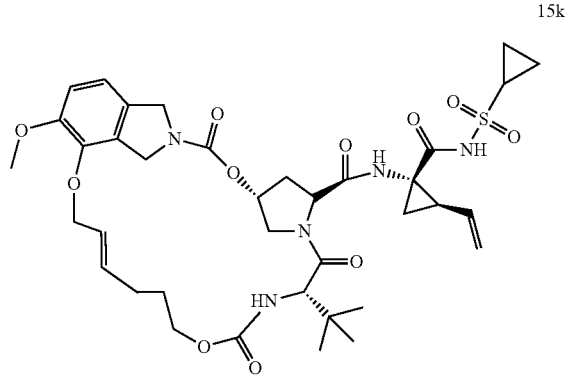
15m
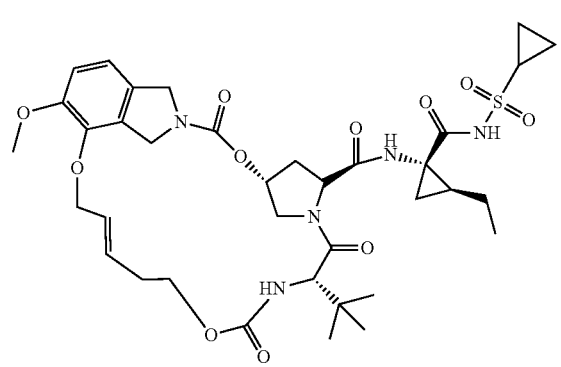
15n
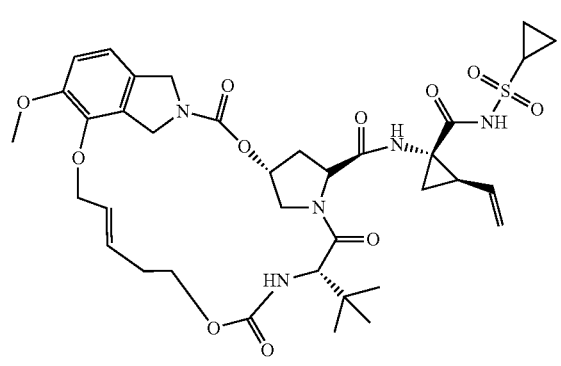
15p
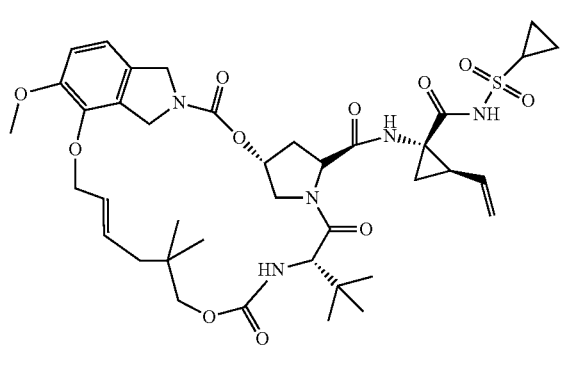
240
-continued
15q
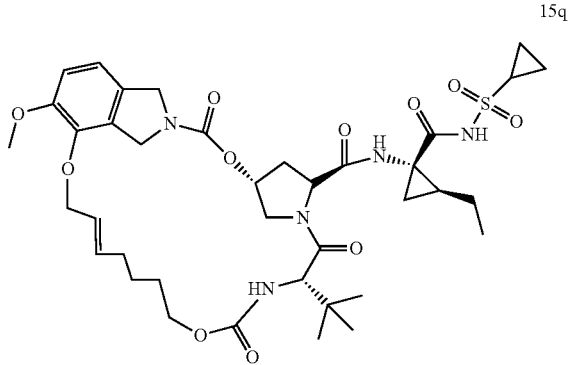
15r
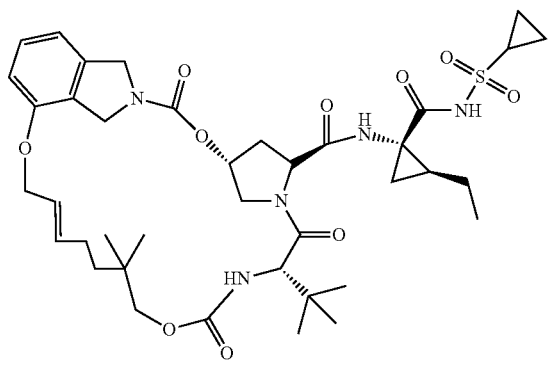
15s
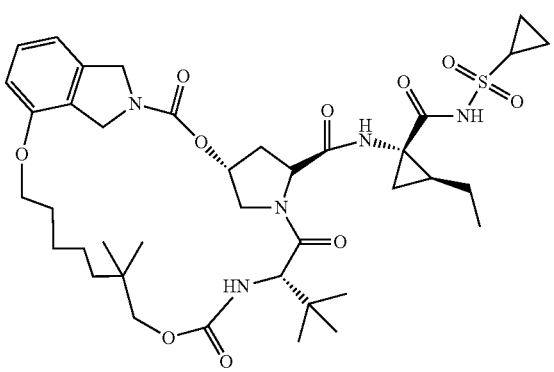
15t
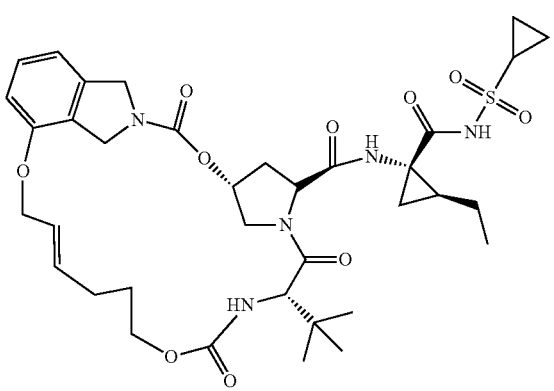

15u
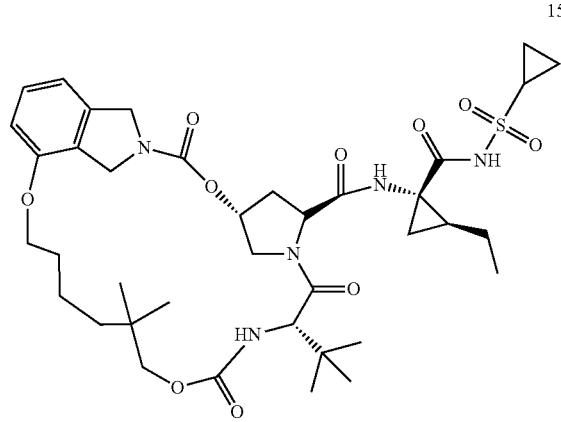
15y
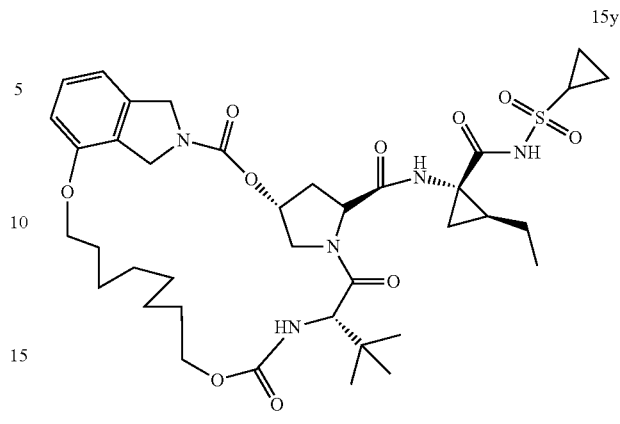
15v
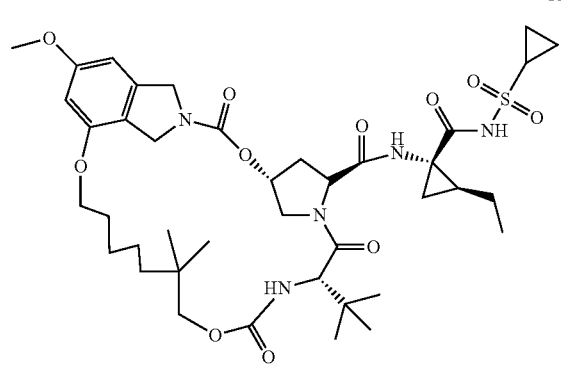
15z
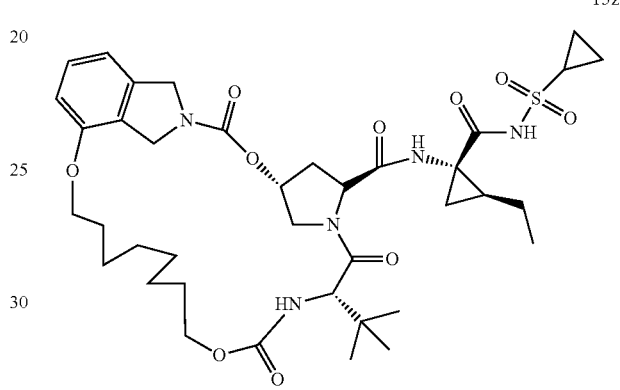
15w
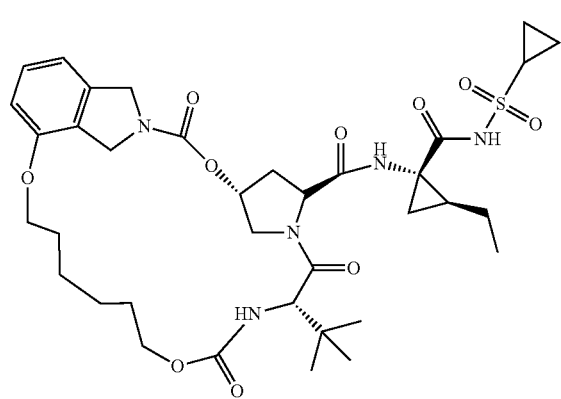
15aa
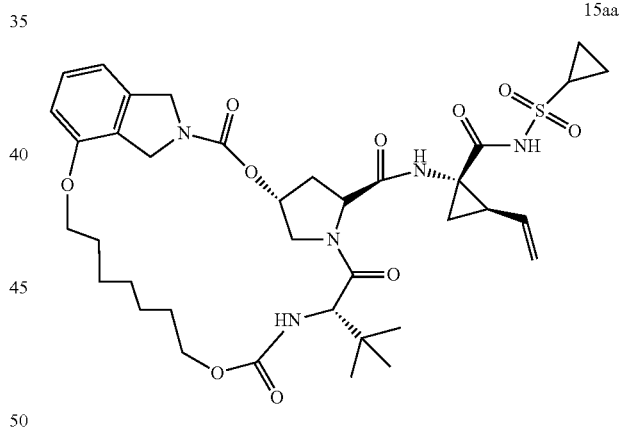
15x
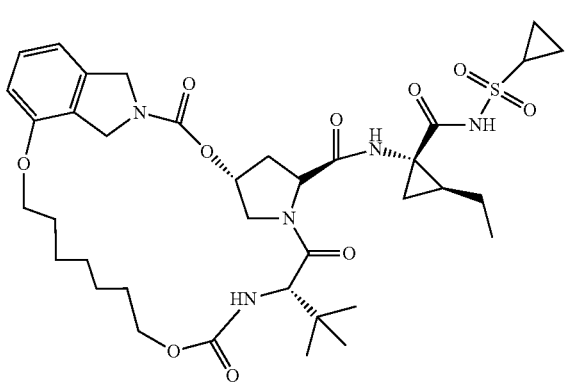
15ab
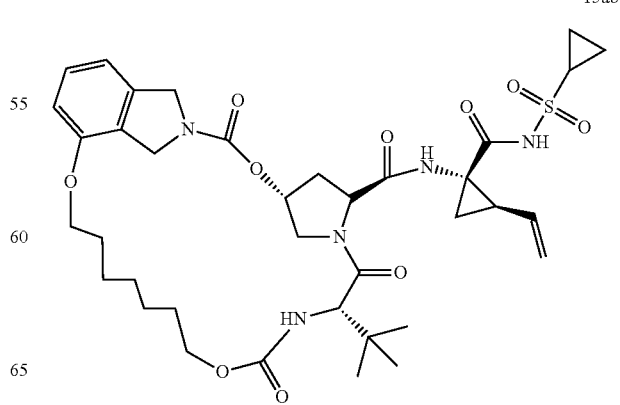

243
-continued
15ac
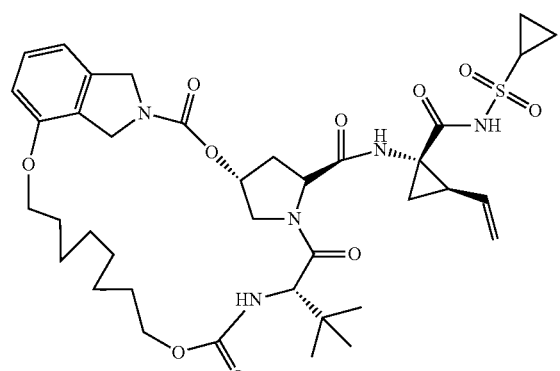
15ad
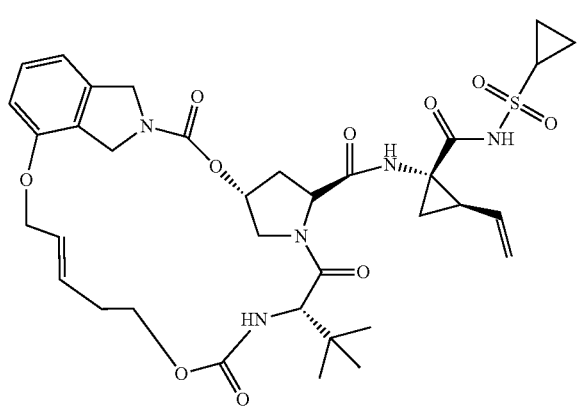
15ae
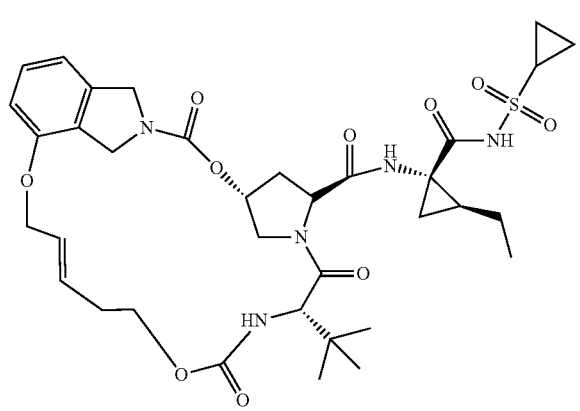
15af
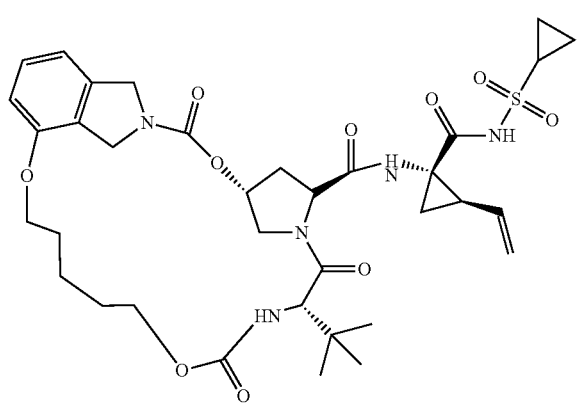
244
-continued
15ag
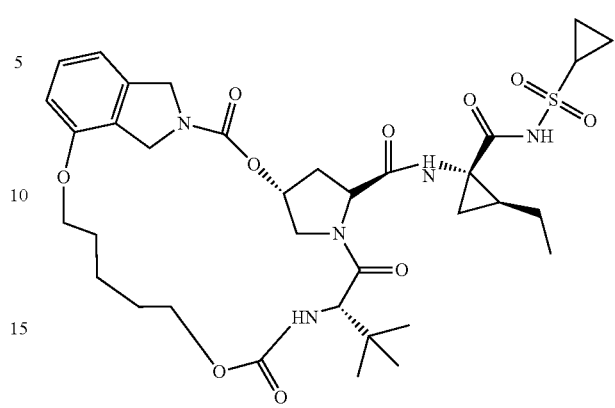
15ah
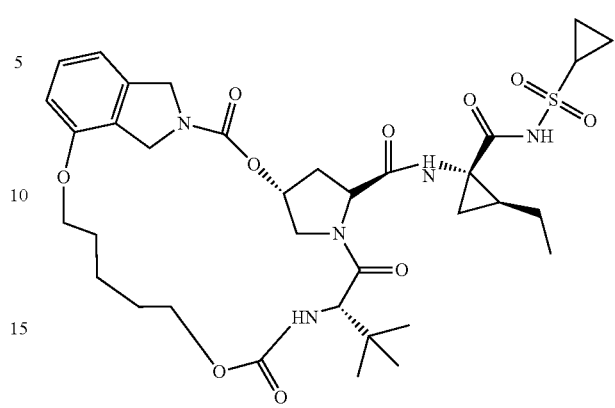
15aj
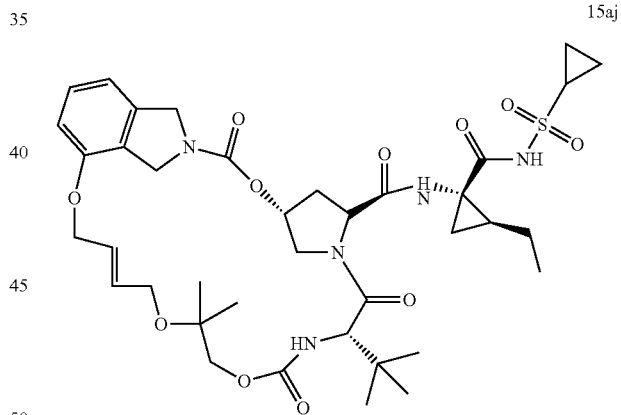
15ak
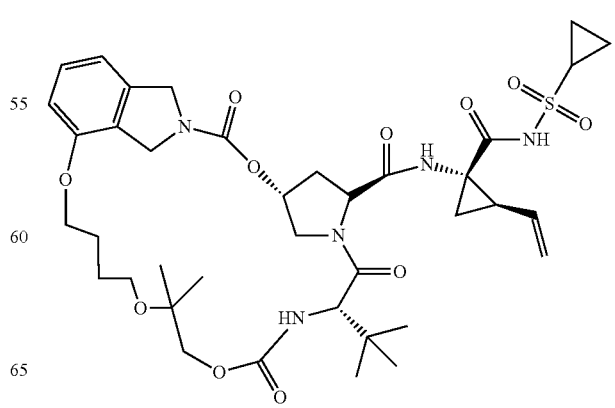

245
-continued
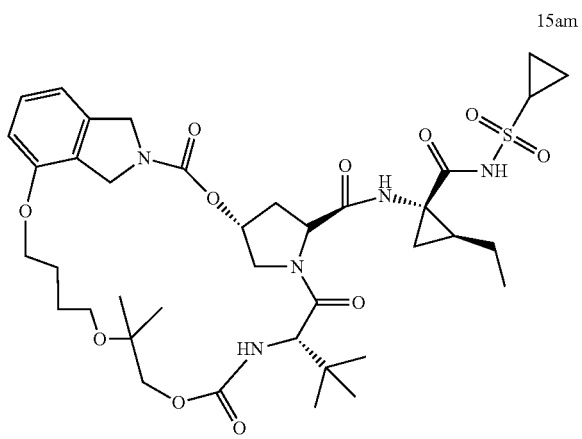
15am
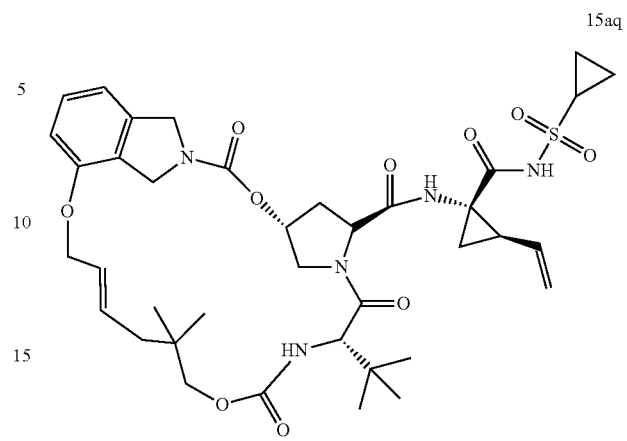
15aq
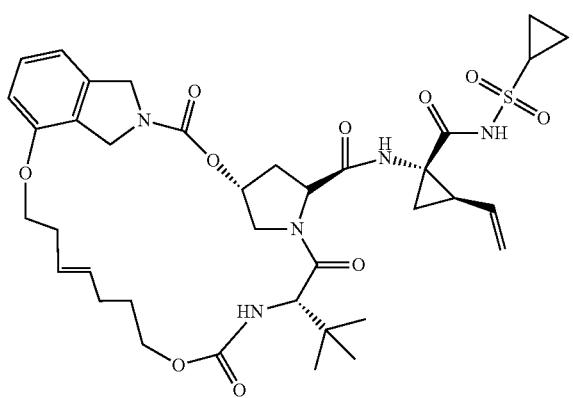
15an
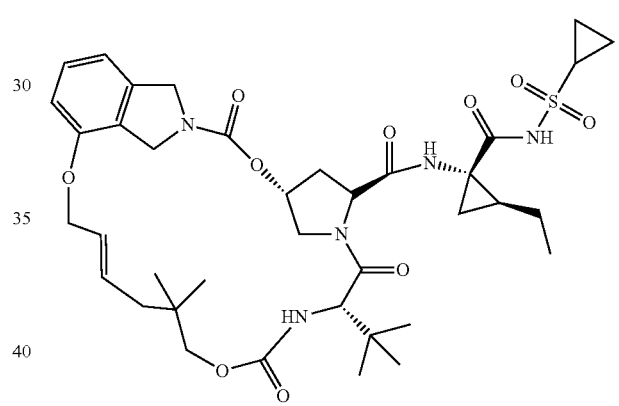
15ar
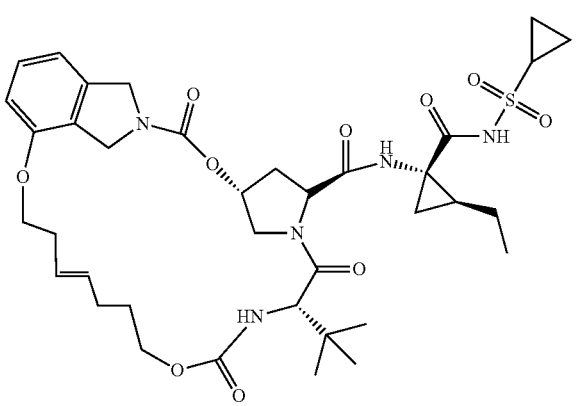
15ap
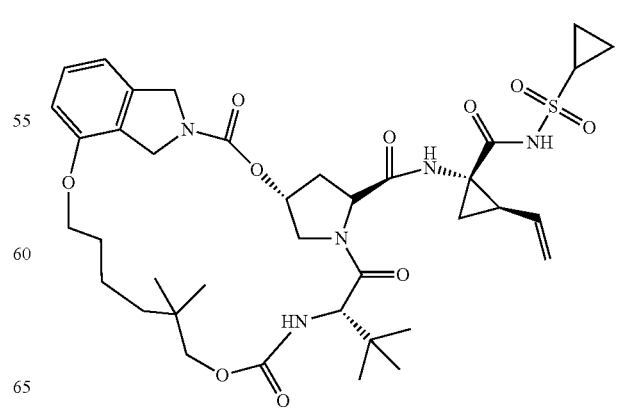
15as 247
-continued
15at
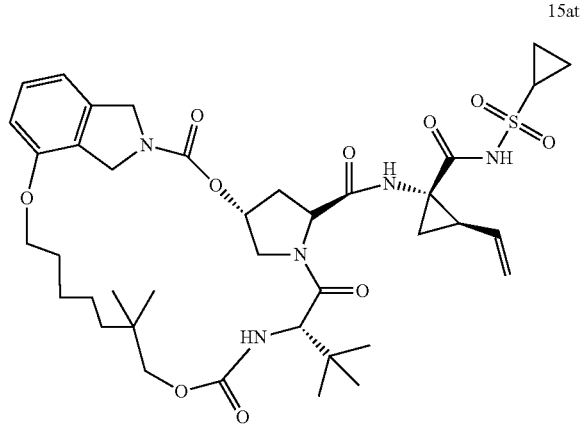
15au
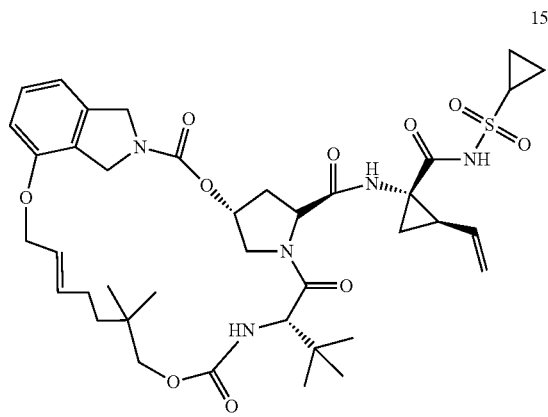
15av
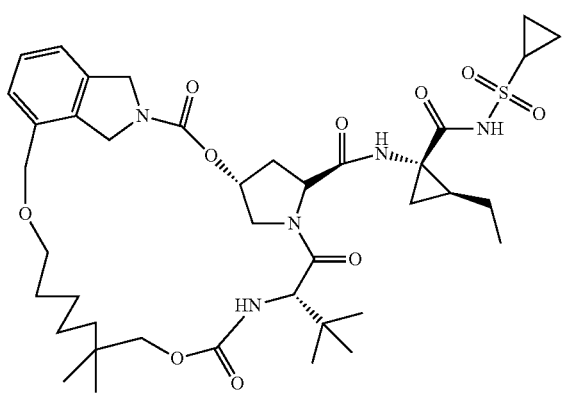
15aw
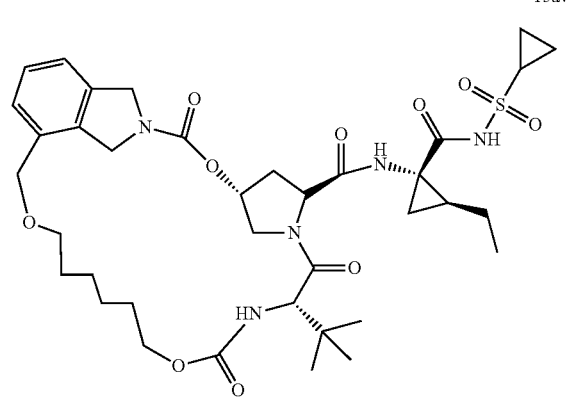
248
-continued
15ax
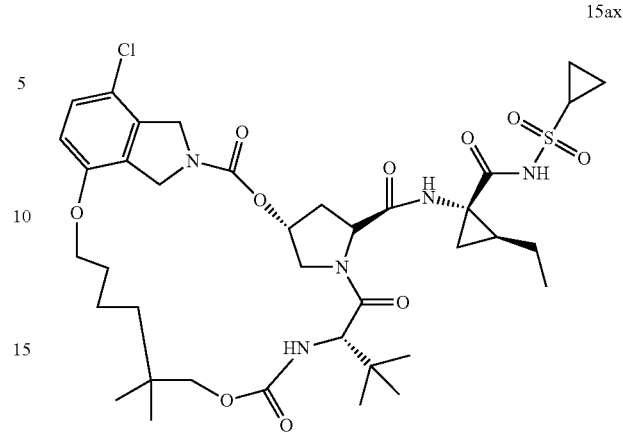
15ba
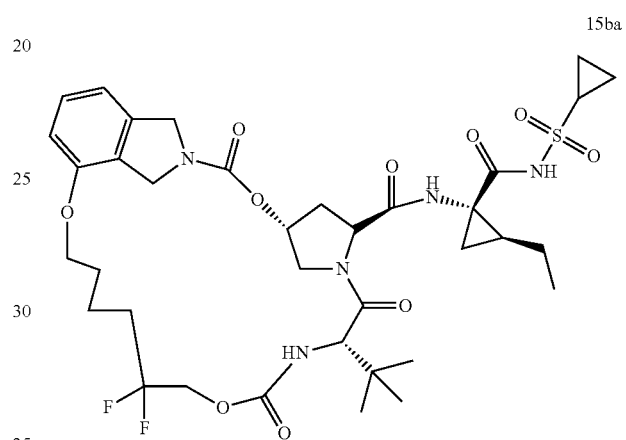
15bb
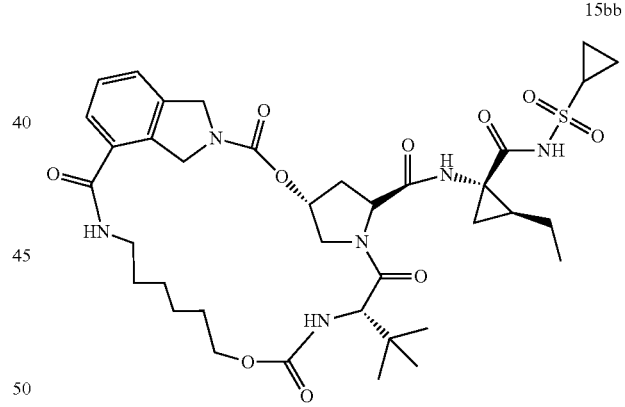
15bc
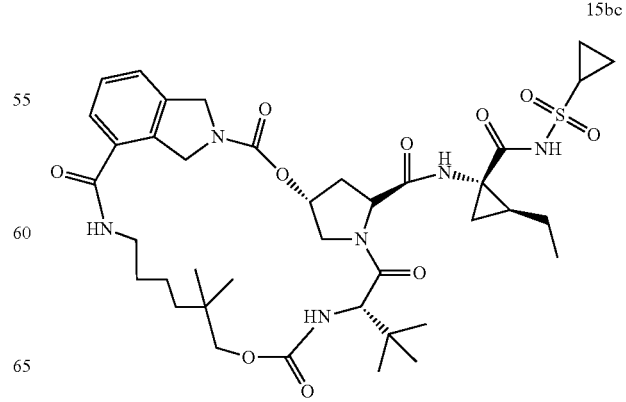

-continued
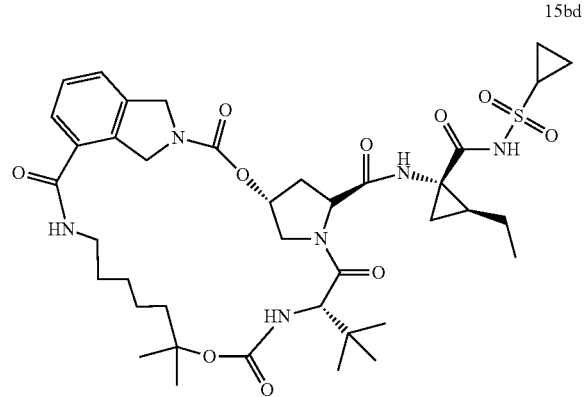
15bd
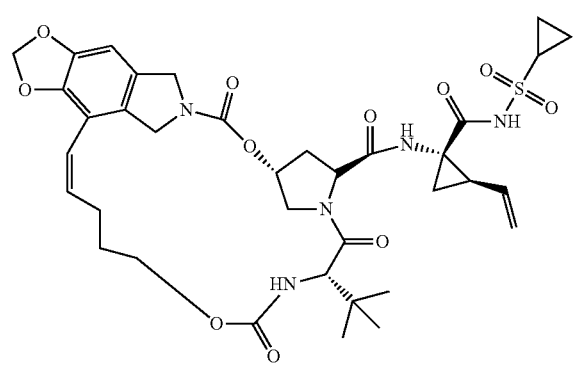
15bt
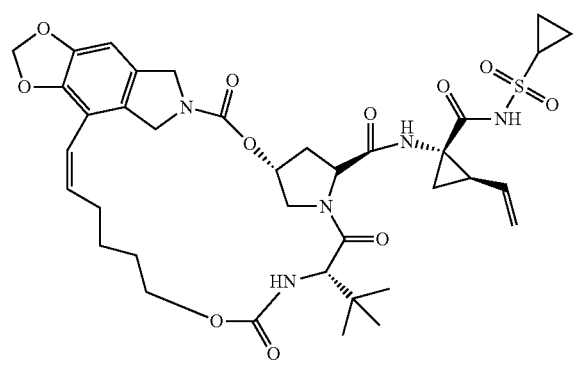
15bu
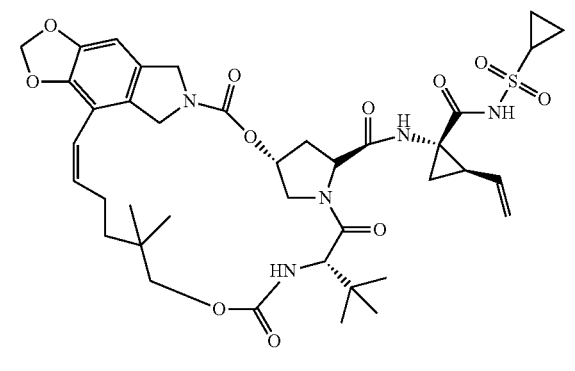
15bv
-continued
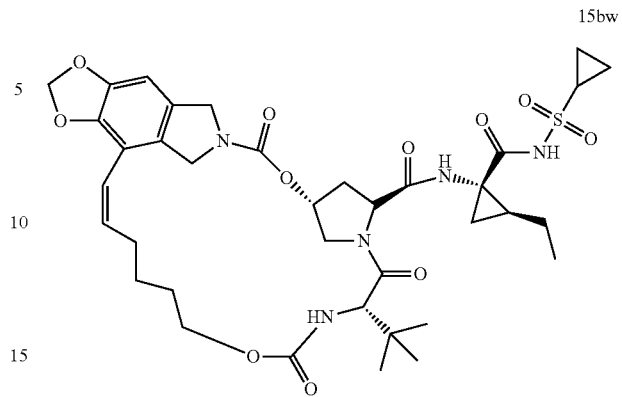
15bw
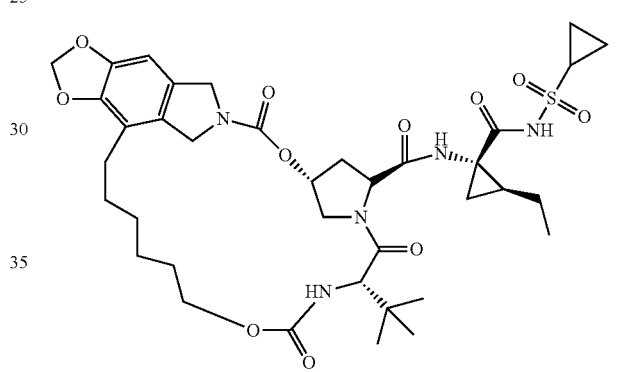
15bx
15by
and the compound of formula Ib is selected from the following structures:

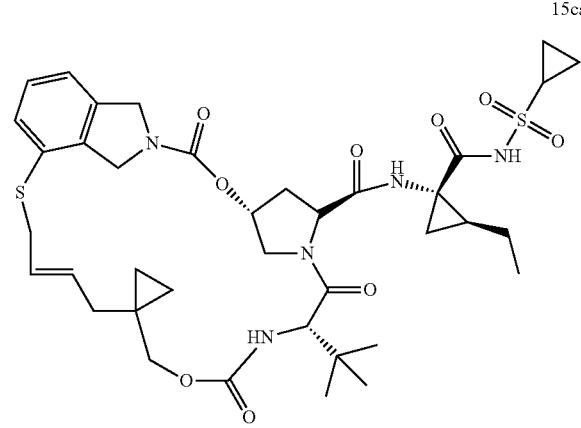
15ca
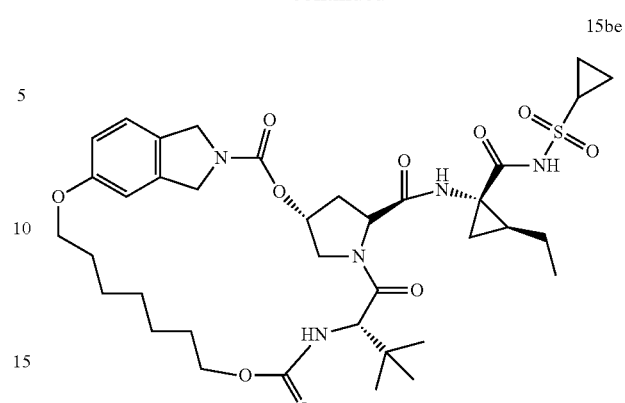
15be
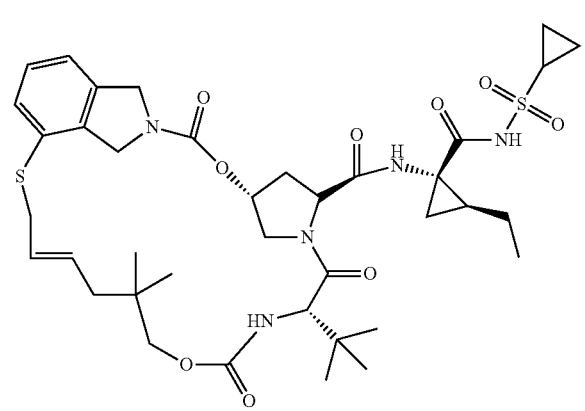
15cb
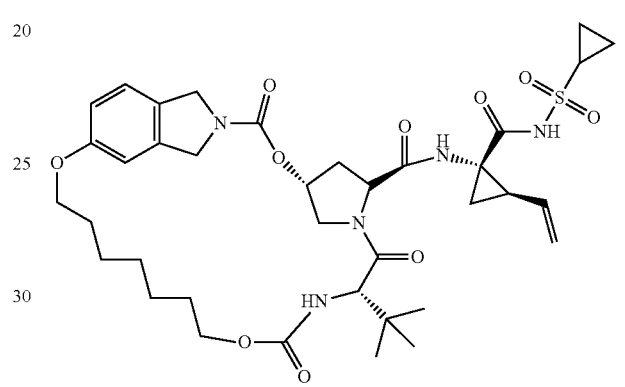
15bf
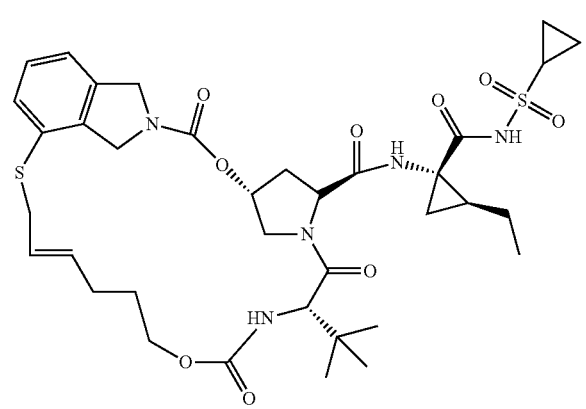
15cc
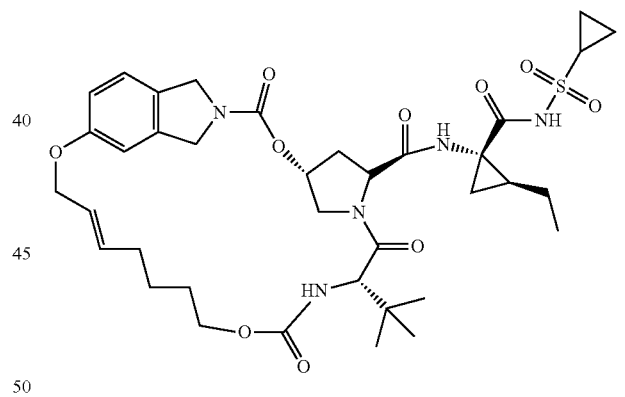
15bg
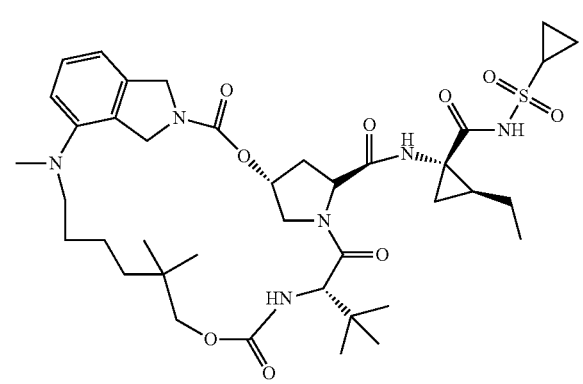
15cd
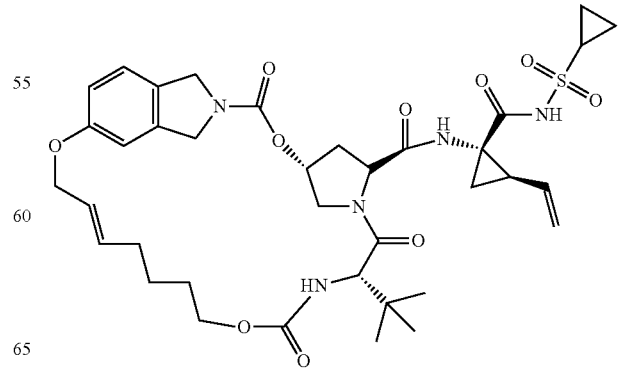
15bh 253
-continued
15bj
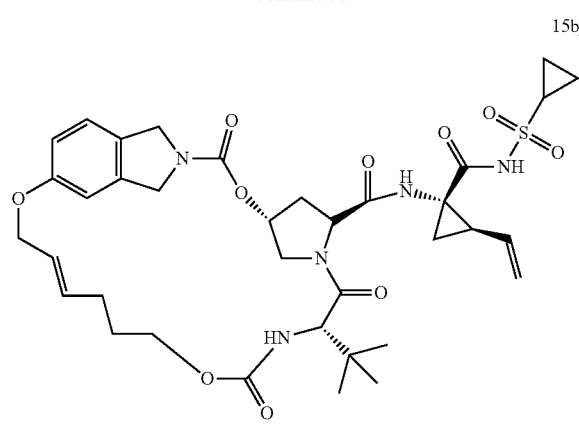
15bk
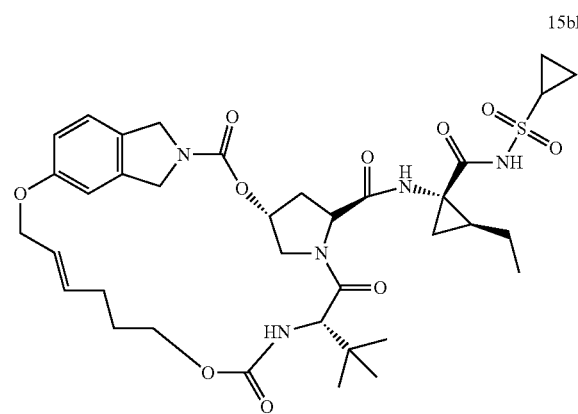
15bm
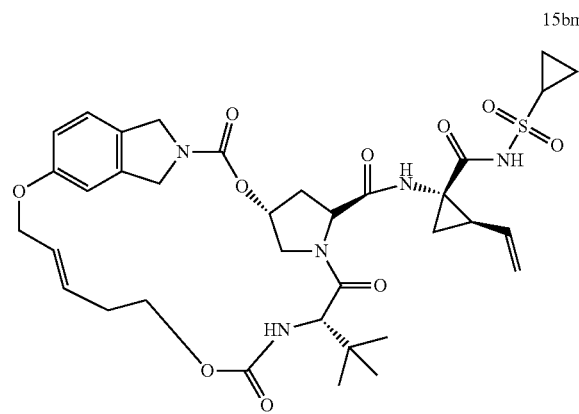
15bn
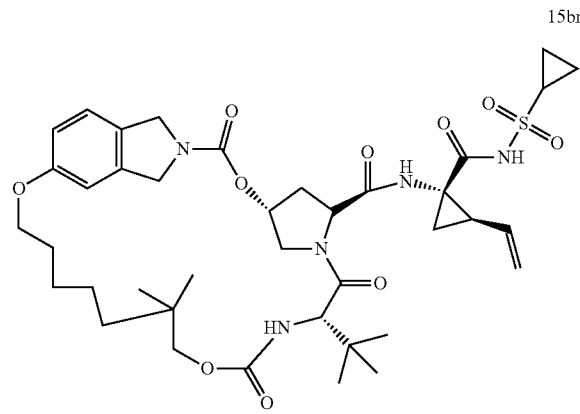
254
-continued
15bp
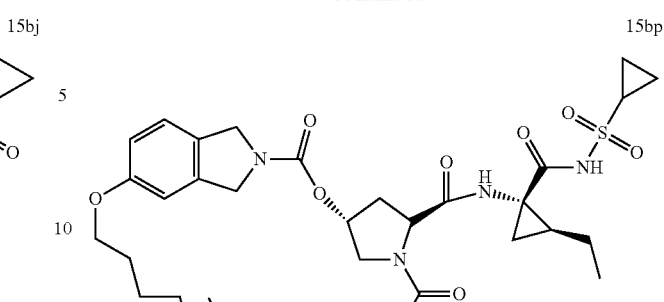
15bq
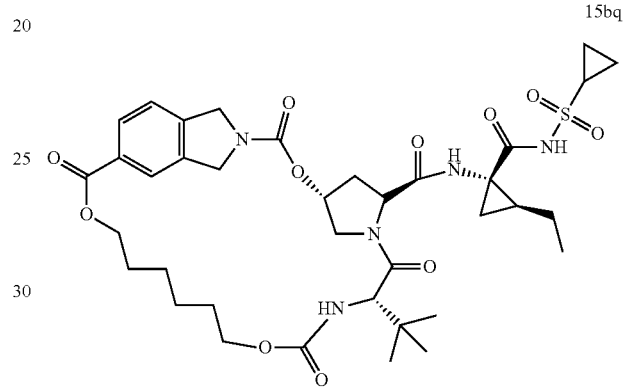
15br
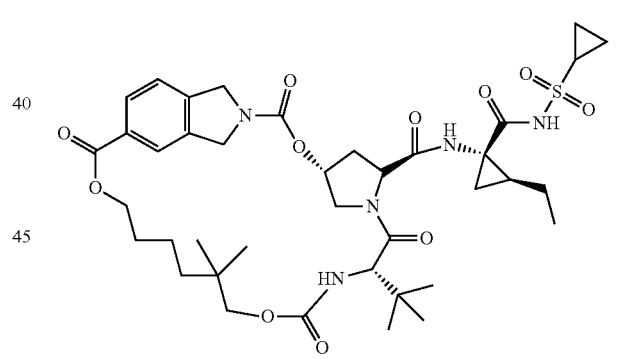
15bs
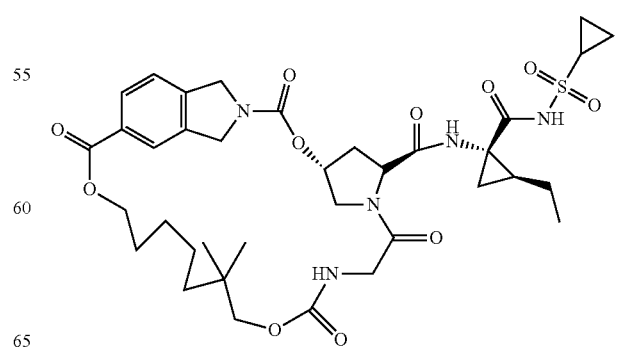

6. A polycyclic compound of formula IIa or IIb:

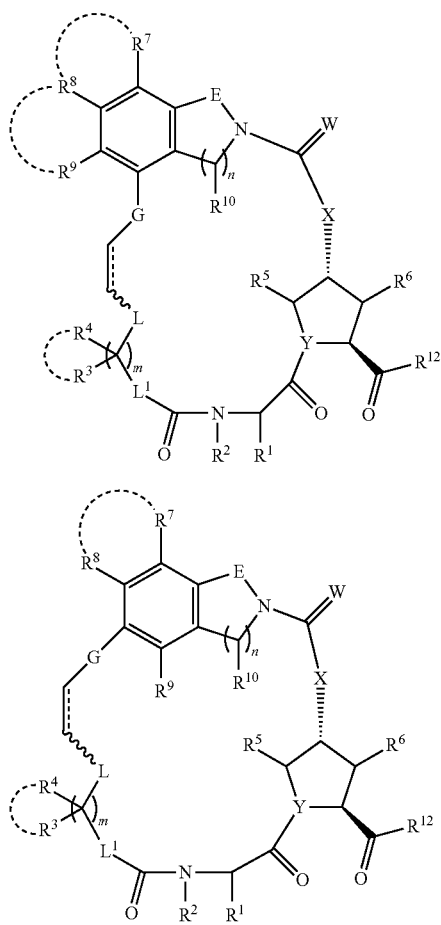

wherein:
m=1 or 2; n=0, 1 or 2;
" ⋯ " is a single bond or double bond;
E, Ra, Rb, Rc, G, L, $L^1$, W, X, Y, $R^1$, $R^2$, $R^3$, $R^4$, $R^5$, $R^6$, $R^7$, $R^8$, $R^9$, and $R^{10}$ are defined as in claim 1; and
$R^{12}$ is selected from hydrogen (H), hydroxyl (OH), amino ($NH_2$), $C_1$-$C_{20}$ alkyl, $C_3$-$C_{20}$ cycloalkyl, $C_1$-$C_{20}$ alkoxyl, $C_3$-$C_{20}$ cycloalkoxyl, $C_1$-$C_{20}$ alkylamino, $C_3$-$C_{20}$ cycloalkylamino, $C_2$-$C_{20}$ heterocyclic amino, $C_6$-$C_{20}$ aryl, $C_6$-$C_{20}$ aryloxyl, $C_3$-$C_{20}$ heterocyclic arylamino, $C_1$-$C_{20}$ alkylsulfonamido, $C_3$-$C_{20}$ cycloalkylsulfonamido, $C_6$-$C_{20}$ arylsulfonamido, $C_1$-$C_{20}$ alkyloxysulfonamido, $C_3$-$C_{20}$ cycloalkyloxysulfonamido, $C_6$-$C_{20}$ aryloxysulfonamido, $C_1$-$C_{20}$ alkylaminosulfonamido, $C_3$-$C_{20}$ cycloalkylaminosulfonamido, or $C_6$-$C_{20}$ arylaminosulfonamido group.

7. The polycyclic compound according to claim 6, wherein in formula IIa or IIb:
m=1 or 2; n=0, 1 or 2;
" ⋯ " is a single bond or double bond;
E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ are describes as E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ in claim 2; and
$R^{12}$ is selected from hydrogen (H), hydroxyl (OH), amino ($NH_2$), $C_1$-$C_{15}$ alkyl, $C_3$-$C_{15}$ cycloalkyl, $C_1$-$C_{15}$ alkoxyl, $C_3$-$C_{15}$ cycloalkoxyl, $C_1$-$C_{15}$ alkylamino, $C_3$-$C_{15}$ cycloalkylamino, $C_2$-$C_{15}$ heterocyclic amino, $C_6$-$C_{15}$ aryl, $C_6$-$C_{15}$ aryloxyl, $C_3$-$C_{15}$ heterocyclic arylamino, $C_1$-$C_{15}$ alkylsulfonamido, $C_3$-$C_{15}$ cycloalkylsulfonamido, $C_6$-$C_{15}$ arylsulfonamido, $C_1$-$C_{15}$ alkyloxysulfonamido, $C_3$-$C_{15}$ cycloalkyloxysulfonamido, $C_6$-$C_{15}$ aryloxysulfonamido, $C_1$-$C_{15}$ alkylaminosulfonamido, $C_3$-$C_{15}$ cycloalkylaminosulfonamido, or $C_6$-$C_{15}$ arylaminosulfonamido.

8. The polycyclic compound according to claim 7, wherein in formula IIa or IIb:
m=1 or 2; n=0, 1 or 2;
" ⋯ " is a single bond or double bond;
E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ are describes as E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ in claim 3; and
$R^{12}$ is selected from hydrogen (H), hydroxyl (OH), amino ($NH_2$), $C_1$-$C_8$ alkyl, $C_3$-$C_8$ cycloalkyl, $C_1$-$C_8$ alkoxyl, $C_3$-$C_8$ cycloalkoxyl, $C_1$-$C_8$ alkylamino, $C_3$-$C_8$ cycloalkylamino, $C_2$-$C_8$ heterocyclic amino, $C_6$-$C_{12}$ aryl, $C_6$-$C_{12}$ aryloxyl, $C_3$-$C_{12}$ heterocyclic arylamino, $C_1$-$C_8$ alkylsulfonamido, $C_3$-$C_8$ cycloalkylsulfonamido, $C_6$-$C_{12}$ arylsulfonamido, $C_1$-$C_8$ alkyloxysulfonamido, $C_3$-$C_8$ cycloalkyloxysulfonamido, $C_6$-$C_{12}$ aryloxysulfonamido, $C_1$-$C_8$ alkylaminosulfonamido, $C_3$-$C_8$ cycloalkylaminosulfonamido, or $C_6$-$C_{12}$ arylaminosulfonamido.

9. The polycyclic compound according to claim 8, wherein in formula IIa or IIb:
m=1; n=1;
" ⋯ " is a single bond or double bond;
E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ are describes as E, Ra, Rb, Rc, G, L, $L^1$, W, X, Y, $R^1$, $R^2$, $R^3$, $R^4$, $R^5$, $R^6$, $R^7$, $R^8$, $R^9$ and $R^{10}$ in claim 4;
$R^3$ and $R^4$ are each independently selected from hydrogen, methyl, fluorine, or $R^3$ and $R^4$ connect each other to be cyclopropyl; and
$R^{12}$ is selected from hydroxyl or $C_1$-$C_3$ alkoxyl group.

10. The polycyclic compound according to claim 9, wherein:
the compound of formula IIa is selected from the following structures:

12ak

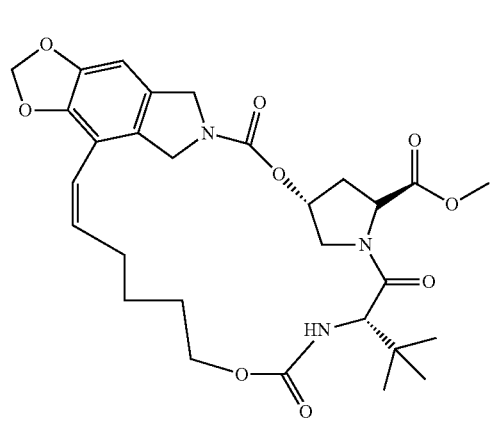

257
-continued
12am
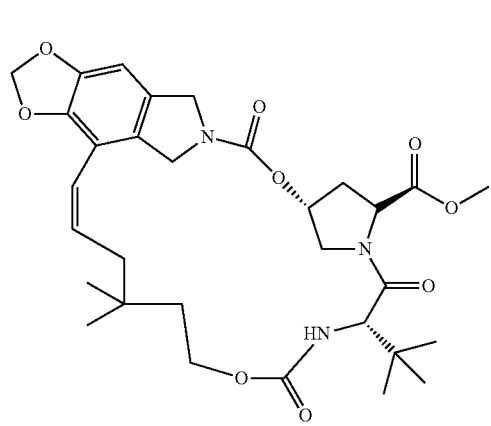
13ak
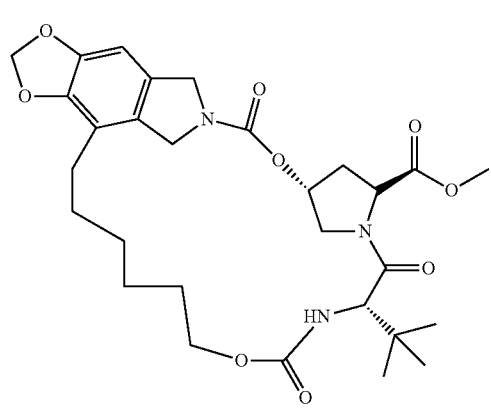
13am
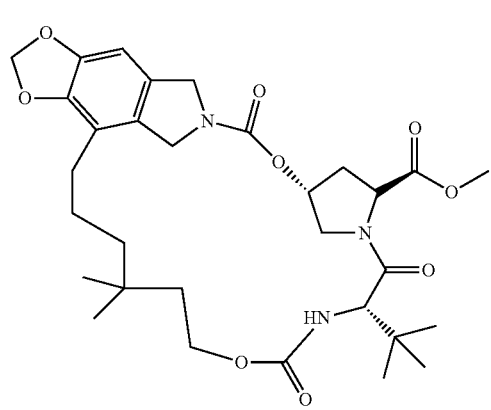
12a
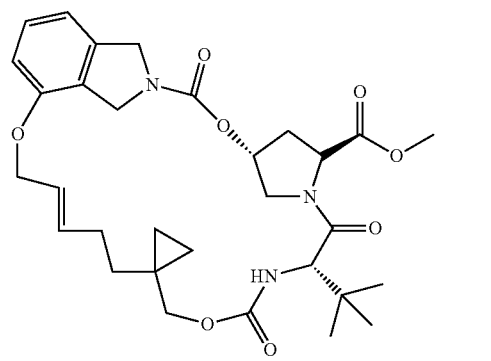
258
-continued
13a
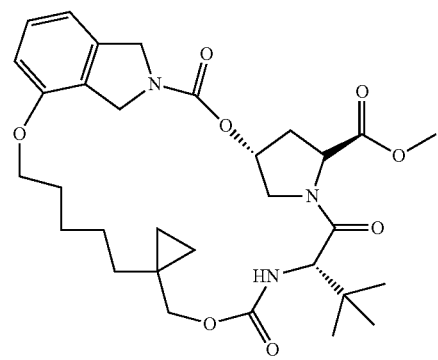
12b
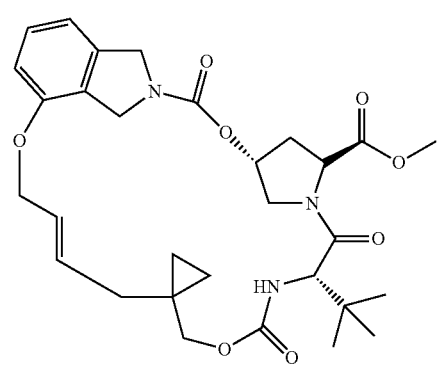
13b
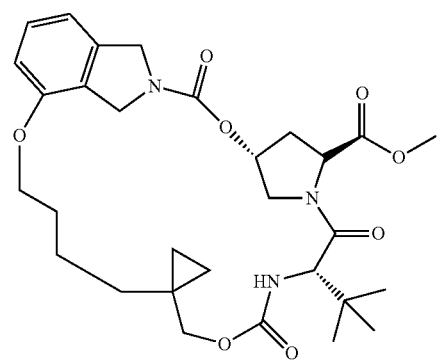
12c
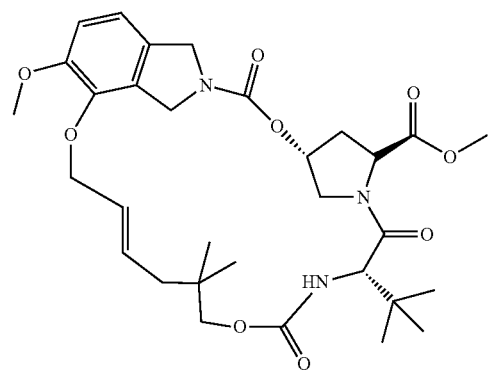

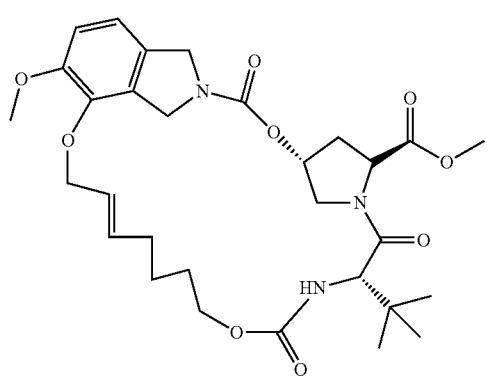
12d
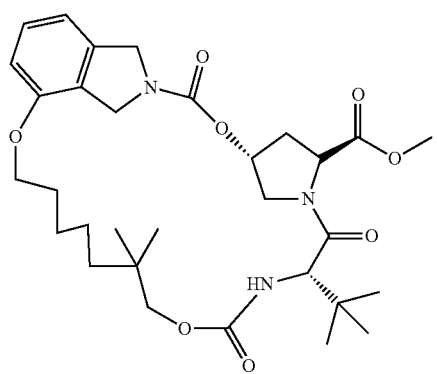
13g
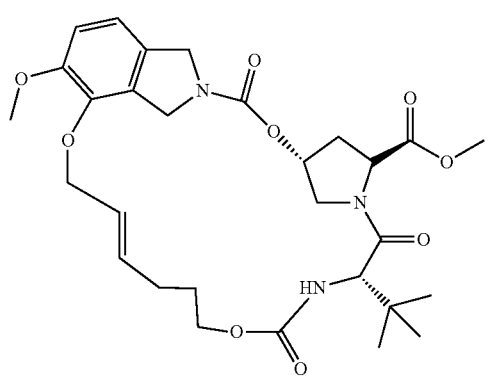
12e
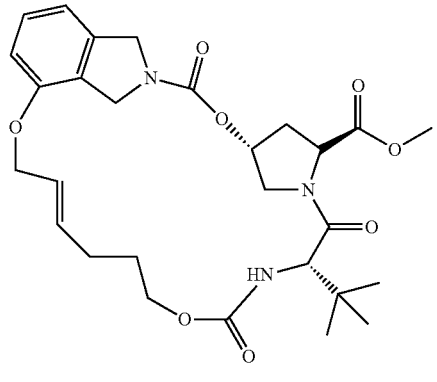
12h
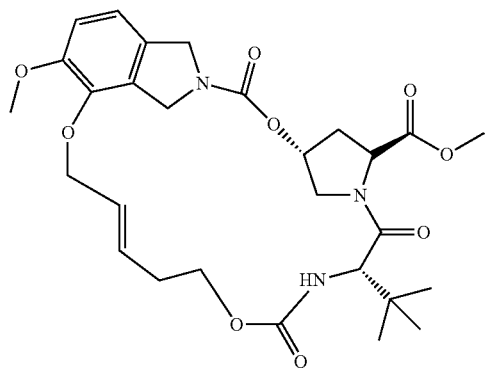
12f
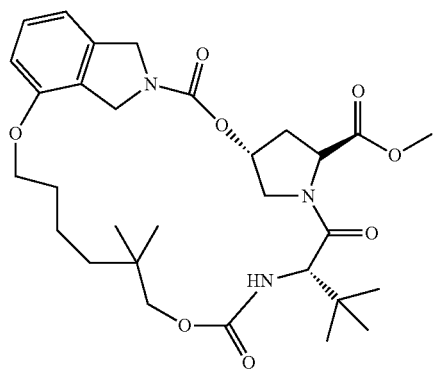
13k
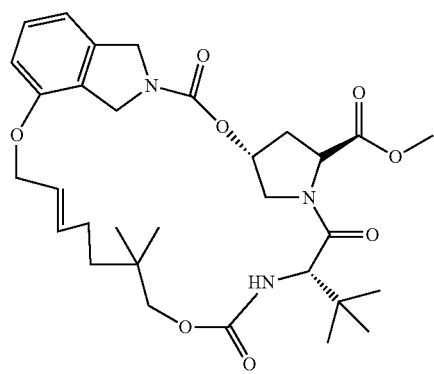
12g
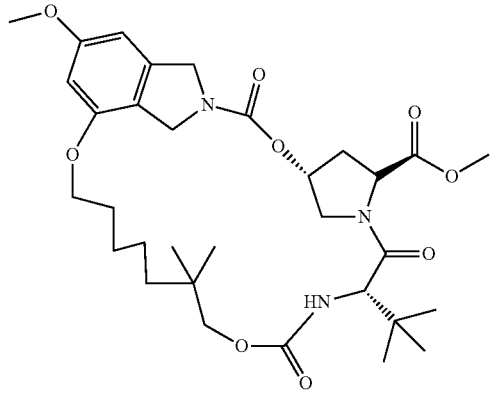
13m 261
-continued
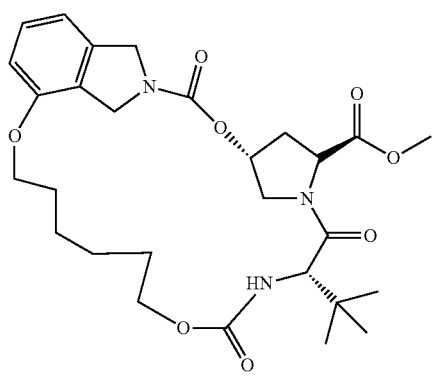
13h
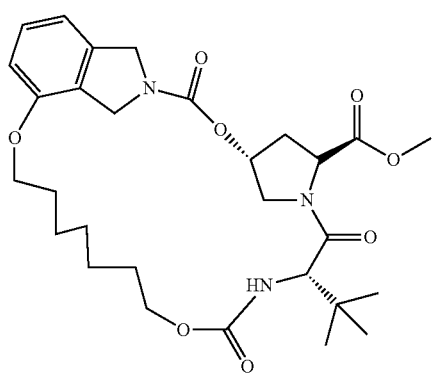
13n
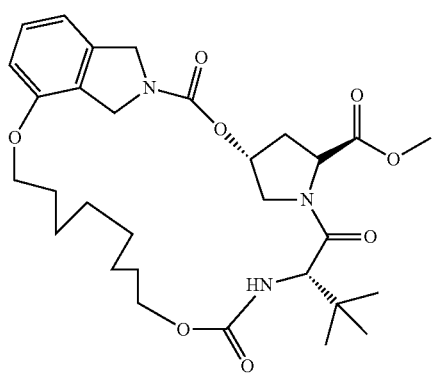
13p
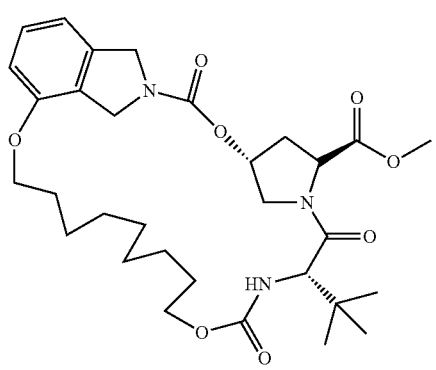
13q
262
-continued
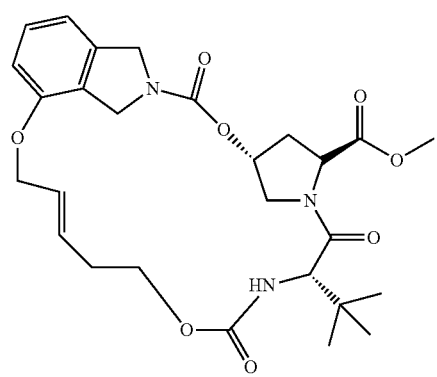
12r
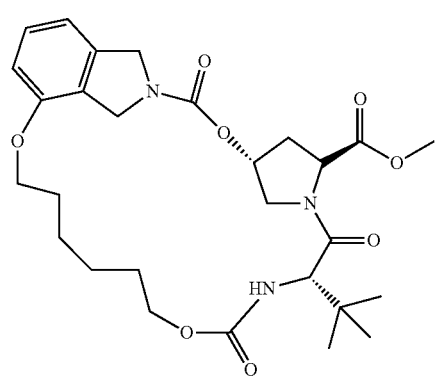
13r
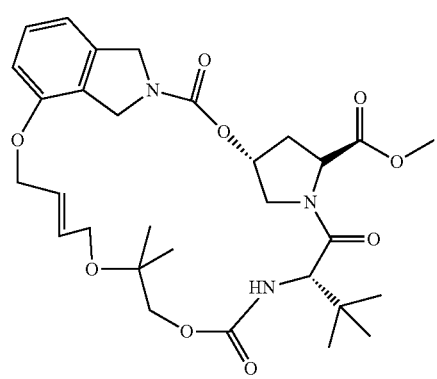
12s
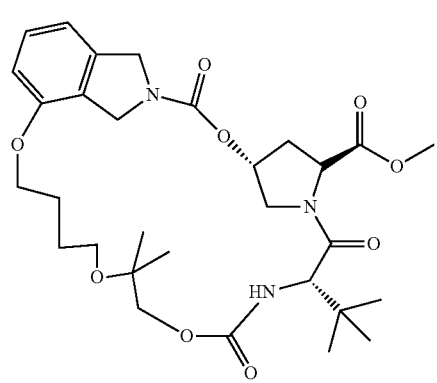
13s 263
-continued
12t
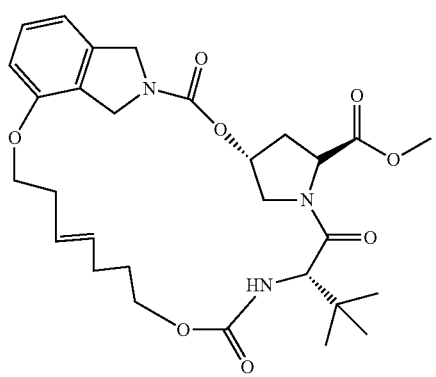
12k
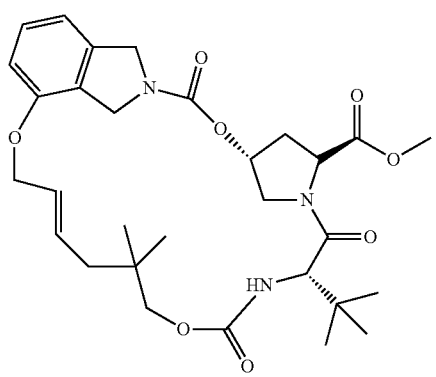
13u
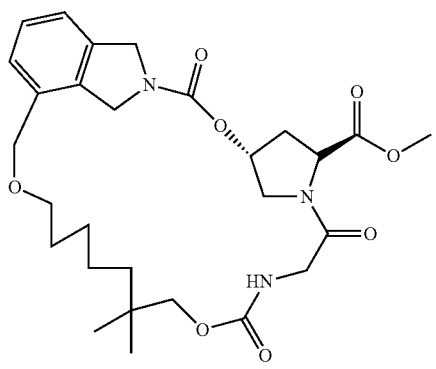
13v
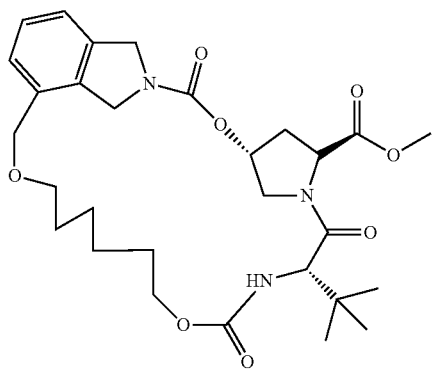
264
-continued
13w
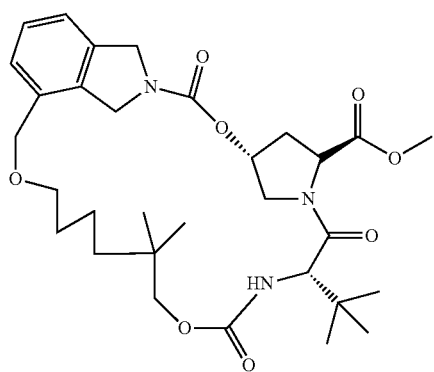
13x
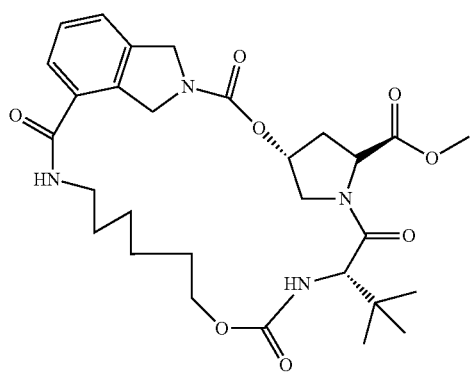
13y
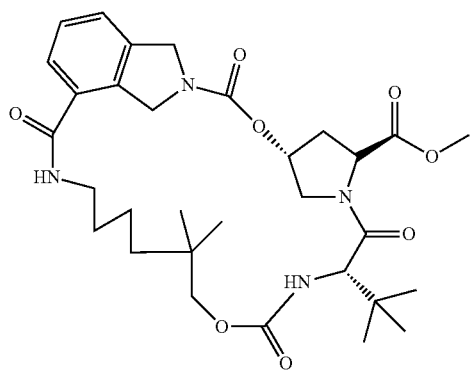
14v
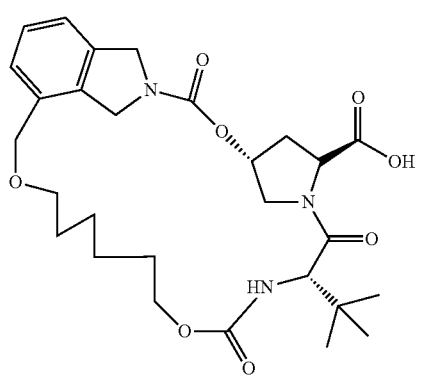

14w
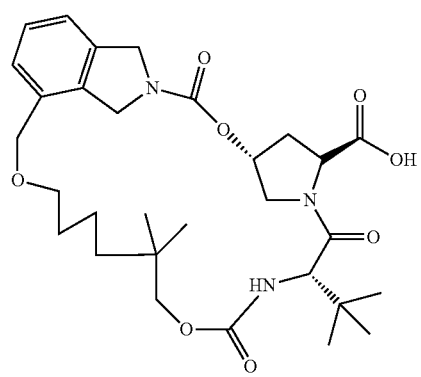
14x
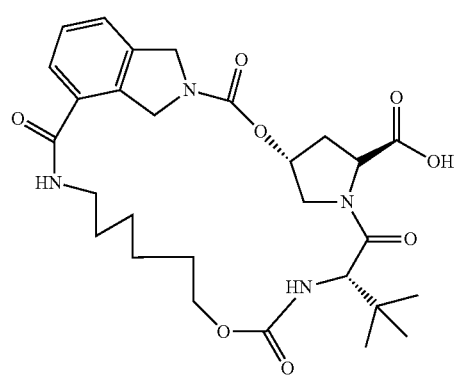
14y
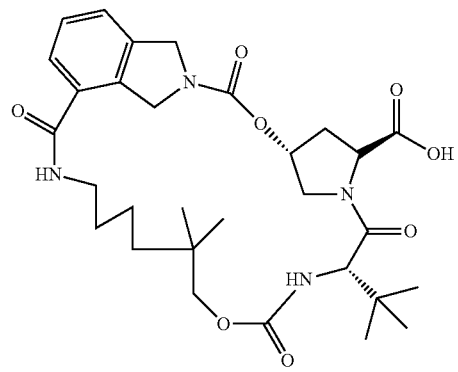
14z
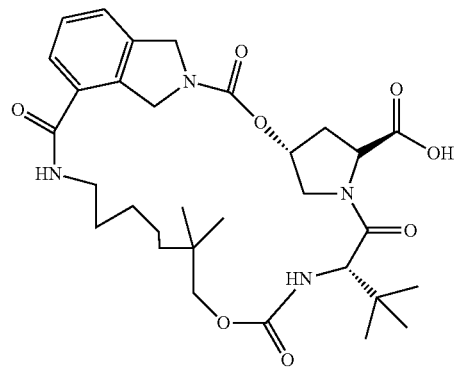
12ah
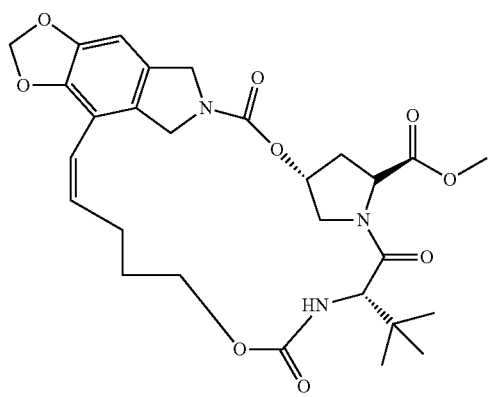
14a-2
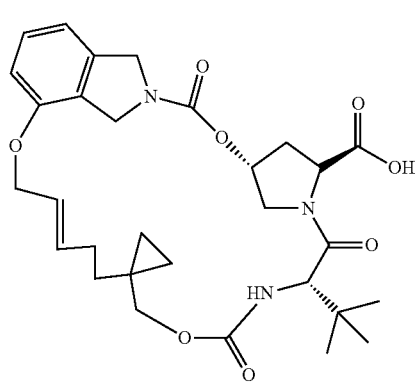
14a
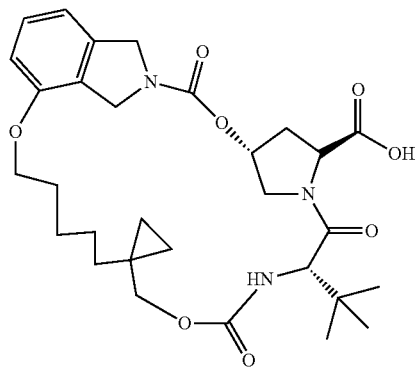
14b-2
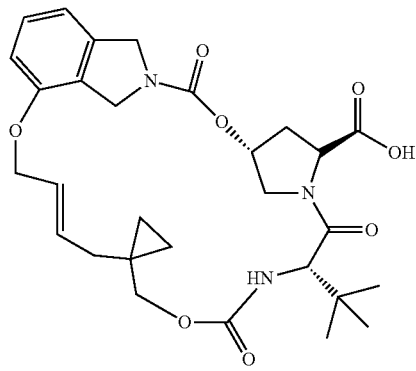

-continued
14b
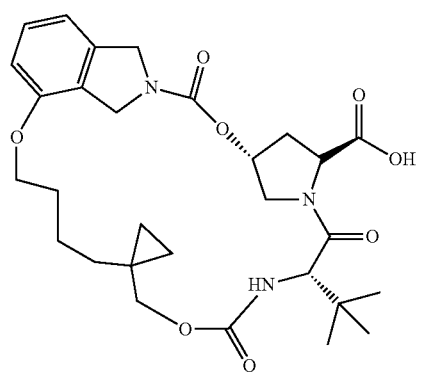
14c-2
14d-2
14e-2
-continued
14f-2
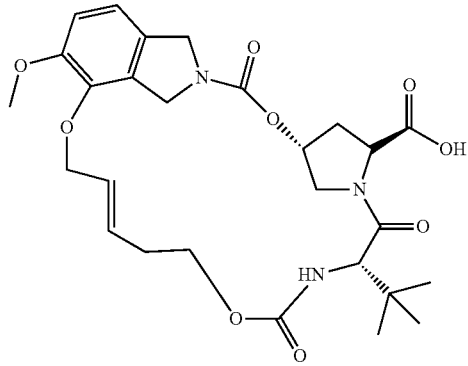
14g-2
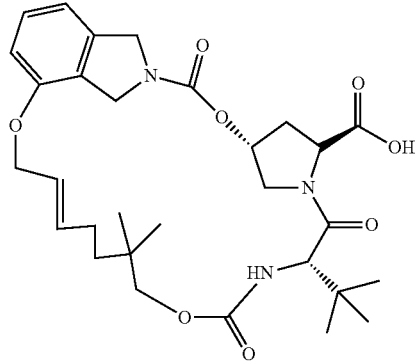
14g
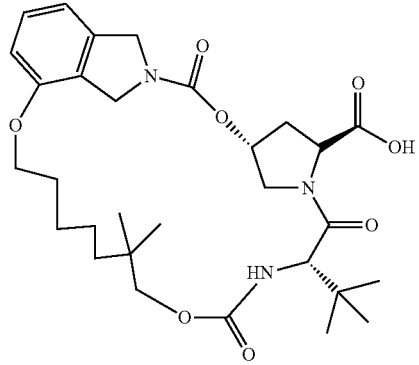
14h-2
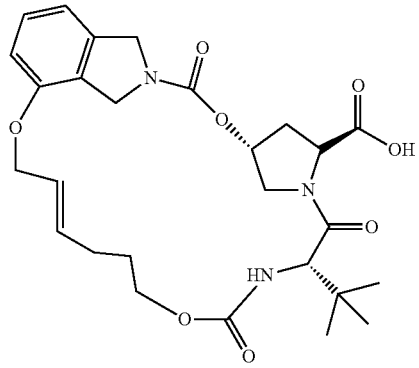

14k
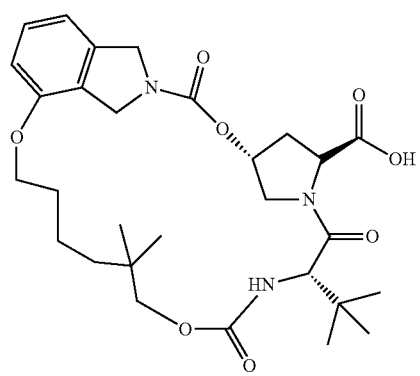
14m
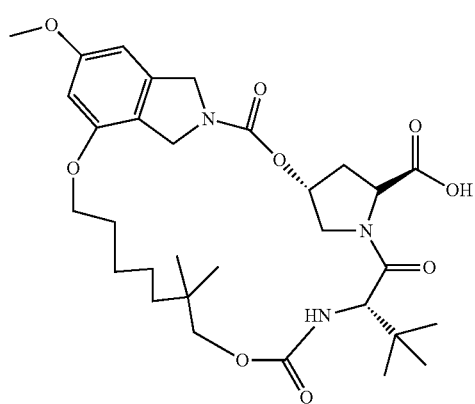
14h
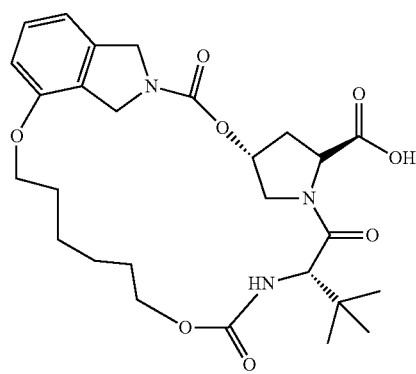
14n
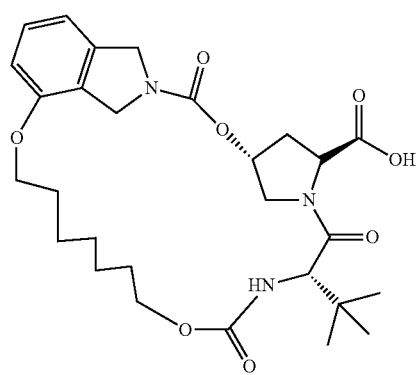
14p
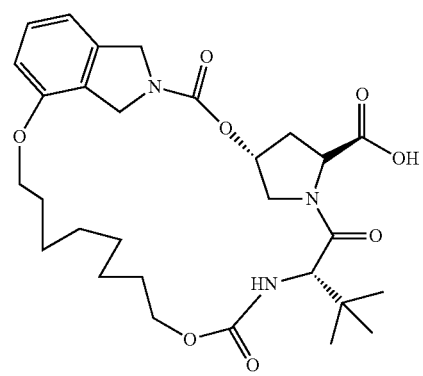
14q
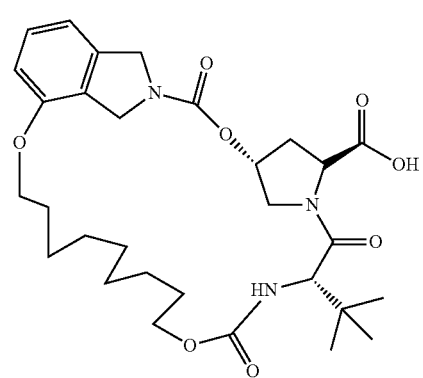
14r2
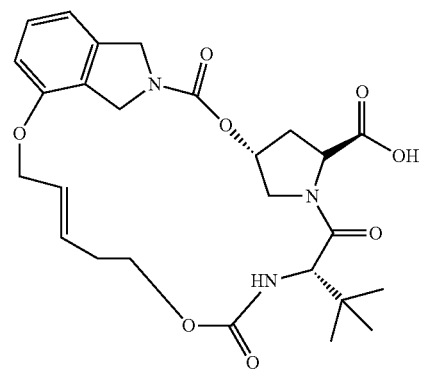
14r
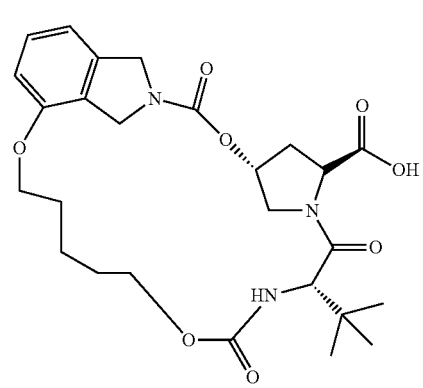

14s-2
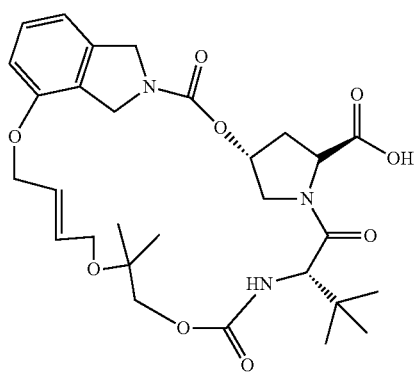
14s
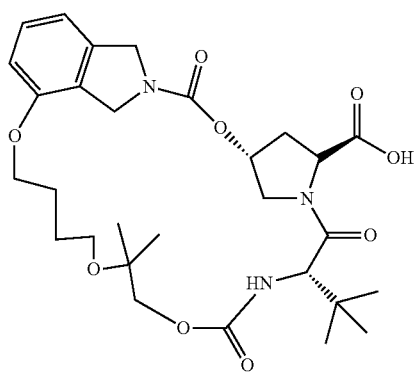
14t-2
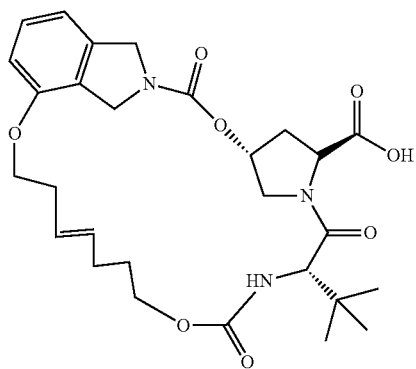
14k-2
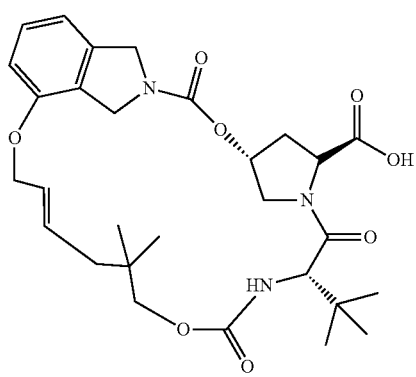
14u
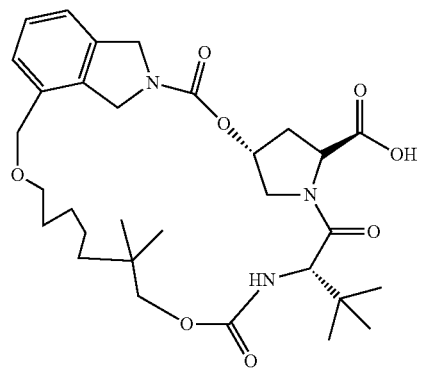
13z
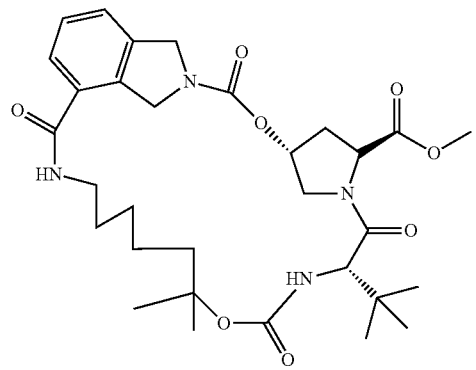
14ah-2
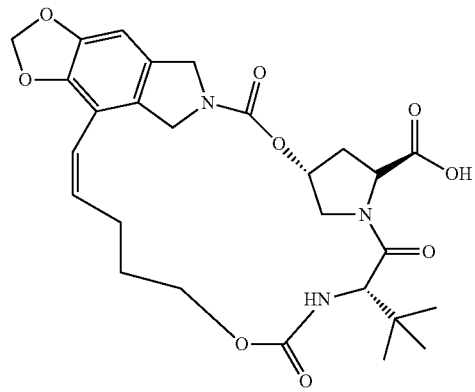
14ak-2
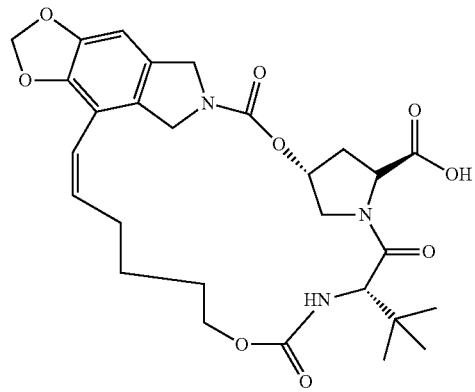

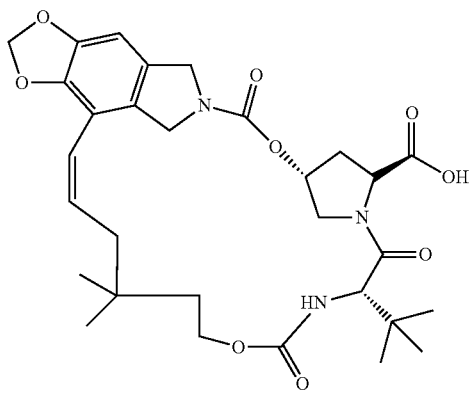
14am-2
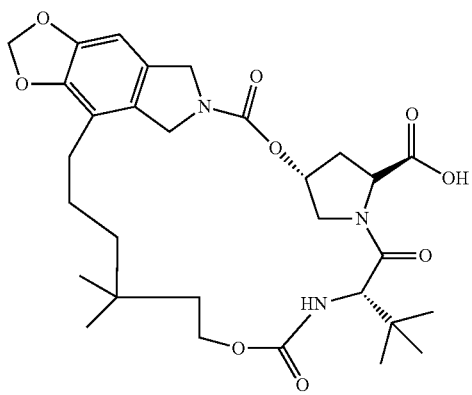
14ak
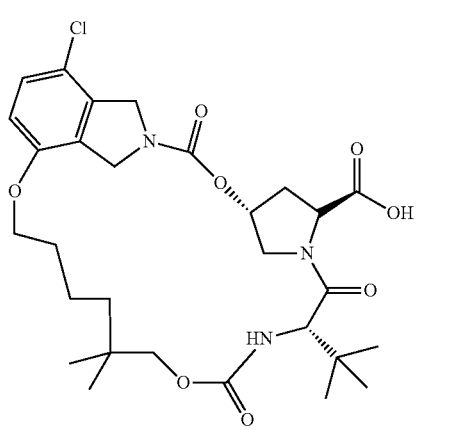
14am
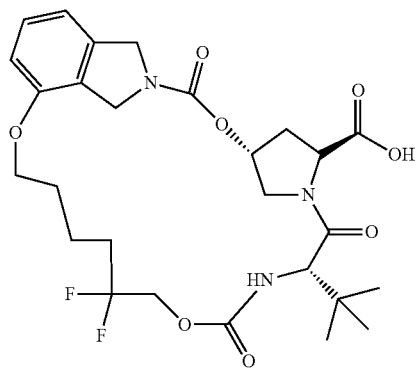
14ba
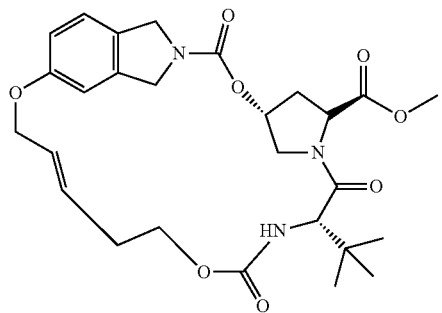
and the compound of formula IIb is selected from the following structures:
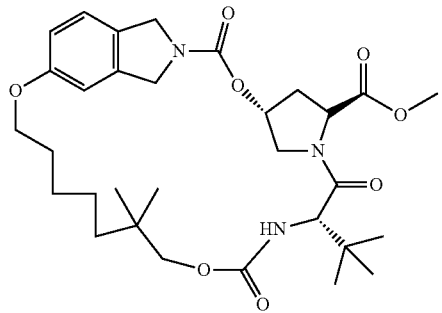
12ac
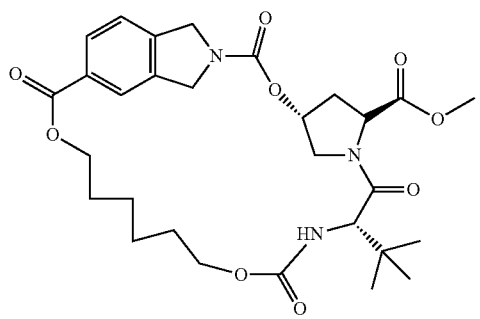
13ad
14ax
13ae 275
-continued
13af
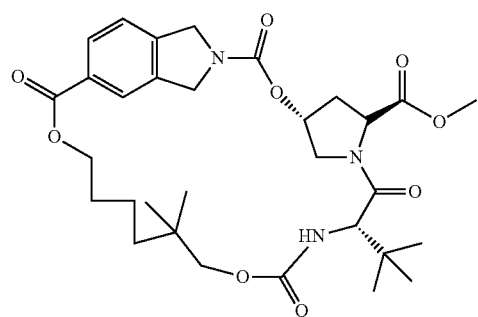
13ag
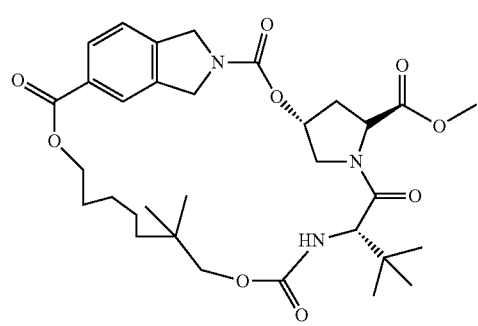
13aa
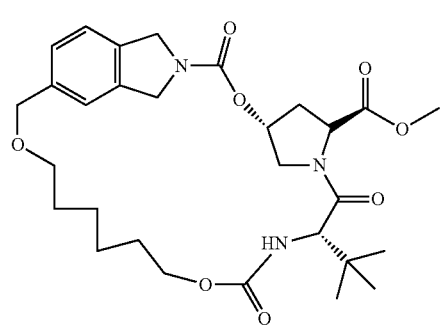
12aa
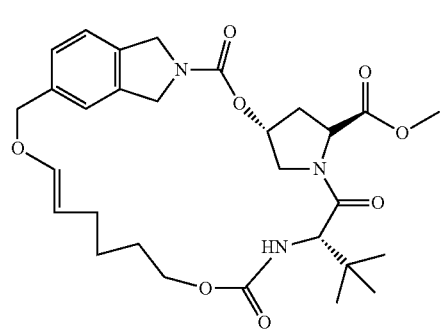
12ab
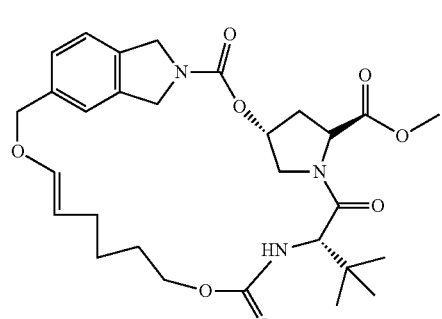
276
-continued
14ae
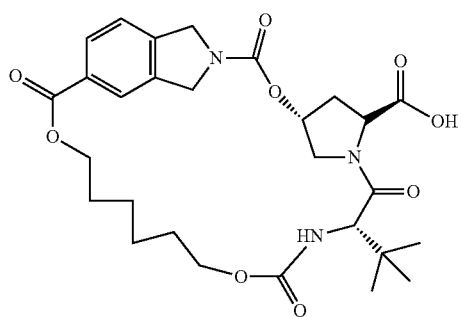
14af
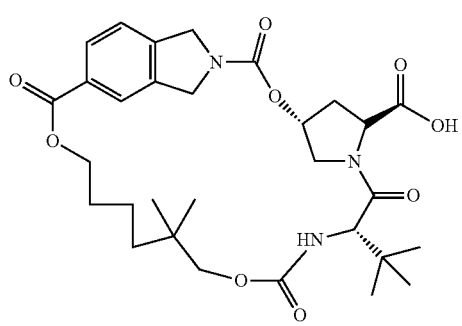
14ag
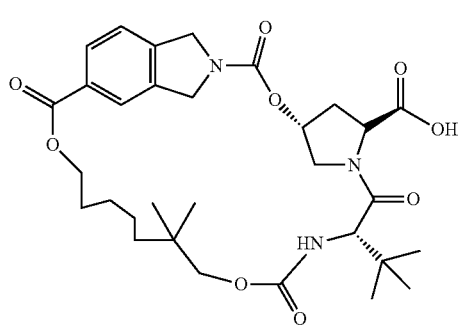
14aa
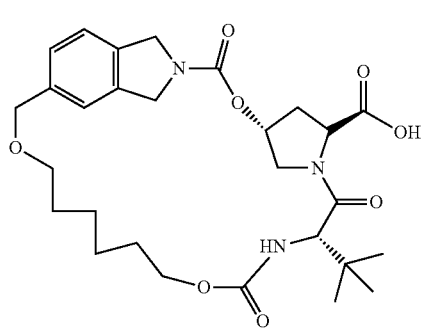
14aa-2
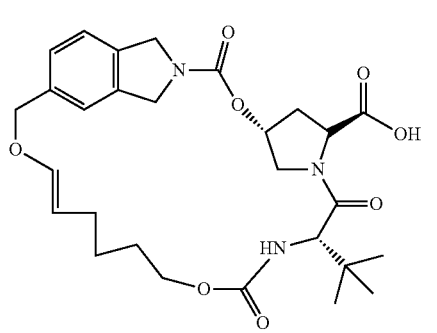

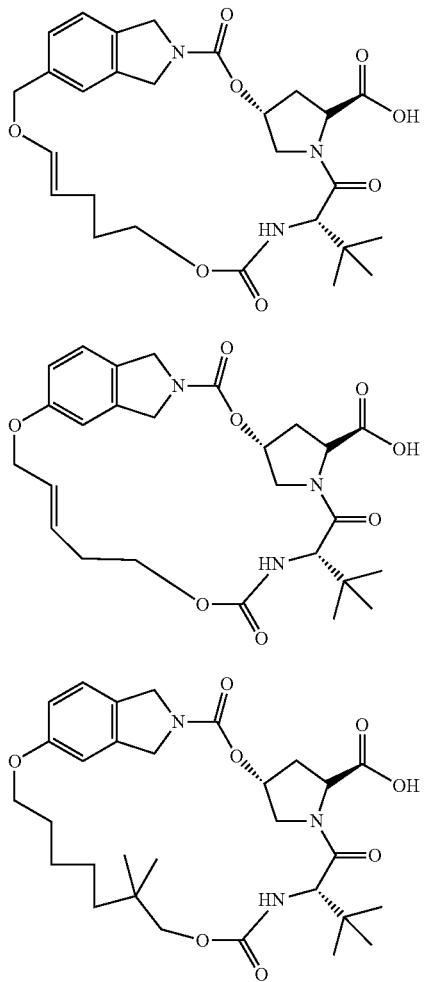

14ab-2

14ac-2

14ad

11. A method of inhibiting HCV, comprising administering to a subject in need thereof an effective amount of the compound of formula Ia or Ib of claim 1, or its stereoisomer, tautomer, esterification or amidation prodrug, pharmaceutically acceptable salt or a mixture thereof.

12. A pharmaceutical composition, which comprises: one or more compounds of formula Ia or Ib of claim 1 or their stereoisomers, tautomers, esterification or amidation prodrugs, pharmaceutically acceptable salts, and pharmaceutically acceptable excipients.

13. A pharmaceutical composition, which comprises the following one or more medicaments, and one or more compounds of formula Ia or Ib of claim 1 or their stereoisomers, tautomers, esterification or amidation prodrugs, or pharmaceutically acceptable salts: (1) immuno-modulators; (2) HCV protease inhibitors; (3) HCV polymerase inhibitors; (4) nucleosides or their derivatives which do not belong to (2)-(3); (5) HBV inhibitors; (6) HIV inhibitors; (7) anti-cancer drugs; (8) anti-inflammation drugs; or (9) other compounds not belonging to (1)-(8).

14. A pharmaceutical composition according to claim 13, wherein the immuno-modulator is an interferon or its derivatives.

15. A pharmaceutical composition according to claim 14, wherein the interferon is polyethylene glycol.

16. A pharmaceutical composition according to claim 13, wherein the HIV inhibitor is Ritonavir.

17. A pharmaceutical composition according to claim 13, wherein the HBV inhibitor is Lamivudine, Telbivudine, Adefovir, Emtricitabine, Entecavir, Tenofovir, or Clevudine.

\* \* \* \* \*